US012715874B2

(12) United States Patent
Zeng et al.

(10) Patent No.: US 12,715,874 B2
(45) **Date of Patent: *Aug. 25, 2026**

(54) ORGANIC ELECTROLUMINESCENT MATERIALS AND DEVICES

(71) Applicant: Universal Display Corporation, Ewing, NJ (US)

(72) Inventors: Lichang Zeng, Ewing, NJ (US); Zhiqiang Ji, Ewing, NJ (US); Walter Yeager, Ewing, NJ (US); Alexey Borisovich Dyatkin, Ewing, NJ (US); Chuanjun Xia, Ewing, NJ (US); Ting-Chih (Carina) Wang, Ewing, NJ (US); Bin Ma, Ewing, NJ (US); Bert Alleyne, Ewing, NJ (US); Vadim Adamovich, Ewing, NJ (US)

(73) Assignee: Universal Display Corporation, Ewing, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/491,066

(22) Filed: Oct. 20, 2023

(65) Prior Publication Data

US 2024/0081147 A1 Mar. 7, 2024

Related U.S. Application Data

(63) Continuation of application No. 15/951,662, filed on Apr. 12, 2018, now Pat. No. 11,818,949, which is a continuation-in-part of application No. 15/283,982, filed on Oct. 3, 2016, now Pat. No. 11,495,749, which is a continuation-in-part of application No. 15/064,023, filed on Mar. 8, 2016, now abandoned.

(60) Provisional application No. 62/274,520, filed on Jan. 4, 2016, provisional application No. 62/254,299, filed on Nov. 12, 2015, provisional application No. 62/245,578, filed on Oct. 23, 2015, provisional application No. 62/143,370, filed on Apr. 6, 2015.

(51) Int. Cl.

| | |
|---|---|
| ***C07D 487/04*** | (2006.01) |
| ***C09K 11/02*** | (2006.01) |
| ***H10K 50/11*** | (2023.01) |
| ***H10K 50/15*** | (2023.01) |
| ***H10K 50/16*** | (2023.01) |
| ***H10K 50/18*** | (2023.01) |
| ***H10K 85/30*** | (2023.01) |
| ***H10K 85/60*** | (2023.01) |
| ***H10K 101/00*** | (2023.01) |
| ***H10K 101/10*** | (2023.01) |

(52) U.S. Cl.

CPC .......... *C07D 487/04* (2013.01); *C09K 11/025* (2013.01); *H10K 85/6572* (2023.02); *C09K 2211/1007* (2013.01); *C09K 2211/1029* (2013.01); *C09K 2211/1033* (2013.01); *C09K 2211/1092* (2013.01); *C09K 2211/185* (2013.01); *C09K 2211/188* (2013.01); *H10K 50/11* (2023.02); *H10K 50/15* (2023.02); *H10K 50/16* (2023.02); *H10K 50/18* (2023.02); *H10K 85/342* (2023.02); *H10K 2101/10* (2023.02); *H10K 2101/90* (2023.02)

(58) Field of Classification Search

CPC ............. H01L 51/0052; H01L 51/0067; H01L 51/0072; H01L 51/0073; H01L 51/0074; H01L 51/5016; H01L 51/5072; H01L 51/0071; H01L 51/0054; H01L 51/5096; H01L 51/5056; H01L 51/0085; H01L 2251/5384; H10K 85/6572; H10K 85/342; H10K 85/615; H10K 85/654; H10K 85/6574; H10K 50/16; H10K 50/11; H10K 50/18; H10K 85/6576; H10K 50/15; H10K 2101/90; C09K 11/025; C09K 11/06; C09K 2211/1007; C09K 2211/1029; C09K 2211/185; C09K 405/14; C09K 487/04

USPC ..... 548/418; 428/690, 691, 917, 411.433, 6; 427/58, 66; 313/500–512; 257/40, 257/88–104, 51.001, 51.052; 252/301.16–301.35

See application file for complete search history.

(56) References Cited

U.S. PATENT DOCUMENTS

| | | | |
|---|---|---|---|
| 4,769,292 | A | 9/1988 | Tang |
| 5,061,569 | A | 10/1991 | Vanslyke |
| 5,247,190 | A | 9/1993 | Friend |
| 5,703,436 | A | 12/1997 | Forrest |
| 5,707,745 | A | 1/1998 | Forrest |
| 5,834,893 | A | 11/1998 | Bulovic |

(Continued)

FOREIGN PATENT DOCUMENTS

| | | |
|---|---|---|
| CN | 103313979 | 9/2013 |
| CN | 103313979 A | 9/2013 |

(Continued)

OTHER PUBLICATIONS

Tung, Yung-Liang et al., "Organic Light-Emitting Diodes Based on Charge-Neutral Ru II PHosphorescent Emitters," Adv. Mater., 17(8):1059-1064 (2005).

(Continued)

*Primary Examiner* — Dylan C Kershner
(74) *Attorney, Agent, or Firm* — Riverside Law LLP

(57) ABSTRACT

The present invention relates in part to compounds containing indolocarbazole and terphenyl building blocks are disclosed in this application. These compounds are useful for application in organic electroluminescent devices wherein the combination of indolocarbazoles with terphenyl groups leads to novel compounds that demonstrate superior device performance.

11 Claims, 2 Drawing Sheets

(56) References Cited

U.S. PATENT DOCUMENTS

| | | | | |
|---|---|---|---|---|
| 5,844,363 | A | 12/1998 | Gu | |
| 6,013,982 | A | 1/2000 | Thompson | |
| 6,087,196 | A | 7/2000 | Sturm | |
| 6,091,195 | A | 7/2000 | Forrest | |
| 6,097,147 | A | 8/2000 | Baldo | |
| 6,294,398 | B1 | 9/2001 | Kim | |
| 6,303,238 | B1 | 10/2001 | Thompson | |
| 6,337,102 | B1 | 1/2002 | Forrest | |
| 6,468,819 | B1 | 10/2002 | Kim | |
| 6,528,187 | B1 | 3/2003 | Okada | |
| 6,687,266 | B1 | 2/2004 | Ma | |
| 6,835,469 | B2 | 12/2004 | Kwong | |
| 6,921,915 | B2 | 7/2005 | Takiguchi | |
| 7,087,321 | B2 | 8/2006 | Kwong | |
| 7,090,928 | B2 | 8/2006 | Thompson | |
| 7,154,114 | B2 | 12/2006 | Brooks | |
| 7,250,226 | B2 | 7/2007 | Tokito | |
| 7,279,704 | B2 | 10/2007 | Walters | |
| 7,332,232 | B2 | 2/2008 | Ma | |
| 7,338,722 | B2 | 3/2008 | Thompson | |
| 7,393,599 | B2 | 7/2008 | Thompson | |
| 7,396,598 | B2 | 7/2008 | Takeuchi | |
| 7,431,968 | B1 | 10/2008 | Shtein | |
| 7,445,855 | B2 | 11/2008 | Mackenzie | |
| 7,534,505 | B2 | 5/2009 | Lin | |
| 7,968,146 | B2 | 6/2011 | Wagner | |
| 8,409,729 | B2 | 4/2013 | Zeng | |
| 8,962,158 | B2 | 2/2015 | Komori | |
| 9,067,947 | B2 | 6/2015 | Lin | |
| 10,593,890 | B2 | 3/2020 | Zeng | |
| 11,094,891 | B2 | 8/2021 | Zeng | |
| 11,245,080 | B2 | 2/2022 | Zeng | |
| 11,495,749 | B2* | 11/2022 | Zeng | C09K 11/025 |
| 11,818,949 | B2* | 11/2023 | Zeng | C07D 487/04 |
| 2002/0034656 | A1 | 3/2002 | Thompson | |
| 2002/0076576 | A1* | 6/2002 | Li | H10K 85/00 428/917 |
| 2002/0121860 | A1 | 9/2002 | Seo | |
| 2002/0134984 | A1 | 9/2002 | Igarashi | |
| 2002/0158242 | A1 | 10/2002 | Son | |
| 2002/0197511 | A1* | 12/2002 | D'Andrade | H10K 50/125 313/506 |
| 2003/0104243 | A1 | 6/2003 | Aziz | |
| 2003/0132704 | A1 | 7/2003 | Aziz | |
| 2003/0137239 | A1 | 7/2003 | Matsuura | |
| 2003/0138657 | A1 | 7/2003 | Li | |
| 2003/0148142 | A1 | 8/2003 | Fryd | |
| 2003/0152802 | A1 | 8/2003 | Tsuboyama | |
| 2003/0162053 | A1 | 8/2003 | Marks | |
| 2003/0175553 | A1 | 9/2003 | Thompson | |
| 2003/0230980 | A1 | 12/2003 | Forrest | |
| 2004/0036077 | A1 | 2/2004 | Ise | |
| 2004/0137267 | A1 | 7/2004 | Igarashi | |
| 2004/0137268 | A1 | 7/2004 | Igarashi | |
| 2004/0164292 | A1 | 8/2004 | Tung | |
| 2004/0174116 | A1 | 9/2004 | Lu | |
| 2004/0263065 | A1 | 12/2004 | Yeh | |
| 2005/0025993 | A1 | 2/2005 | Thompson | |
| 2005/0089715 | A1 | 4/2005 | Cosimbescu | |
| 2005/0112407 | A1 | 5/2005 | Ogasawara | |
| 2005/0238919 | A1 | 10/2005 | Ogasawara | |
| 2005/0244673 | A1 | 11/2005 | Satoh | |
| 2005/0260441 | A1 | 11/2005 | Thompson | |
| 2005/0260449 | A1 | 11/2005 | Walters | |
| 2006/0008670 | A1 | 1/2006 | Lin | |
| 2006/0057423 | A1 | 3/2006 | Steudel | |
| 2006/0202194 | A1 | 9/2006 | Jeong | |
| 2006/0227081 | A1 | 10/2006 | Joo | |
| 2006/0240279 | A1 | 10/2006 | Adamovich | |
| 2006/0251923 | A1 | 11/2006 | Lin | |
| 2006/0263635 | A1 | 11/2006 | Ise | |
| 2006/0280965 | A1 | 12/2006 | Kwong | |
| 2007/0190359 | A1 | 8/2007 | Knowles | |
| 2007/0237982 | A1 | 10/2007 | Inoue | |
| 2007/0252516 | A1 | 11/2007 | Kondakova | |
| 2007/0278938 | A1 | 12/2007 | Yabunouchi | |
| 2008/0015355 | A1 | 1/2008 | Schafer | |
| 2008/0018221 | A1 | 1/2008 | Egen | |
| 2008/0106190 | A1 | 5/2008 | Yabunouchi | |
| 2008/0124572 | A1 | 5/2008 | Mizuki | |
| 2008/0220265 | A1 | 9/2008 | Xia | |
| 2008/0297033 | A1 | 12/2008 | Knowles | |
| 2009/0008605 | A1 | 1/2009 | Kawamura | |
| 2009/0009065 | A1 | 1/2009 | Nishimura | |
| 2009/0017330 | A1 | 1/2009 | Iwakuma | |
| 2009/0030202 | A1 | 1/2009 | Iwakuma | |
| 2009/0039776 | A1 | 2/2009 | Yamada | |
| 2009/0045730 | A1 | 2/2009 | Nishimura | |
| 2009/0045731 | A1 | 2/2009 | Nishimura | |
| 2009/0101870 | A1 | 4/2009 | Prakash | |
| 2009/0108737 | A1 | 4/2009 | Kwong | |
| 2009/0115316 | A1 | 5/2009 | Zheng | |
| 2009/0165846 | A1 | 7/2009 | Johannes | |
| 2009/0167162 | A1 | 7/2009 | Lin | |
| 2009/0179554 | A1 | 7/2009 | Kuma | |
| 2009/0302743 | A1 | 12/2009 | Kato | |
| 2010/0012931 | A1 | 1/2010 | Kato | |
| 2010/0184942 | A1 | 7/2010 | Chen | |
| 2010/0187977 | A1 | 7/2010 | Kai | |
| 2010/0187984 | A1* | 7/2010 | Lin | H10K 50/157 546/89 |
| 2010/0237334 | A1 | 9/2010 | Ma | |
| 2011/0062429 | A1* | 3/2011 | Kai | C09B 47/00 546/88 |
| 2011/0278552 | A1 | 11/2011 | Numata | |
| 2012/0001158 | A1 | 1/2012 | Asari | |
| 2012/0001165 | A1* | 1/2012 | Komori | C07D 487/04 546/276.7 |
| 2012/0056171 | A1 | 3/2012 | Kim | |
| 2012/0104940 | A1 | 5/2012 | Shin | |
| 2012/0175598 | A1 | 7/2012 | Balaganesan | |
| 2012/0205640 | A1 | 8/2012 | Kai | |
| 2013/0026452 | A1 | 1/2013 | Kottas | |
| 2013/0112950 | A1 | 5/2013 | Yokoyama | |
| 2013/0119354 | A1 | 5/2013 | Ma | |
| 2013/0248849 | A1 | 9/2013 | Feldman | |
| 2014/0034914 | A1 | 2/2014 | Saki | |
| 2014/0054564 | A1 | 2/2014 | Kim | |
| 2014/0077179 | A1 | 3/2014 | Shin | |
| 2014/0084273 | A1 | 3/2014 | Nakayama | |
| 2014/0124756 | A1 | 5/2014 | Yokoyama | |
| 2014/0225046 | A1 | 8/2014 | Jatsch | |
| 2014/0374711 | A1 | 12/2014 | Cho | |
| 2015/0021556 | A1 | 1/2015 | Xia | |
| 2015/0041785 | A1 | 2/2015 | Sannomiya | |
| 2015/0053938 | A1 | 2/2015 | Zeng | |
| 2015/0060796 | A1 | 3/2015 | Kim | |
| 2015/0171340 | A1 | 6/2015 | Lee | |
| 2015/0179949 | A1 | 6/2015 | Miyata | |
| 2015/0179955 | A1 | 6/2015 | Miyata | |
| 2015/0228909 | A1 | 8/2015 | Kim | |
| 2015/0228911 | A1 | 8/2015 | Kim | |
| 2015/0236262 | A1 | 8/2015 | Cho | |
| 2015/0255726 | A1 | 9/2015 | Kawamura | |
| 2015/0318487 | A1 | 11/2015 | Ito | |
| 2015/0380662 | A1 | 12/2015 | Kim | |
| 2016/0005979 | A1 | 1/2016 | Kim | |
| 2016/0111663 | A1 | 4/2016 | Kim | |
| 2016/0118590 | A1 | 4/2016 | Ito | |
| 2016/0133844 | A1 | 5/2016 | Kim | |
| 2016/0163995 | A1* | 6/2016 | Kang | H10K 85/654 257/40 |
| 2016/0225992 | A1 | 8/2016 | Ito | |
| 2016/0276596 | A1 | 9/2016 | Jang | |
| 2016/0293853 | A1 | 10/2016 | Zeng | |
| 2016/0293855 | A1* | 10/2016 | Zeng | C09K 11/025 |
| 2017/0025618 | A1 | 1/2017 | Zheng | |
| 2017/0047527 | A1 | 2/2017 | Lee | |
| 2017/0069847 | A1 | 3/2017 | Kim | |
| 2017/0069848 | A1 | 3/2017 | Zeng | |
| 2017/0098784 | A1 | 4/2017 | Kim | |
| 2017/0179406 | A1 | 6/2017 | Kang | |

(56) References Cited

U.S. PATENT DOCUMENTS

2017/0263869 A1 9/2017 Tada
2017/0271598 A1 9/2017 Zeng
2017/0342057 A1 11/2017 Shim

FOREIGN PATENT DOCUMENTS

CN 104926805 A 9/2015
CN 106543205 A 3/2017
CN 107075363 A 8/2017
EP 0650955 5/1995
EP 0908787 4/1999
EP 1238981 9/2002
EP 1725079 11/2006
EP 2034538 3/2009
EP 2551932 1/2013
EP 2617712 7/2013
EP 2977378 1/2016
JP 2003300980 10/2003
JP 200511610 1/2005
JP 2007123392 5/2007
JP 2007254297 10/2007
JP 2008074939 A 4/2008
JP 2010135467 6/2010
JP 2012049518 3/2012
JP 2012056880 A 3/2012
JP 2014077046 A 5/2014
KR 20100082049 7/2010
KR 101003338 12/2010
KR 20100131745 A 12/2010
KR 20110011579 2/2011
KR 20110066766 6/2011
KR 20110102055 A 9/2011
KR 20120021203 3/2012
KR 20120052879 5/2012
KR 20130025268 3/2013
KR 20130132226 12/2013
KR 20140001568 1/2014
KR 20140009019 1/2014
KR 20140023589 A 2/2014
KR 20140127705 11/2014
KR 20140134947 11/2014
KR 20140145355 A 12/2014
KR 20150012835 2/2015
KR 20150133998 A 12/2015
TW 201114743 A 5/2011
WO 0139234 5/2001
WO 0202714 1/2002
WO 0215645 2/2002
WO 03040257 5/2003
WO 03060956 7/2003
WO 2004093207 10/2004
WO 2004107822 12/2004
WO 2004111066 12/2004
WO 2005014551 2/2005
WO 2005019373 3/2005
WO 2005030900 4/2005
WO 2005089025 9/2005
WO 2005123873 12/2005
WO 2006009024 1/2006
WO 2006056418 6/2006
WO 2006067074 6/2006
WO 2006072002 7/2006
WO 2006082742 8/2006
WO 2006098120 9/2006
WO 2006100298 9/2006
WO 2006103874 10/2006
WO 2006114966 11/2006
WO 2006115301 11/2006
WO 2006121811 11/2006
WO 2006128800 12/2006
WO 2006132173 12/2006
WO 2007002683 1/2007
WO 2007004380 1/2007
WO 2007063754 6/2007
WO 2007063796 6/2007
WO 2008044723 4/2008
WO 2008056746 5/2008
WO 2008057394 5/2008
WO 2008101842 8/2008
WO 2008132085 11/2008
WO 2009000673 12/2008
WO 2009003898 1/2009
WO 2009008311 1/2009
WO 2009018009 2/2009
WO 2009021126 A2 2/2009
WO 2009050290 4/2009
WO 2009062578 5/2009
WO 2009063833 5/2009
WO 2009066778 5/2009
WO 2009066779 5/2009
WO 2009086028 7/2009
WO 2009100991 8/2009
WO 2009148016 12/2009
WO 2009148062 12/2009
WO 2010011390 1/2010
WO 2010107244 9/2010
WO 2010111175 9/2010
WO 2010126234 11/2010
WO 2011049325 4/2011
WO 2012029253 3/2012
WO 2012039561 3/2012
WO 2012067425 5/2012
WO 2012087007 6/2012
WO 2013027902 2/2013
WO 2013041176 3/2013
WO 2013109045 7/2013
WO 2013154325 A1 10/2013
WO 2013162284 10/2013
WO 2013165189 11/2013
WO 2013183851 A1 12/2013
WO 2014010910 1/2014
WO 2014044722 A1 3/2014
WO 2014061546 4/2014
WO 2014061961 4/2014
WO 2014088285 6/2014
WO 2014129846 8/2014
WO 2014142467 9/2014
WO 2014142472 9/2014
WO 2014157708 10/2014
WO 2014200244 12/2014
WO 2014208755 12/2014
WO 2015009102 1/2015
WO 2015022835 A1 2/2015
WO 2015022987 2/2015
WO 2015053524 A1 4/2015
WO 2015063046 5/2015
WO 2015099507 7/2015
WO 2015108325 7/2015
WO 2015111848 7/2015
WO 2015152644 10/2015
WO 2015167259 11/2015
WO 2015167259 A1 11/2015
WO 2017056052 4/2017
WO 2014069637 2/2020

OTHER PUBLICATIONS

Van Slyke, S. A. et al., "Organic Electroluminescent Devices with Improved Stability," Appl. Phys. Lett, 69 (15 ):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., "A Novel Class of Phosphorescent Gold(III) Alkynyl-Based Organic Light-Emitting Devices with Tunable Colour," Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Yoshida, Kei et al., Machine translation of JP-2012056880-A (2012) pp. 1-19. (Year: 2012).
Adachi, Chihaya et al., "High-Efficiency Red Electrophosphorescence Devices," Appl. Phys. Lett., 78(11):1622-1624 (2001).

(56) References Cited

OTHER PUBLICATIONS

Adachi, Chihaya et al., "Organic Electroluminescent Device Having a Hole Conductor as an Emitting Layer," Appl. Phys. Lett., 55(15):1489-1491 (1989).
Adachi, Chihaya et al., "Nearly 100% Internal Phosphorescence Efficiency in an Organic Light Emitting Device," J. Appl. Phys., 90(10):5048-5051 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., "Highly Efficient Phosphorescent Emission from Organic Electroluminescent Devices," Nature, vol. 395,151-154, (1998).
Baldo et al., "Very high-efficiency green organic light-emitting devices based on electrophosphorescence," Appl. Phys. Lett., vol. 75, No. 3, 4-6 (1999).
Chae Mi Young et al., machine translation of KR-20110102055-A (2011) pp. 1-69. (Year: 2011).
Chun et al., caplus abstract of U.S. Pat. No. 9,067,947, 2015.
Gao, Zhiqiang et al., "Bright-Blue Electroluminescence From a Silyl-Substituted ter-(phenylene-vinylene) derivative," Appl. Phys. Lett., 74(6):865-867 (1999).
Guo, Tzung-Fang et al., "Highly Efficient Electrophosphorescent Polymer Light-Emitting Devices," Organic Electronics, 1:15-20 (2000).
Hamada, Yuji et al., "High Luminance in Organic Electroluminescent Devices with Bis(10-hydroxybenzo[h]quinolinato)beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185: Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Japanese Office Action (with English language translation) for Application No. 2016-075535, date of mailing May 28, 2019, 6 pages.
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al.,"1,2,4-Triazole Derivative as an Electron Transport Layer in Organic Electroluminescent Devices," Jpn. J. Appl. Phys., 32:L917-L920 (1993).
Kim et al., Machine translation of WO-2014142472-A1 (2014) pp. 1-25. (Year: 2014).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81 (1):162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21):5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Machine translation of KR2014/0134947A (Year: 2014) 33 pages.
Merriam-Webster definition of "single" ("single." Merriam-Webster.com. Merriam-Webster, n.d. Web. Dec. 23, 2019). (Year: 2019) (2 pages).
Mi, Bao-Xiu et al., "Thermally Stable Hole-Transporting Material for Organic Light-Emitting Diode: an Isoindole Derivative," Chem. Mater., 15(16):3148-3151 (2003).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,6-Bis(dinnesitylboryl)-2,2'-bithiophene and 5,5''-Bis(dimesitylbory1)-2,2':5',2''-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Park Seong Je et al., machine translation of WO-2014142472-A1, pp. 1-25. (Year: 2014) (25 pages).
Paulose, Betty Marie Jennifer S, et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Ostergard et al., "Langmuir-Blodgett Light-Emitting Diodes Of Poly(3-Hexylthiophene): Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).
Tanaka et al., machine translation of WO-2014208755-A1 (2014) pp. 1-78. (Year: 2014).

(56) References Cited

OTHER PUBLICATIONS

Tang, C.W. and VanSlyke, S.A., "Organic Electroluminescent Diodes," Appl. Phys. Lett., 51(12):913-915 (1987).
Third Party Preissuance Submissions issued in U.S. Appl. No. 16/802,869, dated Oct. 27, 2020 (pp. 1-37).

* cited by examiner

ORGANIC ELECTROLUMINESCENT MATERIALS AND DEVICES

CROSS-REFERENCE TO RELATED APPLICATIONS

This application is a continuation of U.S. patent application Ser. No. 15/951,662, filed Apr. 12, 2018, now allowed, which is a continuation-in-part of U.S. patent application Ser. No. 15/283,982, filed Oct. 3, 2016, now U.S. Pat. No. 11,495,749, which is a continuation-in-part of U.S. patent application Ser. No. 15/064,023, filed Mar. 8, 2016, which claims priority from U.S. Provisional Patent Application Ser. Nos. 62/143,370, filed Apr. 6, 2015, 62/245,578, filed Oct. 23, 2015, 62/254,299, filed Nov. 12, 2015, and 62/274,520, filed Jan. 4, 2016, all of which applications are incorporated by reference herein in their entireties.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as host materials or electron transporting materials, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

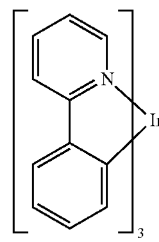

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

Indolocarbazole and oligophenylenes have excellent charge-transport properties, useful for organic electronic devices. Thus, there is a need in the art for novel indolocarbazole, oligophenylenes, and indolocarbazole-oligophenylenes to be used in organic electronic devices.

SUMMARY

According to an embodiment, a composition of materials is provided comprising a first compound, wherein the first compound has a formula selected from the group consisting of Formula I and Formula II:

Formula I

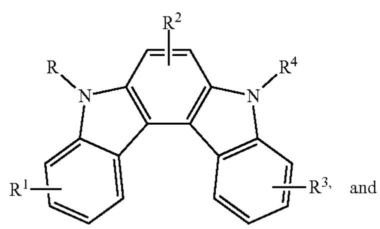

and

Formula II

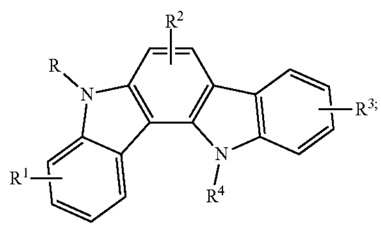

wherein R is selected from the group consisting of:

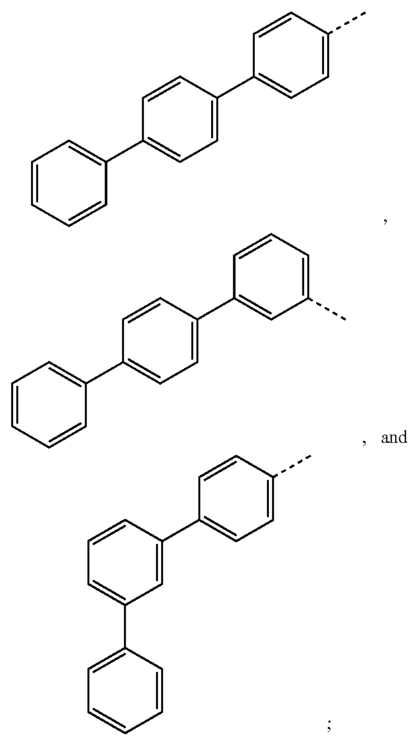

wherein $R^4$ is selected from the group consisting of alkyl, alkoxy, silyl, aryl, heteroaryl, and combinations thereof;

wherein $R^1$, $R^2$ and $R^3$ each independently represents mono to maximum allowable substitutions, or no substitution;

wherein $R^1$, $R^2$ and $R^3$ are each independently selected from the group consisting of hydrogen, deuterium, alkyl, alkenyl, alkyne, alkoxy, halogen, silyl, nitrile, nitro, aryl, heteroaryl and combinations thereof;

wherein any two adjacent substituents are optionally joined or fused into a ring;

wherein $R^4$, $R^1$, $R^2$, and $R^3$ are each independently, optionally, further substituted with one or more substituents selected from the group consisting of hydrogen, deuterium, alkyl, alkenyl, alkyne, alkoxy, halogen, silyl, nitrile, nitro, aryl, heteroaryl, and combinations thereof; and wherein any hydrogen in the compound is optionally replaced with deuterium.

According to another embodiment, an organic light emitting diode/device (OLED) is also provided. The OLED can include an anode, a cathode, and an organic layer, disposed between the anode and the cathode. The organic layer can include a composition of materials comprising a first compound, wherein the first compound has a formula selected from the group consisting of Formula I and Formula II. According to yet another embodiment, the organic light emitting device is incorporated into a device selected from a consumer product, an electronic component module, and/or a lighting panel.

According to another embodiment, a consumer product comprising an organic light-emitting device (OLED) is provided. The OLED can include an anode, a cathode, and an organic layer, disposed between the anode and the cathode. The organic layer can include a composition of materials comprising a first compound, wherein the first compound has a formula selected from the group consisting of Formula I and Formula II.

According to another embodiment, an emissive region or an emissive layer is provided. The emissive region or emissive layer can include a composition of materials comprising a first compound, wherein the first compound has a formula selected from the group consisting of Formula I and Formula II.

According to another embodiment, the invention provides a method for fabricating an organic light emitting device comprising a first electrode, a second electrode, and a first organic layer disposed between the first electrode and the second electrode, wherein the first organic layer comprises a first composition comprising a mixture of a first compound and a second compound, wherein the first compound has a formula selected from the group consisting of Formula I and Formula II, and the second compound has the Formula III.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
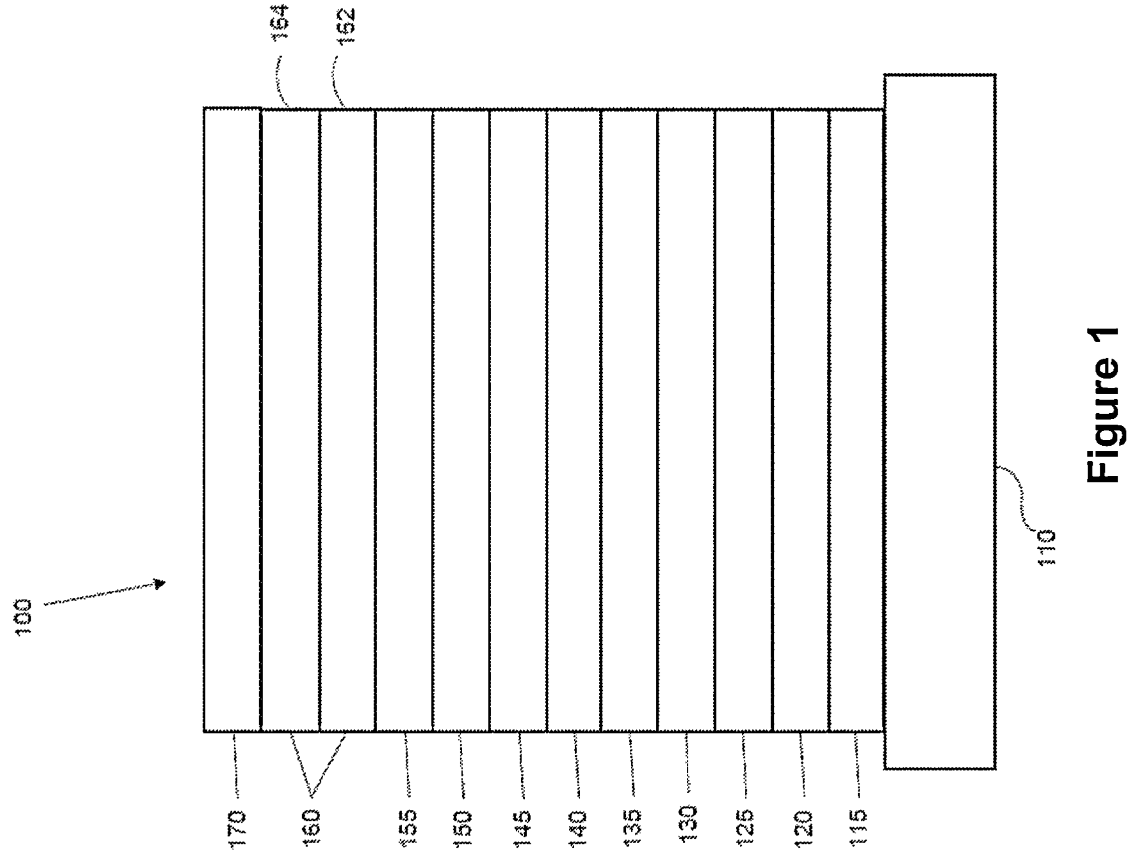
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
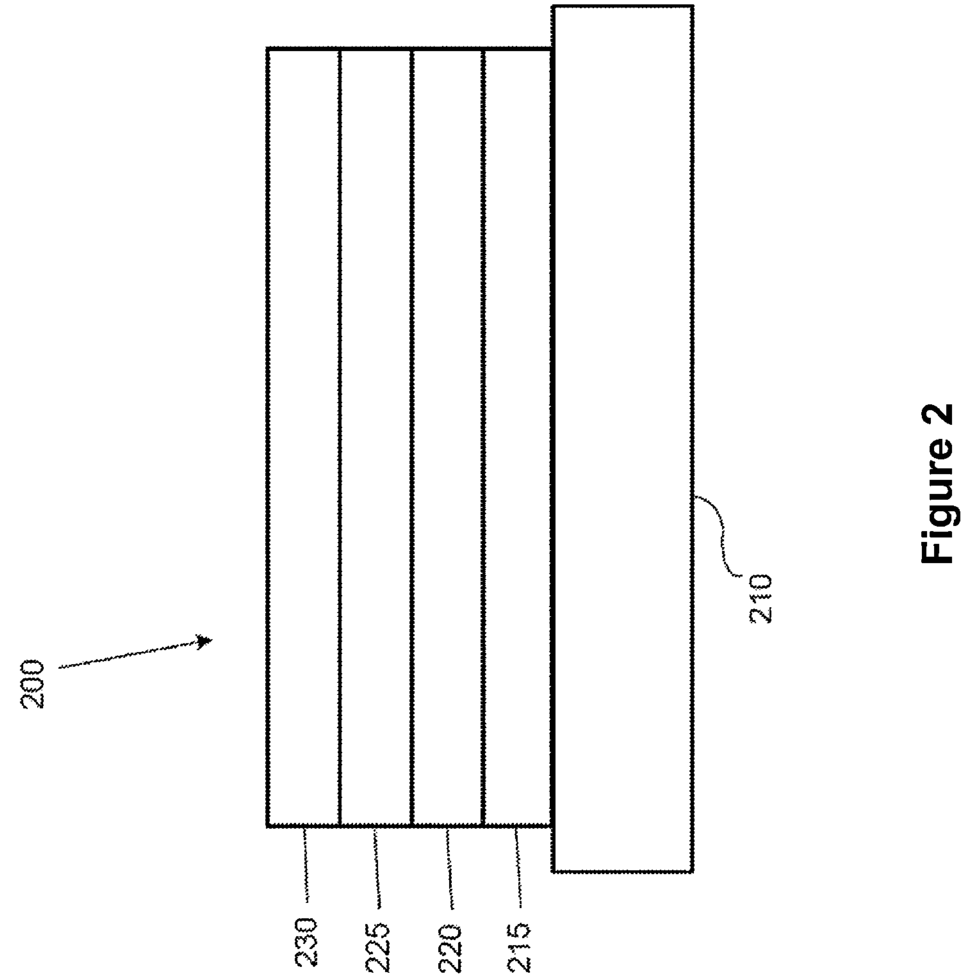
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer"

disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Both indolocarbazole and oligophenylenes have excellent charge-transport properties, useful for organic electronic devices. According to this invention, selected indolocarbazoles with favorable HOMO/LUMO energy levels and high triplet energy are combined with terphenyl to create novel compounds demonstrating superior performance in OLEDs. Further derivatization on these compounds provides additional advantages for this class of compounds.

Often, the emissive layer (EML) of OLED devices exhibiting good lifetime and efficiency requires more than two components (e.g. 3 or 4 components). Fabricating such EMLs using vacuum thermal evaporation (VTE) process then requires evaporating 3 or 4 evaporation source materials in separate VTE sublimation crucibles, which is very complicated and costly compared to a standard two-component EML with a single host and an emitter, which requires only two evaporation sources.

Premixing two or more materials and evaporating them from one VTE sublimation crucible can reduce the complexity of the fabrication process. However, the co-evaporation must be stable and produce an evaporated film having a composition that remains constant through the evaporation process. Variations in the film's composition may adversely affect the device performance. In order to obtain a stable co-evaporation from a mixture of compounds under vacuum, it may be assumed that the materials must have the same evaporation temperature under the same condition. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. Therefore, it is extremely difficult to achieve a stable co-evaporation mixture. So far, there have been very few stable co-evaporation mixture examples. "Evaporation temperature" of a material is measured in a vacuum deposition tool at a constant pressure, normally between $1\times10^{-7}$ Torr to $1\times10^{-8}$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. In one aspect of the invention, it was found that when two materials have similar evaporation temperatures, and similar mass loss rate or similar vapor pressures, the two materials can co-evaporate consistently. "Mass loss rate" of a material is defined as the percentage of mass lost over time ("percentage/minute" or "%/min") and is determined by measuring the time it takes to lose the first 10% of the mass of a sample of the material as measured by thermal gravity analysis (TGA) under a given experimental condition at a given constant temperature for a given material after a steady evaporation state is reached. The given constant temperature is one temperature point that is chosen so that the value of mass loss rate is between about 0.05 to 0.50%/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7, which is incorporated herein by reference in its entirety.

In the state of the art OLED devices, the EML may consist of three or more components. In one example, the EML can consist of two host-type compounds and an emitter combination (e.g. a hole transporting cohost (h-host), an electron transporting cohost (e-host), and a compound capable of functioning as an emitter in an OLED at room temperature). In another example, the EML can consist of one host-type compound and two emitter-type compounds (e.g., a host compound and two compounds each capable of functioning as an emitter in an OLED at room temperature). Conventionally, in order to fabricate such EMLs having three or more components using VTE process, three or more evaporation sources are required, one for each of the components. Because the concentration of the components is important for the device performance, typically, the rate of deposition of each component is measured individually during the deposition process. This makes the VTE process complicated and costly. Thus, it is desired to premix at least two of the components of such EMLs to reduce the number of VTE evaporation sources.

If any two of the three or more components of the EMLs can be premixed and form a stable mixture of co-evaporation source, then the number of evaporation sources required for EML layer fabrication would be reduced. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source.

Compounds of the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the invention relates to a compound having a formula selected from the group consisting of:

Formula I

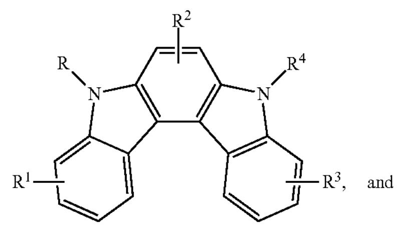

and

Formula II

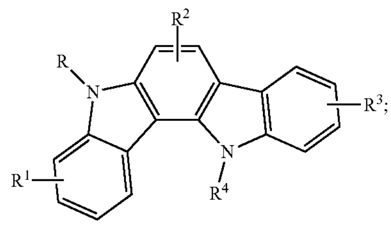

wherein R is selected from the group consisting of:

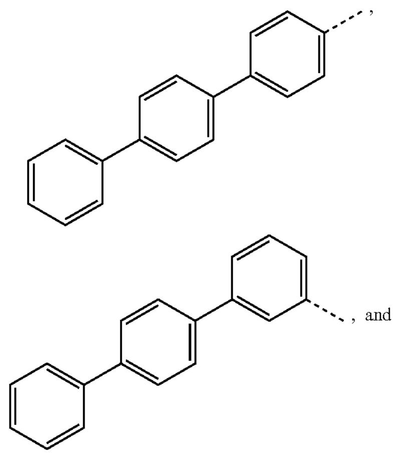

, and

-continued

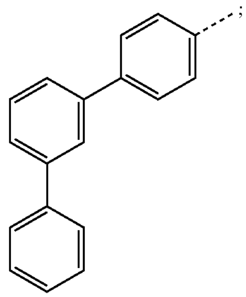

wherein $R^4$ is selected from the group consisting of alkyl, alkoxy, silyl, aryl, heteroaryl, and combinations thereof;

wherein $R^1$, $R^2$ and $R^3$ each independently represents mono to maximum allowable substitutions, or no substitution;

wherein $R^1$, $R^2$ and $R^3$ are each independently selected from the group consisting of hydrogen, deuterium, alkyl, alkenyl, alkyne, alkoxy, halogen, silyl, nitrile, nitro, aryl, heteroaryl and combinations thereof;

wherein any two adjacent substituents are optionally joined or fused into a ring;

wherein $R^4$, $R^1$, $R^2$, and $R^3$ are each independently, optionally, further substituted with one or more substituents selected from the group consisting of hydrogen, deuterium, alkyl, alkenyl, alkyne, alkoxy, halogen, silyl, nitrile, nitro, aryl, heteroaryl, and combinations thereof; and wherein any hydrogen in the compound is optionally replaced with deuterium.

In one embodiment, the formula is Formula I. In another embodiment, the formula is Formula II. In another embodiment, $R^1$, $R^2$ and $R^3$ are each a hydrogen.

In one embodiment, $R^4$ is selected from the group consisting of:

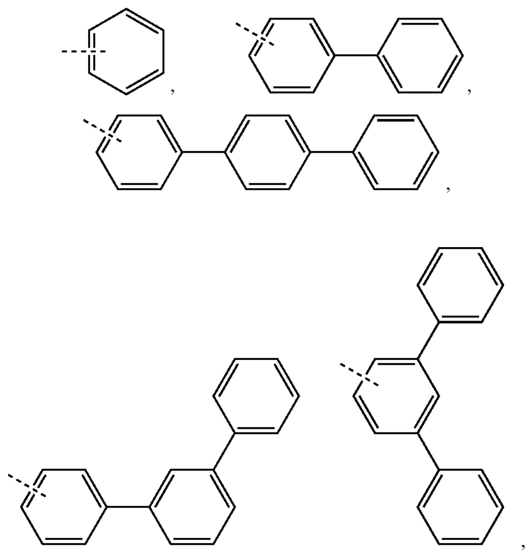

-continued

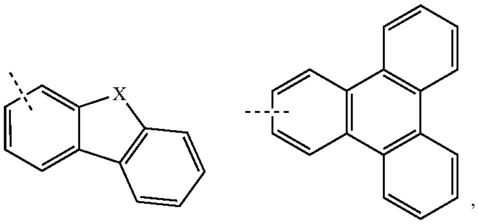

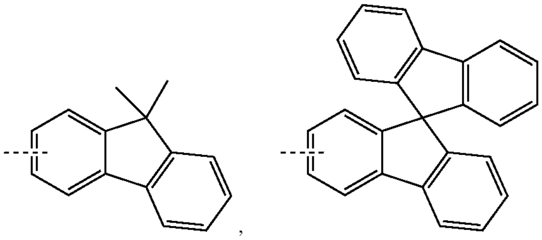

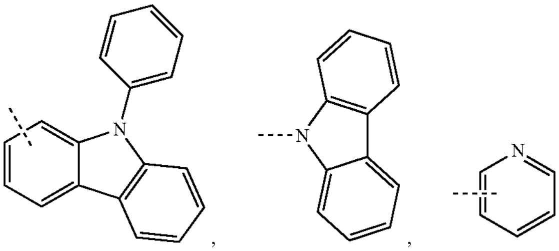

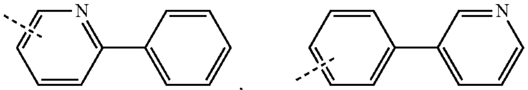

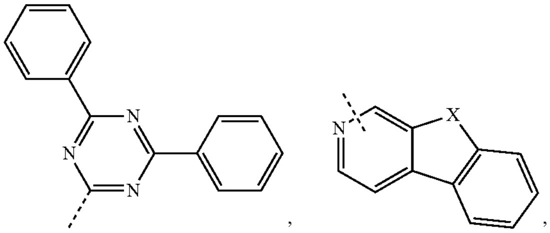

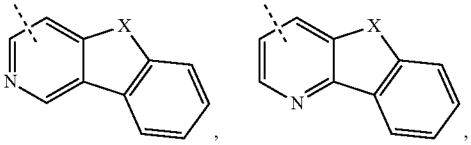

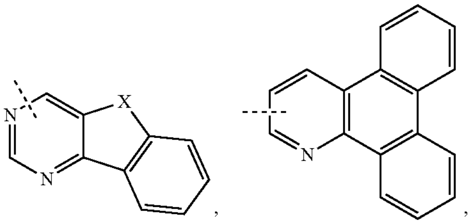

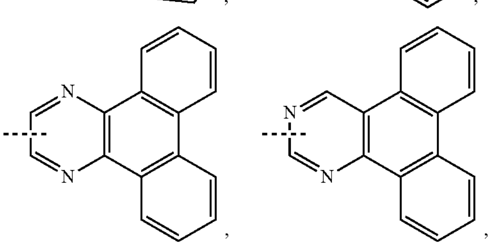

-continued
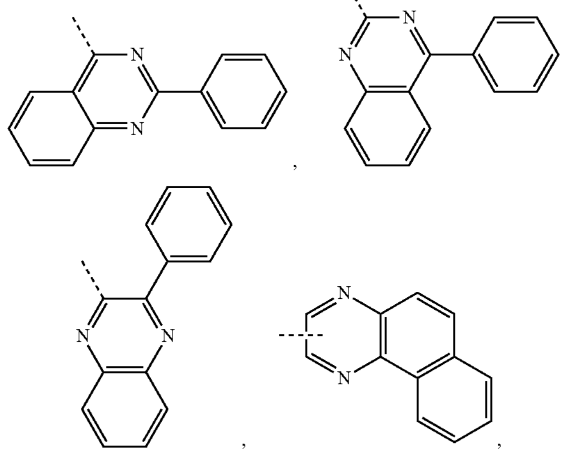
and combinations thereof.
wherein X is selected from a group consisting of O, S and Se.
In another aspect, the invention relates to a compound selected from the group consisting of:
Compound A1
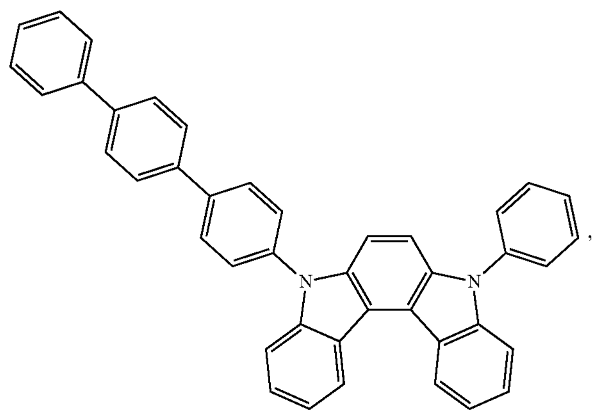
Compound A2
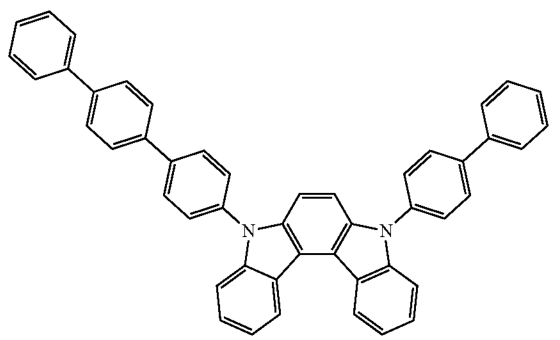
Compound A3
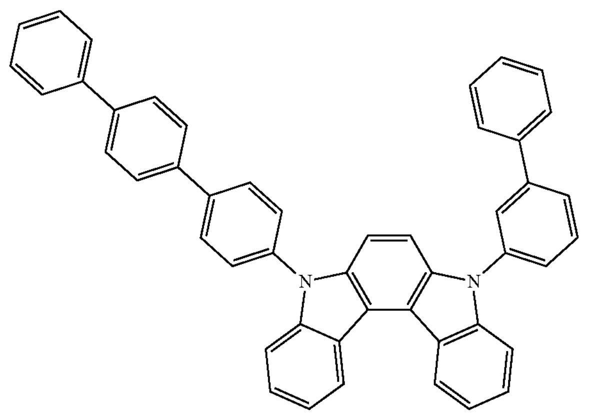

-continued
Compound A4
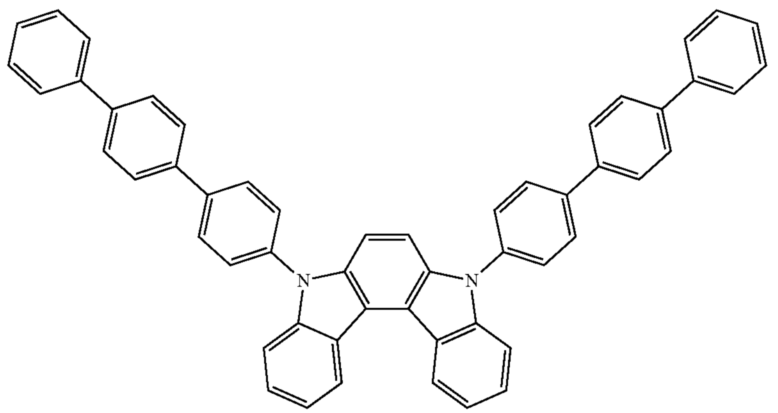
,
Compound A5
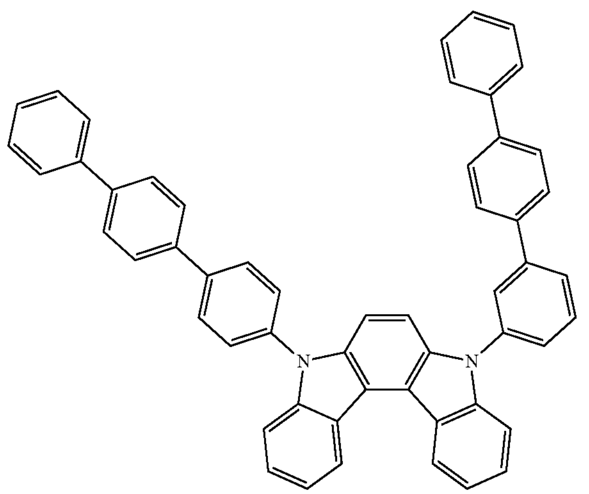
,
Compound A6
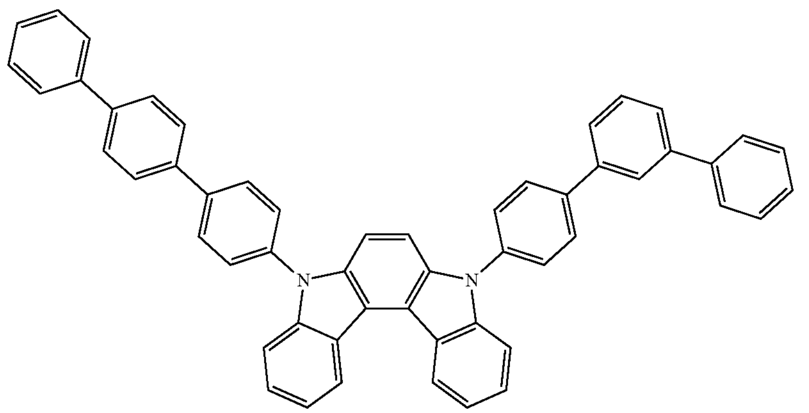
, -continued
Compound A7
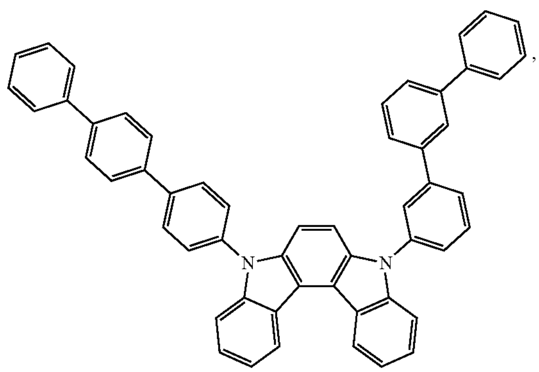
,
Compound A8
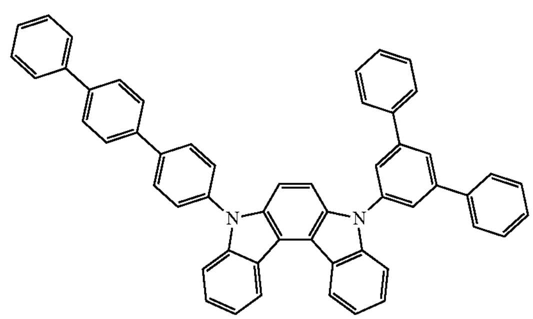
,
Compound A9
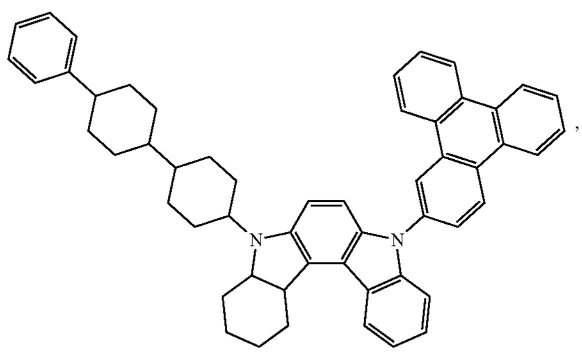
,
Compound A10
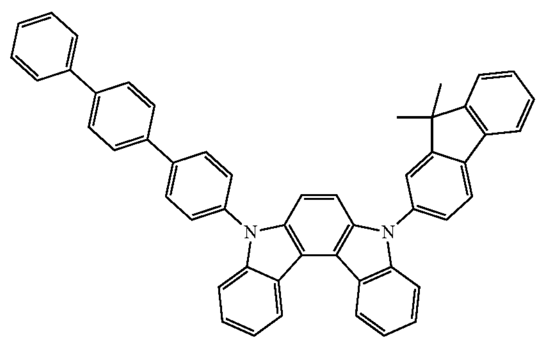
,
Compound A11
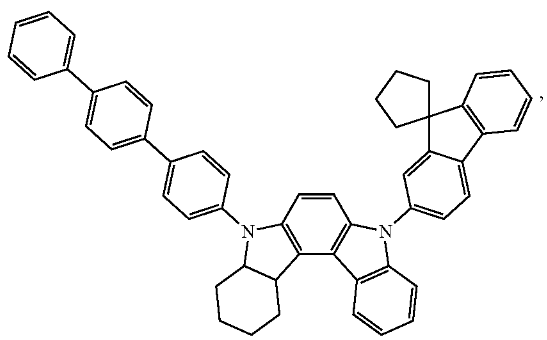
,
Compound A12
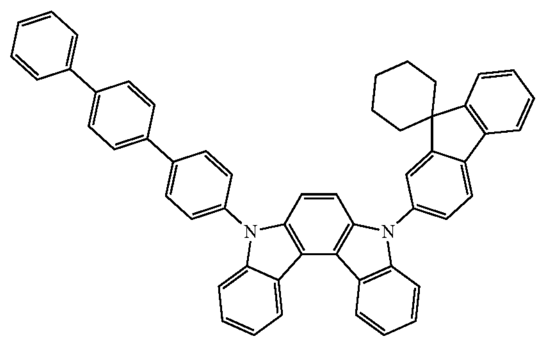
,
Compound A13
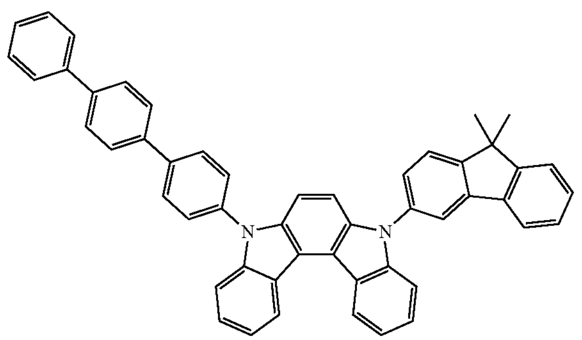
,
Compound A14
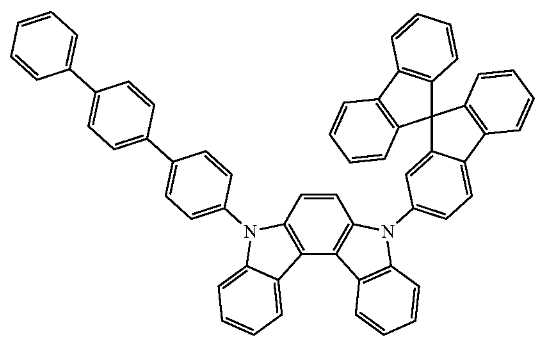
, -continued
Compound A15
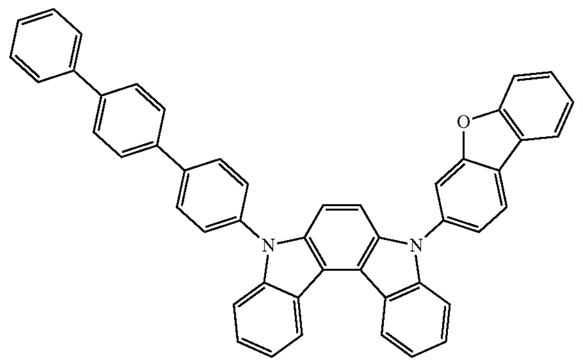
,
Compound A16
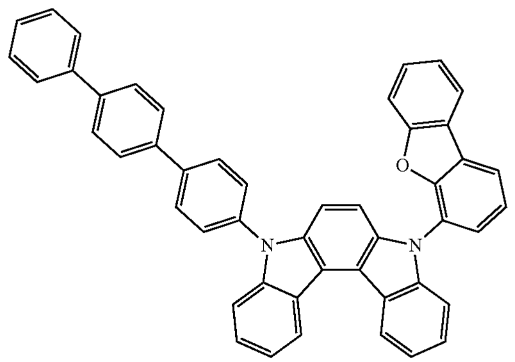
,
Compound A17
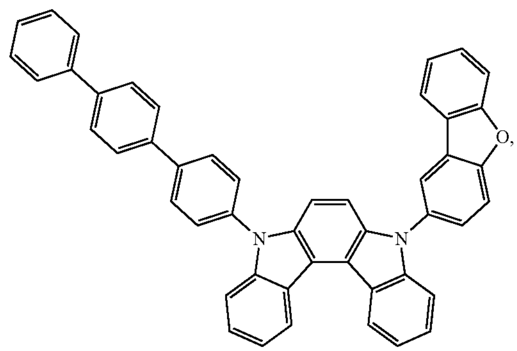
,
Compound A18
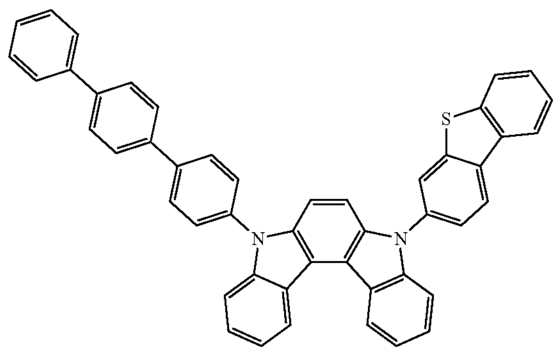
,
Compound A19
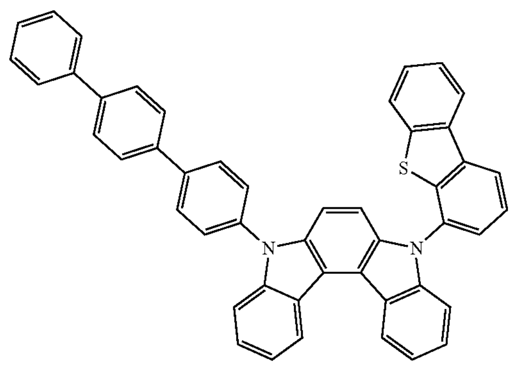
,
Compound A20
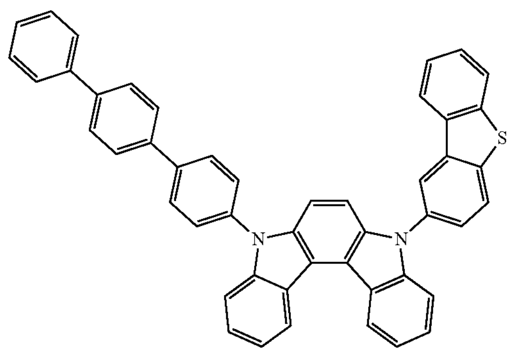
,
Compound A21
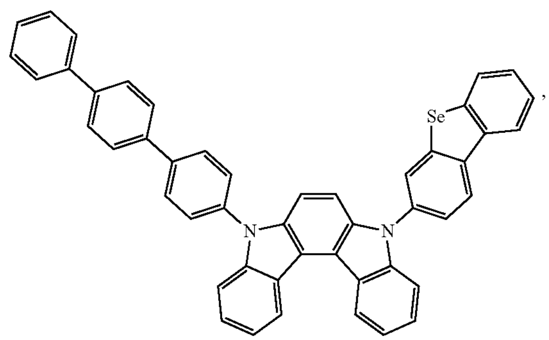
,
Compound A22
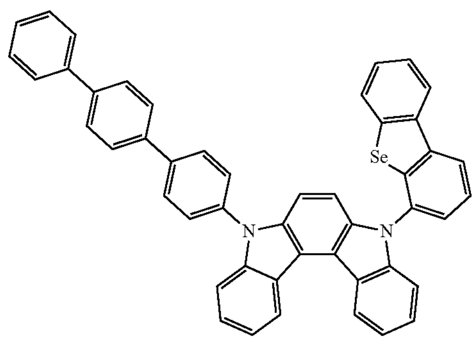
, -continued
Compound A23
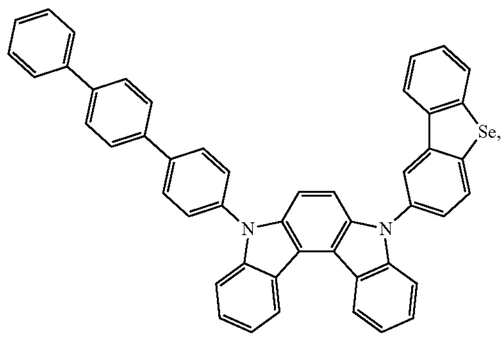
Compound A24
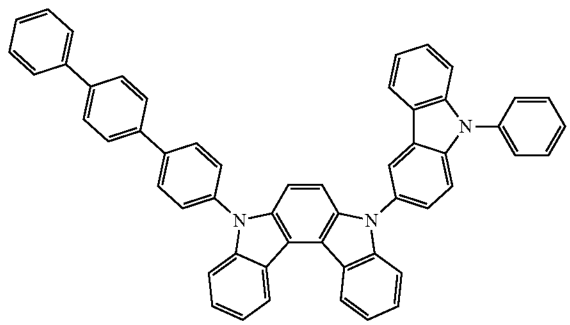
Compound A25
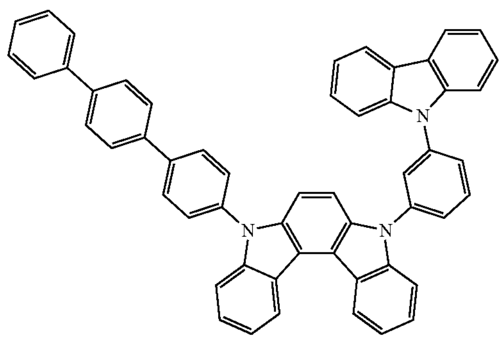
Compound A26
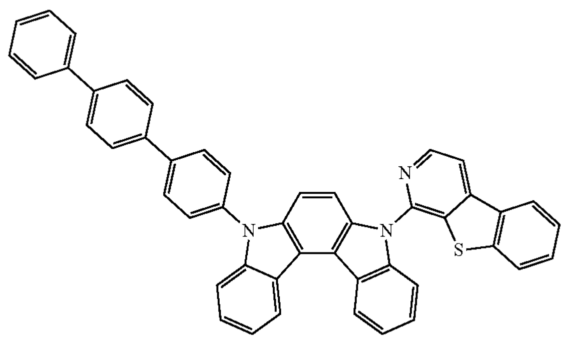
Compound A27
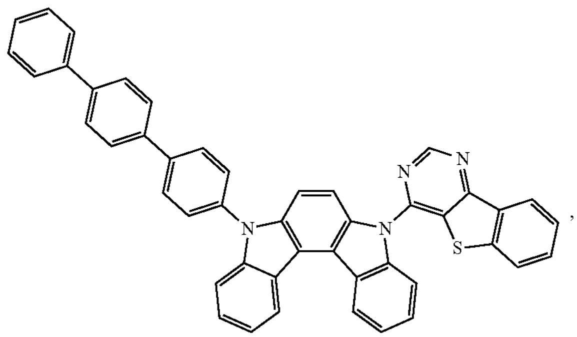
Compound A28
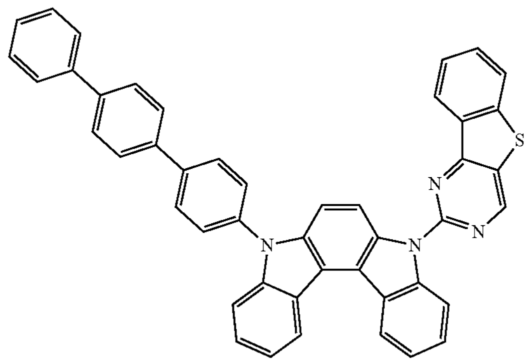
Compound A29
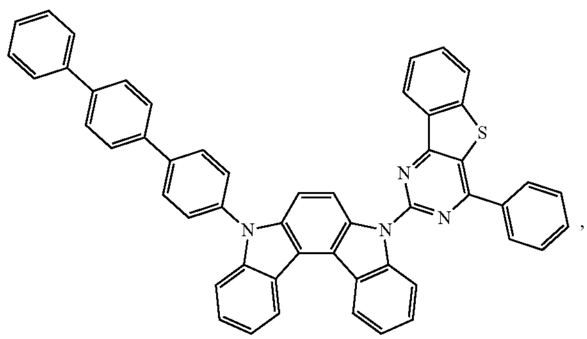
Compound A30
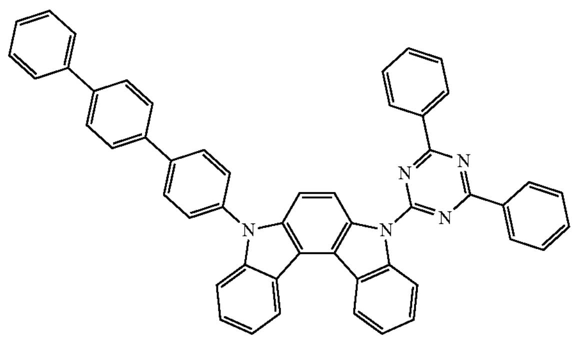

-continued
Compound A31
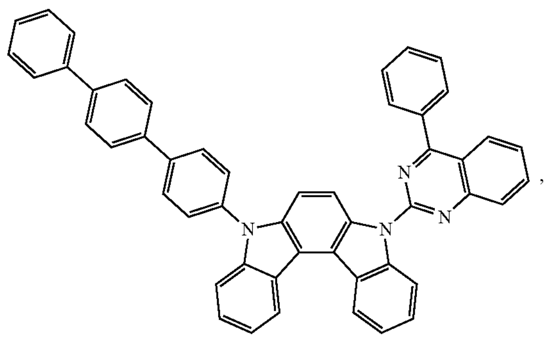
,
Compound A32
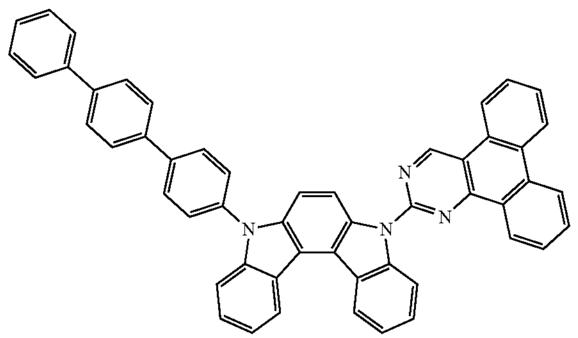
,
Compound A33
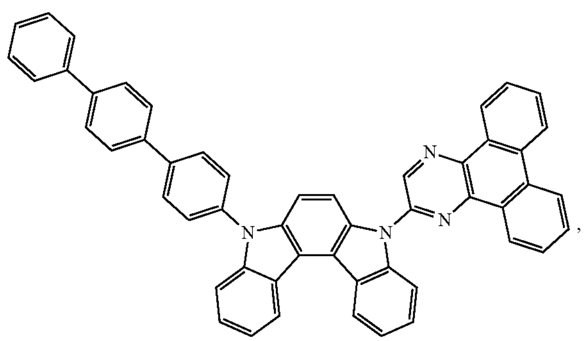
,
Compound A34
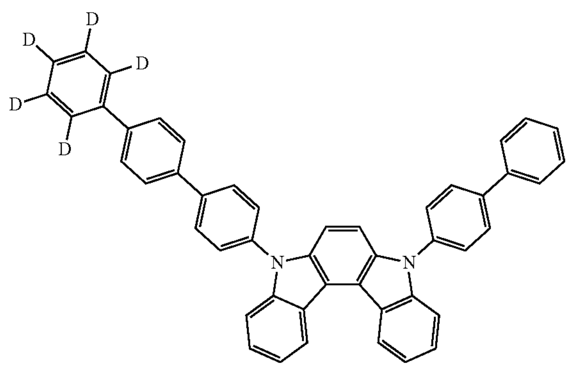
,
Compound A35
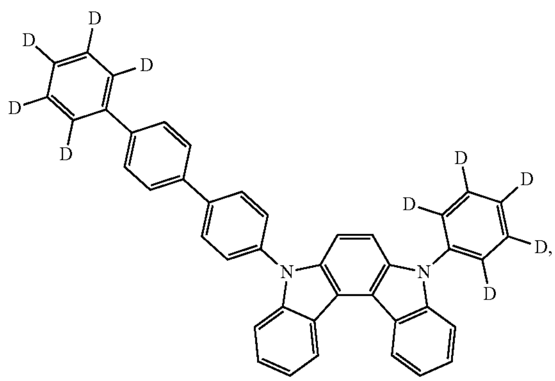
Compound A36
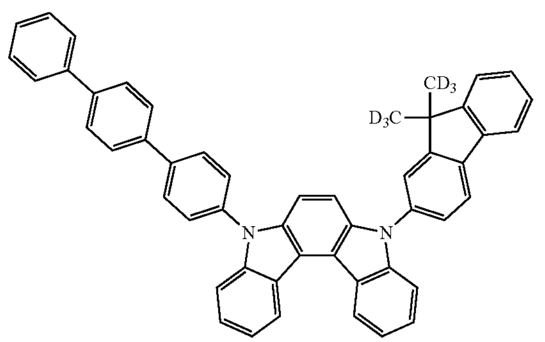
,
Compound A37
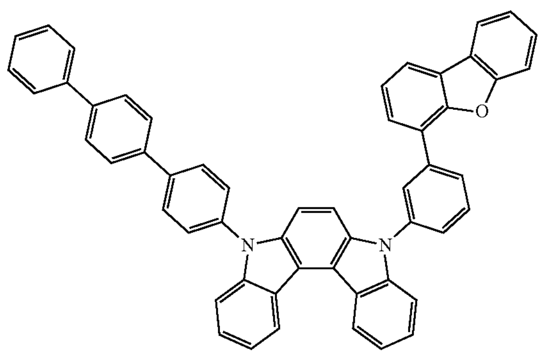
,
Compound A38
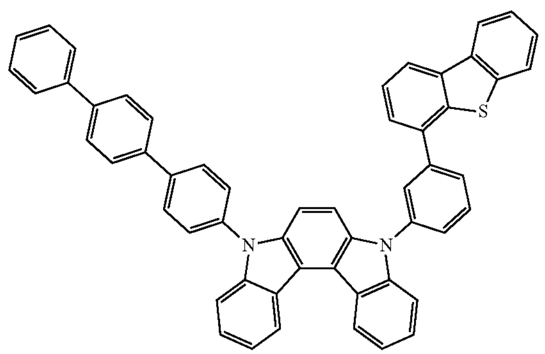
, -continued
Compound A39
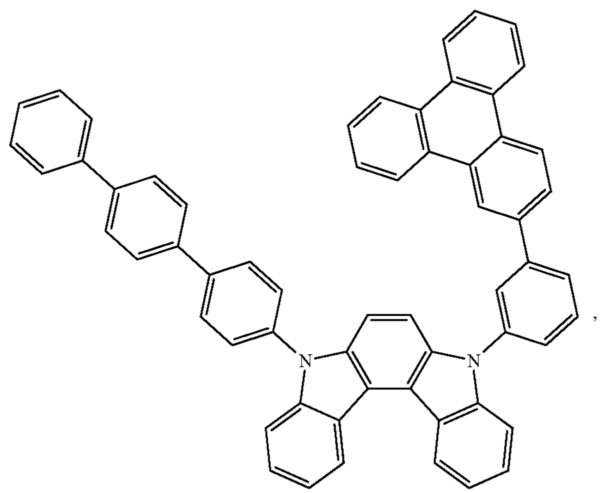
,
Compound A40
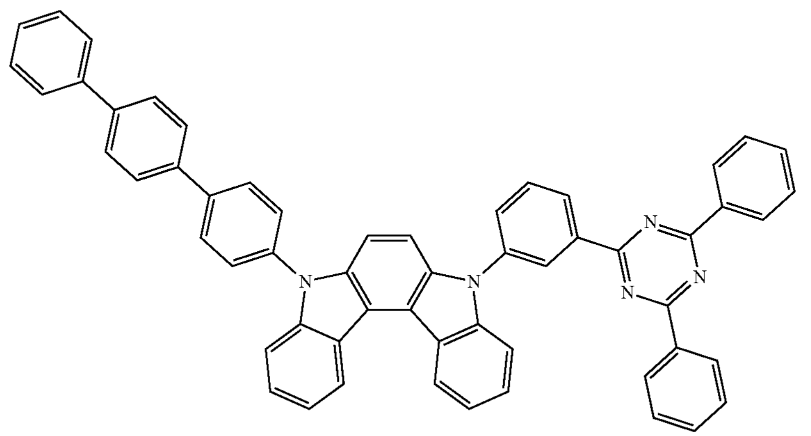
,
Compound B1
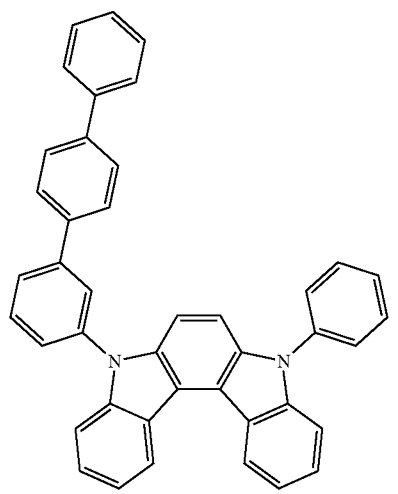
,
Compound B2
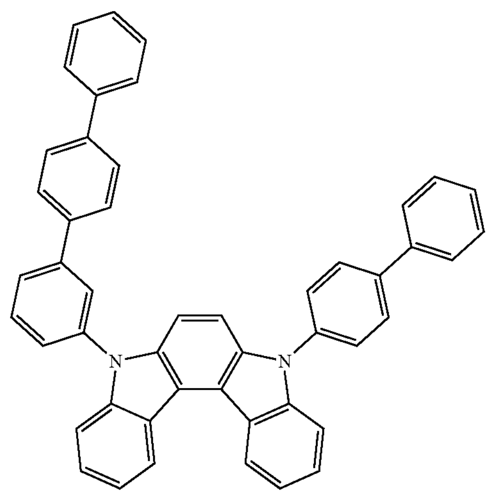
, -continued
Compound B3
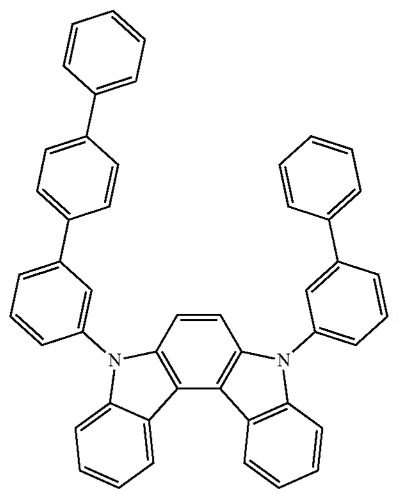
,
Compound B4
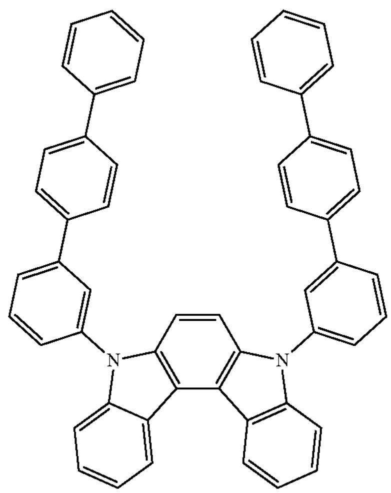
,
Compound B5
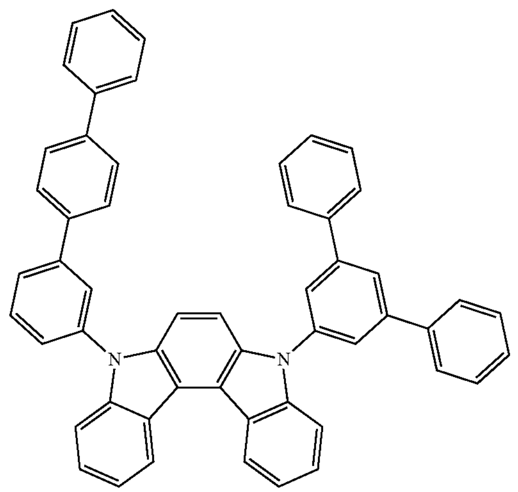
,
Compound B6
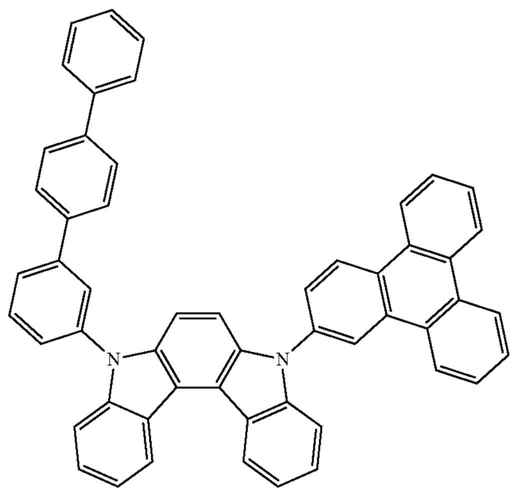
,
Compound B7
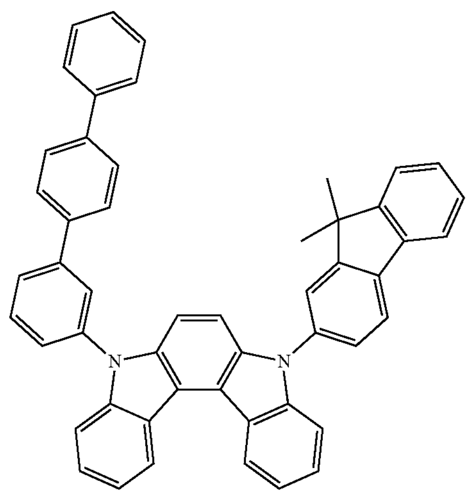
,
Compound B8
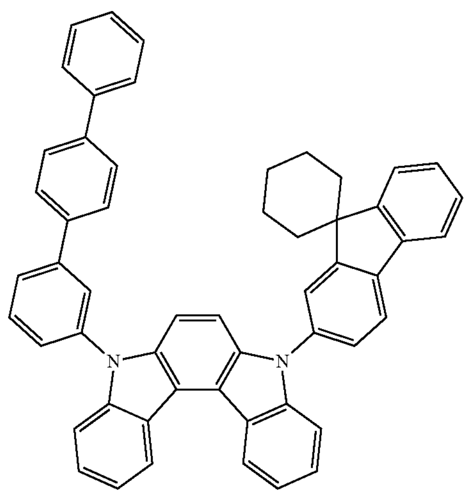
, -continued
Compound B9
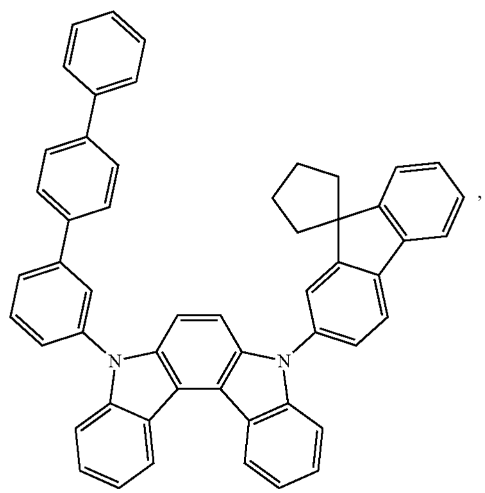
,
Compound B10
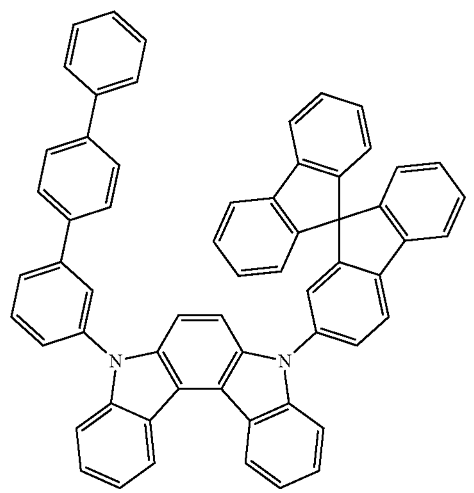
,
Compound B11
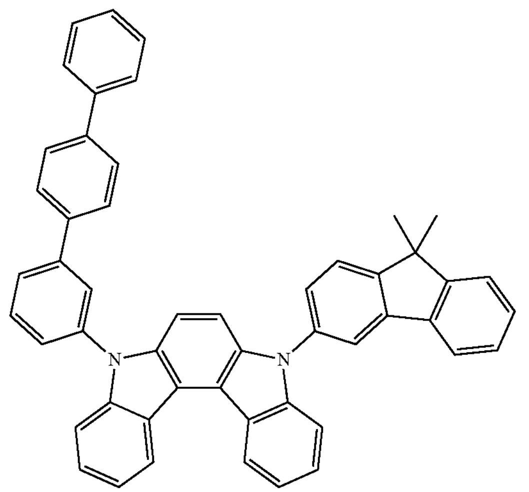
,
Compound B12
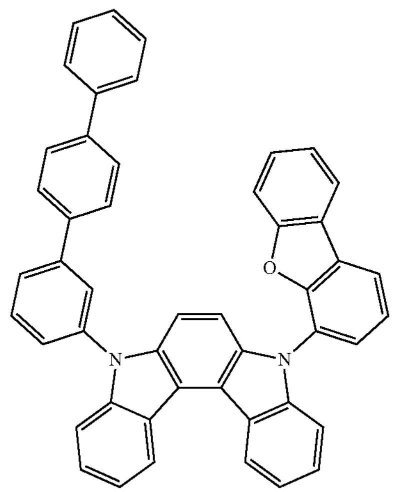
,
Compound B13
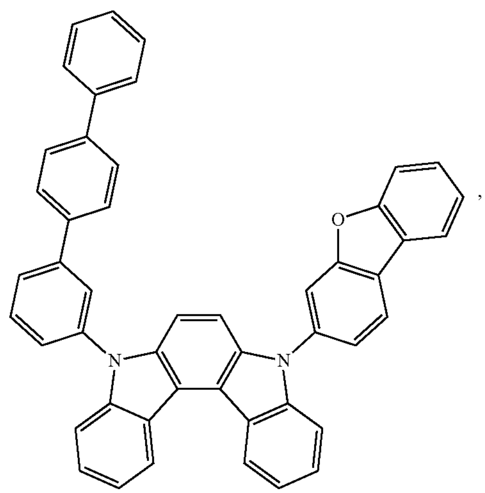
,
Compound B14
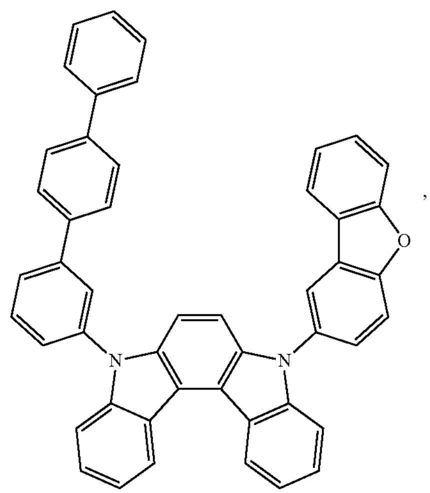
, -continued
Compound B15
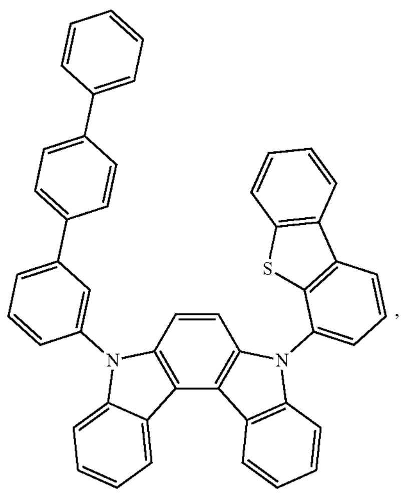
,
Compound B16
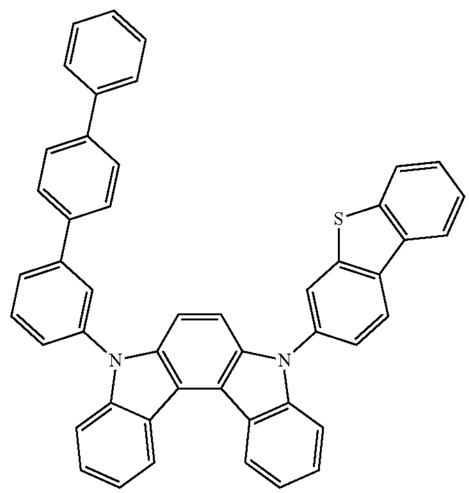
,
Compound B17
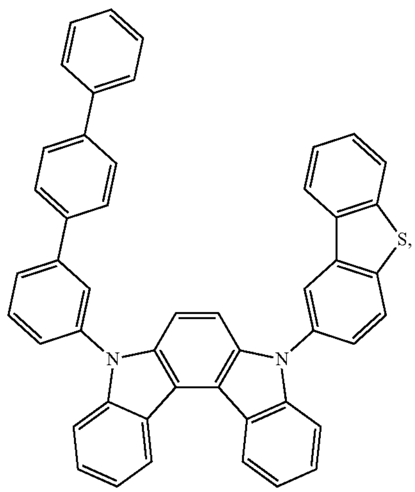
,
Compound B18
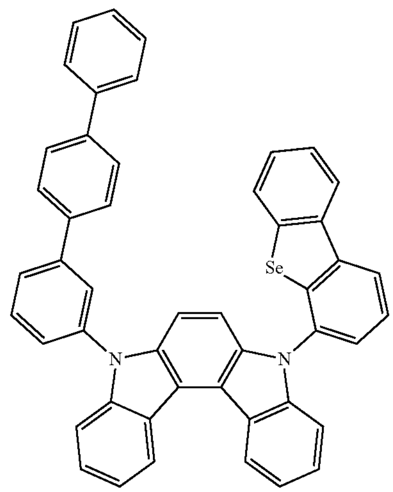
,
Compound B19
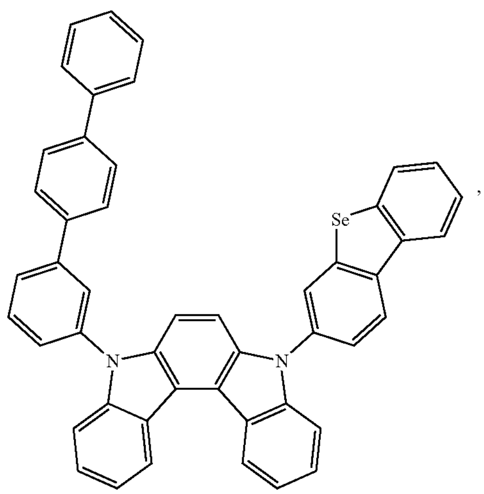
,
Compound B20
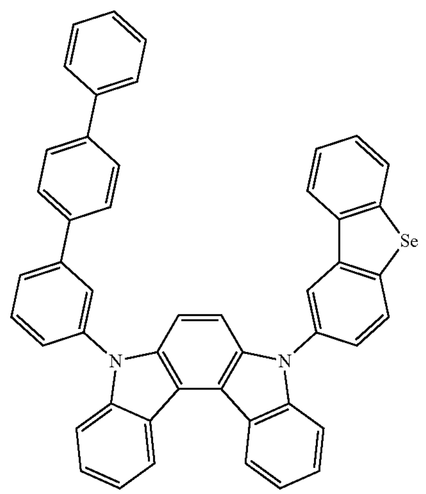
, -continued
Compound B21
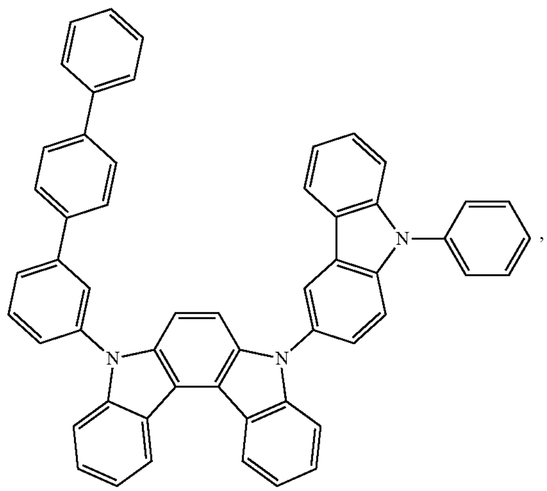
,
Compound B22
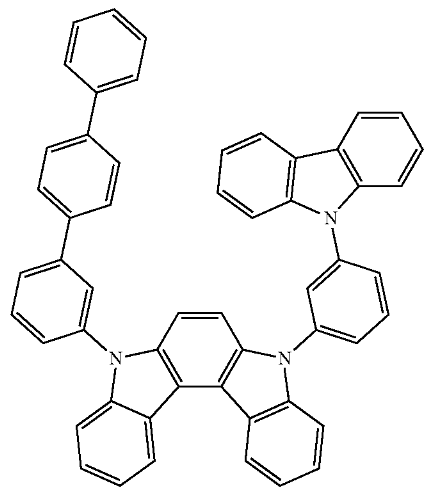
,
Compound B23
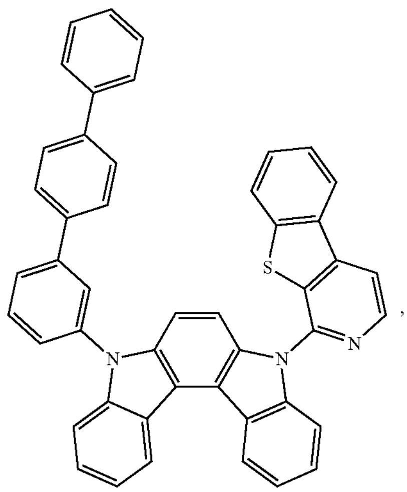
Compound B24
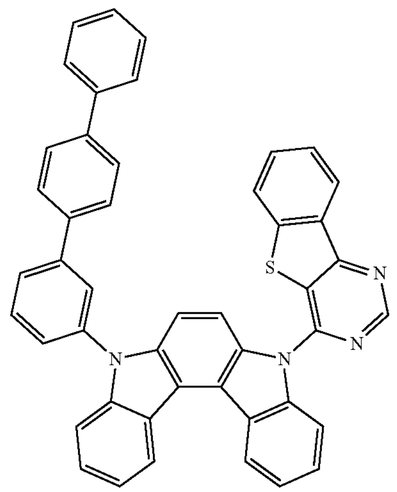
Compound B25
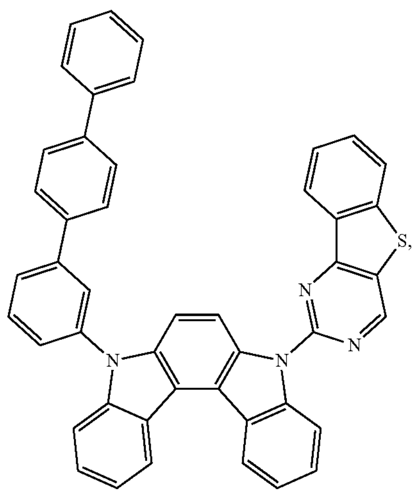
Compound B26
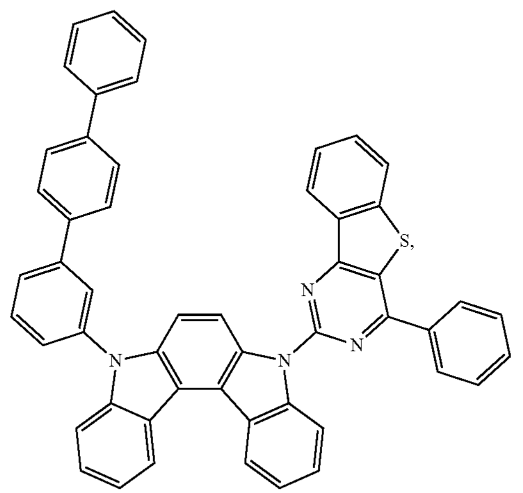
, -continued
Compound B27
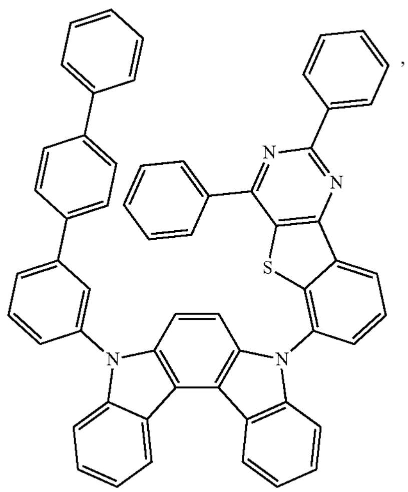
,
Compound B28
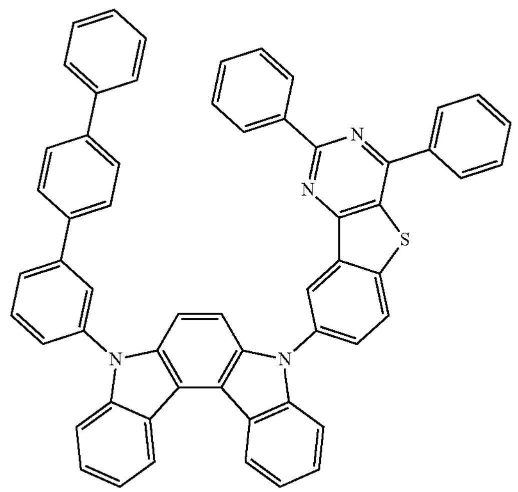
,
Compound B29
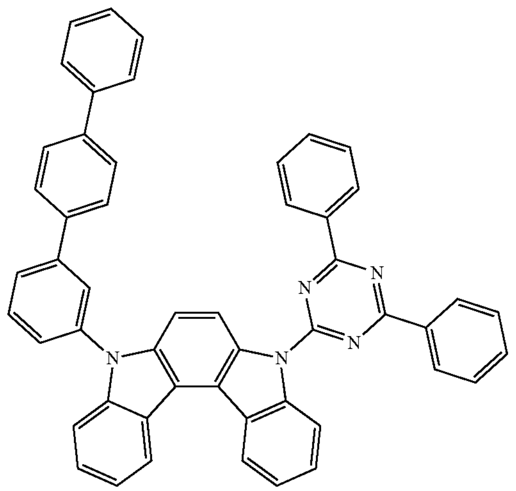
,
Compound B30
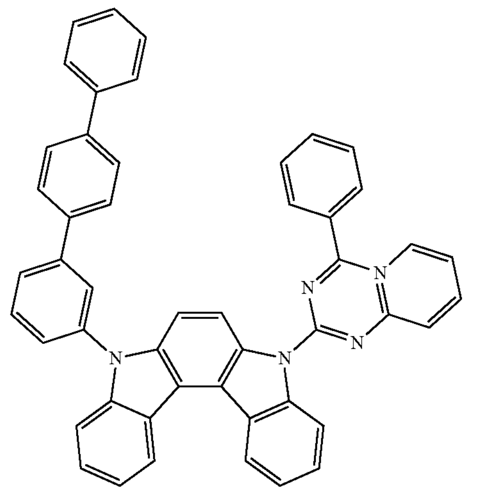
,
Compound B31
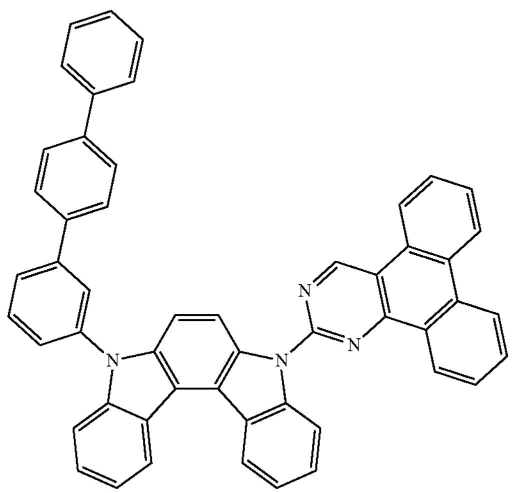
,
Compound B32
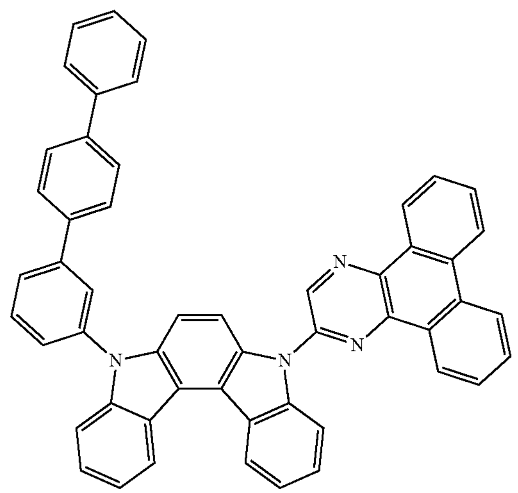
, -continued
Compound B33
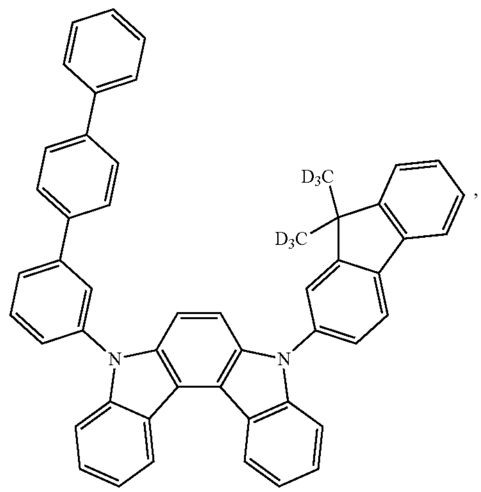
,
Compound B34
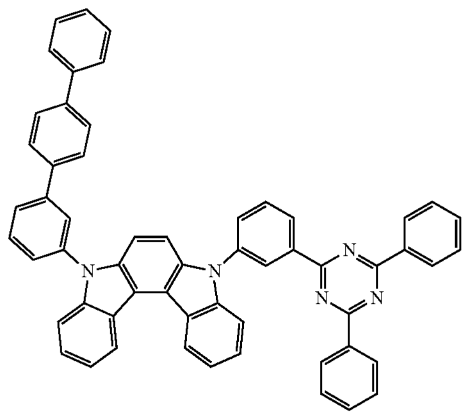
,
Compound B35
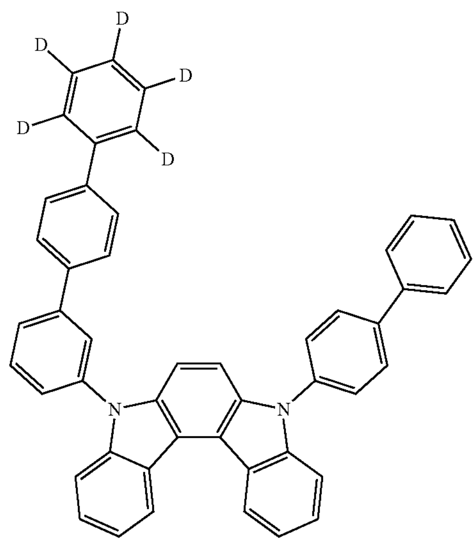
Compound B36
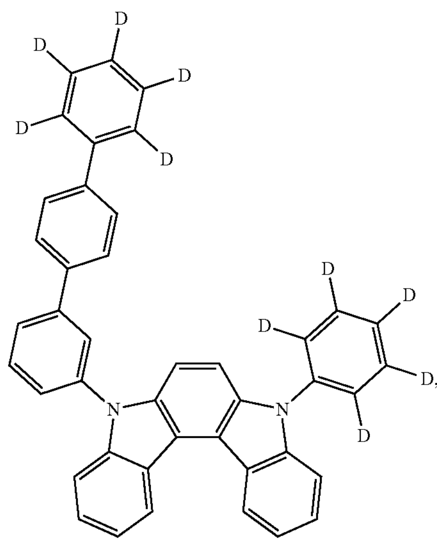
Compound C1
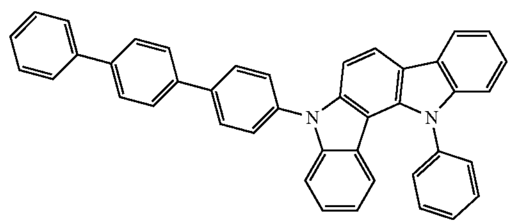
,
Compound C2
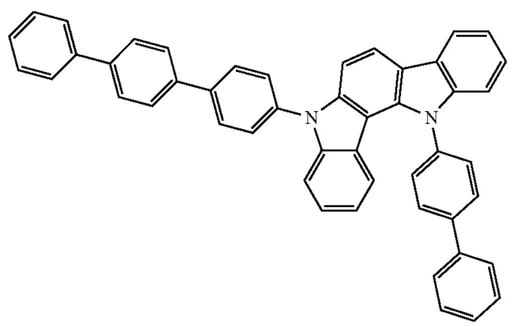
, -continued
Compound C3
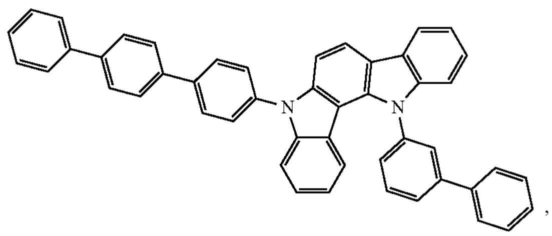
,
Compound C4
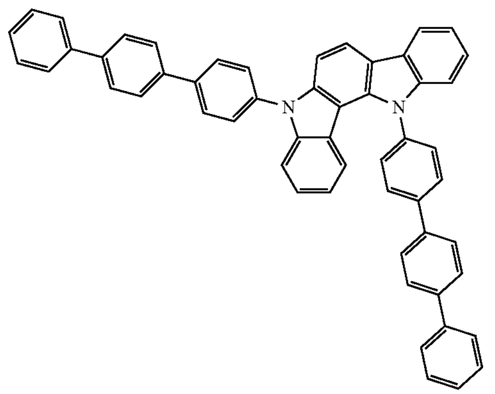
,
Compound C5
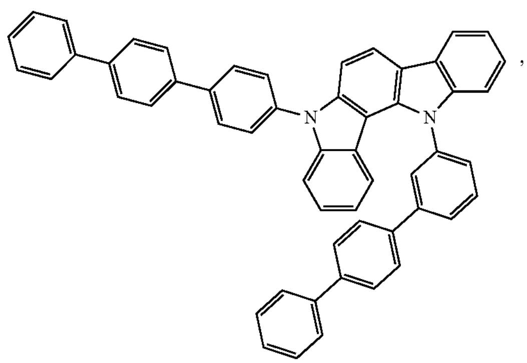
,
Compound C6
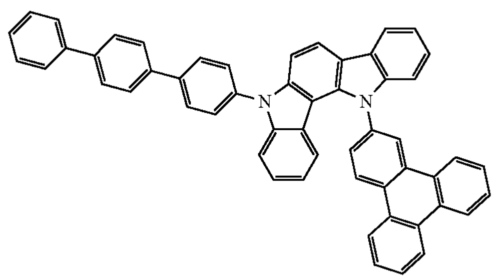
,
Compound C7
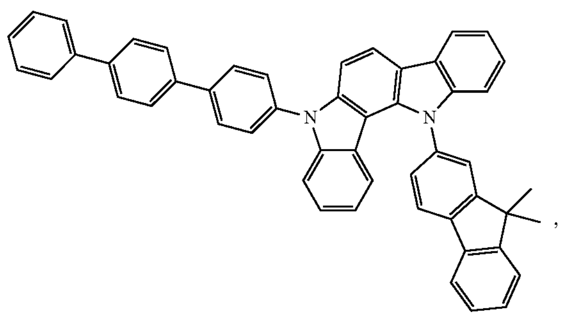
,
Compound C8
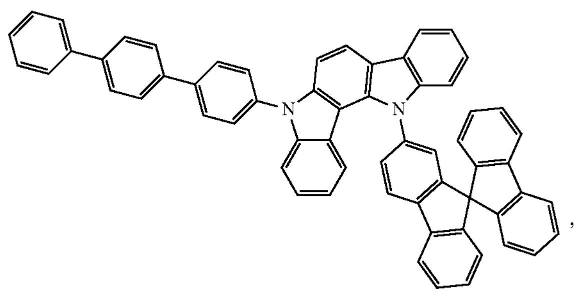
,
Compound C9
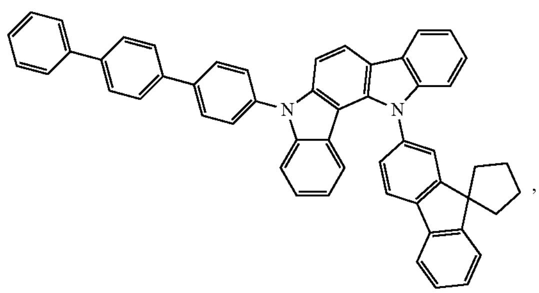
,
Compound C10
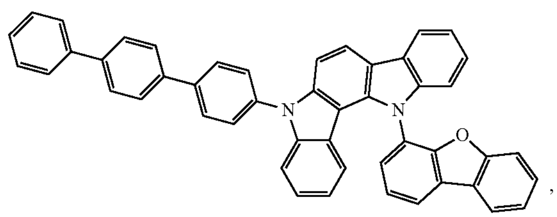
, -continued
Compound C11
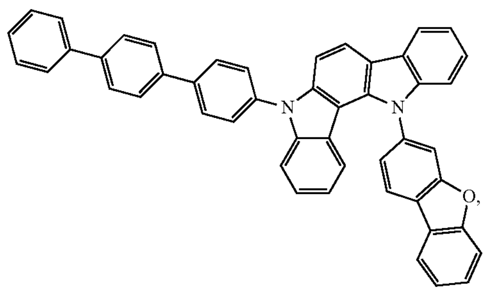
Compound C12
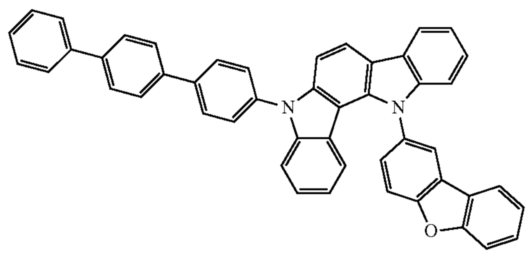
Compound C13
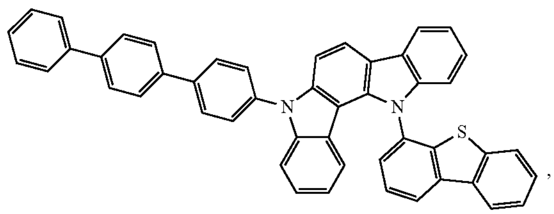
Compound C14
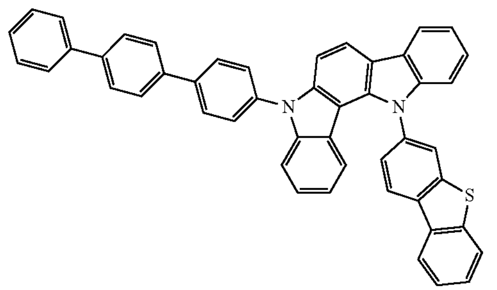
Compound C15
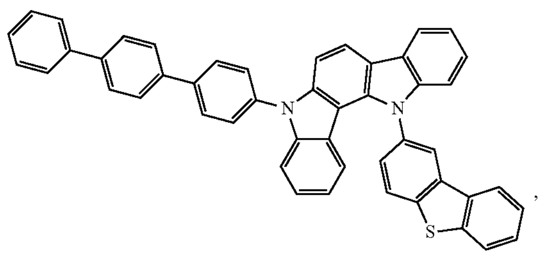
Compound C16
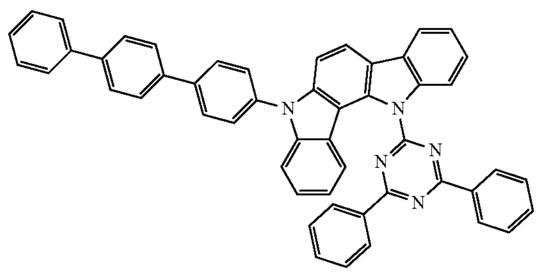
Compound C17
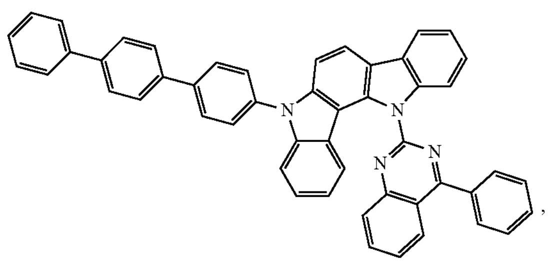
Compound C18
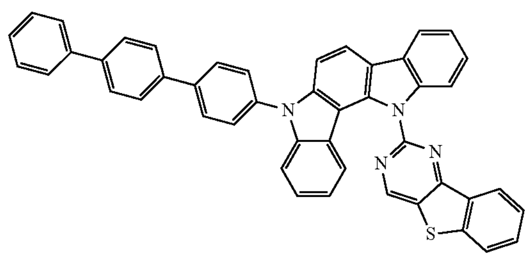
Compound D1
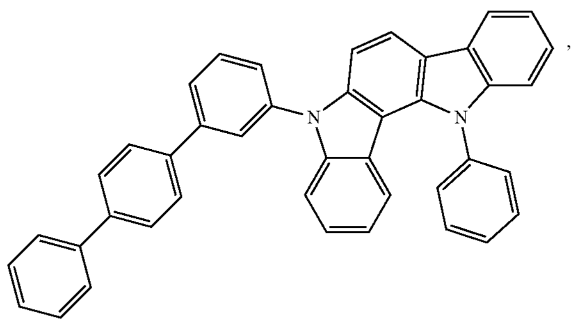
Compound D2
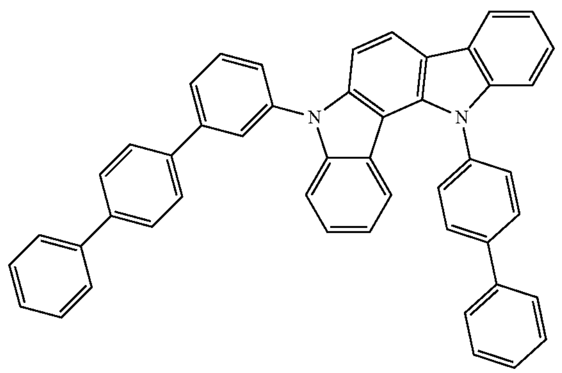

-continued
Compound D3
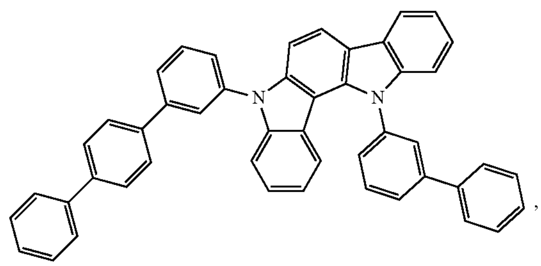
,
Compound D4
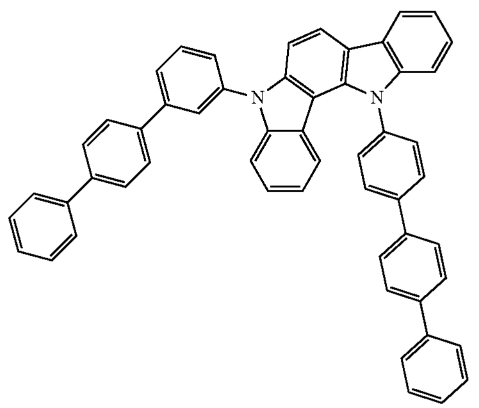
,
Compound D5
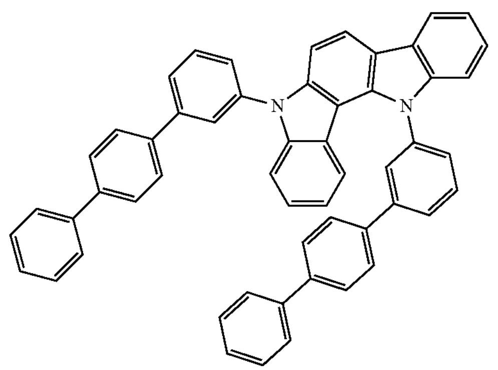
,
Compound D6
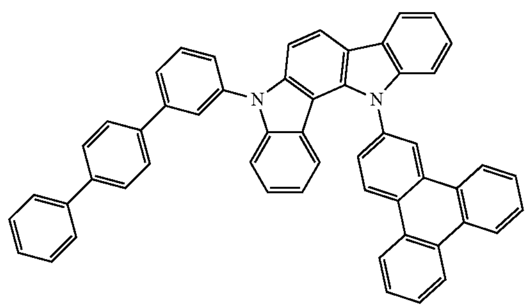
,
Compound D7
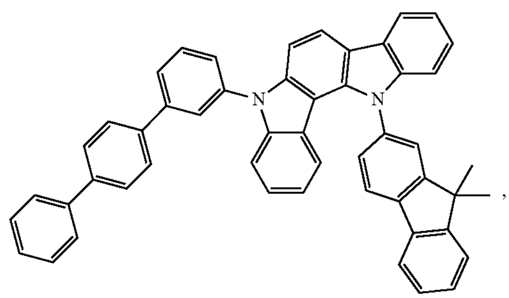
,
Compound D8
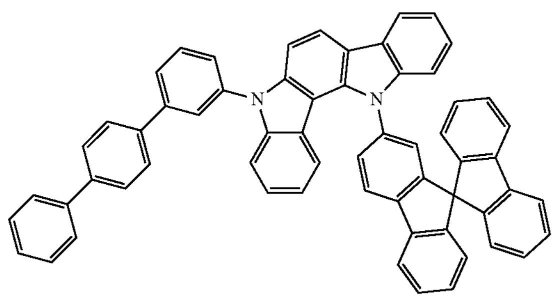
,
Compound D9
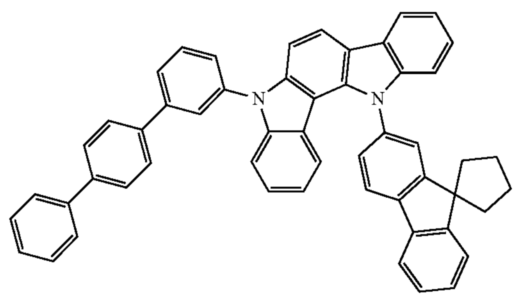
,
Compound D10
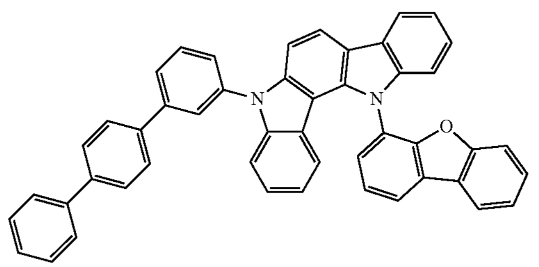
, -continued
Compound D11
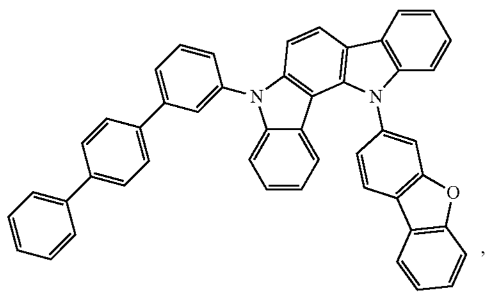
,
Compound D12
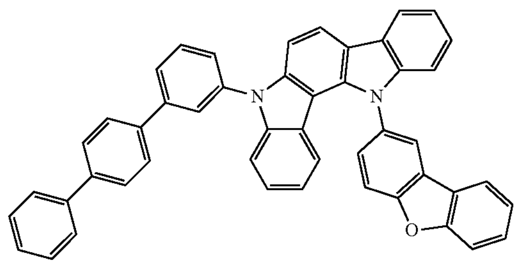
,
Compound D13
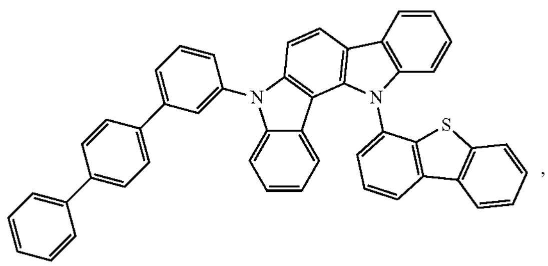
,
Compound D14
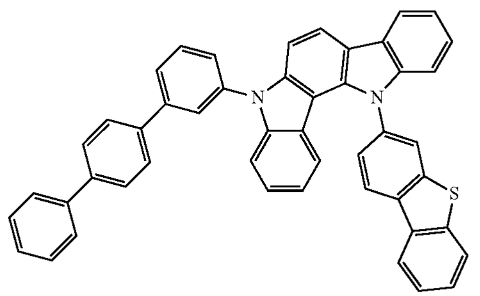
,
Compound D15
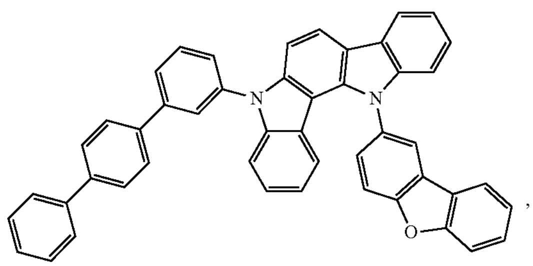
,
Compound D16
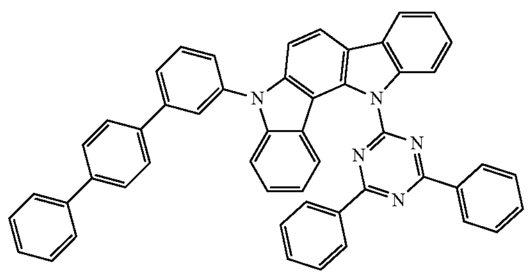
,
Compound D17
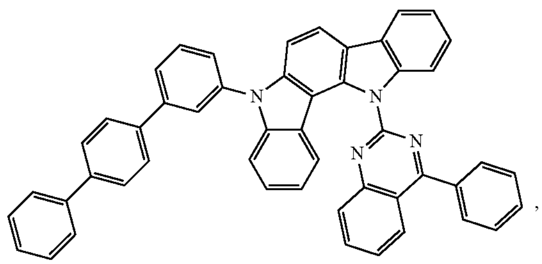
,
Compound D18
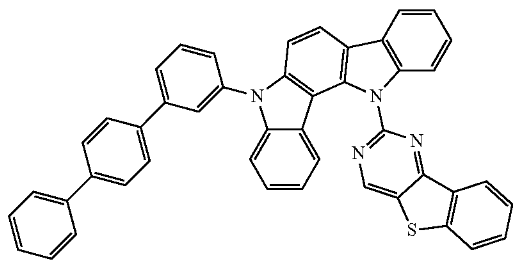
,
Compound E1
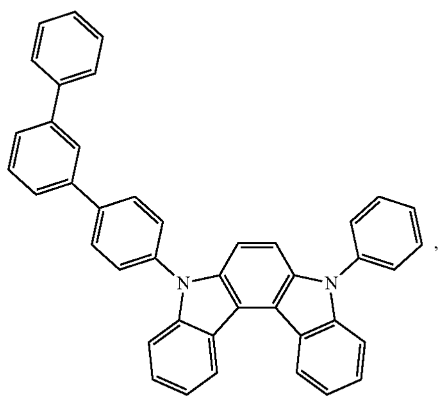
,
Compound E2
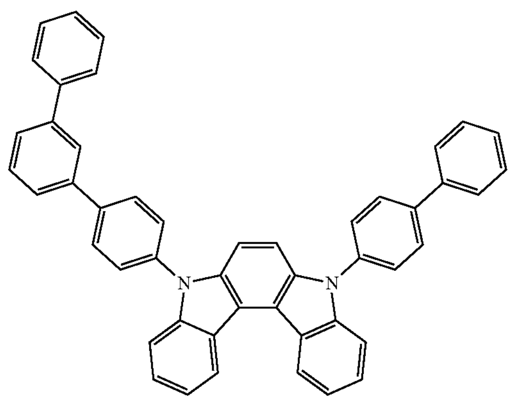
, -continued
Compound E3
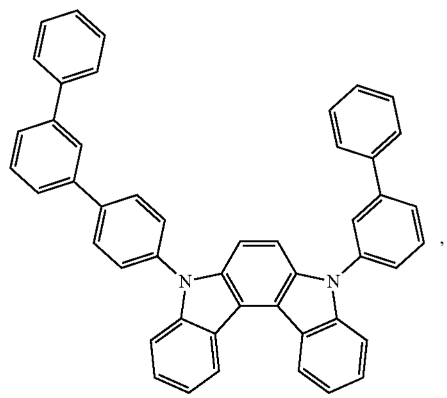
,
Compound E4
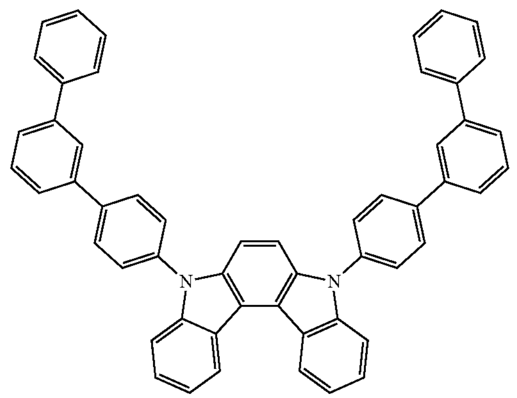
,
Compound E5
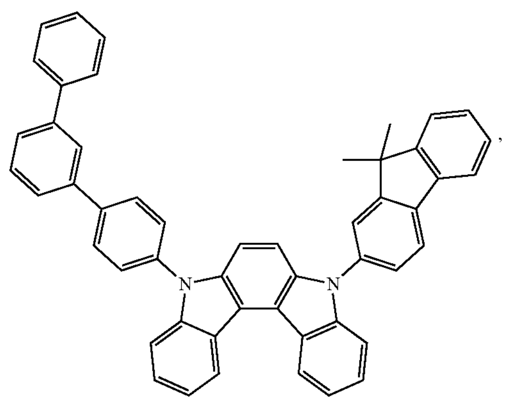
,
Compound E6
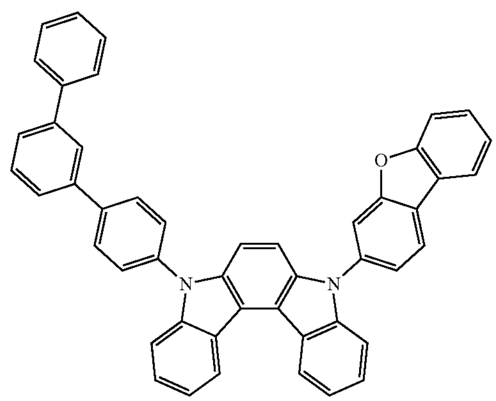
,
Compound E7
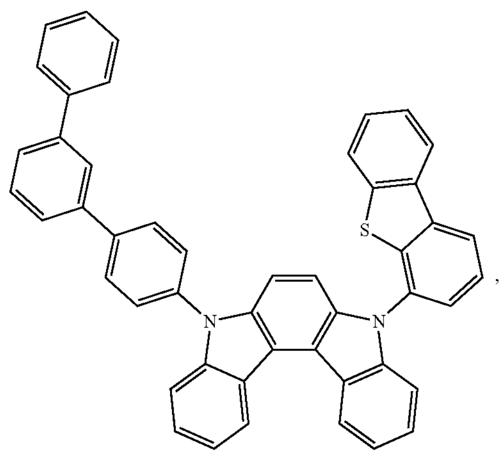
,
Compound E8
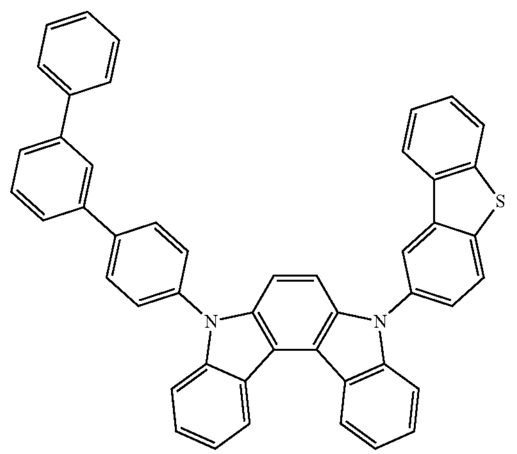
, -continued
Compound E9
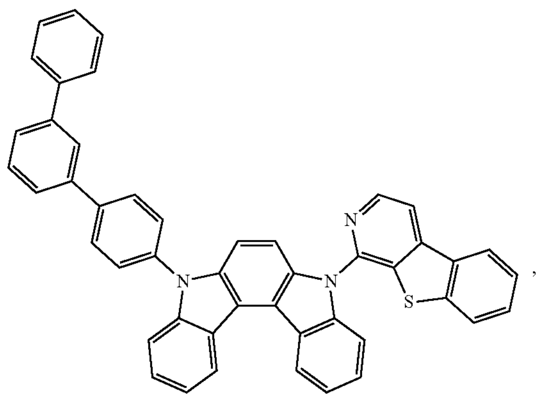
,
Compound E10
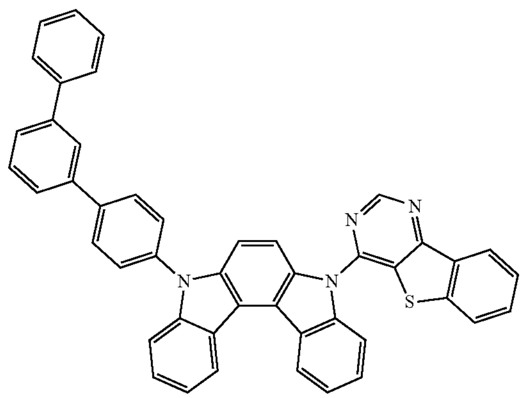
,
Compound E11
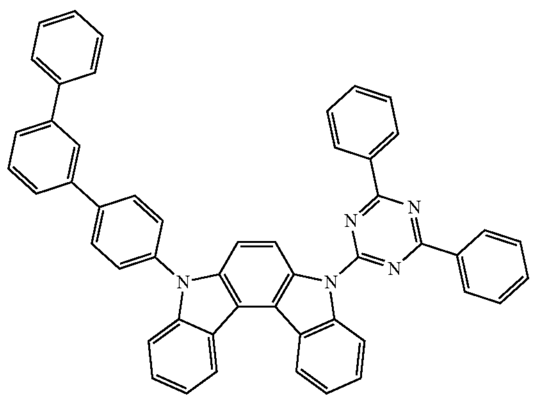
,
Compound E12
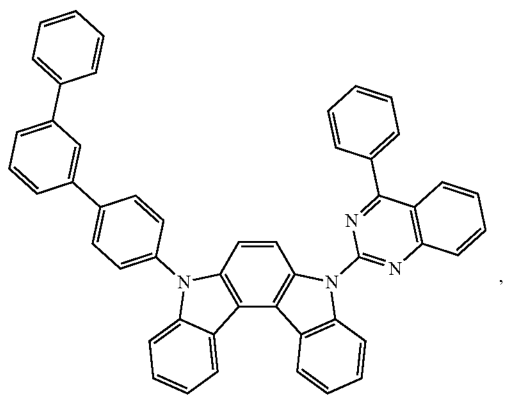
,
Compound E13
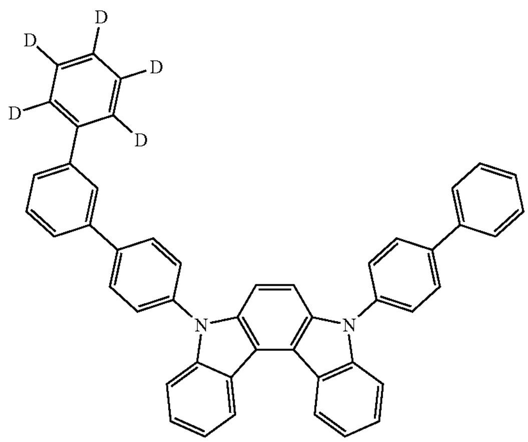
Compound E14
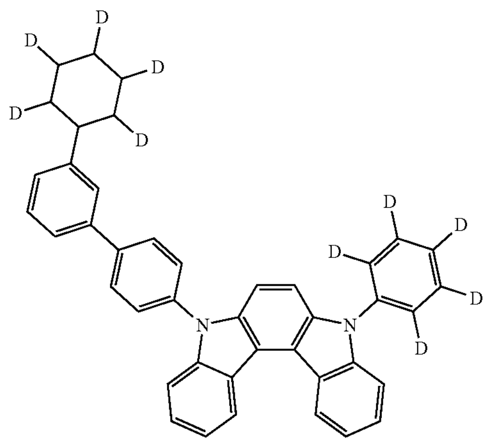

-continued
Compound E15
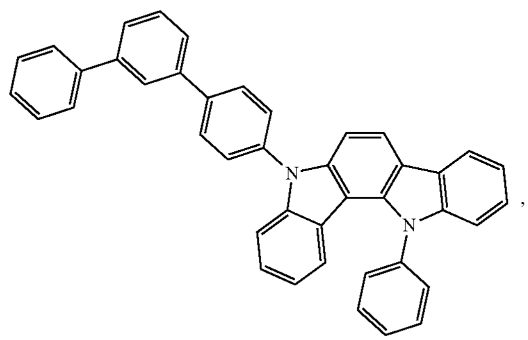
,
Compound E16
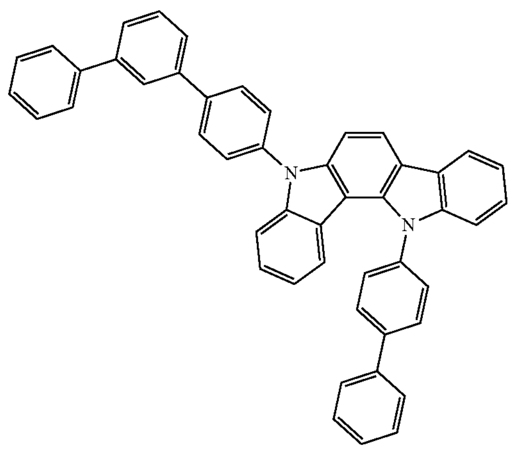
,
Compound E17
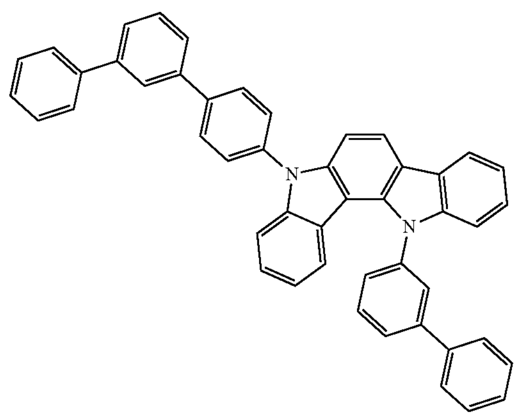
,
Compound E18
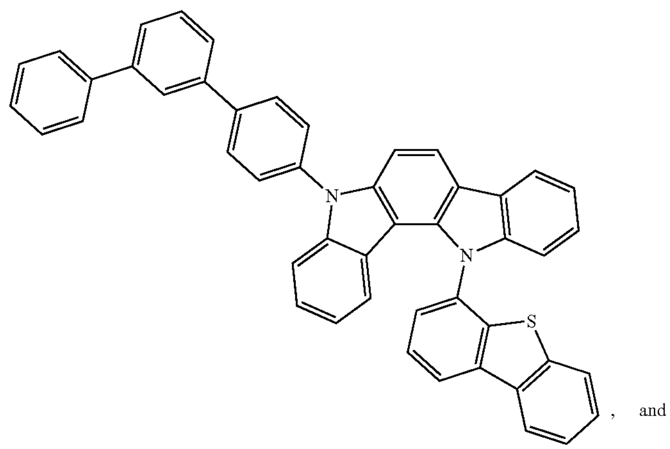
, and -continued Compound E19

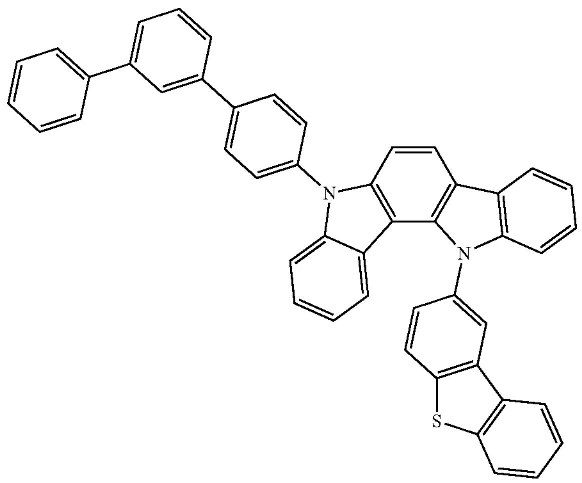

In another aspect, the present invention includes a composition of materials comprising a first compound, wherein the first compound has a formula selected from the group consisting of Formula I and Formula II.

In one embodiment, the composition comprises a second compound, wherein the second compound is selected from the group consisting of:

Formula III

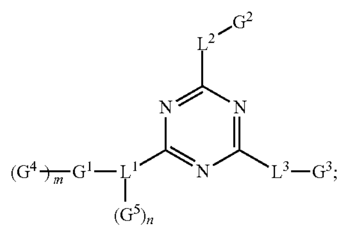

wherein $G^1$ is selected from the group consisting of dibenzofuran, dibenzothiophene, dibenzoselenophene, triphenylene, and fluorene;

wherein $L^1$, $L^2$, and $L^3$ are each independently selected from the group consisting of a direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, triphenylene, pyridine, pyrimidine, pyrazine, quinoline, isoquinoline, phenanthroline, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, carbazole, and combinations thereof;

wherein $G^1$, $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7, wherein n is an integer from 0 to 4;

wherein, when m or n is larger than 1, each $G^4$ or $G^5$ can be the same or different;

wherein when n is 0, then m is equal to or greater than 1, and each $G^4$ is selected from the group consisting of phenyl and biphenyl;

wherein when n is equal to or greater than 1, $L^1$ is not a direct bond; and wherein when m and n are both 0, $L^1$ is biphenyl; and Formula IV

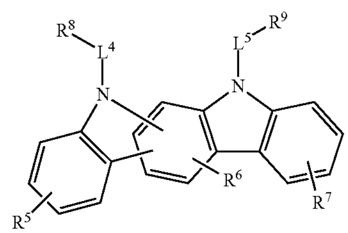

wherein $L^4$ and $L^5$ are each independently selected from the group consisting of a direct bond, phenyl, biphenyl, terphenyl, pyridine, pyrimidine, and combinations thereof;

wherein $R^5$, $R^6$, and $R^7$ each represent mono to the maximum allowable substitution, or no substitution;

wherein $R^8$ and $R^9$ are each independently a substituted or unsubstituted aryl or heteroaryl group;

wherein at least one of $R^8$ and $R^9$ is selected from the group consisting of:

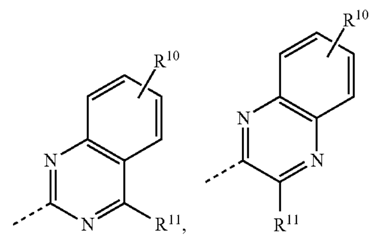

-continued

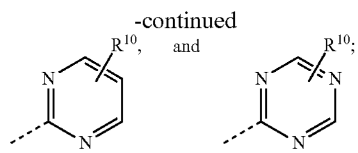

wherein $R^{10}$ represents mono to the maximum allowable substitution, or no substitution;

wherein $R^5$, $R^6$, $R^7$, $R^{10}$, and $R^{11}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two substituents may be joined or fused together to form a ring.

In one embodiment, each $R^5$, $R^6$, $R^7$, $R^{10}$, and $R^{11}$ is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

In one embodiment, $G^2$, $G^3$ and $G^5$ are independently selected from the group consisting of:

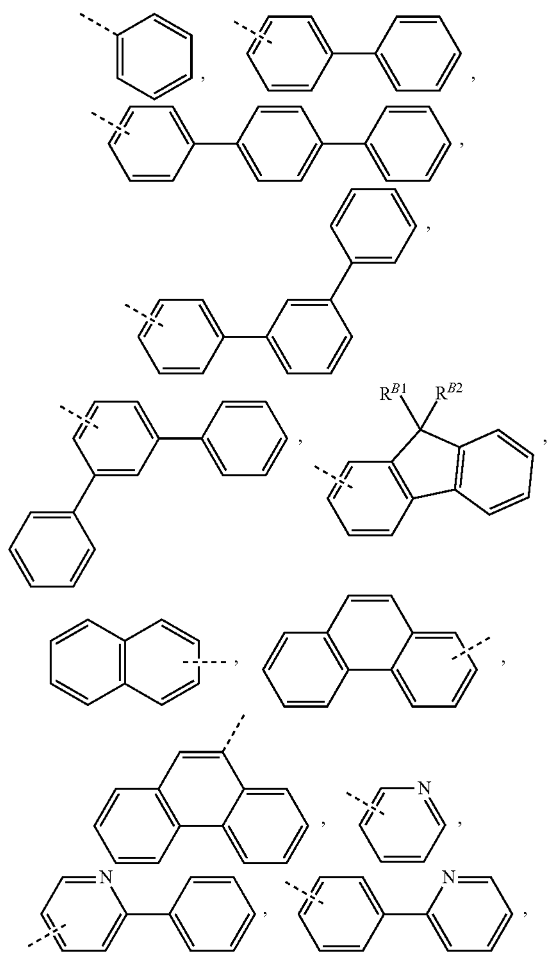

-continued

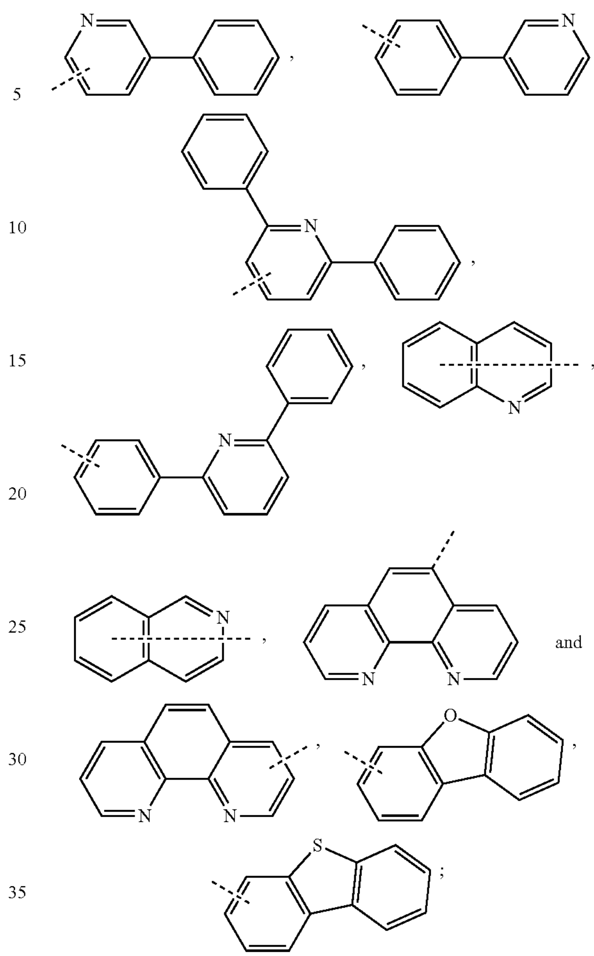

wherein $R^{B1}$ and $R^{B2}$ are independently selected from a group consisting of hydrogen, deuterium, alkyl, alkenyl, cycloalkyl, alkoxyl, aryl, heteraryl, halogen, and combinations thereof; and wherein $R^{B1}$ and $R^{B2}$ are optionally joined to form a ring.

In one embodiment, $R^8$ and $R^9$ are independently selected from the group consisting of:

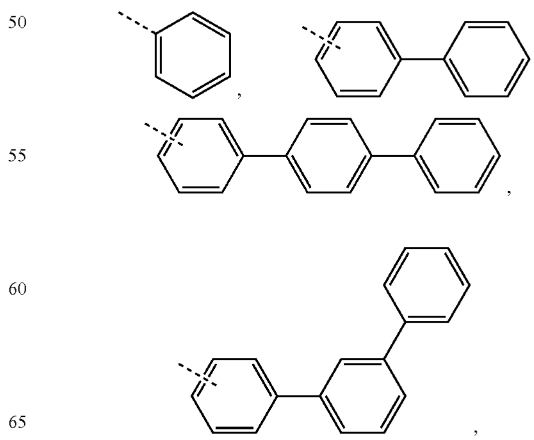

-continued

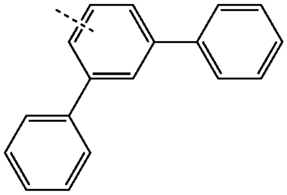,

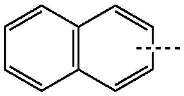,

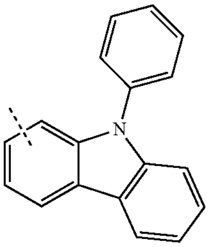,

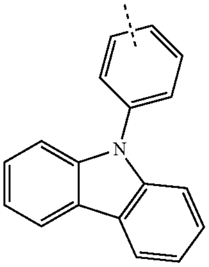

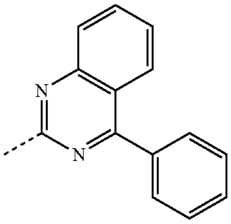,

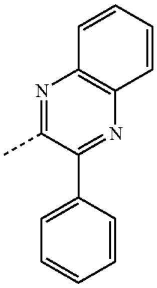,

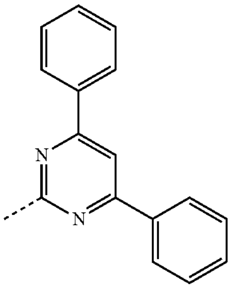,

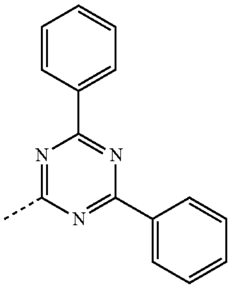,

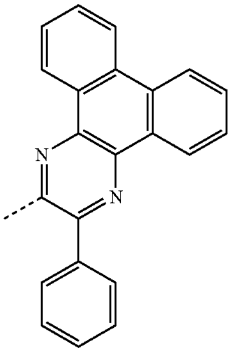,

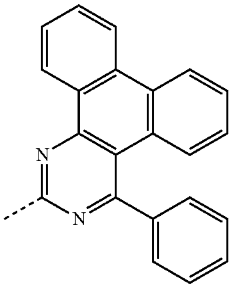,

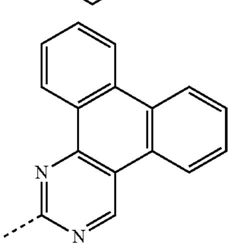, and

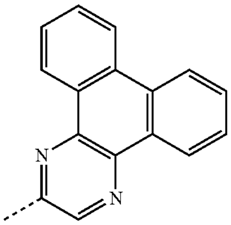.

In one embodiment, $L^4$ is a direct bond, and $L^5$ is a phenyl ring.

In one embodiment, at least one of $R^8$ or $R^9$ is

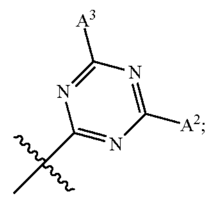

wherein $A^2$ and $A^3$ are each independently selected from the group consisting of hydrogen, phenyl, biphenyl, terphenyl, naphthalene, and combinations thereof.

In one embodiment, $L^4$ and $R^8$ are fused together to form a ring. In one embodiment, $L^5$ and $R^9$ are fused together to form a ring.

In one embodiment, the second compound has the formula:

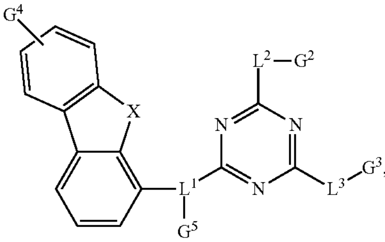

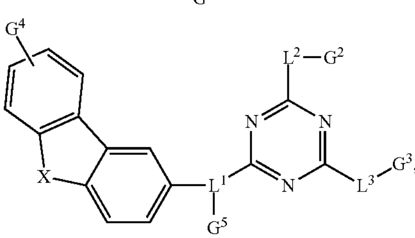

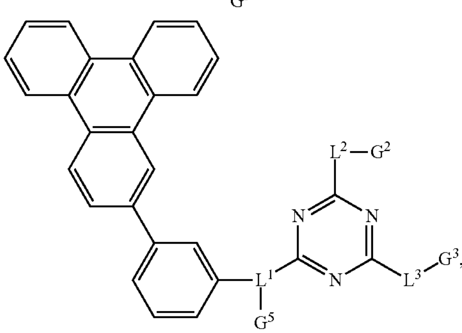

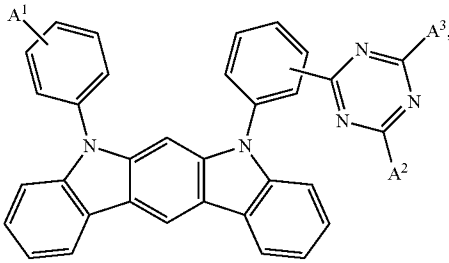

-continued

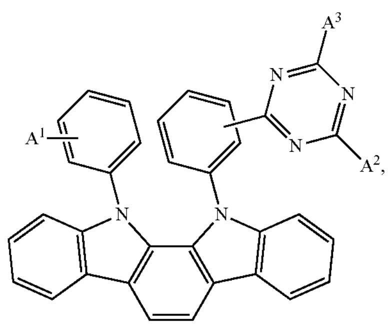

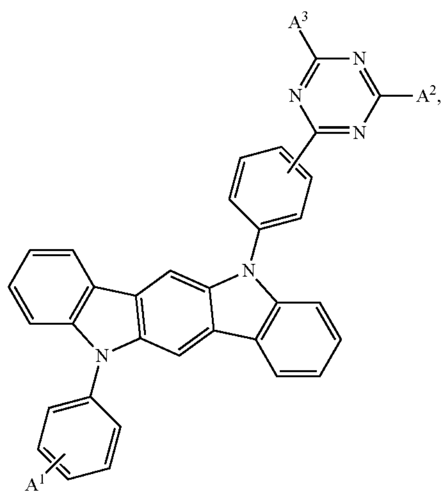

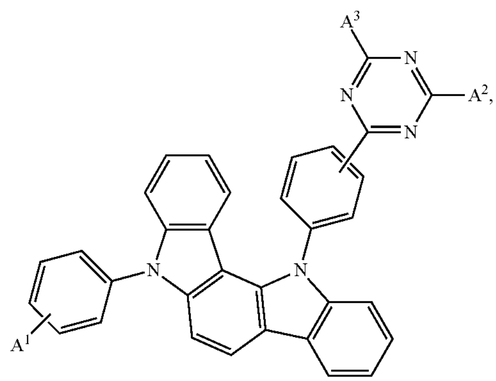

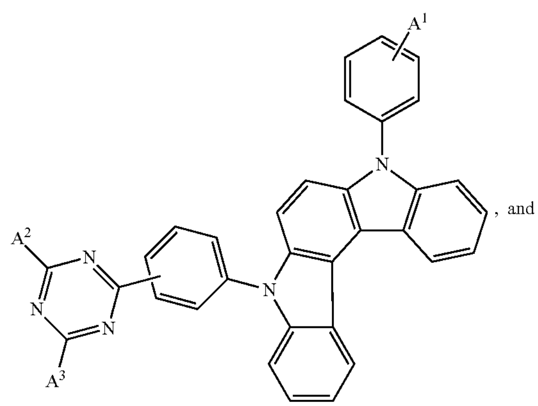

, and

-continued

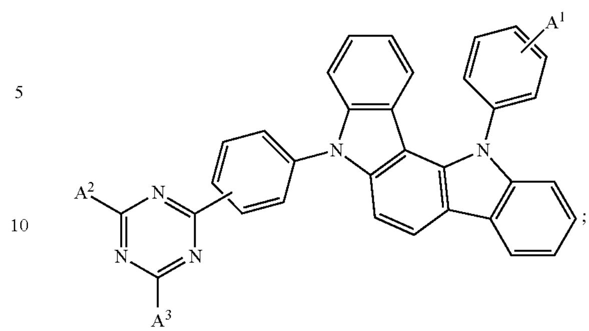

;

wherein X is selected from the group consisting of O, S and Se;

wherein $A^1$ represents mono to the maximum allowable substitution, or no substitution; and wherein each $A^1$, $A^2$, and $A^3$ is independently selected from the group consisting of hydrogen, phenyl, biphenyl, terphenyl, naphthalene, and combinations thereof.

In one embodiment, the second compound is selected from the group consisting of:

Compound F1 through F3, each represented by the formula

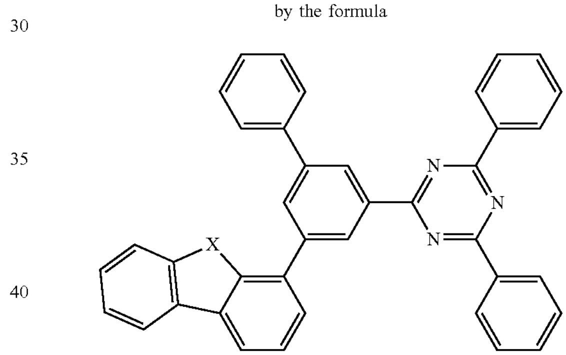

wherein in Compound F1: X = O,
in Compound F2: X = S,
in Compound F3: X = Se,

Compound F4 through F6, each represented by the formula

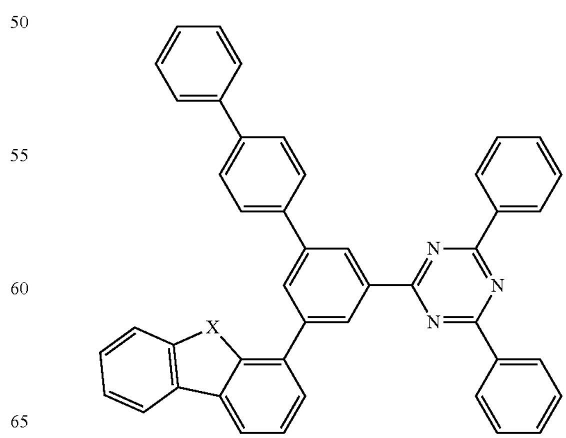

-continued wherein in Compound F4: X = O,
in Compound F5: X = S,
in Compound F6: X = Se, Compound F7 through F9, each represented by the formula

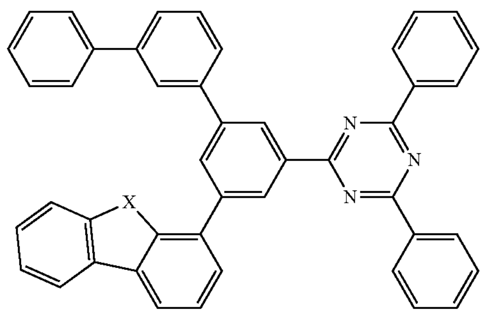

wherein in Compound F7: X = O,
in Compound F8: X = S,
in Compound F9: X = Se,

Compound F10 through F12, each represented by the formula

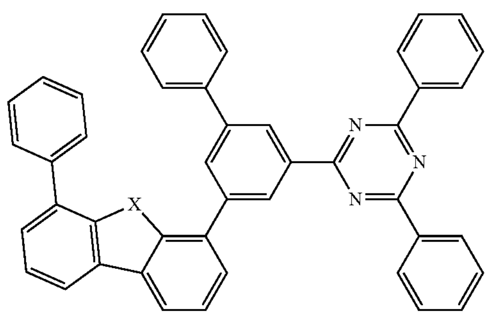

wherein in Compound F10: X = O,
in Compound F11: X = S,
in Compound F12: X = Se, Compound F13 through F15, each represented by the formula

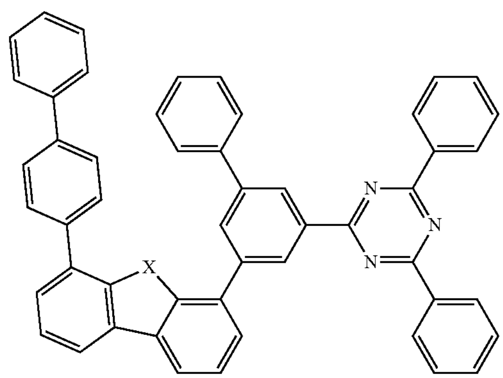

wherein in Compound F13: X = O,
in Compound F14: X = S,
in Compound F15: X = Se, -continued Compound F16 through F18, each represented by the formula

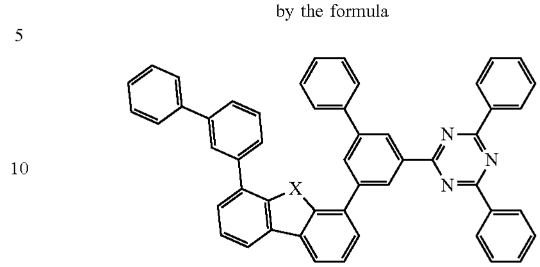

wherein in Compound F16: X = O,
in Compound F17: X = S,
in Compound F18: X = Se, Compound F19 through F21, each represented by the formula

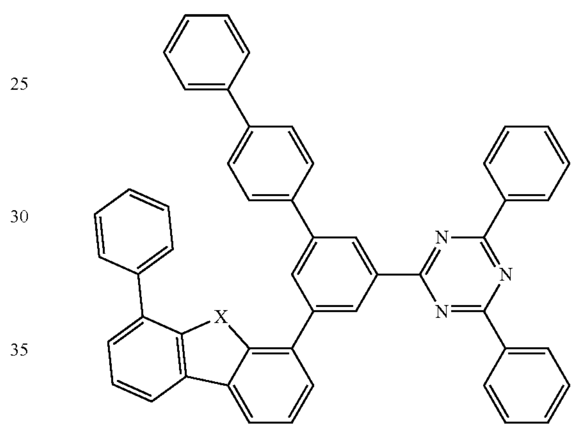

wherein in Compound F19: X = O,
in Compound F20: X = S,
in Compound F21: X = Se, Compound F22 through F24, each represented by the formula

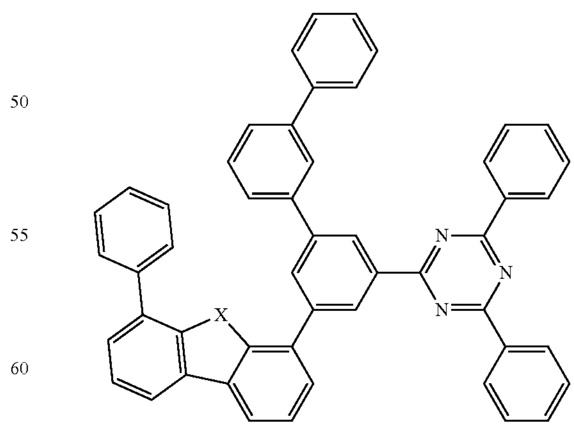

wherein in Compound F22: X = O,
in Compound F23: X = S,
in Compound F24: X = Se, Compound F25 through F27, each represented by the formula

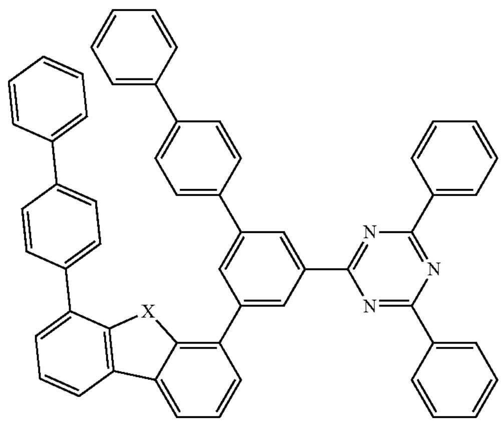

wherein in Compound F25: X = O,
in Compound F26: X = S,
in Compound F27: X = Se, Compound F28 through F30, each represented by the formula

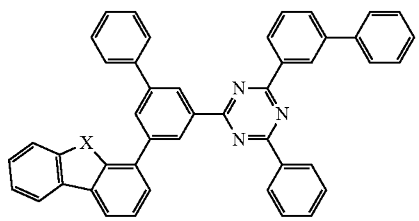

wherein in Compound F28: X = O,
in Compound F29: X = S,
in Compound F30: X = Se, Compound F31 through F33, each represented by the formula

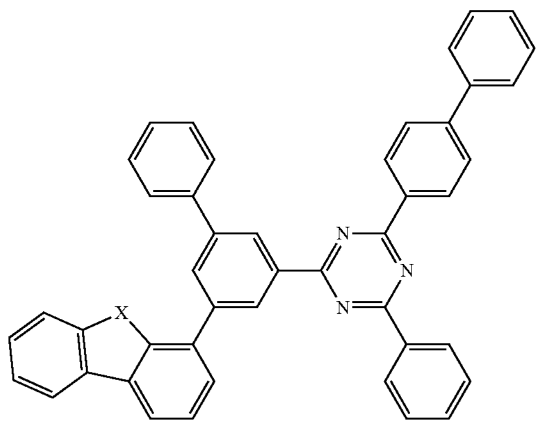

wherein in Compound F31: X = O,
in Compound F32: X = S,
in Compound F33: X = Se, Compound F34 through F36, each represented by the formula

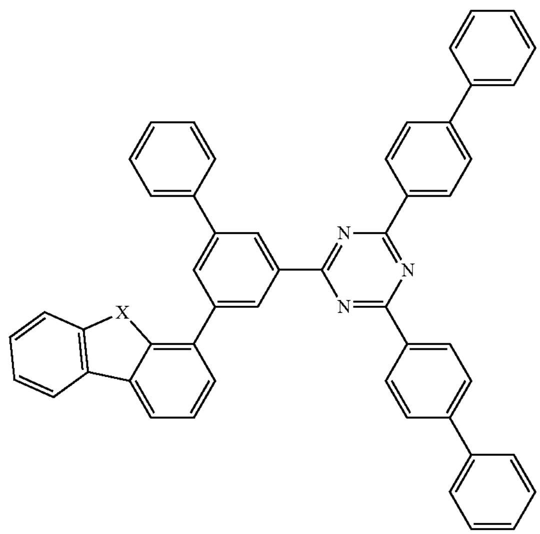

wherein in Compound F34: X = O,
in Compound F35: X = S,
in Compound F36: X = Se, Compound F37 through F39, each represented by the formula

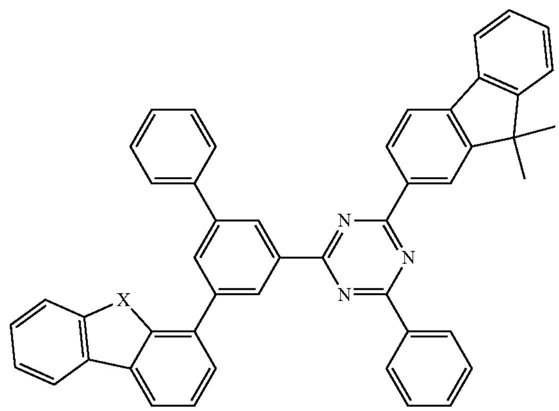

wherein in Compound F37: X = O,
in Compound F38: X = S,
in Compound F39: X = Se, Compound F40 through F42, each represented by the formula

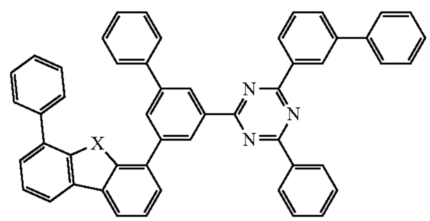

wherein in Compound F40: X = O,
in Compound F41: X = S,
in Compound F42: X = Se, Compound F43 through F45, each represented by the formula

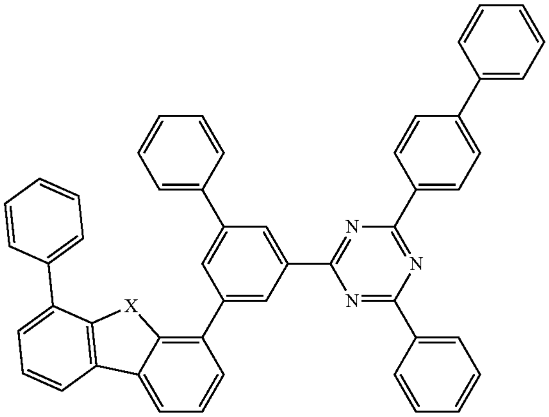

wherein in Compound F43: X = O, in Compound F44: X = S, in Compound F45: X = Se, Compound F46 through F48, each represented by the formula

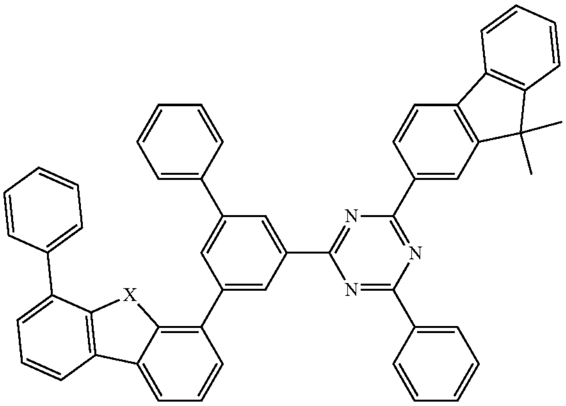

wherein in Compound F46: X = O, in Compound F47: X = S, in Compound F48: X = Se, Compound F49 through F51, each represented by the formula

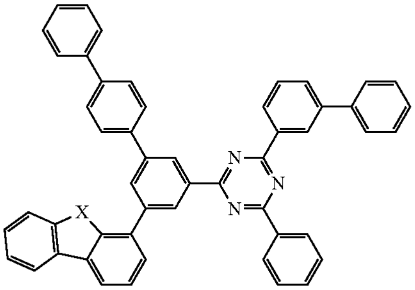

wherein in Compound F49: X = O, in Compound F50: X = S, in Compound F51: X = Se, Compound F52 through F54, each represented by the formula

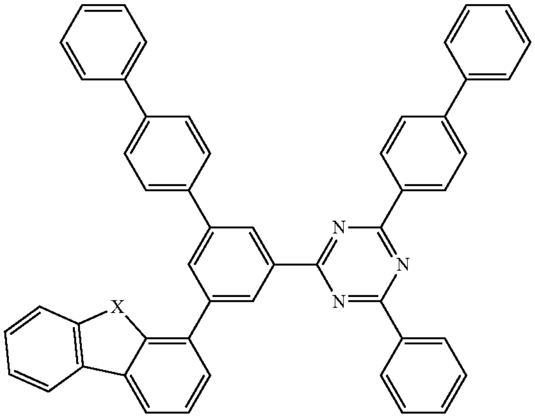

wherein in Compound F52: X = O, in Compound F53: X = S, in Compound F54: X = Se, Compound F55 through F57, each represented by the formula

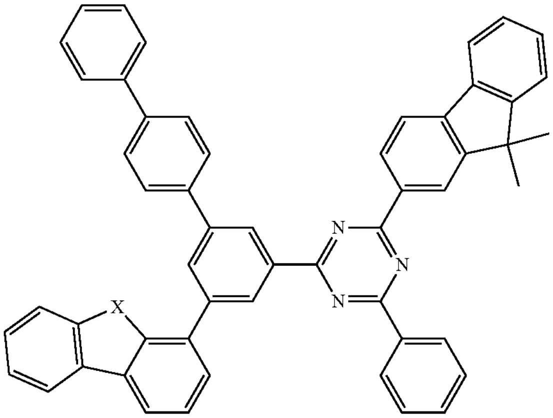

wherein in Compound F55: X = O, in Compound F56: X = S, in Compound F57: X = Se, Compound F58 through F60, each represented by the formula

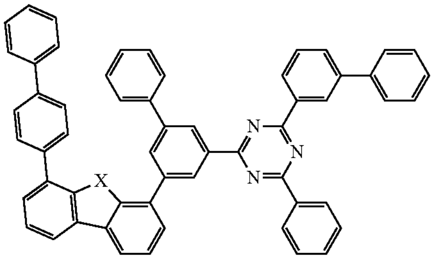

wherein in Compound F58: X = O, in Compound F59: X = S, in Compound F60: X = Se, Compound F61 through F63, each represented by the formula

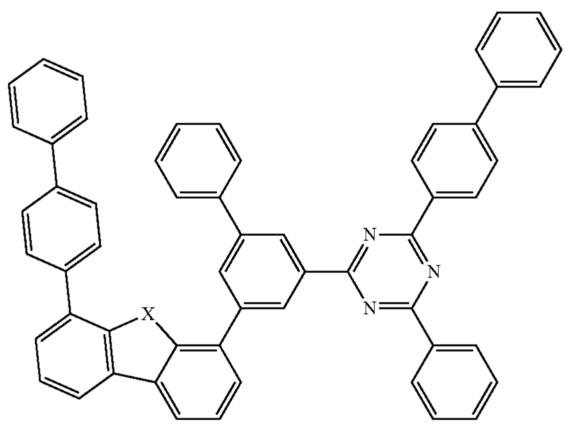

wherein in Compound F61: X = O,
in Compound F62: X = S,
in Compound F63: X = Se, Compound F64 through F66, each represented by the formula

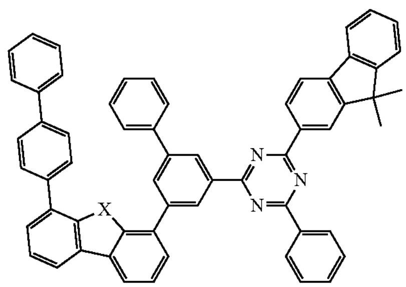

wherein in Compound F64: X = O,
in Compound F65: X = S,
in Compound F66: X = Se, Compound F67 through F69, each represented by the formula

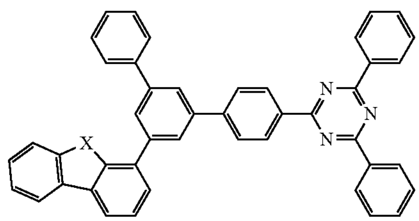

wherein in Compound F67: X = O,
in Compound F68: X = S,
in Compound F69: X = Se, Compound F70 through F72, each represented by the formula

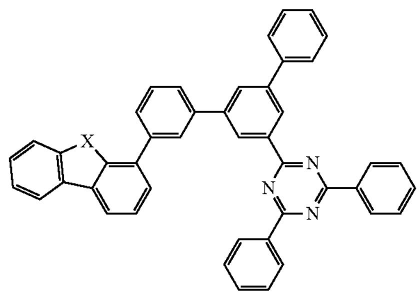

wherein in Compound F70: X = O,
in Compound F71: X = S,
in Compound F72: X = Se, Compound F73 through F75, each represented by the formula

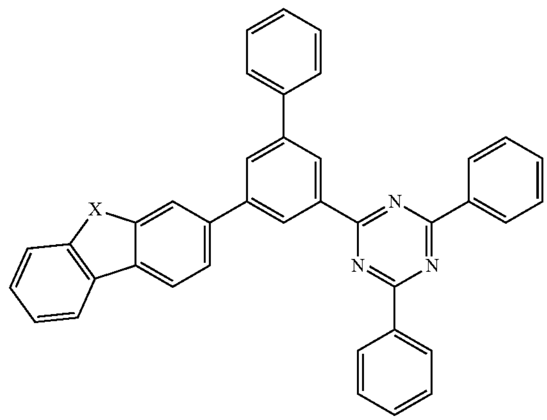

wherein in Compound F73: X = O,
in Compound F74: X = S,
in Compound F75: X = Se, Compound F76 through F78, each represented by the formula

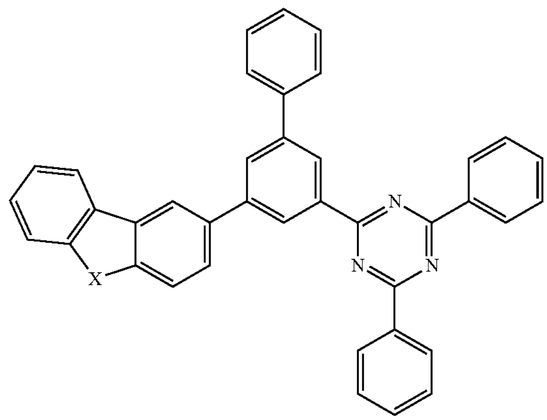

wherein in Compound F76: X = O,
in Compound F77: X = S,
in Compound F78: X = Se, -continued Compound F79 through F81, each represented by the formula

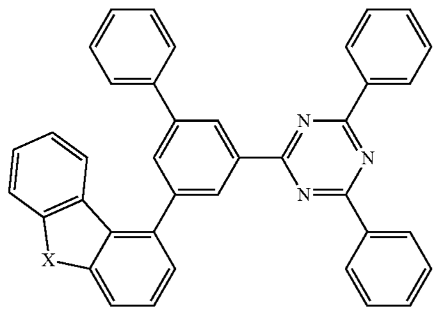

wherein in Compound F79: X = O,
in Compound F80: X = S,
in Compound F81: X = Se, Compound F82 through F84, each represented by the formula

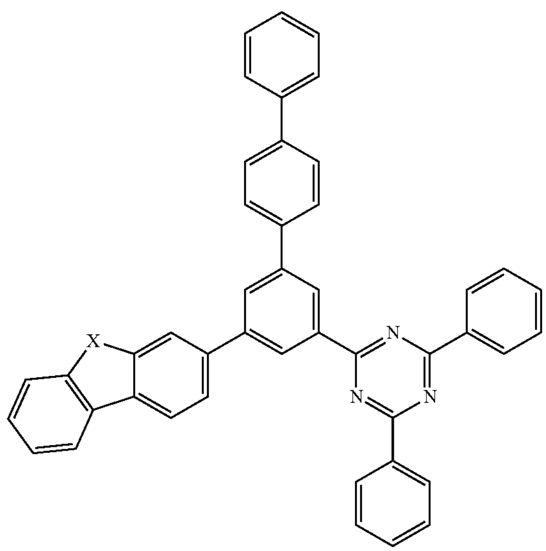

wherein in Compound F82: X = O,
in Compound F83: X = S,
in Compound F84: X = Se, -continued Compound F85 through F87, each represented by the formula

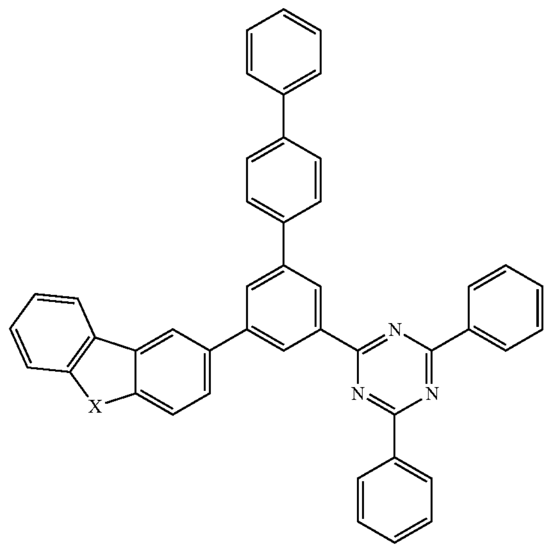

wherein in Compound F85: X = O,
in Compound F86: X = S,
in Compound F87: X = Se, Compound F88 through F90, each represented by the formula

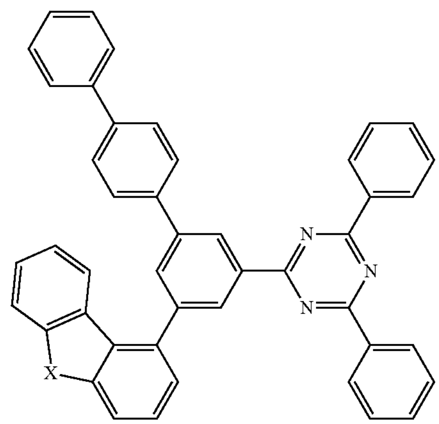

wherein in Compound F88: X = O,
in Compound F89: X = S,
in Compound F90: X = Se, Compound F91 through F93, each represented by the formula

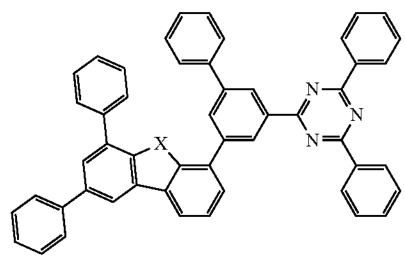

wherein in Compound F91: X = O,
in Compound F92: X = S,
in Compound F93: X = Se, Compound F94 through F96, each represented by the formula

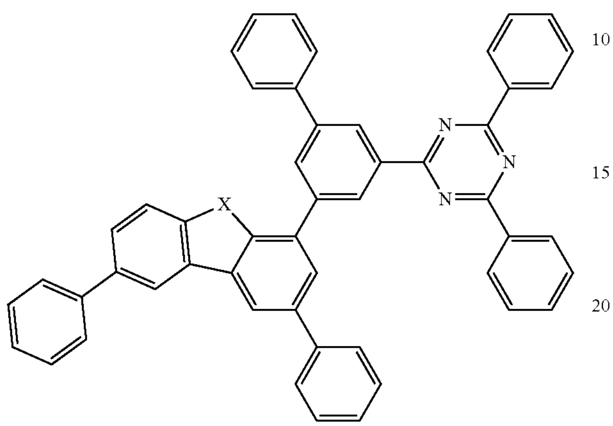

wherein in Compound F94: X = O,
in Compound F95: X = S,
in Compound F96: X = Se, Compound F97 through F99, each represented by the formula

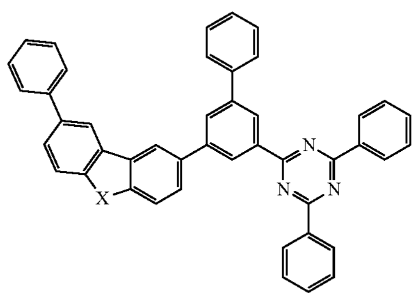

wherein in Compound F97: X = O,
in Compound F98: X = S,
in Compound F99: X = Se, Compound F100 through F102, each represented by the formula

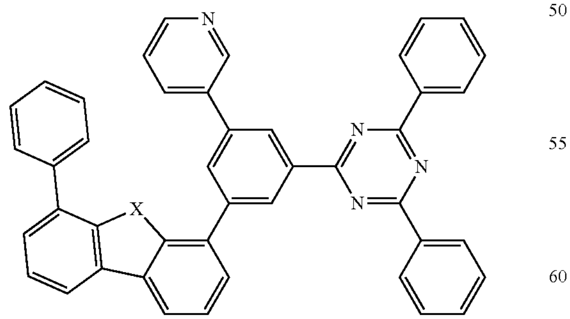

wherein in Compound F100: X = O,
in Compound F101: X = S,
in Compound F102: X = Se, Compound F103 through F105, each represented by the formula

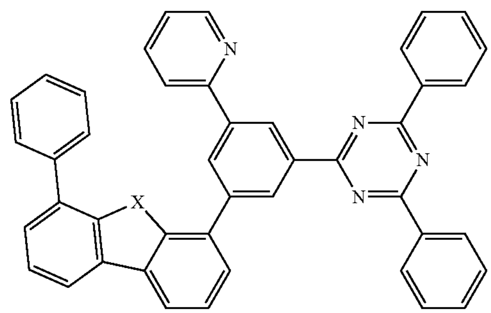

wherein in Compound F103: X = O,
in Compound F104: X = S,
in Compound F105: X = Se, Compound F106 through F108, each represented by the formula

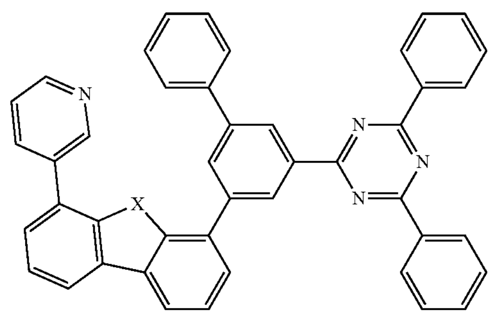

wherein in Compound F106: X = O,
in Compound F107: X = S,
in Compound F108: X = Se, Compound F109 through F111, each represented by the formula

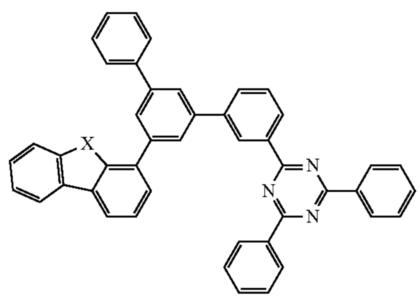

wherein in Compound F109: X = O,
in Compound F110: X = S,
in Compound F111: X = Se, -continued
Compound F112 through F114, each represented by the formula
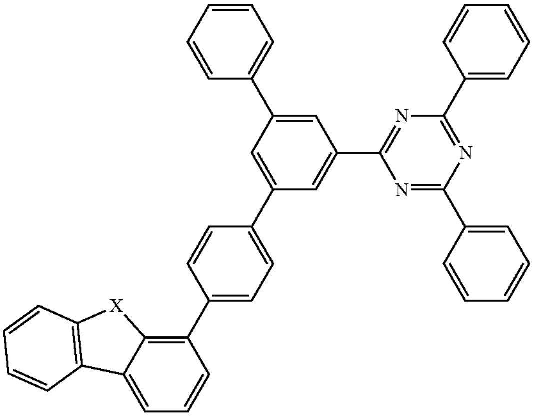
wherein in Compound F112: X = O,
in Compound F113: X = S,
in Compound F114: X = Se,
Compound F115 through F117, each represented by the formula
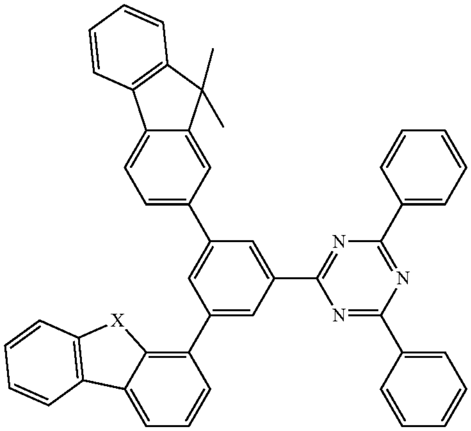
wherein in Compound F115: X = O,
in Compound F116: X = S,
in Compound F117: X = Se,
Compound G1
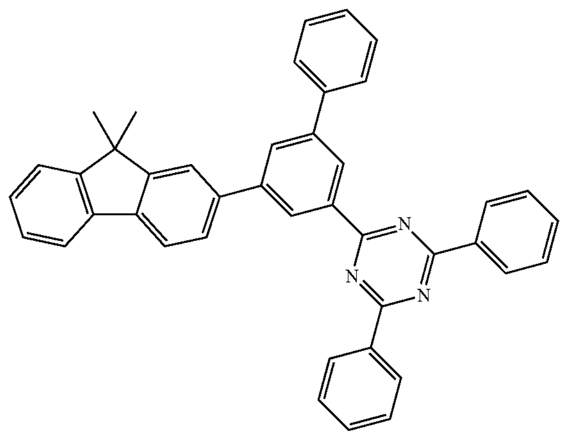
,
Compound G2
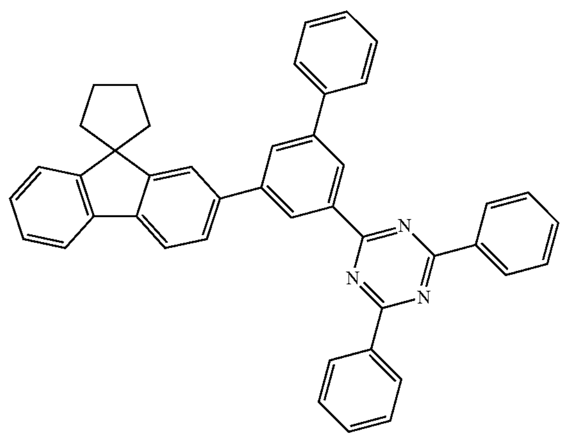
,
Compound G3
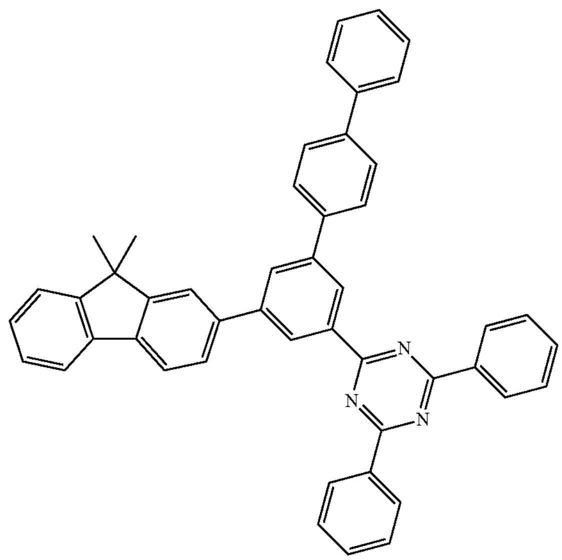
, -continued
Compound G4
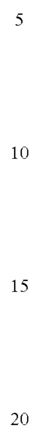
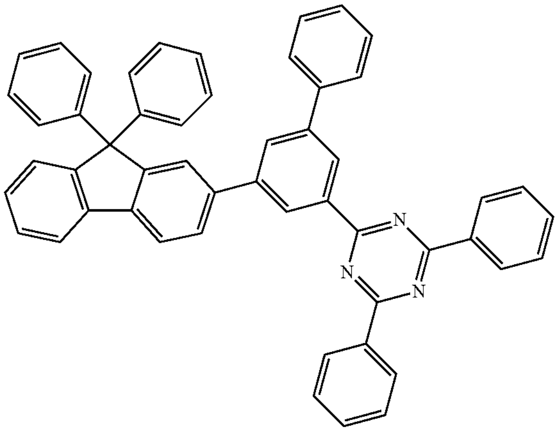
,
Compound G5
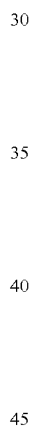
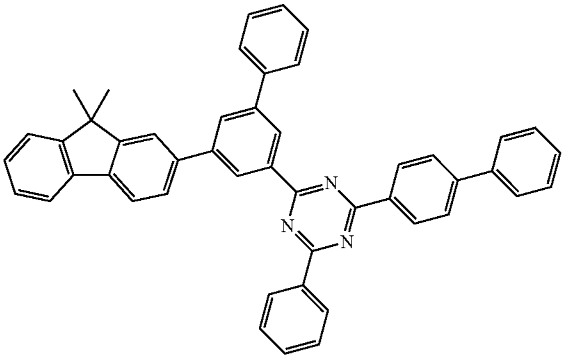
,
Compound G6
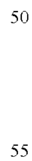
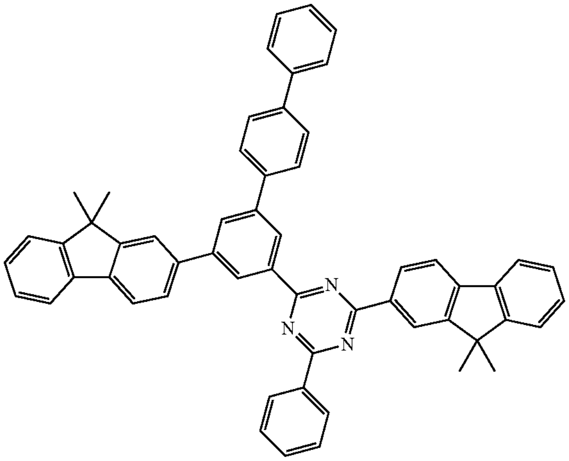
,
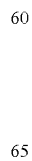
-continued
Compound G7
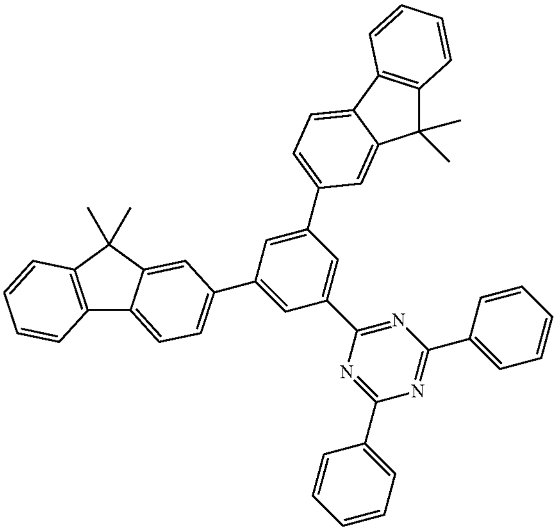
,
Compound G8
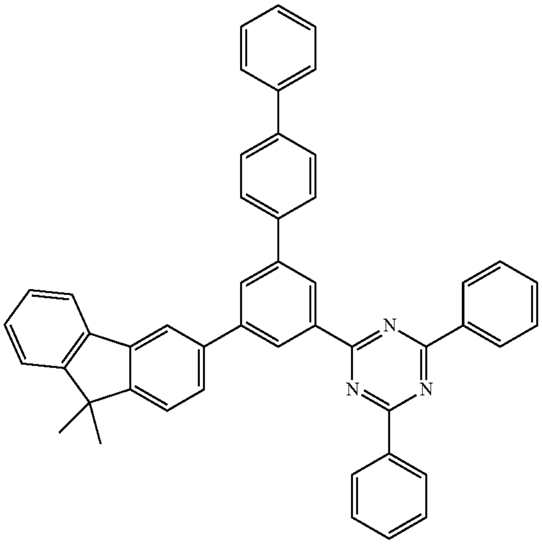
,
Compound G9
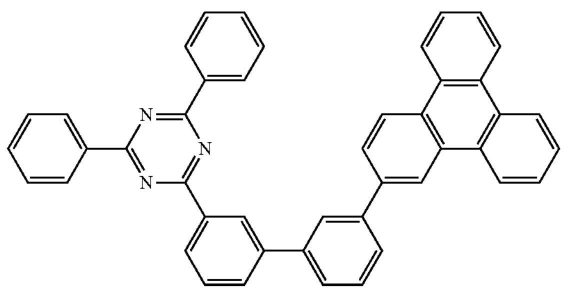
, -continued
Compound G10
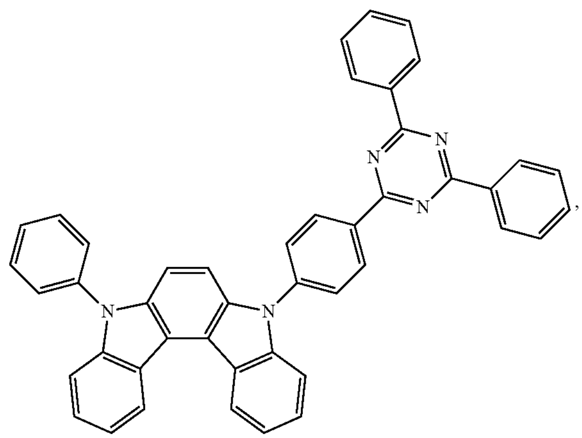
Compound G11
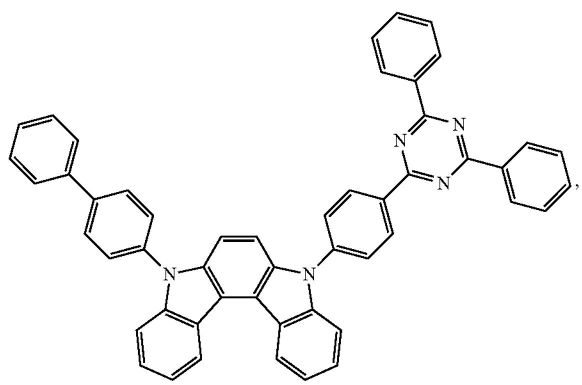
Compound G12
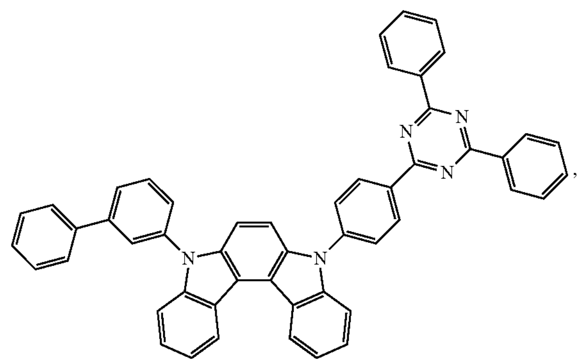
Compound G13
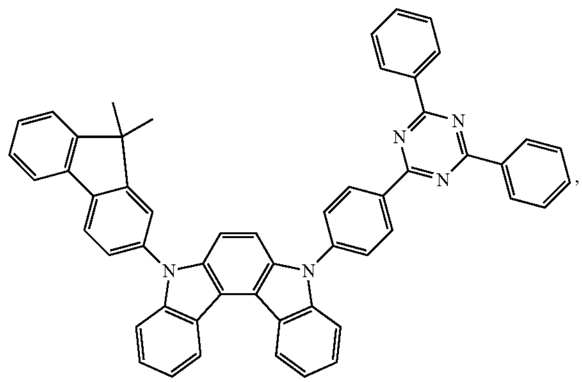
-continued
Compound G14
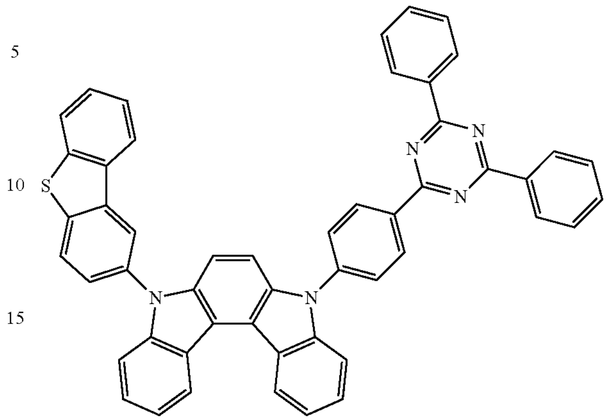
Compound G15
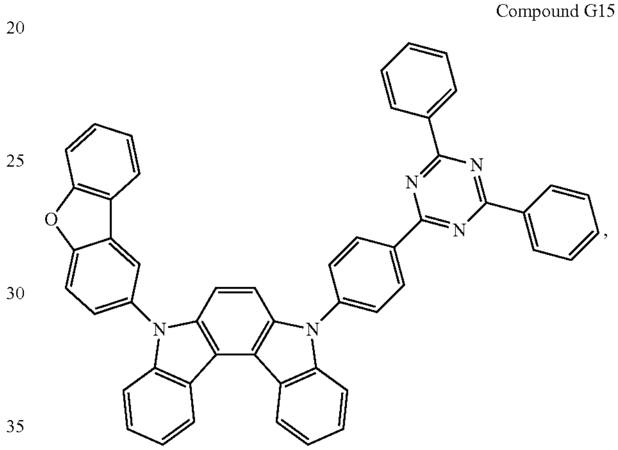
Compound G16
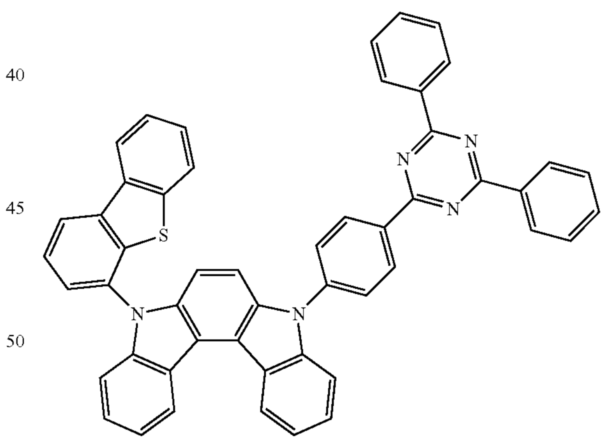
Compound G17
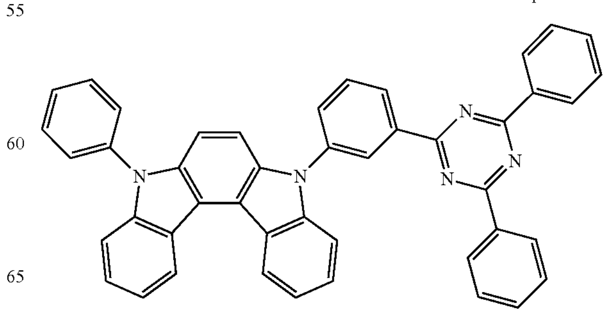

-continued
Compound G18
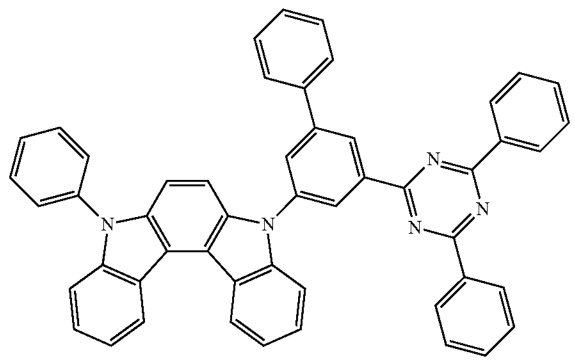
,
Compound G19
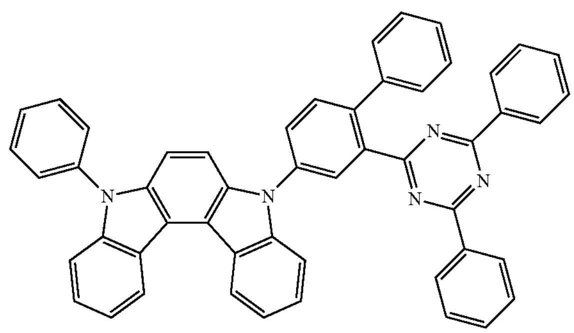
,
Compound G20
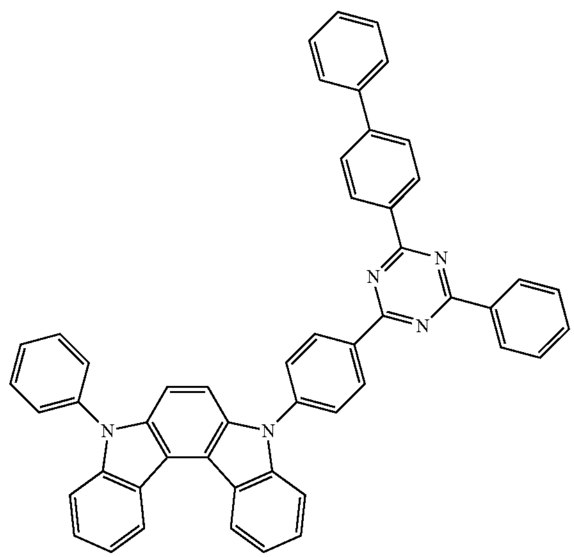
,
-continued
Compound G21
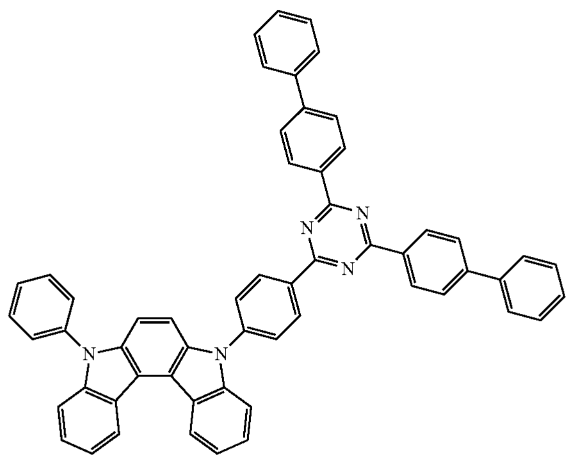
,
Compound G22
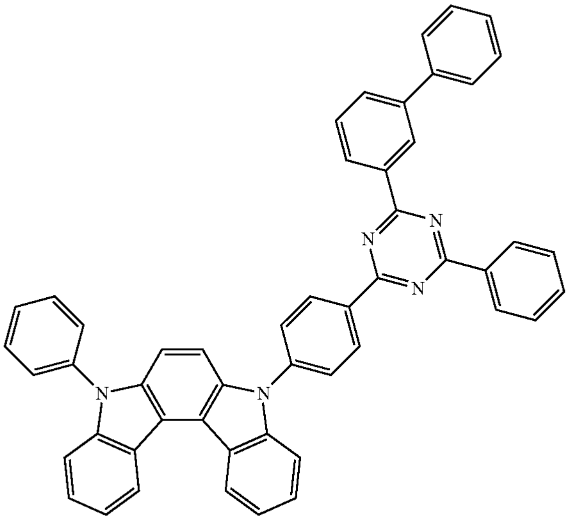
,
Compound G23
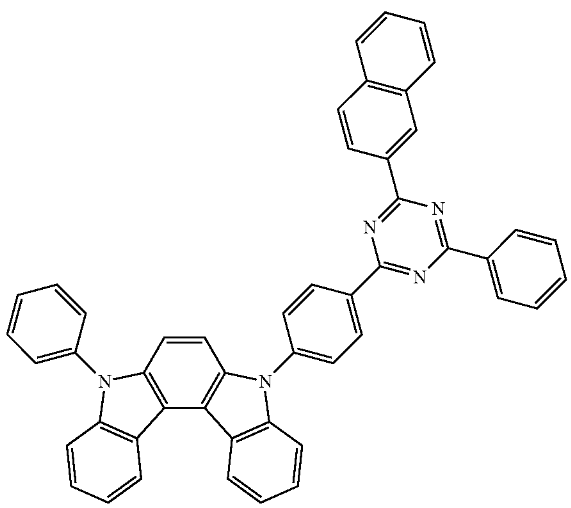
, -continued
Compound G24
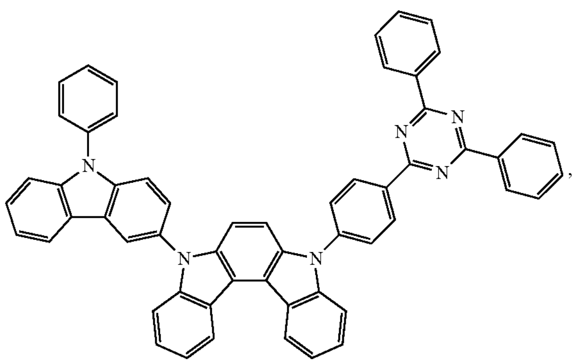
Compound G25
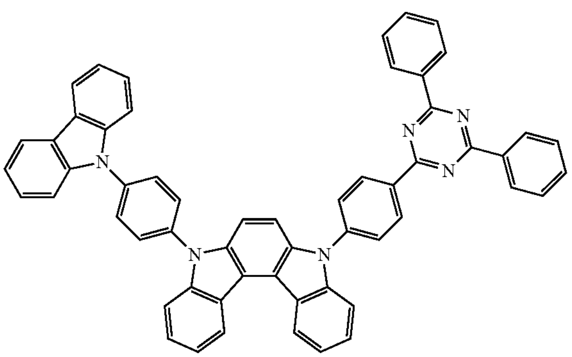
Compound G26
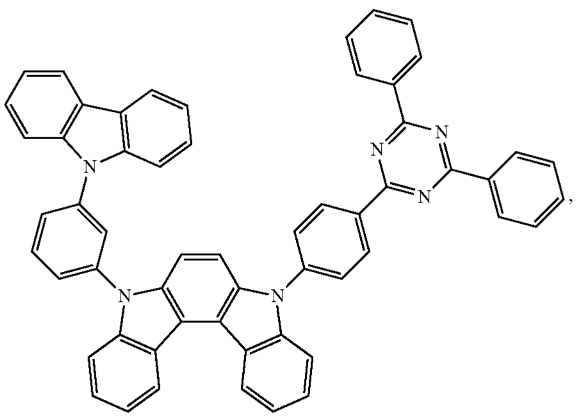
Compound G27
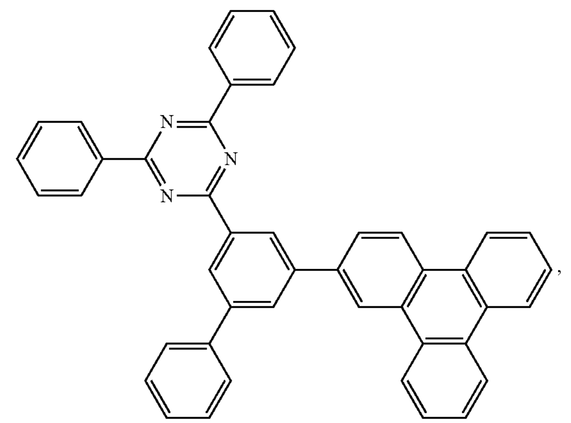
-continued
Compound G28
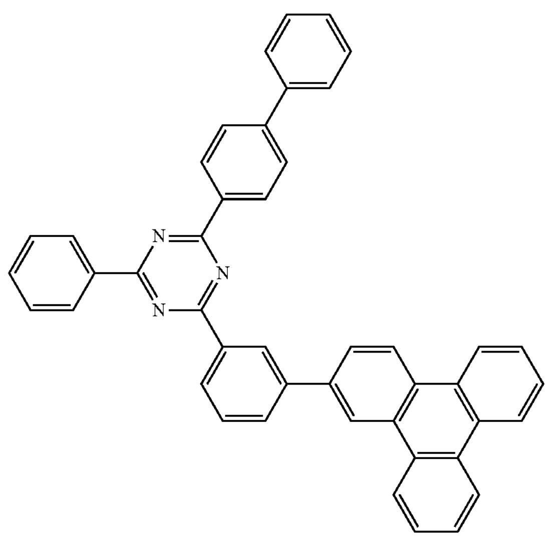
Compound G29
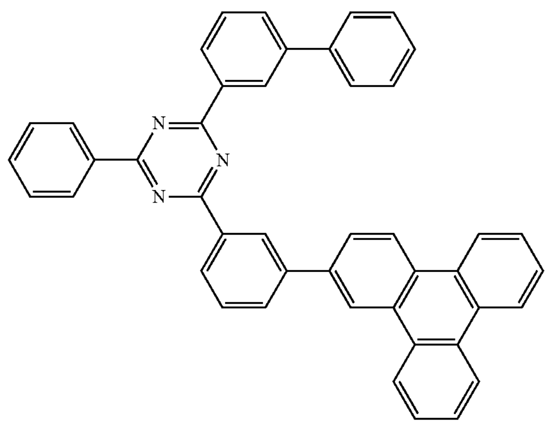
Compound G30
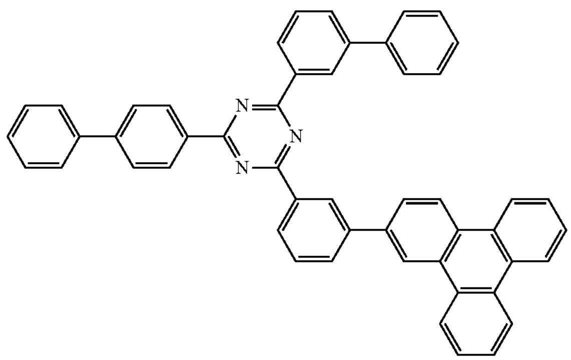

-continued
Compound G31
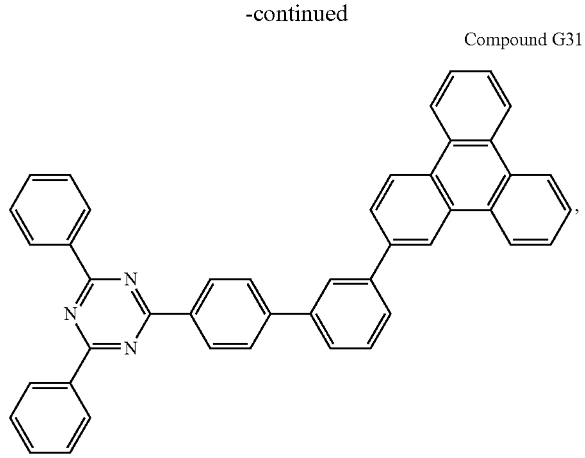
Compound G32
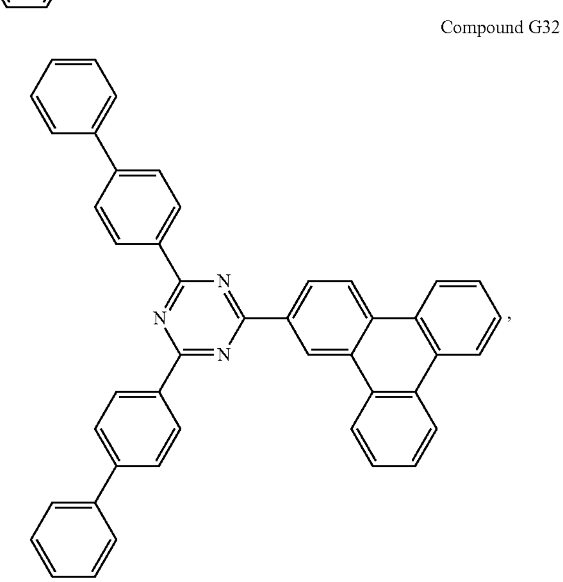
Compound G33
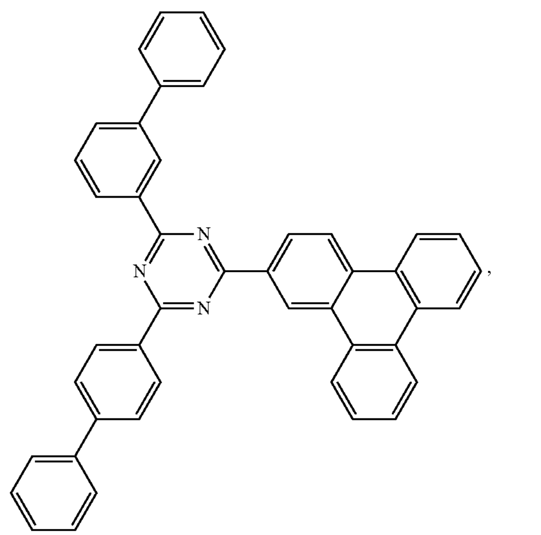
-continued
Compound G34
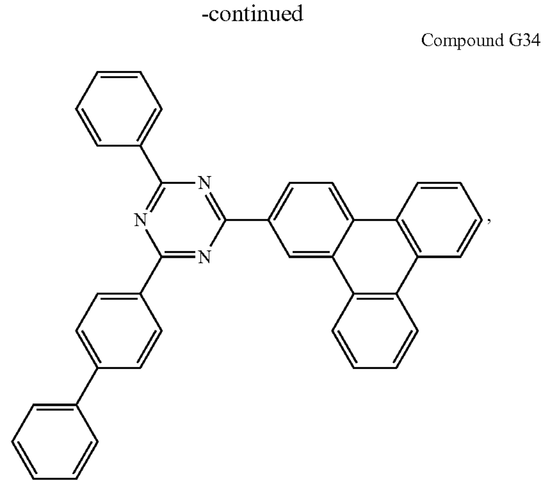
Compound G35
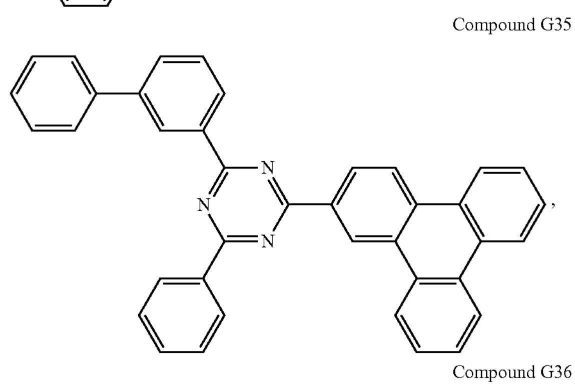
Compound G36
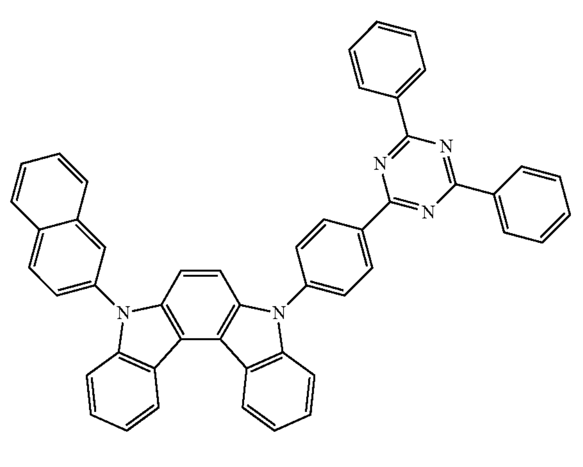
Compound H1 through H3, each represented by the formula
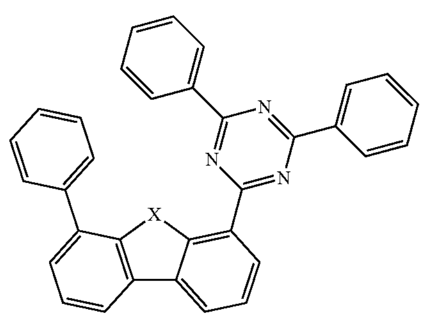

-continued wherein in Compound H1: X = O,
in Compound H2: X = S,
in Compound H3: X = Se, Compound H4 through H6, each represented by the formula

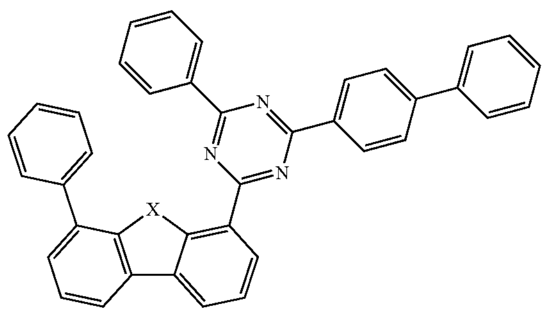

wherein in Compound H4: X = O,
in Compound H5: X = S,
in Compound H6: X = Se,

Compound H7 through H9, each represented by the formula

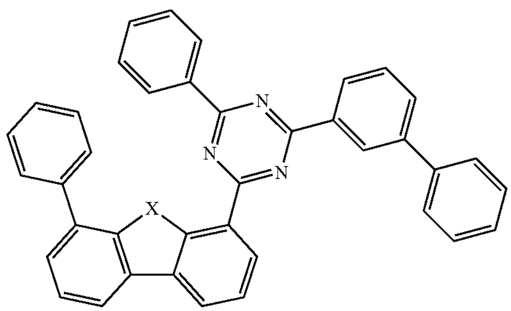

wherein in Compound H7: X = O,
in Compound H8: X = S,
in Compound H9: X = Se,

Compound H10 through H12, each represented by the formula

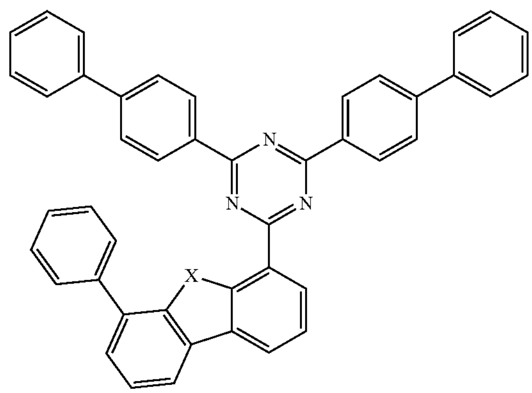

wherein in Compound H10: X = O,
in Compound H11: X = S,
in Compound H12: X = Se, -continued Compound H13 through H15, each represented by the formula

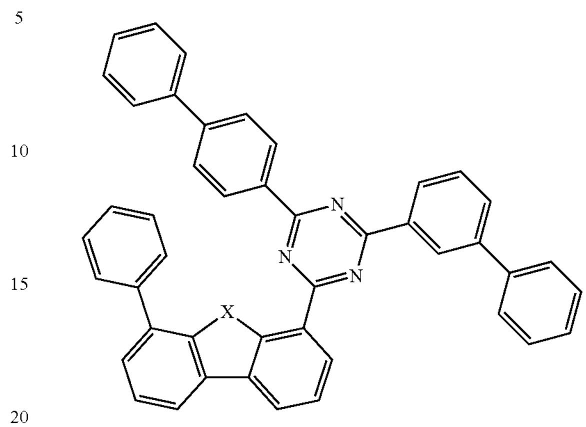

wherein in Compound H13: X = O,
in Compound H14: X = S,
in Compound H15: X = Se, Compound H16 through H18, each represented by the formula

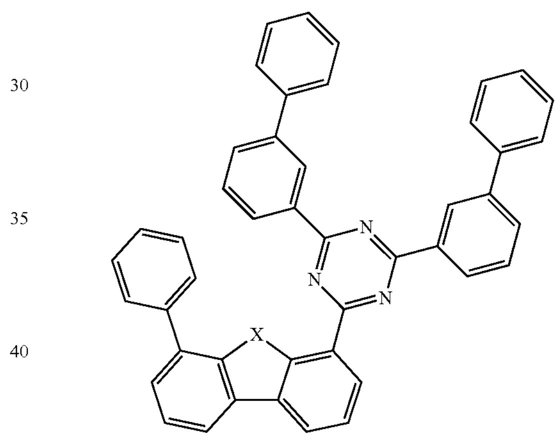

wherein in Compound H16: X = O,
in Compound H17: X = S,
in Compound H18: X = Se, Compound H19 through H21, each represented by the formula

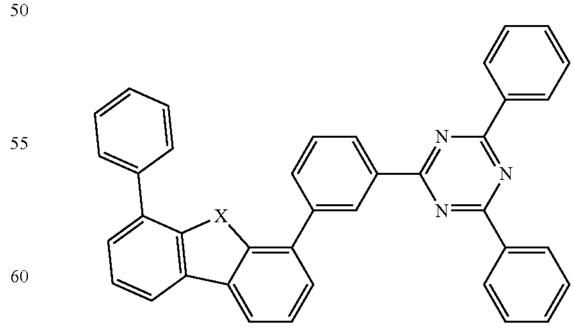

wherein in Compound H19: X = O,
in Compound H20: X = S,
in Compound H21: X = Se, -continued Compound H22 through H24, each represented by the formula

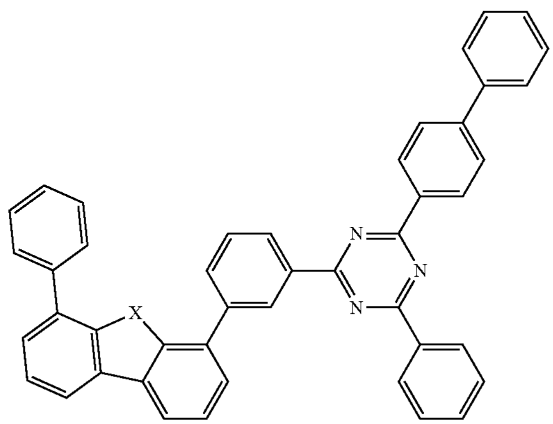

wherein in Compound H22: X = O,
in Compound H23: X = S,
in Compound H24: X = Se, Compound H25 through H27, each represented by the formula

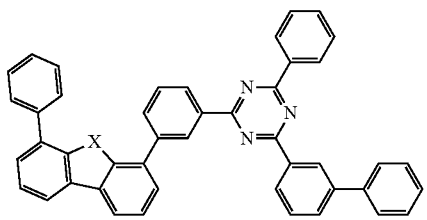

wherein in Compound H25: X = O,
in Compound H26: X = S,
in Compound H27: X = Se, Compound H28 through H30, each represented by the formula

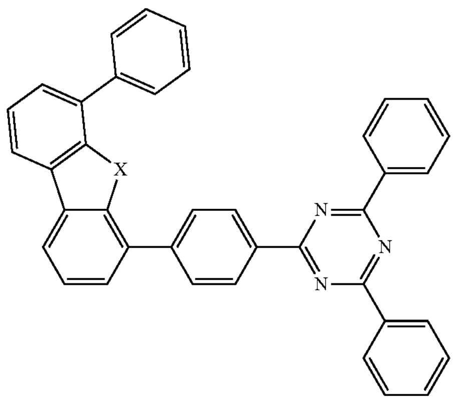

wherein in Compound H28: X = O,
in Compound H29: X = S,
in Compound H30: X = Se, -continued Compound H31 through H33, each represented by the formula

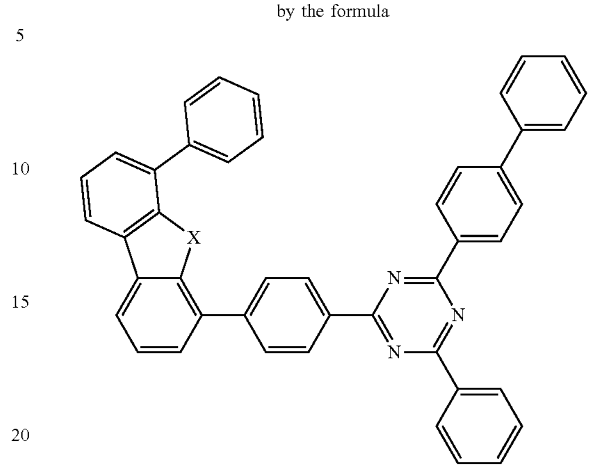

wherein in Compound H31: X = O,
in Compound H32: X = S,
in Compound H33: X = Se, Compound H34 through H36, each represented by the formula

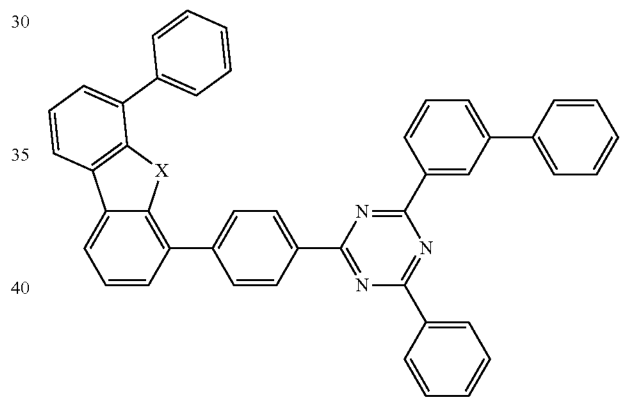

wherein in Compound H34: X = O,
in Compound H35: X = S,
in Compound H36: X = Se, Compound H37 through H39, each represented by the formula

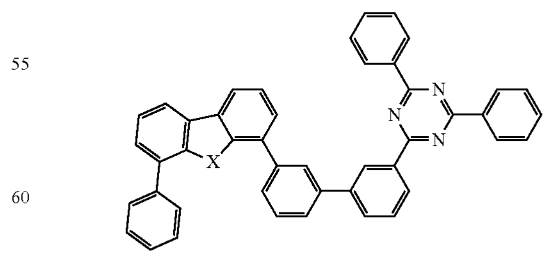

wherein in Compound H37: X = O,
in Compound H38: X = S,
in Compound H39: X = Se, -continued Compound H40 through H42, each represented by the formula

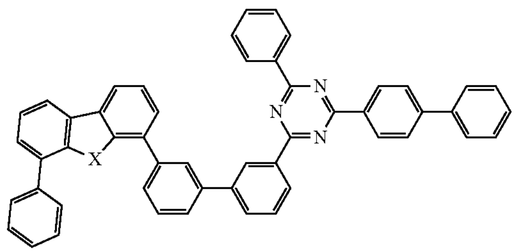

wherein in Compound H40: X = O,
in Compound H41: X = S,
in Compound H42: X = Se, Compound H43 through H45, each represented by the formula

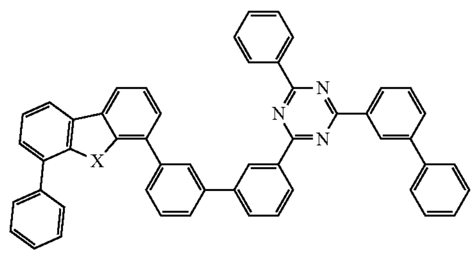

wherein in Compound H43: X = O,
in Compound H44: X = S,
in Compound H45: X = Se, Compound H46 through H48, each represented by the formula

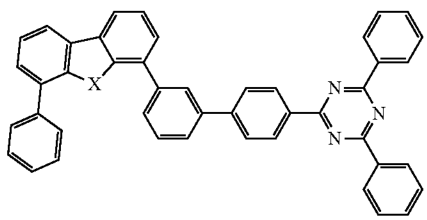

wherein in Compound H46: X = O,
in Compound H47: X = S,
in Compound H48: X = Se, Compound H49 through H51, each represented by the formula

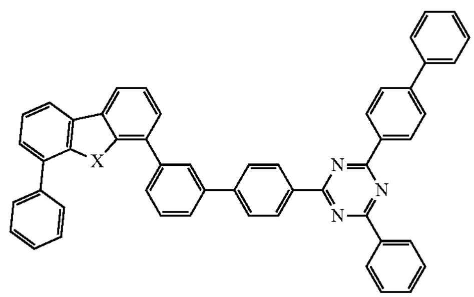

wherein in Compound H49: X = O,
in Compound H50: X = S,
in Compound H51: X = Se, -continued Compound H52 through H54, each represented by the formula

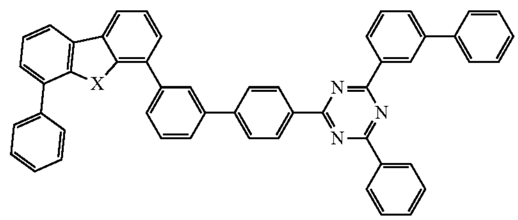

wherein in Compound H52: X = O,
in Compound H53: X = S,
in Compound H54: X = Se, Compound H55 through H57, each represented by the formula

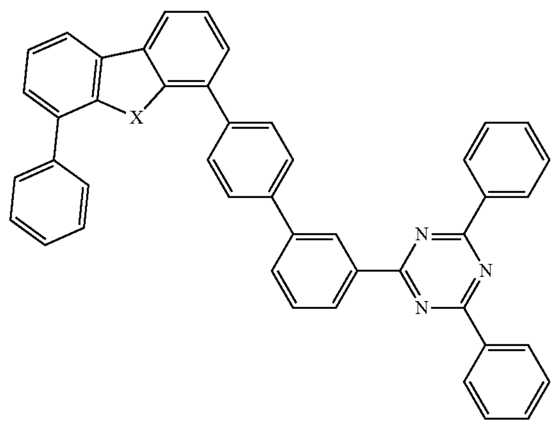

wherein in Compound H55: X = O,
in Compound H56: X = S,
in Compound H57: X = Se, Compound H58 through H60, each represented by the formula

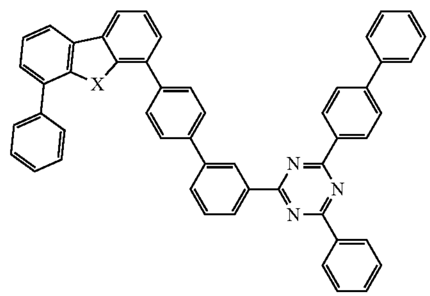

wherein in Compound H58: X = O,
in Compound H59: X = S,
in Compound H60: X = Se, Compound H61 through H63, each represented by the formula

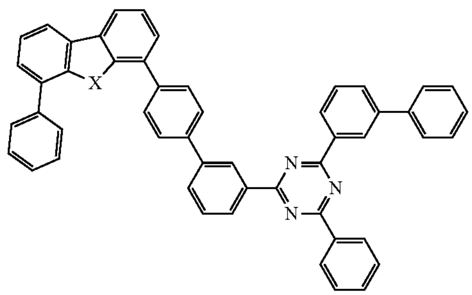

wherein in Compound H61: X = O,
in Compound H62: X = S,
in Compound H63: X = Se, Compound H64 through H66, each represented by the formula

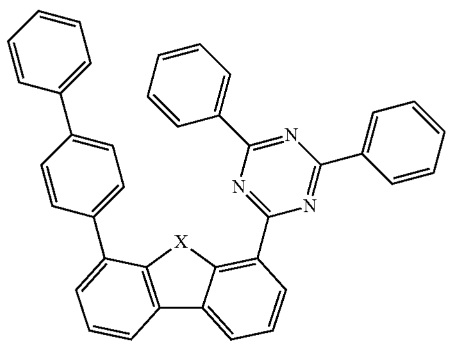

wherein in Compound H64: X = O,
in Compound H65: X = S,
in Compound H66: X = Se, Compound H67 through H69, each represented by the formula

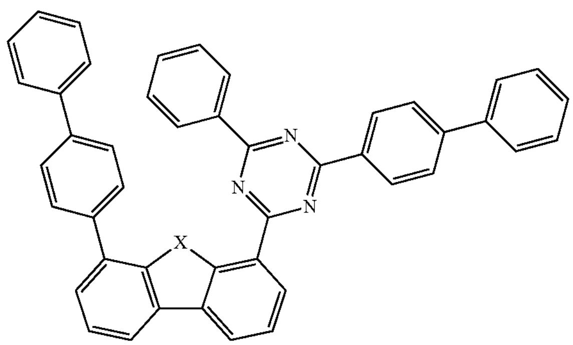

wherein in Compound H67: X = O,
in Compound H68: X = S,
in Compound H69: X = Se, Compound H70 through H72, each represented by the formula

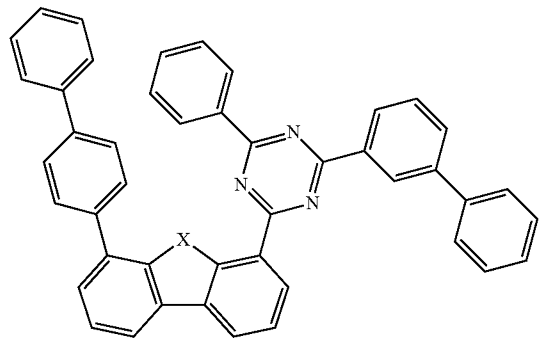

wherein in Compound H70: X = O,
in Compound H71: X = S,
in Compound H72: X = Se, Compound H73 through H75, each represented by the formula

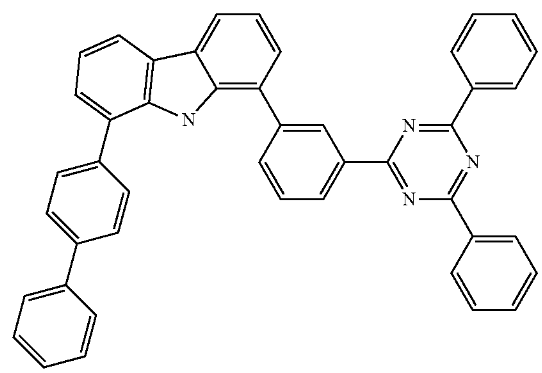 [SMILES: c1ccc(-c2ccc(-c3cccc4c3[nH]c3c(-c5cccc(-c6nc(-c7ccccc7)nc(-c7ccccc7)n6)c5)cccc34)cc2)cc1]

wherein in Compound H73: X = O,
in Compound H74: X = S,
in Compound H75: X = Se, Compound H76 through H78, each represented by the formula

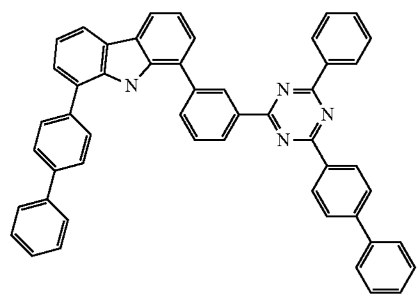 [SMILES: c1ccc(-c2ccc(-c3nc(-c4ccccc4)nc(-c4cccc(-c5cccc6c5[nH]c5c(-c7ccc(-c8ccccc8)cc7)cccc56)c4)n3)cc2)cc1]

wherein in Compound H76: X = O,
in Compound H77: X = S,
in Compound H78: X = Se, -continued Compound H79 through H81, each represented by the formula

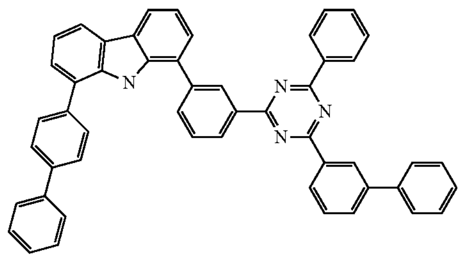 [SMILES: c1ccc(-c2ccc(-c3cccc4c3[nH]c3c(-c5cccc(-c6nc(-c7ccccc7)nc(-c7cccc(-c8ccccc8)c7)n6)c5)cccc34)cc2)cc1]

wherein in Compound H79: X = O, in Compound H80: X = S, in Compound H81: X = Se, Compound H82 through H84, each represented by the formula

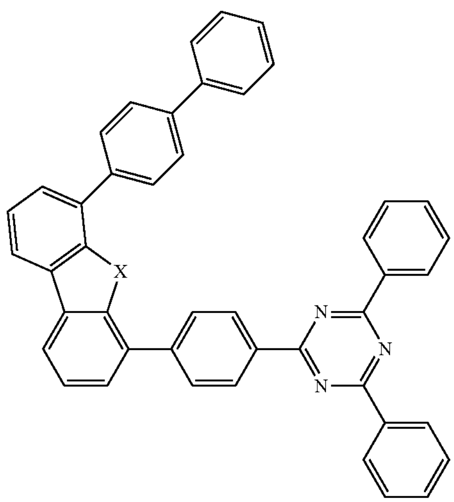

wherein in Compound H82: X = O, in Compound H83: X = S, in Compound H84: X = Se, Compound H85 through H87, each represented by the formula

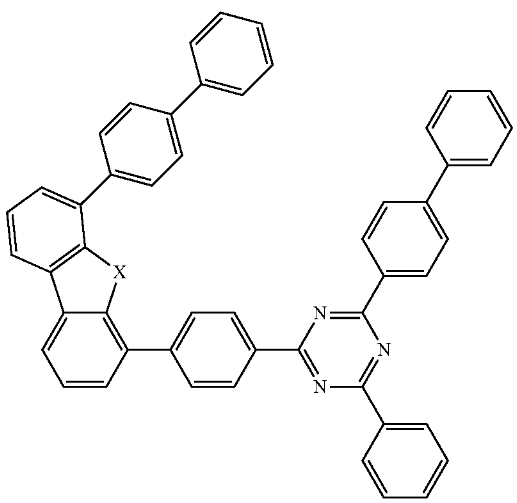

-continued wherein in Compound H85: X = O, in Compound H86: X = S, in Compound H87: X = Se, Compound H88 through H90, each represented by the formula

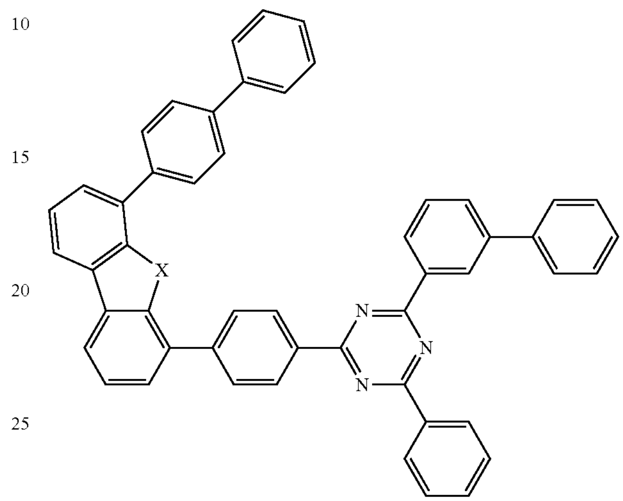

wherein in Compound H88: X = O, in Compound H89: X = S in Compound H90: X = Se,

Compound H91 through H93, each represented by the formula

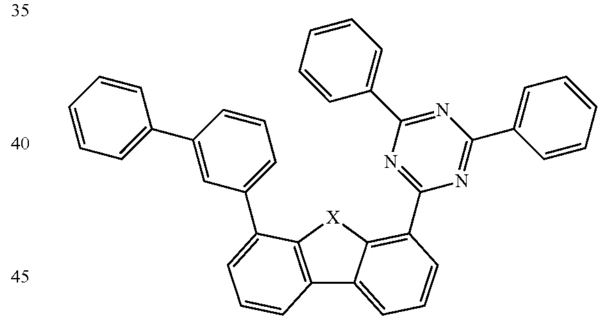

wherein in Compound H91: X = O, in Compound H92: X = S, in Compound H93: X = Se, Compound H94 through H96, each represented by the formula

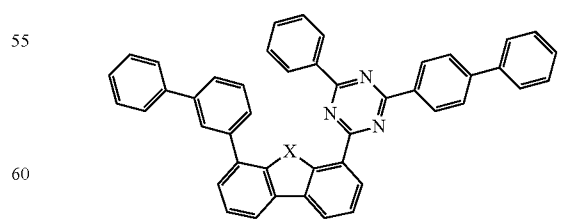

wherein in Compound H94: X = O, in Compound H95: X = S, in Compound H96: X = Se, -continued Compound H97 through H99, each represented by the formula

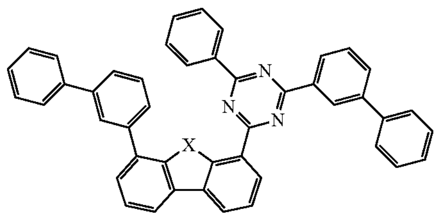

wherein in Compound H97: X = O,
in Compound H98: X = S,
in Compound H99: X = Se, Compound H100 through H102, each represented by the formula

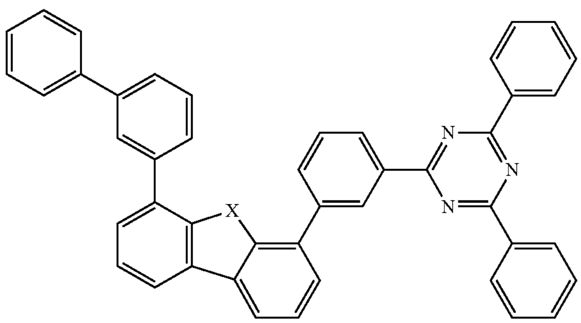

wherein in Compound H100: X = O,
in Compound H101: X = S,
in Compound H102: X = Se, Compound H103 through H105, each represented by the formula

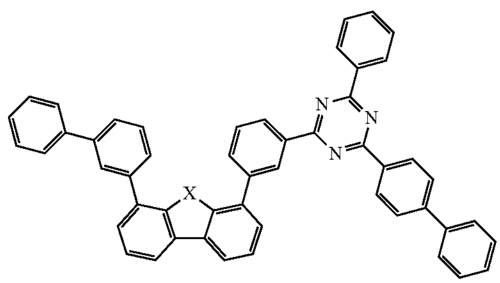

wherein in Compound H103: X = O,
in Compound H104: X = S,
in Compound H105: X = Se, Compound H106 through H108, each represented by the formula

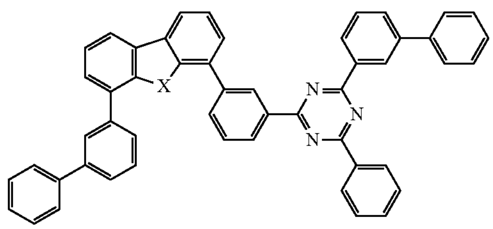

wherein in Compound H106: X = O,
in Compound H107: X = S,
in Compound H108: X = Se, -continued Compound H109 through H111, each represented by the formula

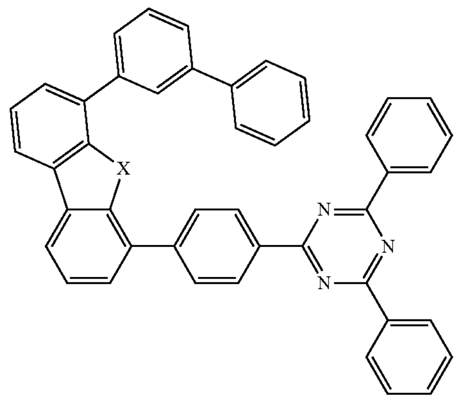

wherein in Compound H109: X = O,
in Compound H110: X = S,
in Compound H111: X = Se, Compound H112 through H114, each represented by the formula

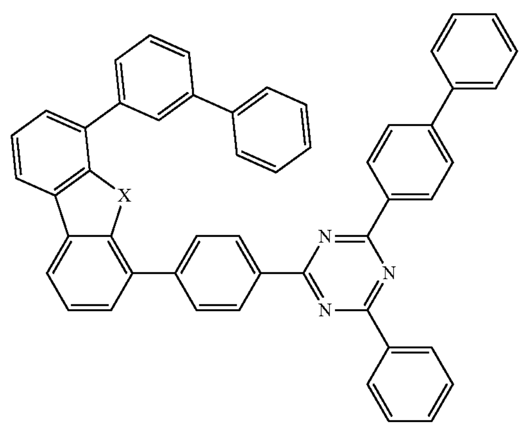

wherein in Compound H112: X = O,
in Compound H113: X = S,
in Compound H114: X = Se, Compound H115 through H117, each represented by the formula

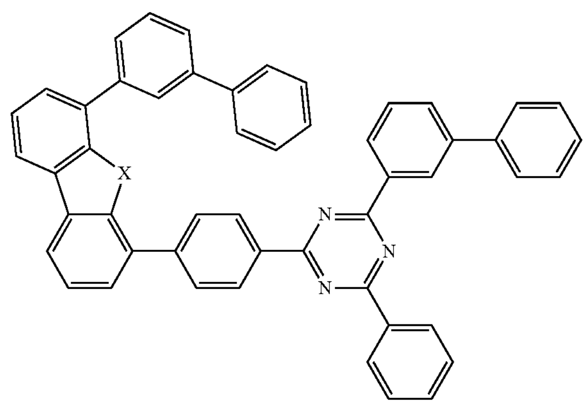

-continued wherein in Compound H115: X = O,
in Compound H116: X = S,
in Compound H117: X = Se, Compound H118 through H120, each represented by the formula

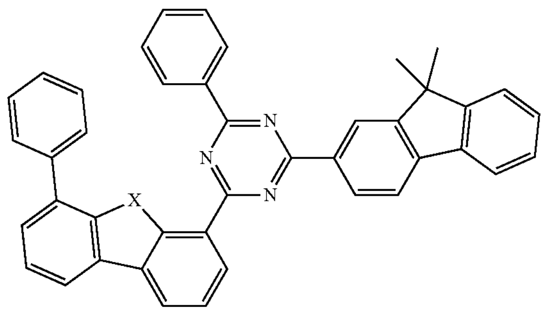

wherein in Compound H118: X = O,
in Compound H119: X = S,
in Compound H120: X = Se, Compound H121 through H123, each represented by the formula

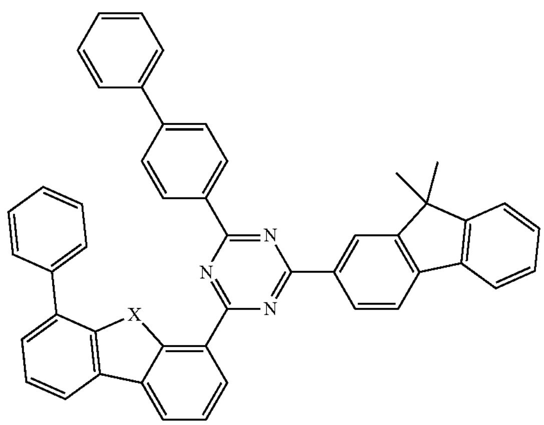

wherein in Compound H121: X = O,
in Compound H122: X = S,
in Compound H123: X = Se, Compound H124 through H126, each represented by the formula

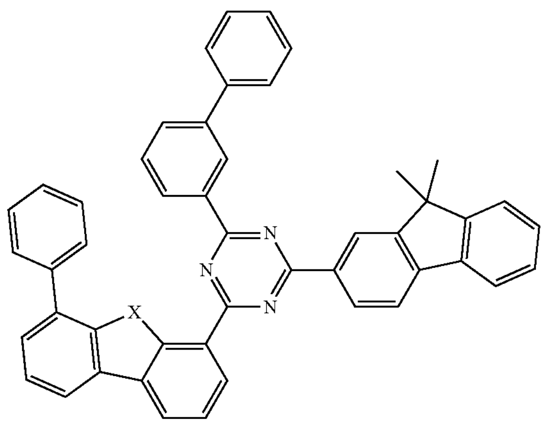

-continued wherein in Compound H124: X = O,
in Compound H125: X = S,
in Compound H126: X = Se, Compound H127 through H129, each represented by the formula

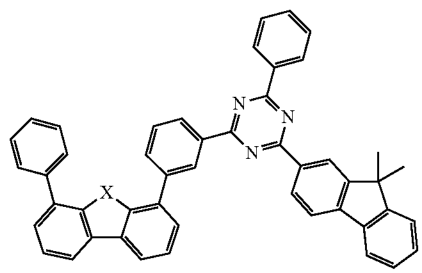

wherein in Compound H127: X = O,
in Compound H128: X = S,
in Compound H129: X = Se, Compound H130 through H132, each represented by the formula

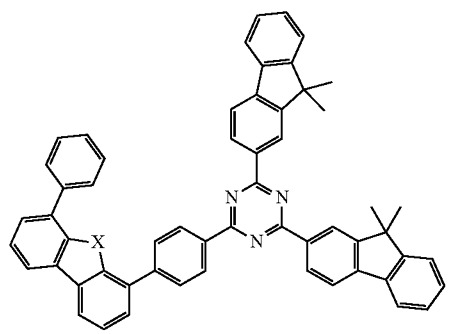

wherein in Compound H130: X = O,
in Compound H131: X = S,
in Compound H132: X = Se, Compound H133 through H135, each represented by the formula

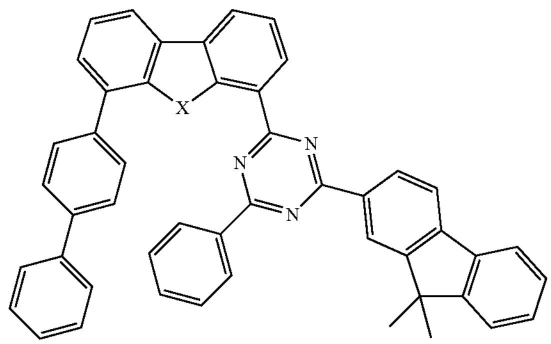

wherein in Compound H133: X = O,
in Compound H134: X = S,
in Compound H135: X = Se, -continued Compound H136 through H138, each represented by the formula

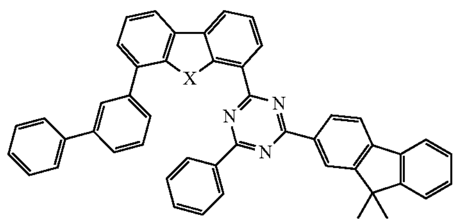

wherein in Compound H136: X = O,
in Compound H137: X = S,
in Compound H138: X = Se, Compound H139 through H141, each represented by the formula

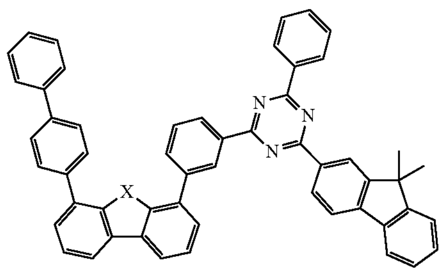

wherein in Compound H139: X = O,
in Compound H140: X = S,
in Compound H141: X = Se, Compound H142 through H144, each represented by the formula

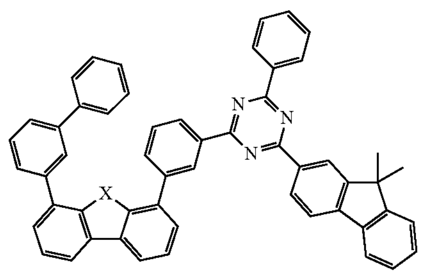

wherein in Compound H142: X = O,
in Compound H143: X = S,
in Compound H144: X = Se, Compound H145 through H147, each represented by the formula

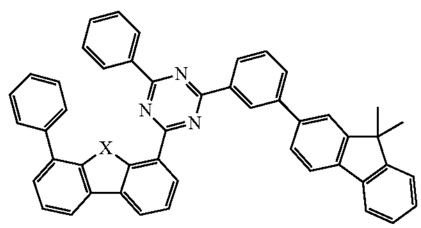

wherein in Compound H145: X = O,
in Compound H146: X = S,
in Compound H147: X = Se, -continued Compound H148 through H150, each represented by the formula

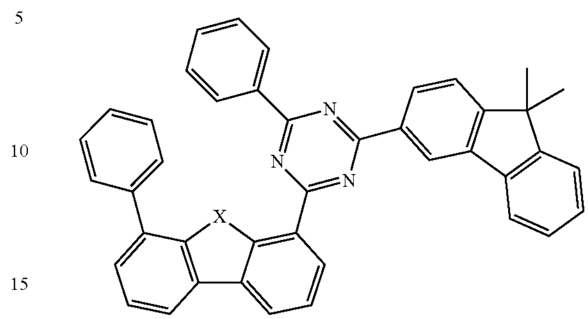

wherein in Compound H148: X = O,
in Compound H149: X = S,
in Compound H150: X = Se, Compound H151 through H153, each represented by the formula

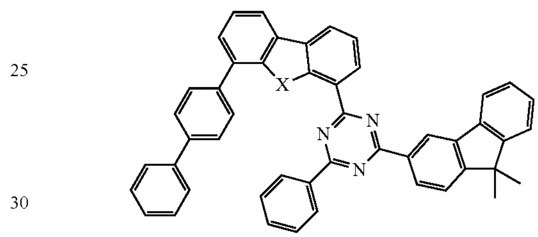

wherein in Compound H151: X = O,
in Compound H152: X = S,
in Compound H152: X = Se, Compound H154 through H156, each represented by the formula

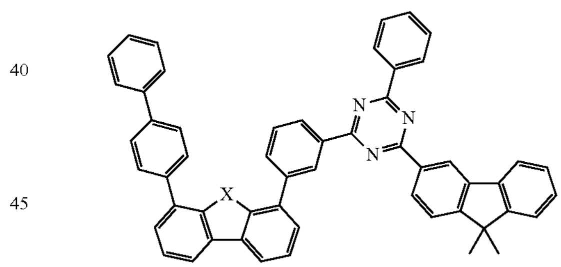

wherein in Compound H154: X = O,
in Compound H155: X = S,
in Compound H156: X = Se, Compound H157 through H159, each represented by the formula

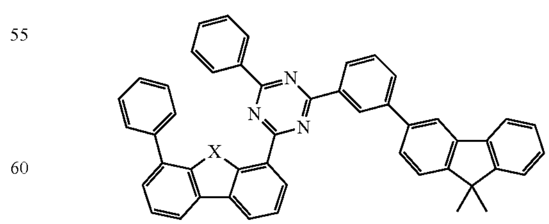

wherein in Compound H157: X = O,
in Compound H158: X = S,
in Compound H159: X = Se, -continued Compound H160 through H162, each represented by the formula

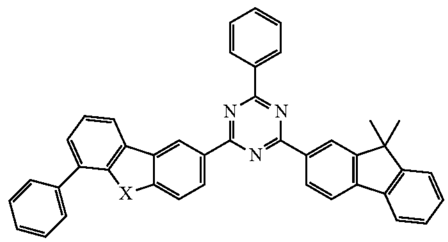

wherein in Compound H160: X = O,
in Compound H161: X = S,
in Compound H162: X = Se, Compound H163 through H165, each represented by the formula

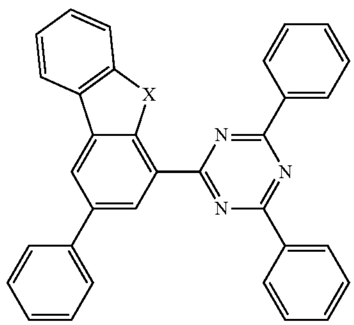

wherein in Compound H163: X = O,
in Compound H164: X = S,
in Compound H165: X = Se, Compound H166 through H168, each represented by the formula

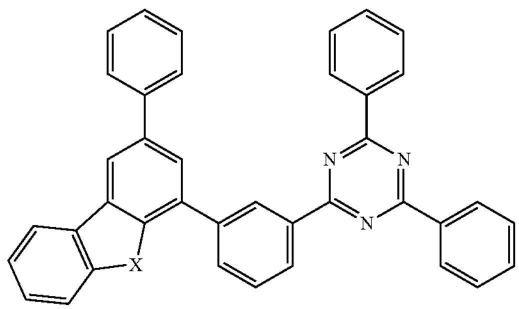

wherein in Compound H166: X = O,
in Compound H167: X = S,
in Compound H168: X = Se, -continued Compound H169 through H171, each represented by the formula

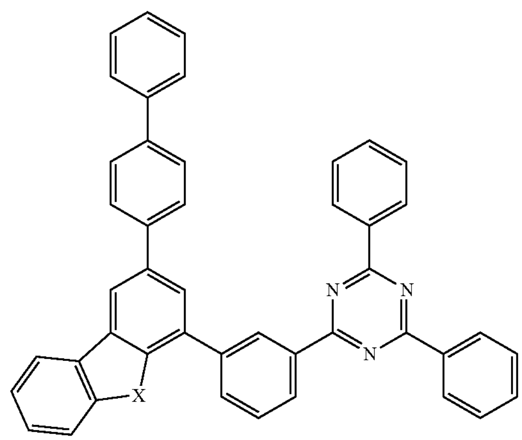

wherein in Compound H169: X = O,
in Compound H170: X = S,
in Compound H171: X = Se, Compound H172 through H174, each represented by the formula

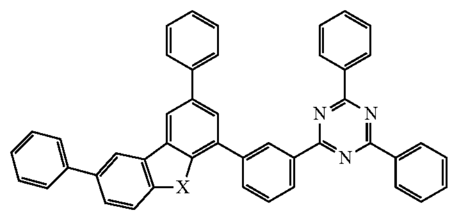

wherein in Compound H172: X = O,
in Compound H173: X = S,
in Compound H174: X = Se, Compound H175 through H177, each represented by the formula

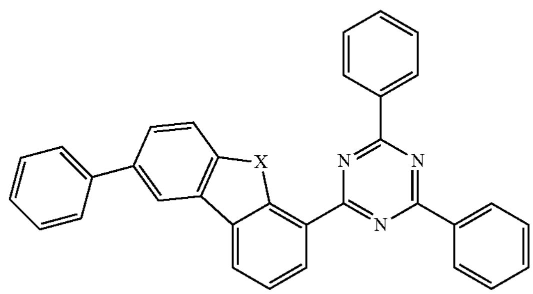

wherein in Compound H175: X = O,
in Compound H176: X = S,
in Compound H177: X = Se, -continued Compound H178 through H180, each represented by the formula

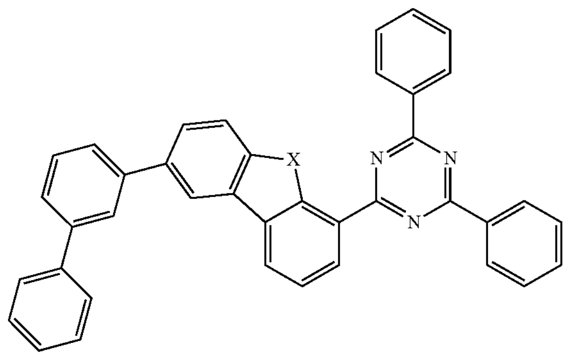

wherein in Compound H178: X = O,
in Compound H179: X = S,
in Compound H180: X = Se, Compound H181 through H183, each represented by the formula

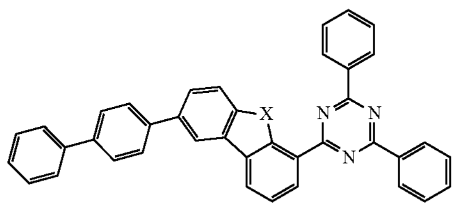

wherein in Compound H181: X = O,
in Compound H182: X = S,
in Compound H183: X = Se, Compound H184 through H186, each represented by the formula

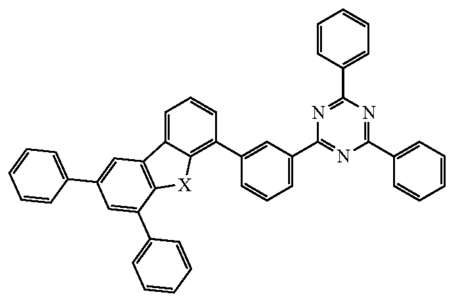

wherein in Compound H184: X = O,
in Compound H185: X = S,
in Compound H186: X = Se, Compound H187 through H189, each represented by the formula

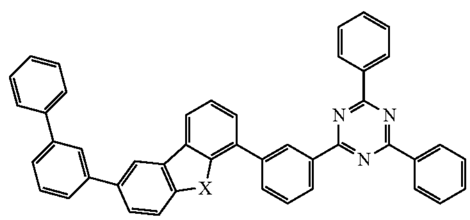

-continued wherein in Compound H187: X = O,
in Compound H188: X = S,
in Compound H189: X = Se, Compound H190 through H192, each represented by the formula

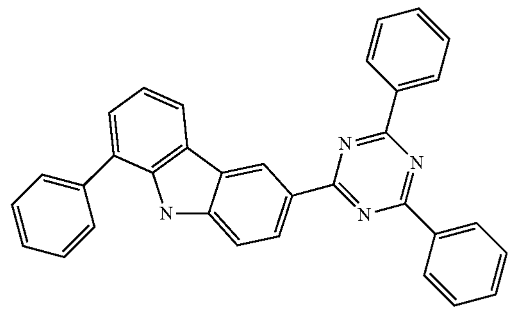 [SMILES: c1ccc(-c2nc(-c3ccccc3)nc(-c3ccc4[nH]c5c(-c6ccccc6)cccc5c4c3)n2)cc1]

wherein in Compound H190: X = O,
in Compound H191: X = S,
in Compound H192: X = Se, Compound H193 through H195, each represented by the formula

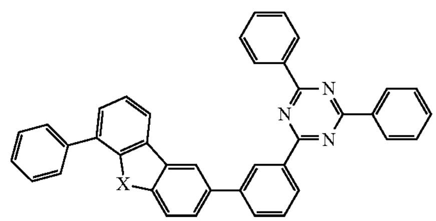

wherein in Compound H193: X = O,
in Compound H194: X = S,
in Compound H195: X = Se, Compound H196 through H198, each represented by the formula

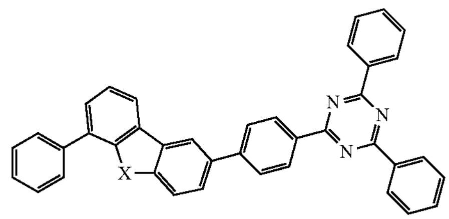

wherein in Compound H196: X = O,
in Compound H197: X = S,
in Compound H198: X = Se, Compound H199 through H201, each represented by the formula

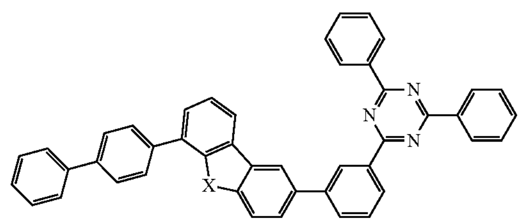

wherein in Compound H199: X = O,
in Compound H200: X = S,
in Compound H201: X = Se, Compound H202 through H204, each represented by the formula

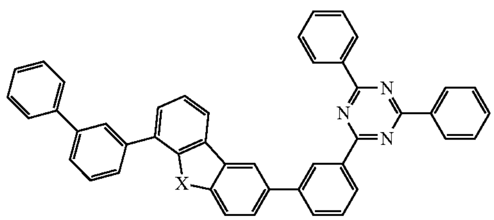

wherein in Compound H202: X = O,
in Compound H203: X = S,
in Compound H204: X = Se, Compound H205 through H207, each represented by the formula

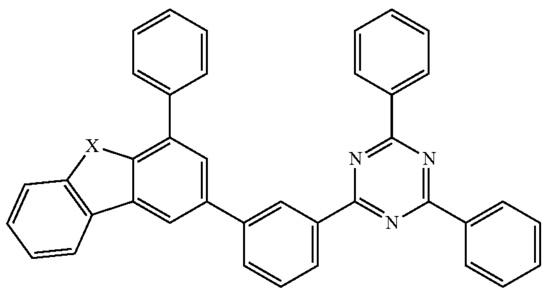

wherein in Compound H205: X = O,
in Compound H206: X = S,
in Compound H207: X = Se, Compound H208 through H210, each represented by the formula

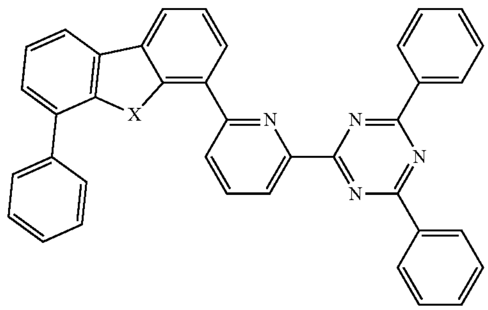

wherein in Compound H208: X = O,
in Compound H209: X = S,
in Compound H210: X = Se, Compound H211 through H213, each represented by the formula

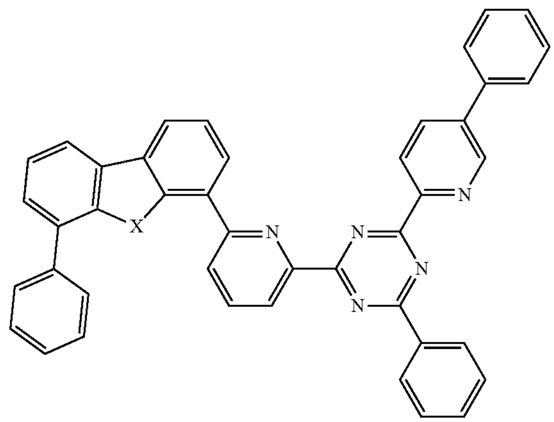

wherein in Compound H211: X = O,
in Compound H212: X = S,
in Compound H213: X = Se, Compound H214 through H216, each represented by the formula

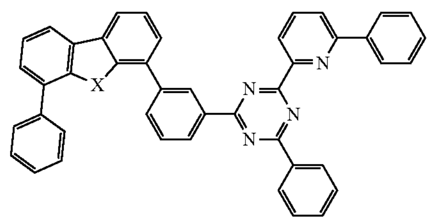

wherein in Compound H214: X = O,
in Compound H215: X = S,
in Compound H216: X = Se, Compound H217 through H219, each represented by the formula

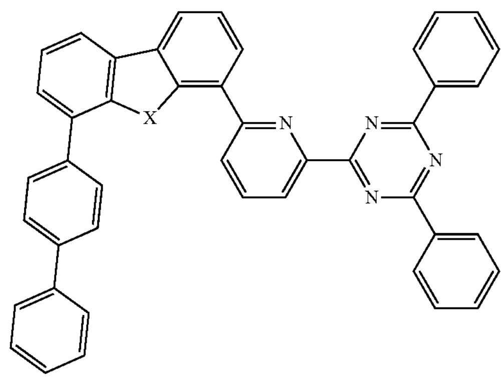

wherein in Compound H217: X = O,
in Compound H218: X = S,
in Compound H219: X = Se, -continued Compound H220 through H222, each represented by the formula

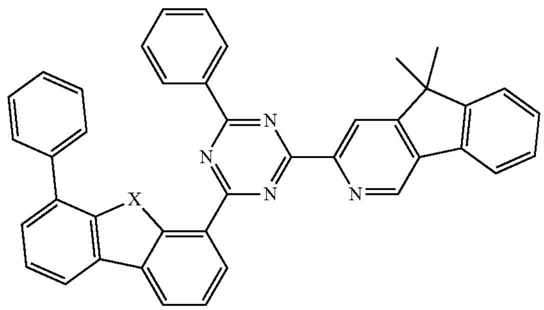

wherein in Compound H220: X = O,
in Compound H221: X = S,
in Compound H222: X = Se, Compound H223 through H225, each represented by the formula

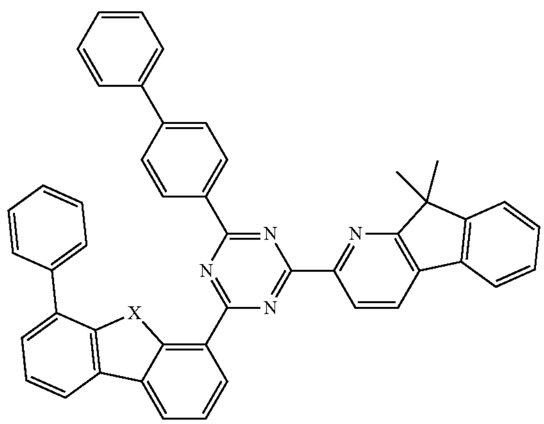

wherein in Compound H223: X = O,
in Compound H224: X = S,
in Compound H225: X = Se, Compound H226 through H228, each represented by the formula

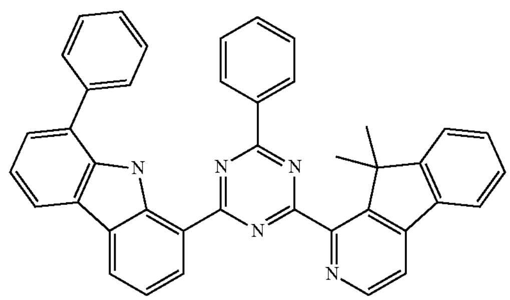 [SMILES: CC1(C)c2ccccc2-c2ccnc(-c3nc(-c4ccccc4)nc(-c4cccc5c4[nH]c4c(-c6ccccc6)cccc45)n3)c21]

wherein in Compound H226: X = O,
in Compound H227: X = S,
in Compound H228: X = Se, -continued Compound H229 through H231, each represented by the formula

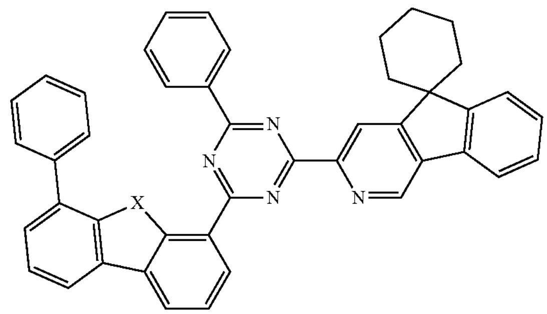

wherein in Compound H229: X = O,
in Compound H230: X = S,
in Compound H231: X = Se, Compound H232 through H234, each represented by the formula

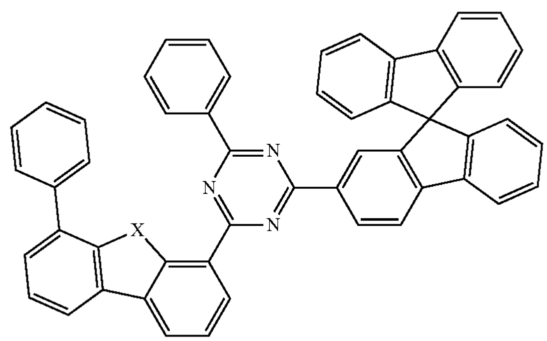

wherein in Compound H232: X = O,
in Compound H233: X = S,
in Compound H234: X = Se, Compound H235 through H237, each represented by the formula

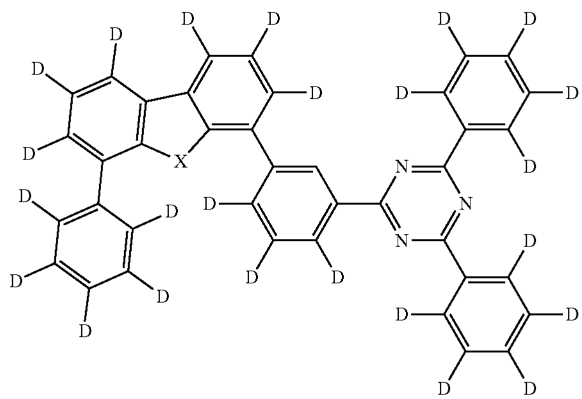

wherein in Compound H235: X = O,
in Compound H236: X = S,
in Compound H237: X = Se, -continued Compound H238 through H240, each represented by the formula

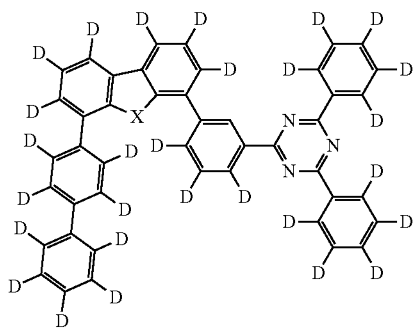

wherein in Compound H238: X = O,
in Compound H239: X = S,
in Compound H240: X = Se, Compound H241 through H243, each represented by the formula

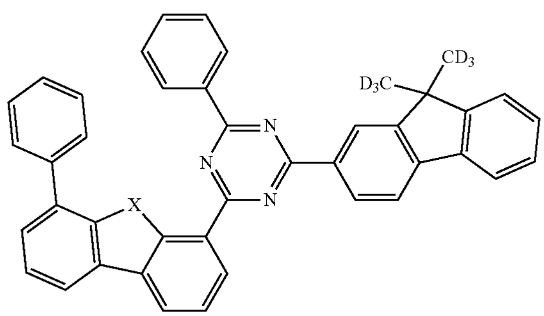

wherein in Compound H241: X = O,
in Compound H242: X = S,
in Compound H243: X = Se, Compound H244 through H246, each represented by the formula

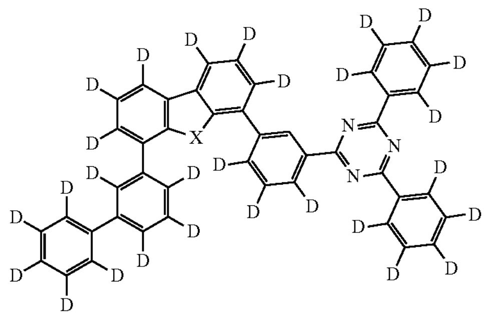

wherein in Compound H244: X = O,
in Compound H245: X = S,
in Compound H246: X = Se, -continued Compound H247 through H249, each represented by the formula

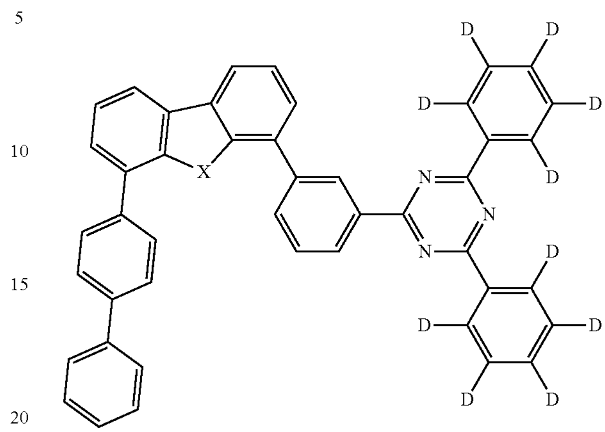

wherein in Compound H247: X = O,
in Compound H248: X = S,
in Compound H249: X = Se, Compound H250 through H252, each represented by the formula

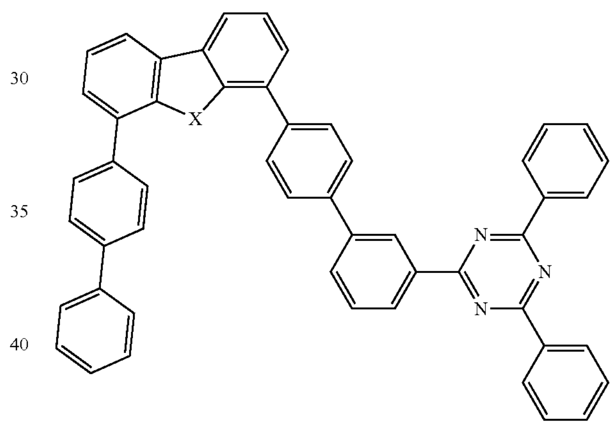

wherein in Compound H250: X = O,
in Compound H251: X = S,
in Compound H252: X = Se, Compound H253 through H255, each represented by the formula

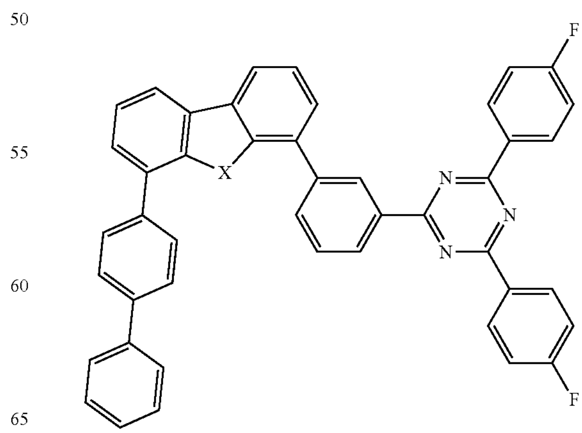

wherein in Compound H253: X = O,
in Compound H254: X = S,
in Compound H255: X = Se, Compounds M1 through M3, each represented by the formula:

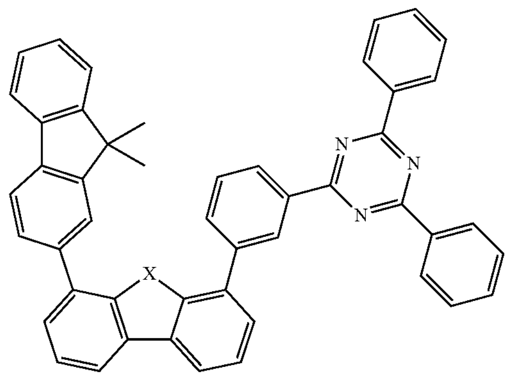

where in Compound M1: X = O,
in Compound M2, X = S, and
in Compound M3, X = Se,

Compounds M4 through M6, each represented by the formula:

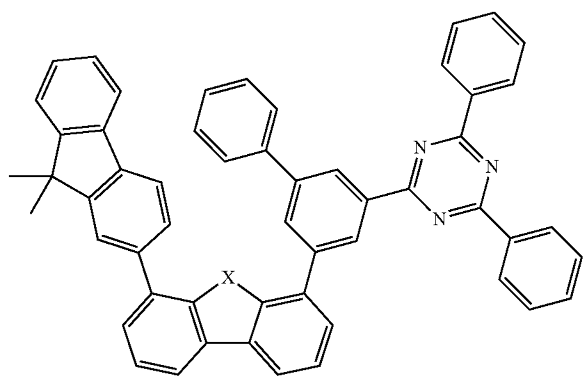

where in Compound M4: X = O,
in Compound M5, X = S, and
in Compound M6, X = Se,

Compounds M7 through M9, each represented by the formula:

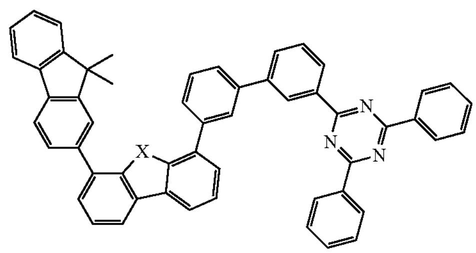

where in Compound M7: X = O,
in Compound M8, X = S, and
in Compound M9, X = Se,

Compounds M10 through M12, each represented by the formula:

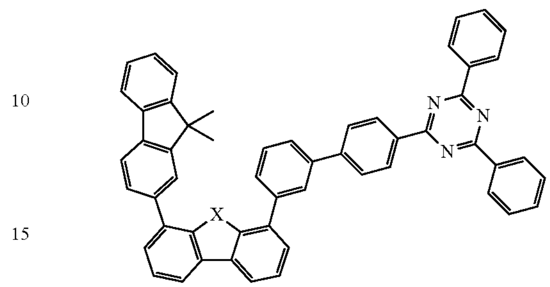

where in Compound M10: X = O,
in Compound M11, X = S, and
in Compound M12, X = Se, Compounds M13 through M15, each represented by the formula:

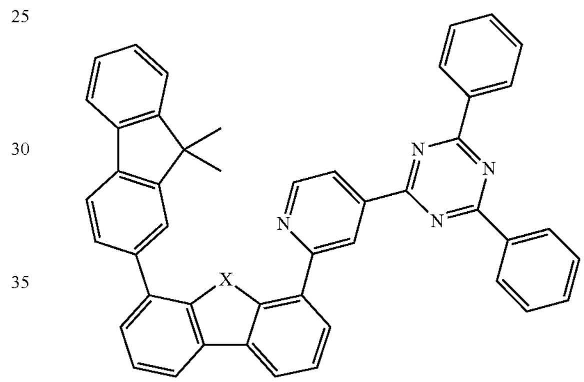

where in Compound M13: X = O,
in Compound M14, X = S, and
in Compound M15, X = Se, Compounds M16 through M18, each represented by the formula:

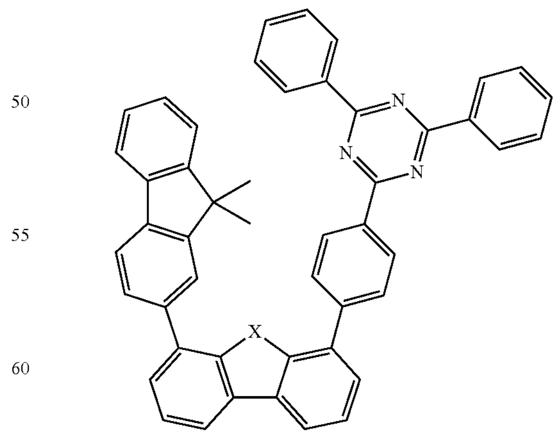

where in Compound M16: X = O,
in Compound M17, X = S, and
in Compound M18, X = Se, -continued Compounds M19 through M21, each represented by the formula:

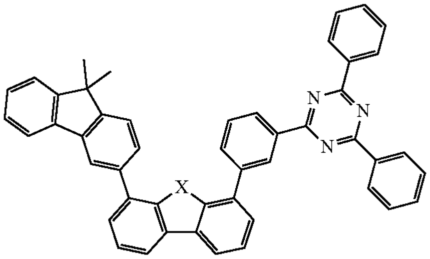

where in Compound M19: X = O, in Compound M20, X = S, and in Compound M21, X = Se, Compounds M22 through M24, each represented by the formula:

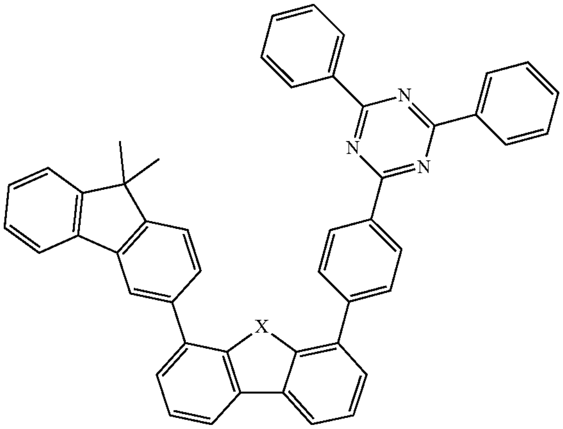

where in Compound M22: X = O, in Compound M23, X = S, and in Compound M24, X = Se, Compounds M25 through M27, each represented by the formula:

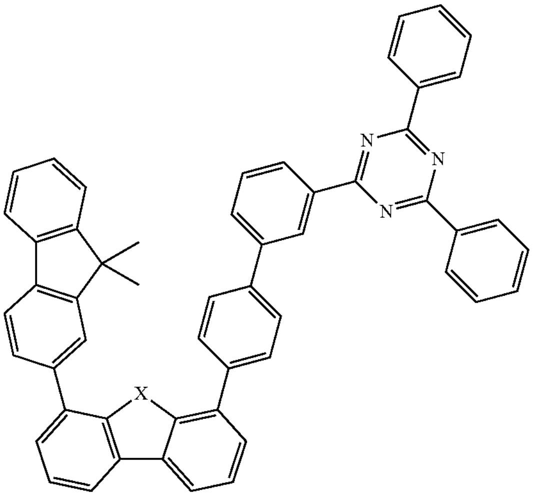

where in Compound M25: X = O, in Compound M26, X = S, and in Compound M27, X = Se, -continued Compounds M28 through M30, each represented by the formula:

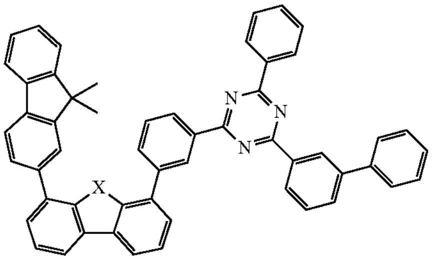

where in Compound M28: X = O, in Compound M29, X = S, and in Compound M30, X = Se, Compounds M31 through M33, each represented by the formula:

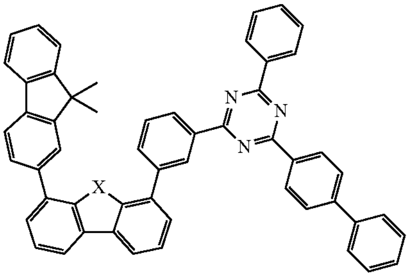

where in Compound M31: X = O, in Compound M32, X = S, and in Compound M33, X = Se, Compounds M34 through M36, each represented by the formula:

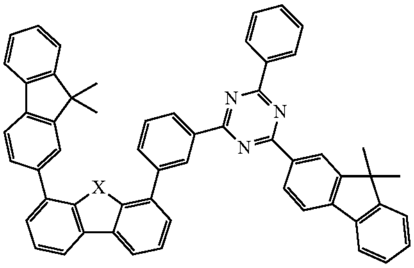

where in Compound M34: X = O, in Compound M35, X = S, and in Compound M36, X = Se, Compounds M37 through M39, each represented by the formula:

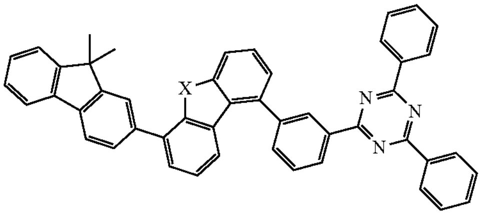

where in Compound M37: X = O, in Compound M38, X = S, and in Compound M39, X = Se, Compounds M40 through M42, each represented by the formula:

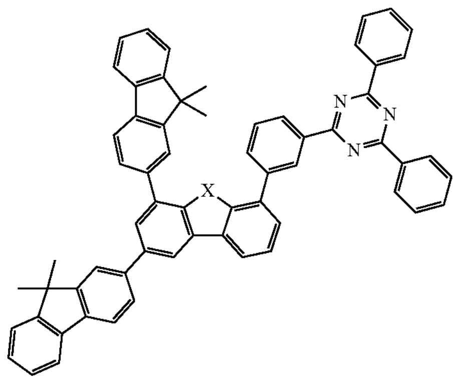

where in Compound M40: X = O, in Compound M41, X = S, and in Compound M42, X = Se, Compounds M43 through M45, each represented by the formula:

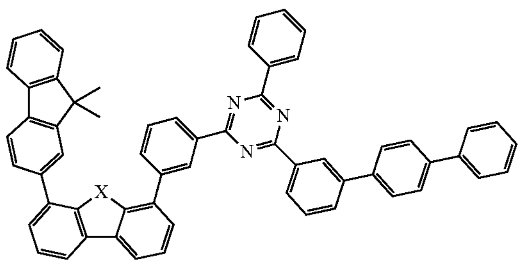

where in Compound M43: X = O, in Compound M44, X = S, and in Compound M45, X = Se, Compounds M46 through M48, each represented by the formula:

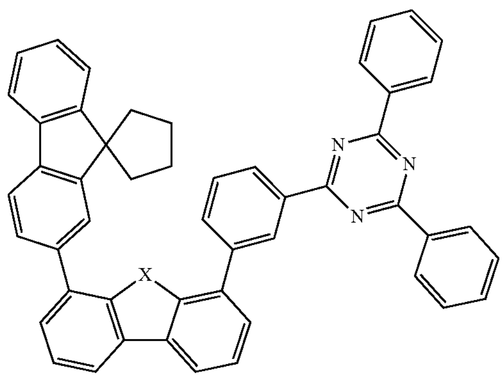

where in Compound M46: X = O, in Compound M47, X = S, and in Compound M48, X = Se, Compounds M49 through M51, each represented by the formula:

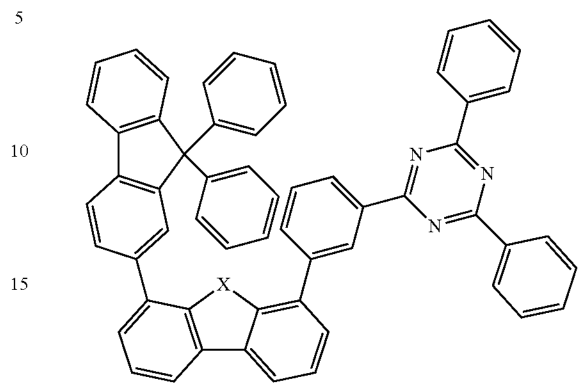

where in Compound M49: X = O, in Compound M50, X = S, and in Compound M51, X = Se, Compounds M49 through M51, each represented by the formula:

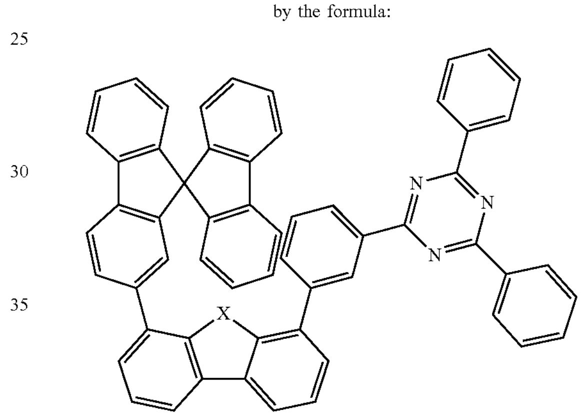

where in Compound M52: X = O, in Compound M53, X = S, and in Compound M54, X = Se, Compounds M55 through M57, each represented by the formula:

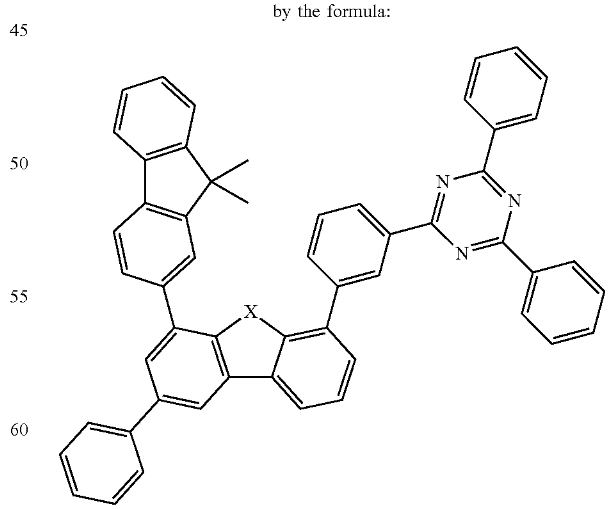

where in Compound M55: X = O, in Compound M56, X = S, and in Compound M57, X = Se, -continued Compounds M58 through M60, each represented by the formula:

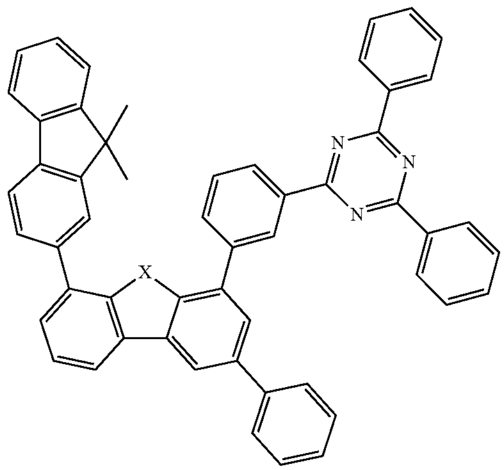

where in Compound M58: X = O, in Compound M59, X = S, and in Compound M60, X = Se, Compounds M61 through M63, each represented by the formula:

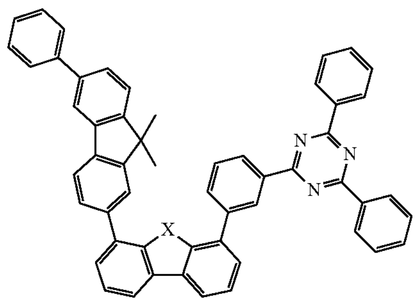

where in Compound M61: X = O, in Compound M62, X = S, and in Compound M63, X = Se, Compounds M64 through M66, each represented by the formula:

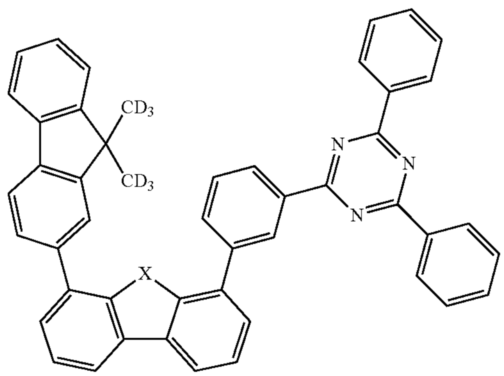

where in Compound M64: X = O, in Compound M65, X = S, and in Compound M66, X = Se, -continued Compounds M67 through M69, each represented by the formula:

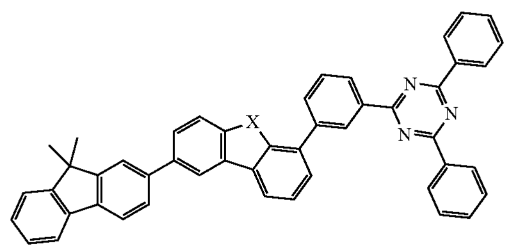

where in Compound M67: X = O, in Compound M68, X = S, and in Compound M69, X = Se, Compounds M70 through M72, each represented by the formula:

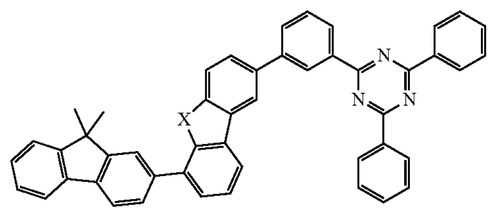

where in Compound M70: X = O, in Compound M71, X = S, and in Compound M72, X = Se, Compounds M73 through M75, each represented by the formula:

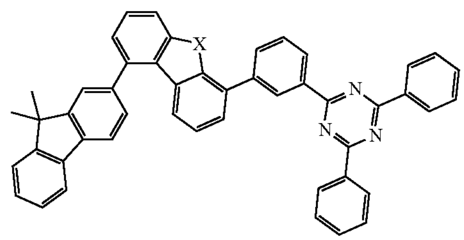

where in Compound M73: X = O, in Compound M74, X = S, and in Compound M75, X = Se, Compounds M76 through M78, each represented by the formula:

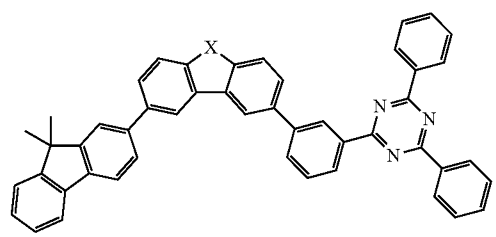

where in Compound M76: X = O, in Compound M77, X = S, and in Compound M78, X = Se, -continued Compounds M79 through M81, each represented by the formula:

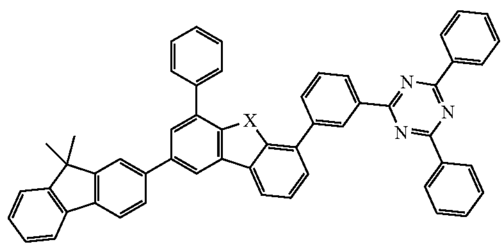

where in Compound M79: X = O,
in Compound M80, X = S, and
in Compound M81, X = Se, Compounds M82 through M84, each represented by the formula:

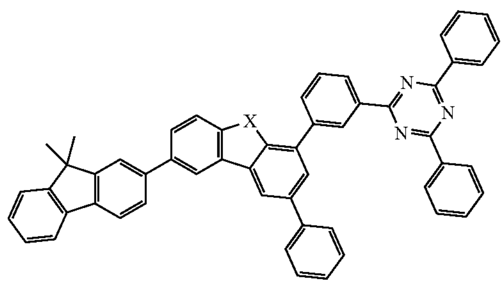

where in Compound M82: X = O,
in Compound M83, X = S, and
in Compound M84, X = Se, Compounds M85 through M87, each represented by the formula:

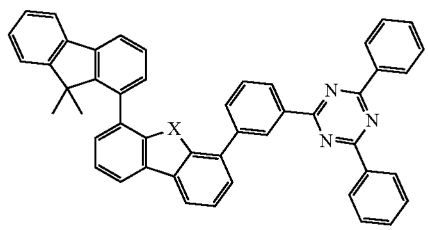

where in Compound M85: X = O,
in Compound M86, X = S, and
in Compound M87, X = Se, -continued Compounds M88 through M90, each represented by the formula:

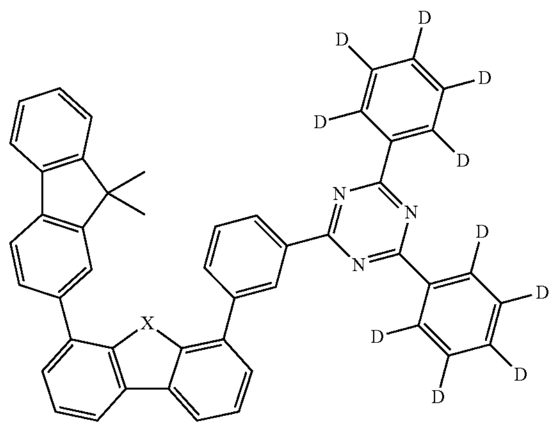

where in Compound M88: X = O,
in Compound M89, X = S, and
in Compound M90, X = Se, Compounds M91 through M93, each represented by the formula:

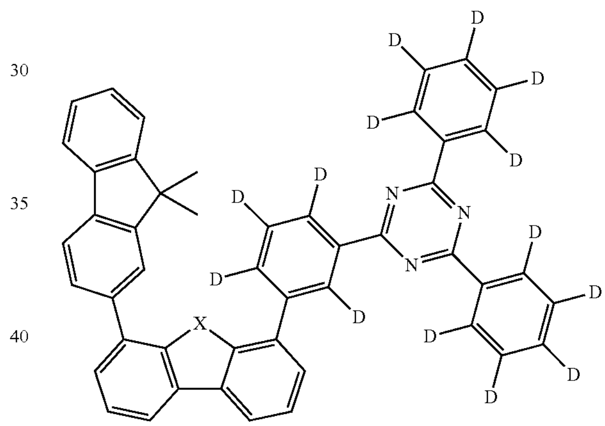

where in Compound M91: X = O,
in Compound M92, X = S, and
in Compound M93, X = Se, Compounds M94 through M96, each represented by the formula:

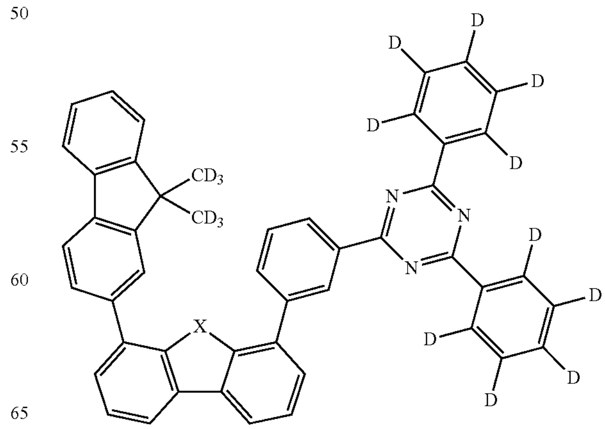

-continued where in Compound M94: X = O,
in Compound M95, X = S, and
in Compound M96, X = Se, Compounds M97 through M99, each represented by the formula:

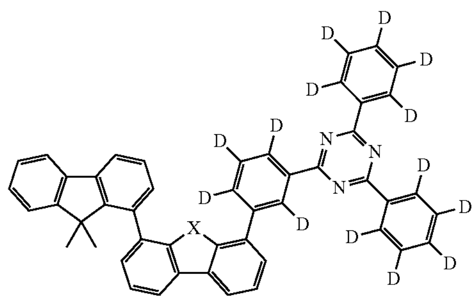

where in Compound M97: X = O,
in Compound M98, X = S, and
in Compound M99, X = Se, Compounds M100 through M102, each represented by the formula:

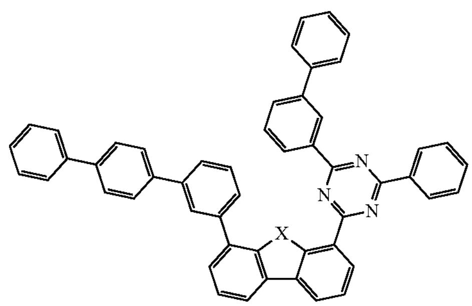

where in Compound M100: X = O,
in Compound M101, X = S, and
in Compound M102, X = Se, Compounds M103 through M105, each represented by the formula:

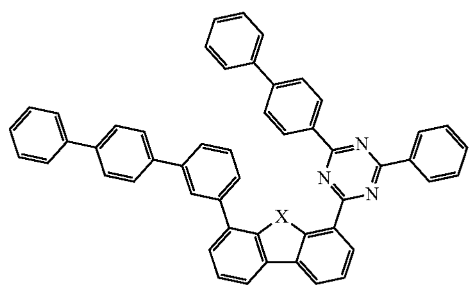

where in Compound M103: X = O,
in Compound M104, X = S, and
in Compound M105, X = Se, -continued Compounds M106 through M108, each represented by the formula:

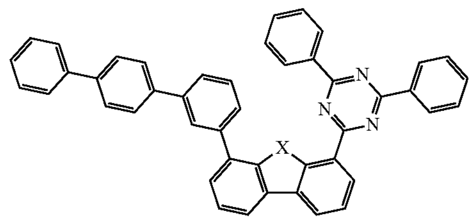

where in Compound M106: X = O,
in Compound M107, X = S, and
in Compound M108, X = Se, Compounds M109 through M111, each represented by the formula:

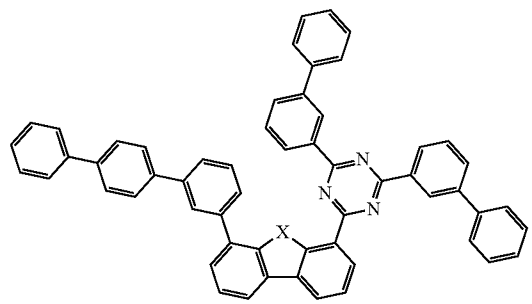

where in Compound M109: X = O,
in Compound M110, X = S, and
in Compound M111, X = Se, Compounds M112 through M114, each represented by the formula:

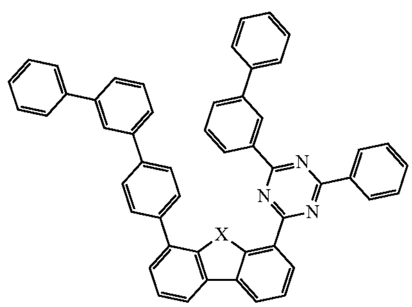

where in Compound M112: X = O,
in Compound M113, X = S, and
in Compound M114, X = Se, Compounds M115 through M117, each represented by the formula:

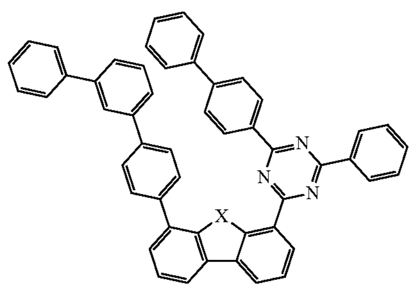

where in Compound M115: X = O,
in Compound M116, X = S, and
in Compound M117, X = Se, Compounds M118 through M120, each represented by the formula:

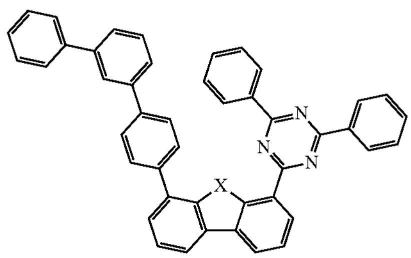

where in Compound M118: X = O,
in Compound M119, X = S, and
in Compound M120, X = Se, Compounds M121 through M123, each represented by the formula:

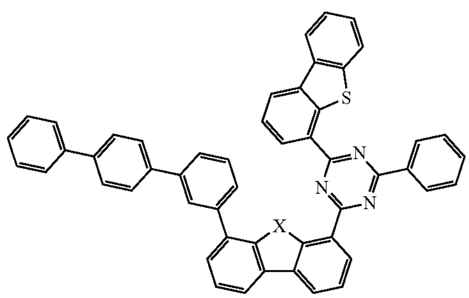

where in Compound M121: X = O,
in Compound M122, X = S, and
in Compound M123, X = Se, Compounds M124 through M126, each represented by the formula:

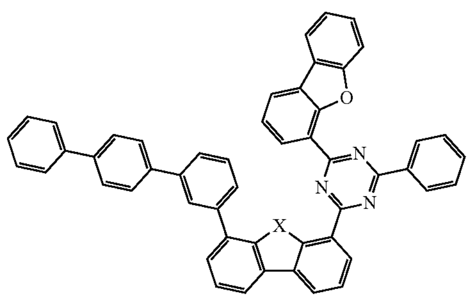

where in Compound M124: X = O,
in Compound M125, X = S, and
in Compound M126, X = Se, Compounds M127 through M129, each represented by the formula:

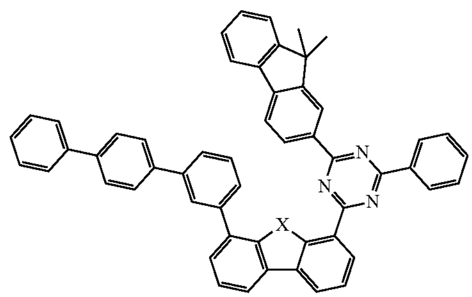

where in Compound M127: X = O,
in Compound M128, X = S, and
in Compound M129, X = Se, Compounds M130 through M132, each represented by the formula:

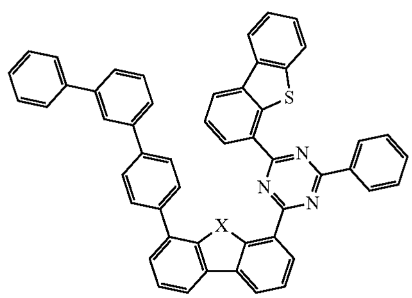

where in Compound M130: X = O,
in Compound M131, X = S, and
in Compound M132, X = Se, Compounds M133 through M135, each represented by the formula:

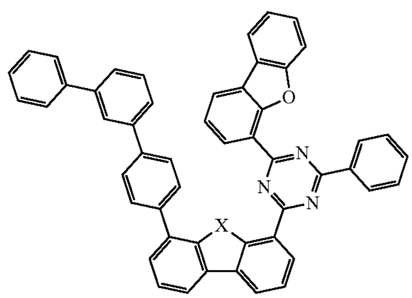

where in Compound M133: X = O,
in Compound M134, X = S, and
in Compound M135, X = Se, -continued Compounds M136 through M138, each represented by the formula:

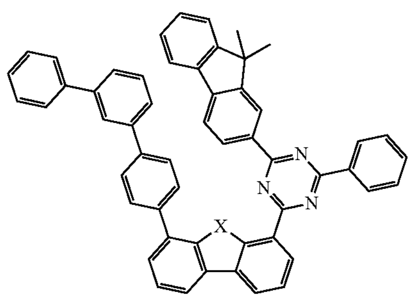

where in Compound M136: X = O,
in Compound M137, X = S, and
in Compound M138, X = Se, Compounds M139 through M141, each represented by the formula:

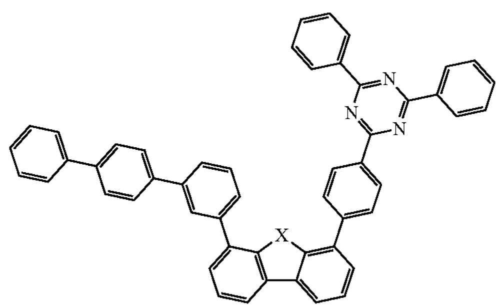

where in Compound M139: X = O,
in Compound M140, X = S, and
in Compound M141, X = Se, Compounds M142 through M144, each represented by the formula:

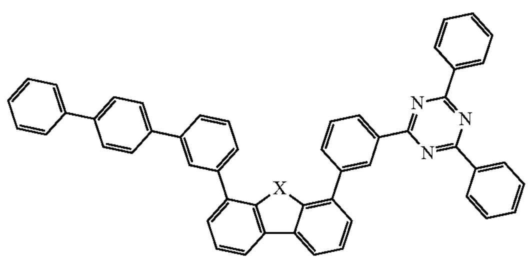

where in Compound M142: X = O,
in Compound M143, X = S, and
in Compound M144, X = Se, -continued Compounds M145 through M147, each represented by the formula:

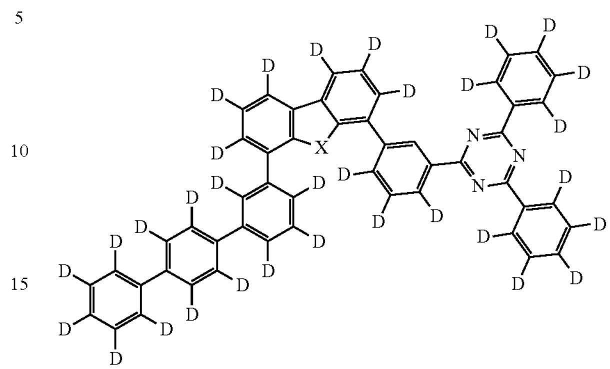

where in Compound M145: X = O,
in Compound M146, X = S, and
in Compound M147, X = Se, Compounds M148 through M150, each represented by the formula:

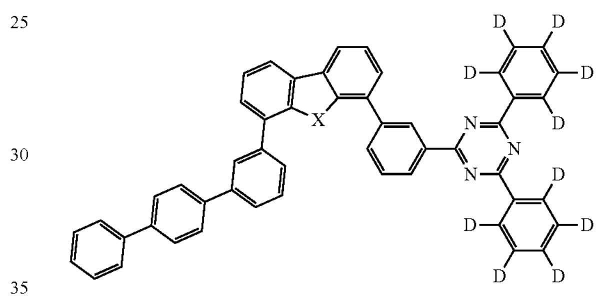

where in Compound M148: X = O,
in Compound M149, X = S, and
in Compound M150, X = Se, and Compounds M151 through M153, each represented by the formula:

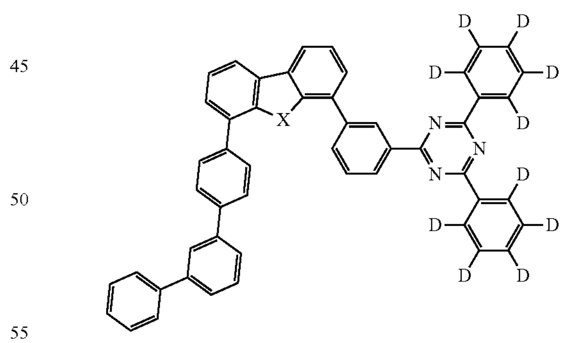

where in Compound M151: X = O,
in Compound M152, X = S, and
in Compound M153, X = Se.

In one embodiment, the first compound is Formula I.

In one embodiment, the first compound has an evaporation temperature T1 of 150 to 350° C.;

wherein the second compound has an evaporation temperature T2 of 150 to 350° C.;

wherein the absolute value of T1-T2 is less than 20° C.;

wherein the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the mixture being evaporated; and wherein the absolute value of (C1−C2)/C1 is less than 5%.

In one embodiment, the first compound has evaporation temperature T1 of 200 to 350° C. and the second compound has evaporation temperature T2 of 200 to 350° C.

In one embodiment, the absolute value of (C1−C2)/C1 is less than 3%.

In one embodiment, the first compound has a vapor pressure of P1 at T1 at 1 atm, the second compound has a vapor pressure of P2 at T2 at 1 atm; and wherein the ratio of P1/P2 is within the range of 0.90 to 1.10.

In one embodiment, the first compound has a first mass loss rate and the second compound has a second mass loss rate, wherein the ratio between the first mass loss rate and the second mass loss rate is within the range of 0.90 to 1.10. In another embodiment, the first compound has a first mass loss rate and the second compound has a second mass loss rate, wherein the ratio between the first mass loss rate and the second mass loss rate is within the range of 0.95 to 1.05. In another embodiment, the first compound has a first mass loss rate and the second compound has a second mass loss rate, wherein the ratio between the first mass loss rate and the second mass loss rate is within the range of 0.97 to 1.03.

In one embodiment, the first compound and the second compound each has a purity in excess of 99% as determined by high pressure liquid chromatography.

In one embodiment, the composition further comprises a third compound, wherein the third compound has a different chemical structure than the first and second compounds, wherein the third compound has an evaporation temperature T3 of 150 to 350° C., and wherein absolute value of T1-T3 is less than 20° C.

In one embodiment, the composition further comprises a third compound, wherein the third compound has a different chemical structure than the first and second compounds, wherein the third compound has a third mass loss rate and the ratio between the first mass loss rate and third mass loss rate is within the range of 0.90 to 1.10

In one embodiment, the composition is in liquid form at a temperature less than T1 and T2.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Devices of the Invention

According to another aspect of the present disclosure, an OLED is also provided. The OLED includes an anode, a cathode, and an organic layer disposed between the anode and the cathode. The organic layer may include a host and a phosphorescent dopant. The organic layer can include a compound having a formula selected from the group consisting of Formula I and Formula II, and their variations as described herein. The organic layer can also include a composition of materials comprising a first compound, wherein the first compound has a formula selected from the group consisting of Formula I and Formula II.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the present invention relates to an emissive region or an emissive layer. The emissive region or emissive layer can include a compound of the present invention. In one embodiment, the compound of the present invention is a host.

The organic layer can also include an emissive dopant. In some embodiments, two or more emissive dopants are preferred. In some embodiments of the emissive region, the emissive region further comprises a phosphorescent emissive dopant. In one embodiment, the emissive dopant is a transition metal complex having at least one ligand or part of the ligand if the ligand is more than bidentate selected from the group consisting of:

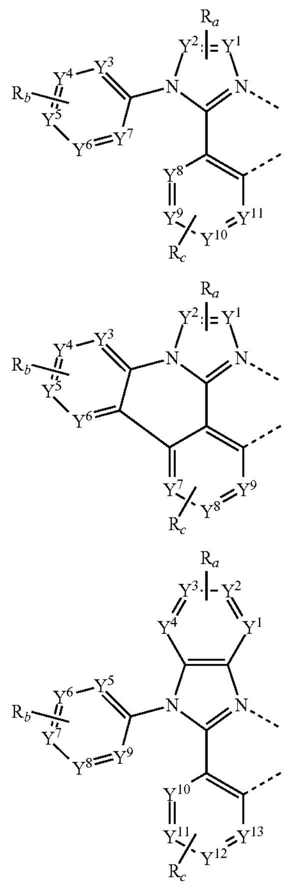

, , ,

-continued

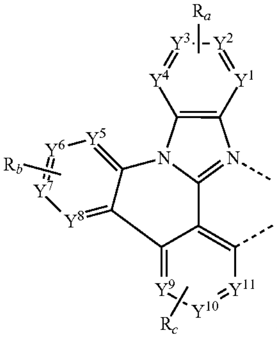, 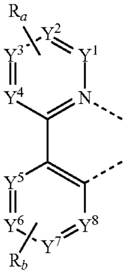,

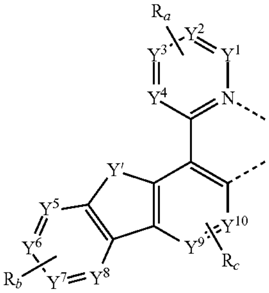, 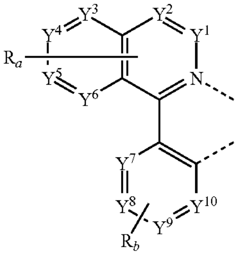,

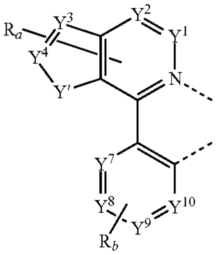, 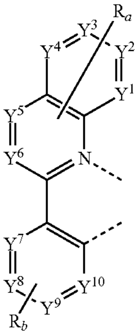, 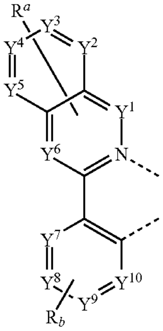,

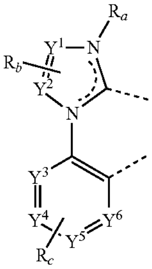, 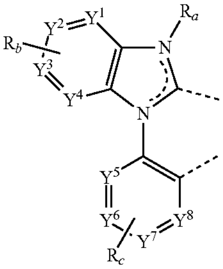,

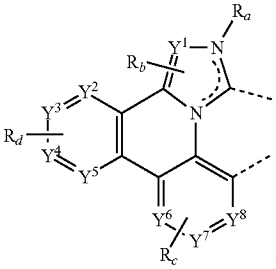, 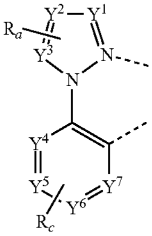,

-continued

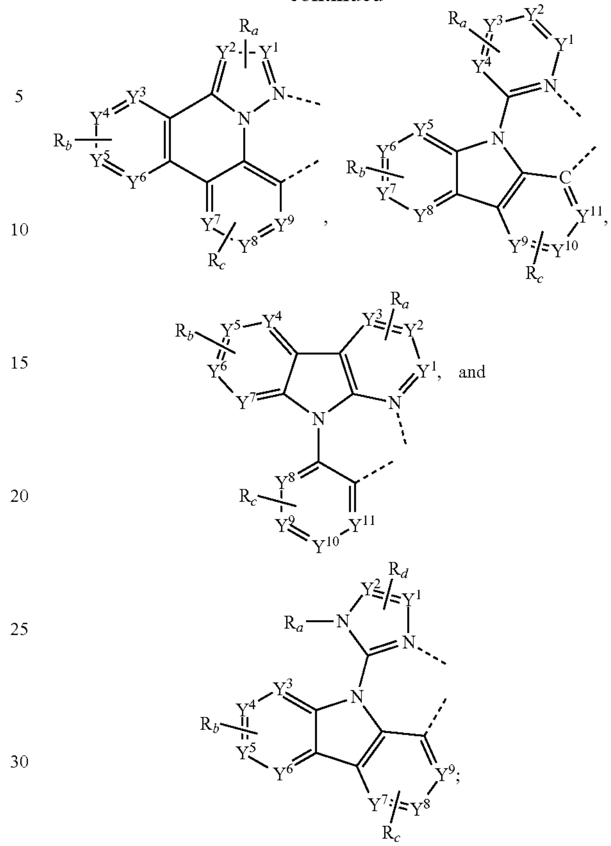

wherein each $Y^1$ to $Y^{13}$ are independently selected from the group consisting of carbon and nitrogen;

wherein Y' is selected from the group consisting of $BR_e$, $NR_e$, $PR_e$, O, S, Se, C═O, S═O, $SO_2$, $CR_eR_f RR$, $SiR_eR_f$, and $G_eR_eR_f$;

wherein $R_e$ and $R_f$ are optionally fused or joined to form a ring;

wherein each $R_a$, $R_b$, $R_c$, and $R_d$ may independently represent from mono substitution to the maximum possible number of substitution, or no substitution;

wherein each $R_a$, $R_b$, $R_c$, $R_d$, $R_e$, and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

Additional information on possible emissive dopants is provided below.

The OLED disclosed herein can be incorporated into one or more of a consumer product, an electronic component module, and a lighting panel.

In one embodiment, the consumer product is selected from the group consisting of a flat panel display, a curved display, a computer monitor, a medical monitor, a television, a billboard, a light for interior or exterior illumination and/or signaling, a heads-up display, a fully or partially transparent display, a flexible display, a rollable display, a foldable display, a stretchable display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video walls comprising multiple displays tiled together, a theater or stadium screen, and a sign.

In one embodiment, the organic layer is an emissive layer and the compound of Formula I or Formula II is a host. In some embodiments the organic layer is a blocking layer and the compound of Formula I or Formula II is a blocking material in the organic layer. In other embodiments the organic layer is a transporting layer and the compound of Formula I or Formula II is a transporting material in the organic layer In some embodiments, the organic layer further comprises a phosphorescent emissive dopant. In one embodiment, the emissive dopant is a transition metal complex having at least one ligand or part of the ligand if the ligand is more than bidentate selected from the group consisting of:

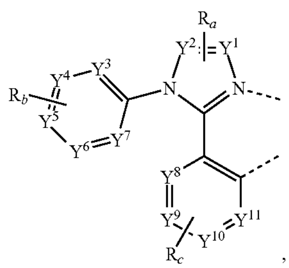

,

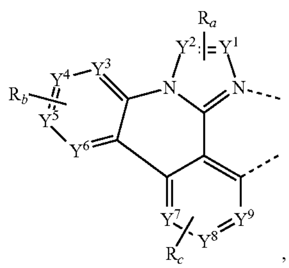

,

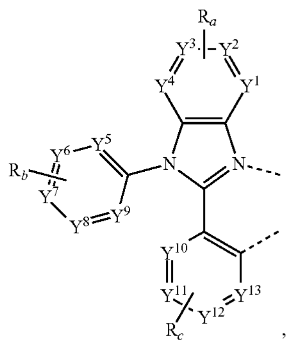

,

-continued

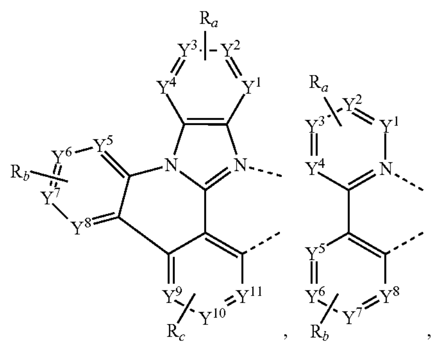

,

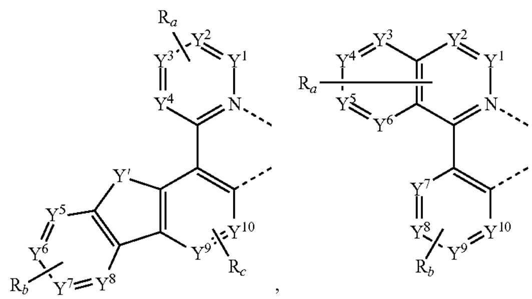

,

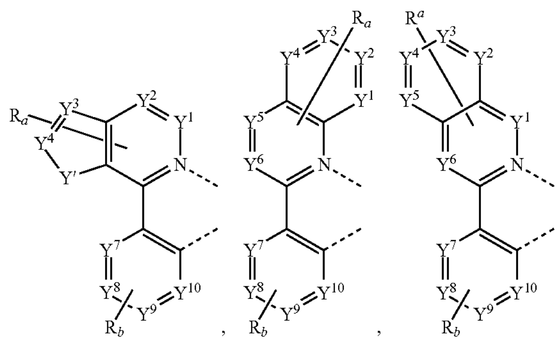

,

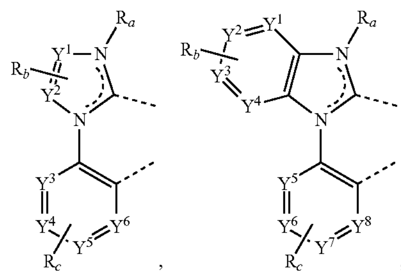

,

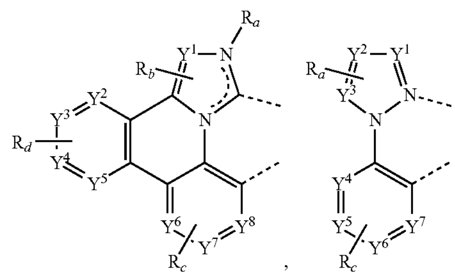

,

-continued

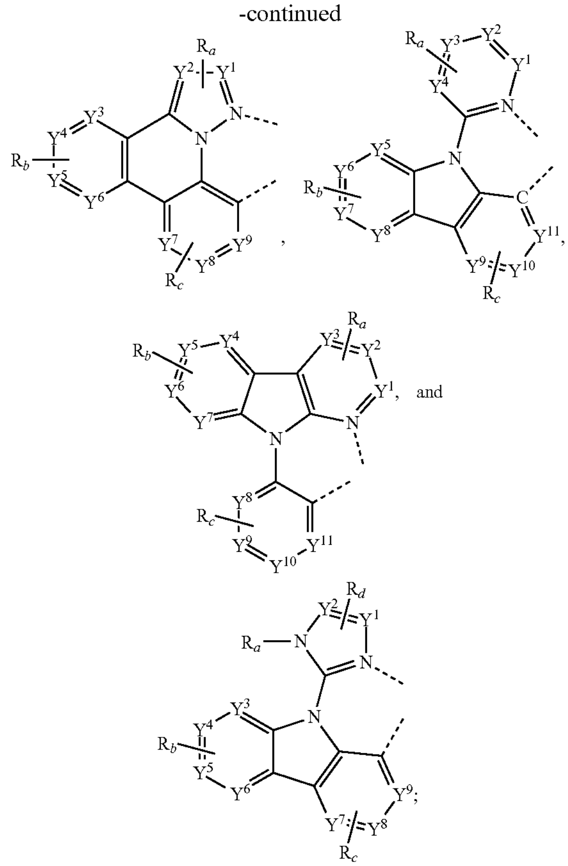

, , and ;

wherein each $Y^1$ to $Y^{13}$ are independently selected from the group consisting of carbon and nitrogen;

wherein Y' is selected from the group consisting of $BR_e$, $NR_e$, $PR_e$, O, S, Se, C═O, S═O, $SO_2$, $CR_eR_fRR$, $SiR_eR_f$, and $G_eR_eR_f$;

wherein $R_e$ and $R_f$ are optionally fused or joined to form a ring;

wherein each $R_a$, $R_b$, $R_c$, and $R_d$ may independently represent from mono substitution to the maximum possible number of substitution, or no substitution;

wherein each $R_a$, $R_b$, $R_c$, $R_d$, $R_e$, and $R_f$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

In one embodiment, each $R_a$, $R_b$, $R_c$, $R_d$, $R_e$, and $R_f$ is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

According to another aspect, a formulation comprising a composition of materials comprising a first compound described herein is also disclosed.

The emitter dopants can be phosphorescent dopants and/or fluorescent dopants. The organic layer can include a composition of materials comprising a first compound, wherein the first compound has a formula selected from the group consisting of Formula I and Formula II and its variations as described herein as a host.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

In yet another aspect of the present disclosure, a method for fabricating an organic light emitting device comprising a first electrode, a second electrode, and a first organic layer disposed between the first electrode and the second electrode is also described, wherein the first organic layer comprises a first composition comprising a mixture of a first compound and a second compound, wherein the first compound has a formula selected from the group consisting of Formula I and Formula II, and wherein the second compound has the Formula III. The method may include the steps of providing a substrate having the first electrode disposed thereon, depositing the first composition over the first electrode, and depositing the second electrode over the first organic layer.

In yet another aspect of the present disclosure, a formulation that comprises a compound according to Formula I or Formula II is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer. Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

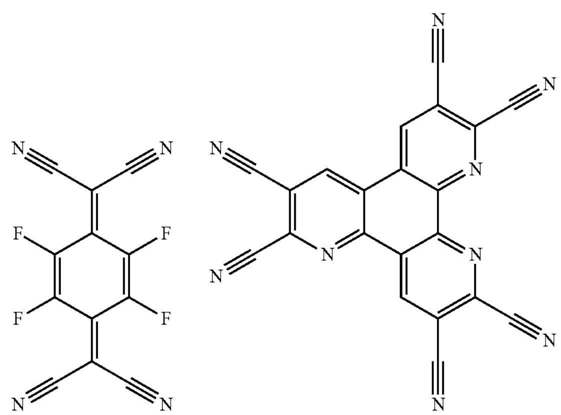
,
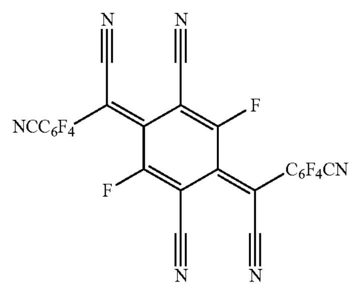
,
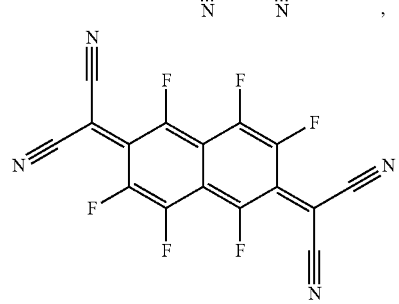
,
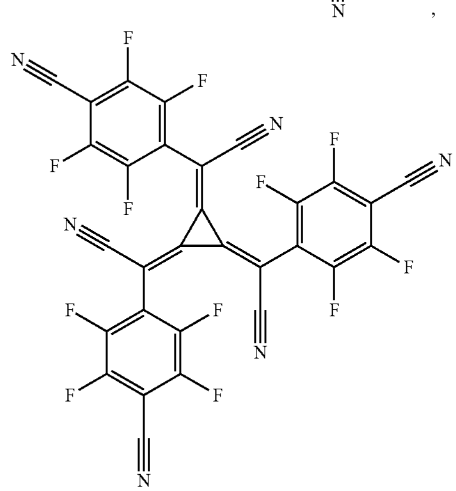
,
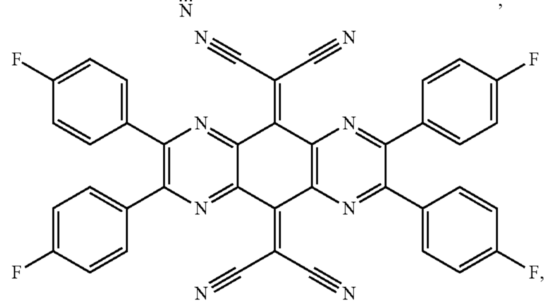
-continued
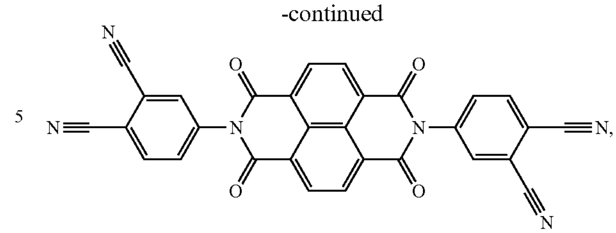
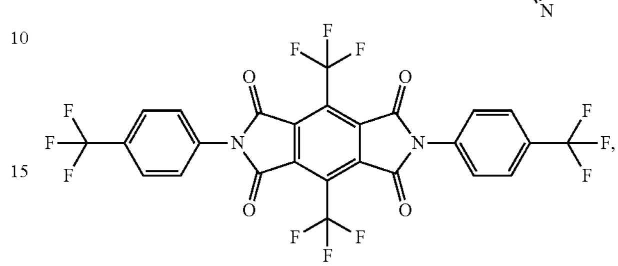
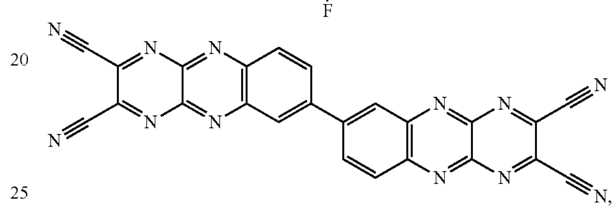
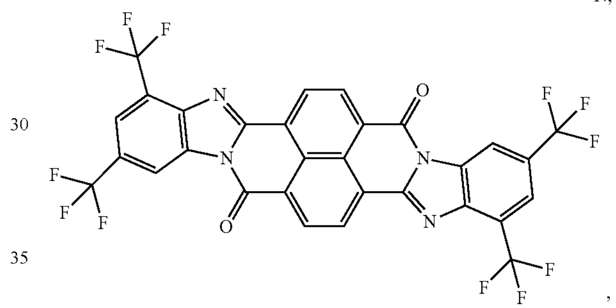
,
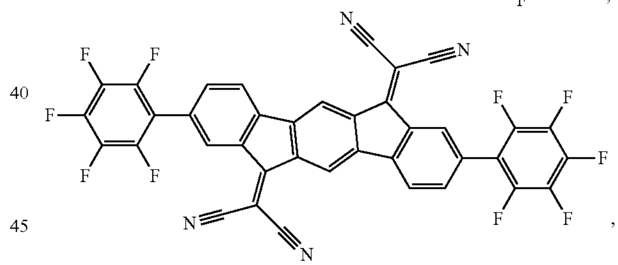
,
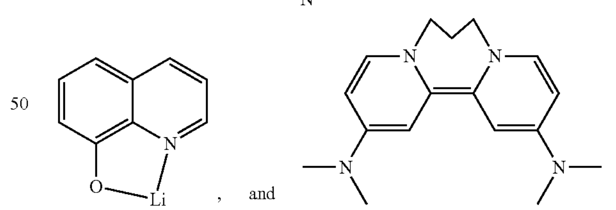
, and
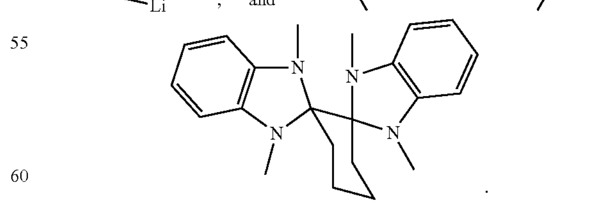
.
HIL/HTL:
A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silyl derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

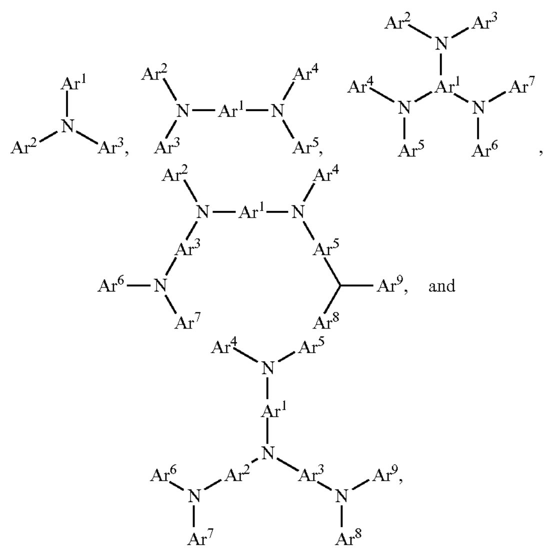

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

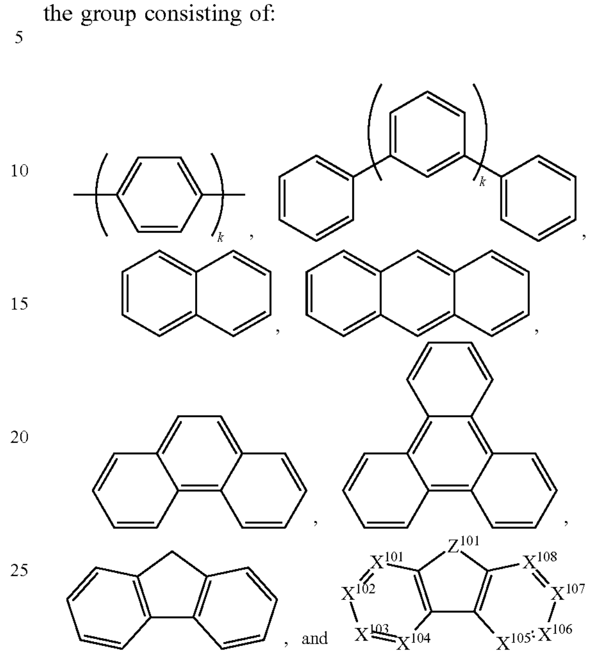

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

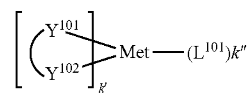

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.
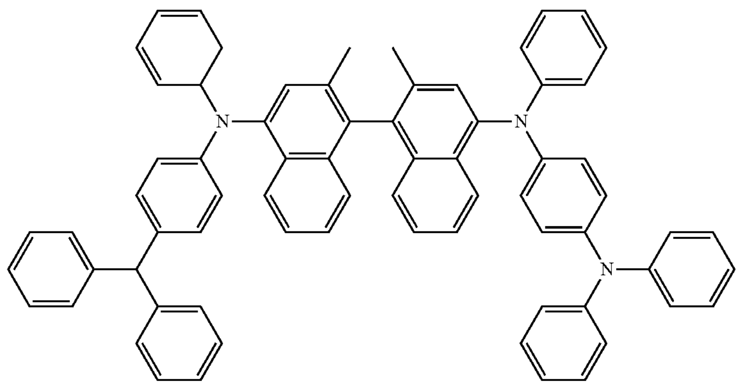
,
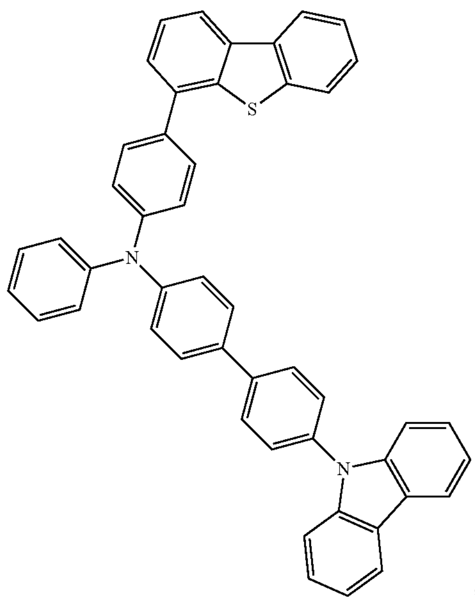
, -continued
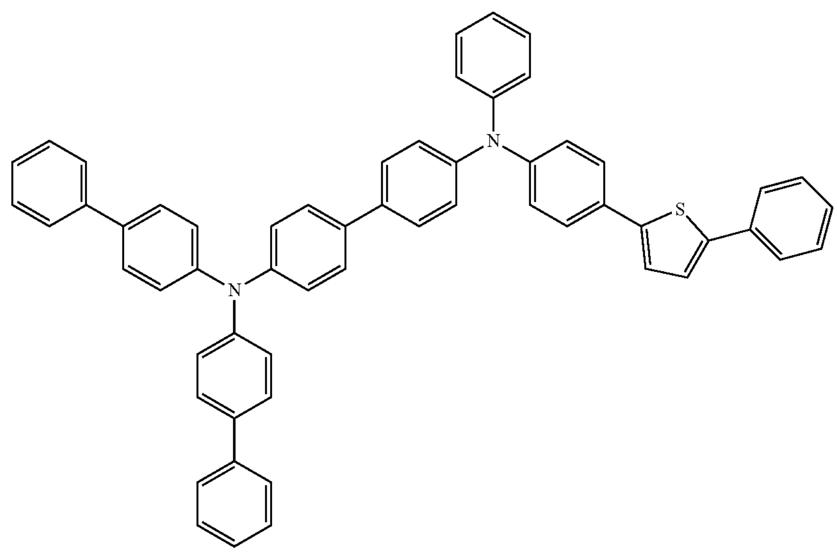
,
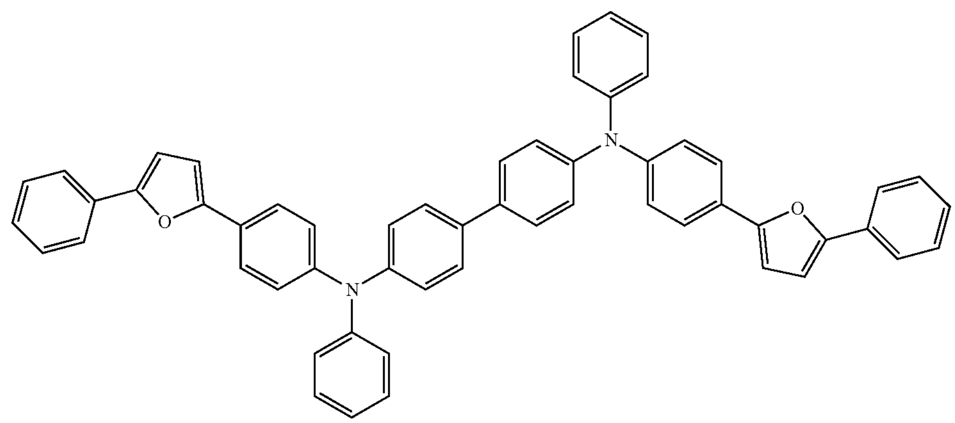
,
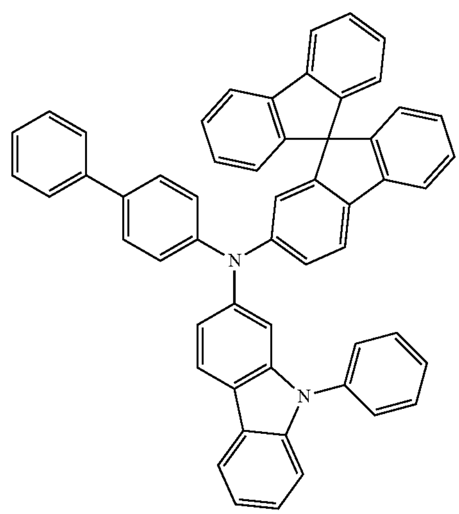
, -continued
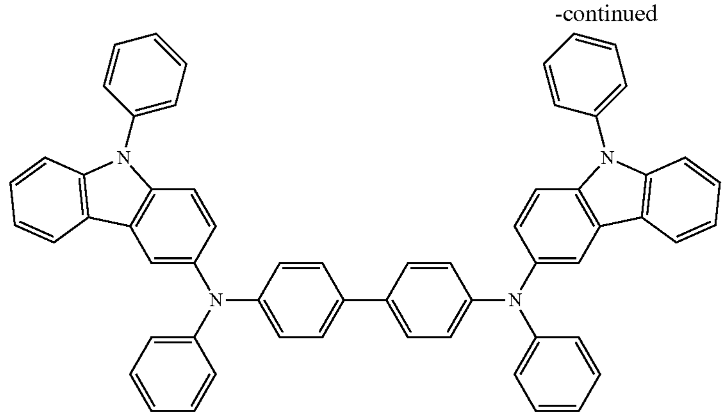
,
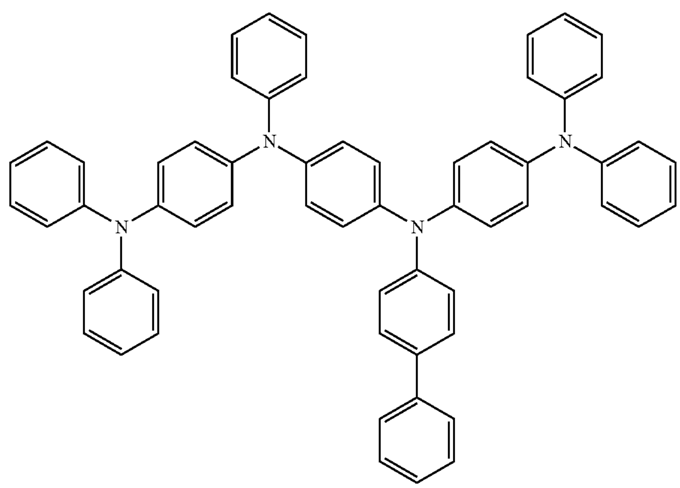
,
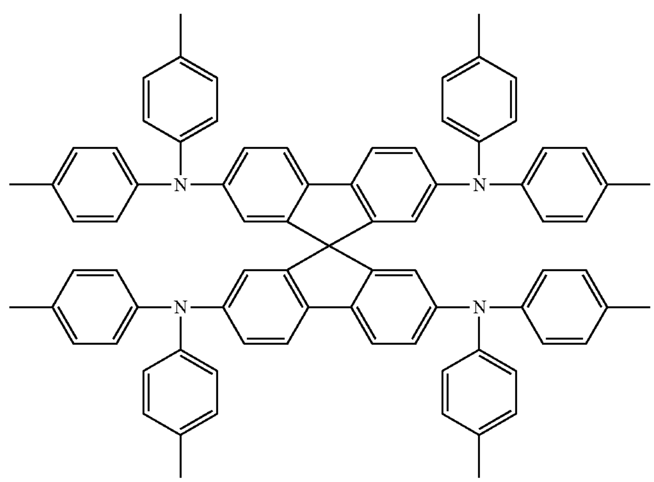
, -continued
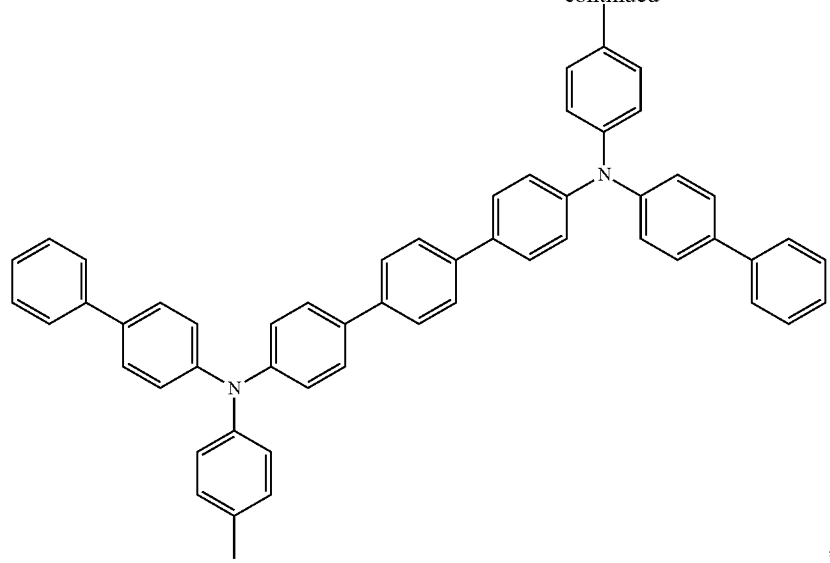
,
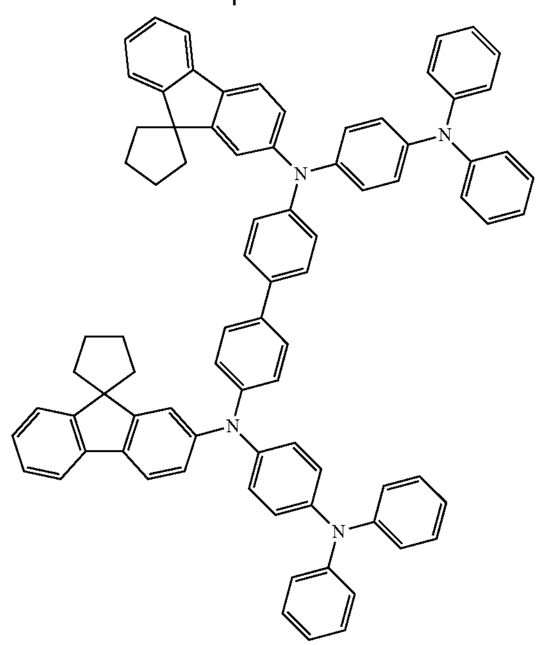
,
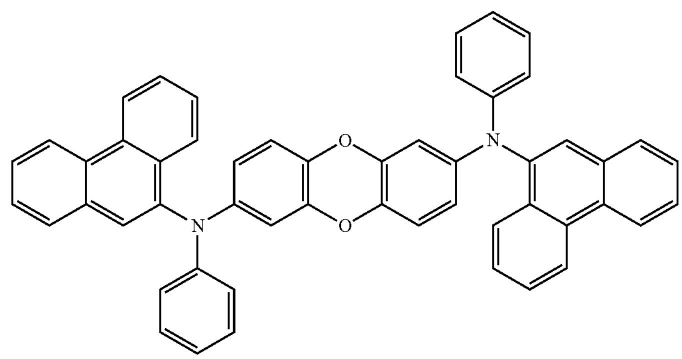
, -continued
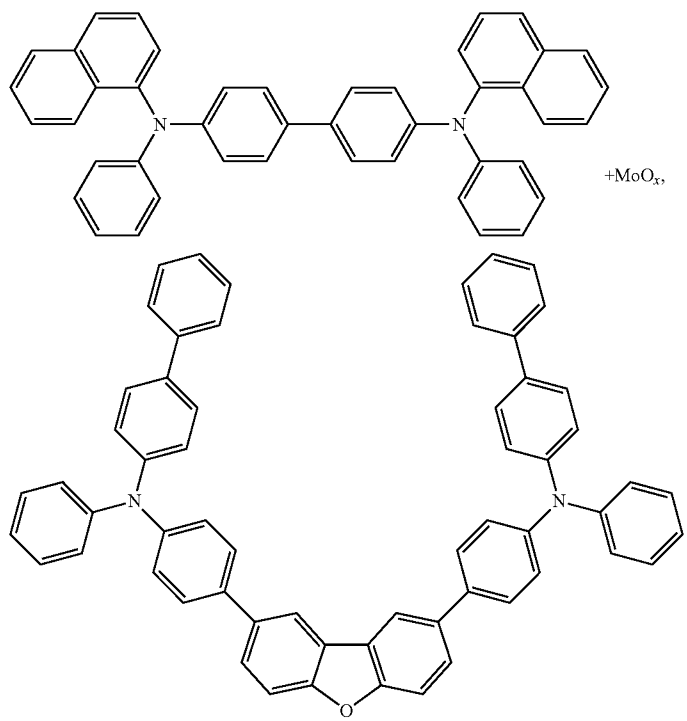
+MoO$_x$,
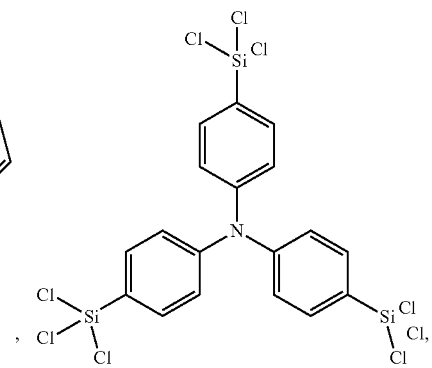
, Cl,
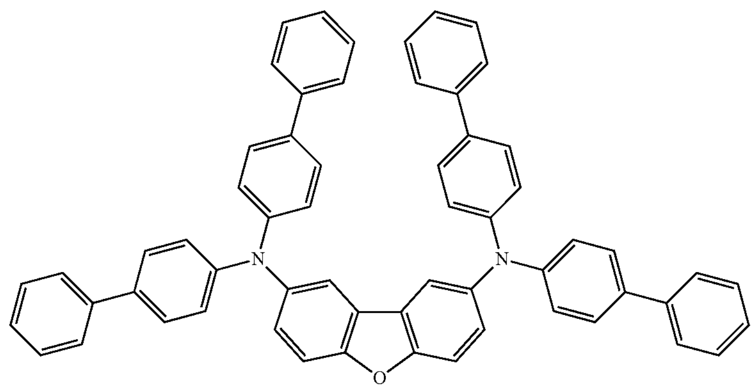
,
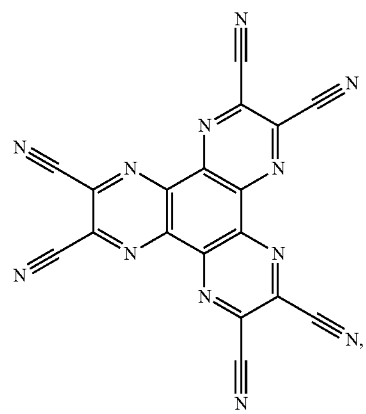
N,
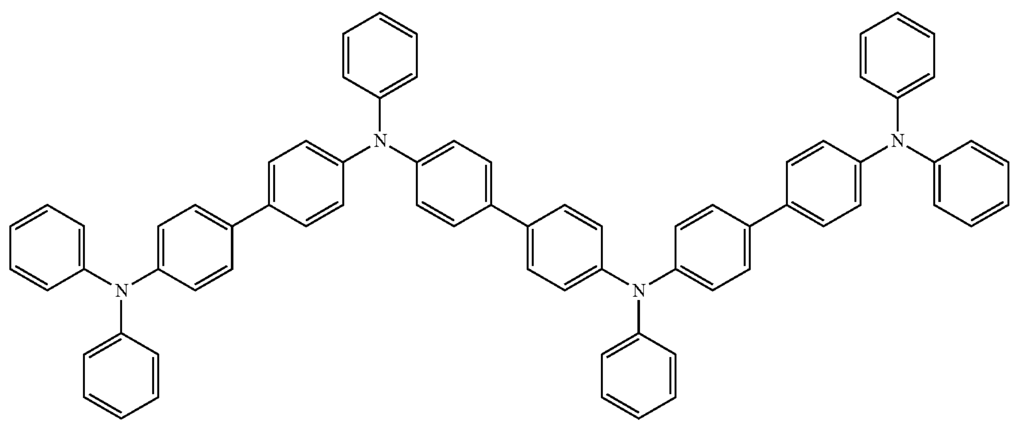
,
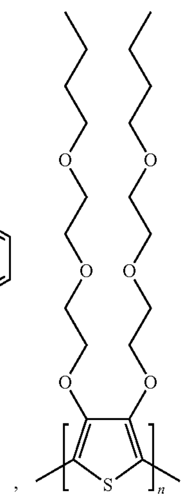
, -continued
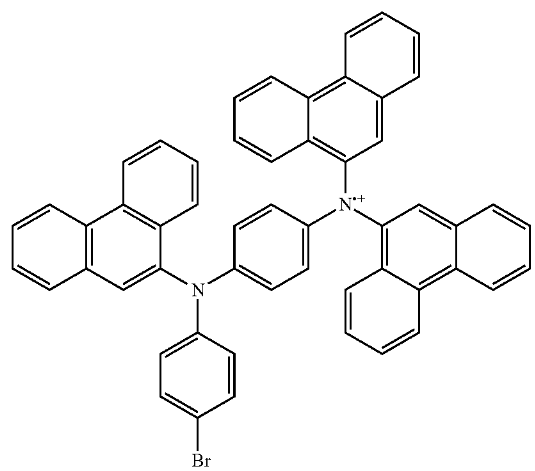
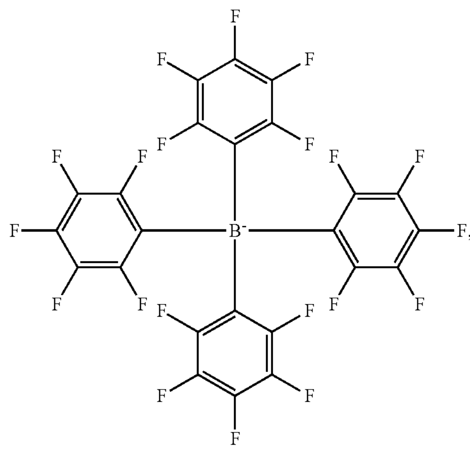
,
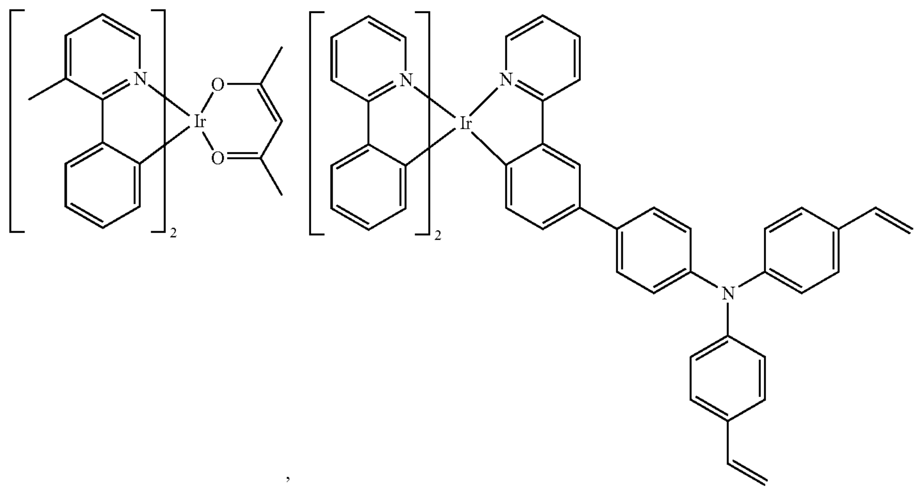
, ,
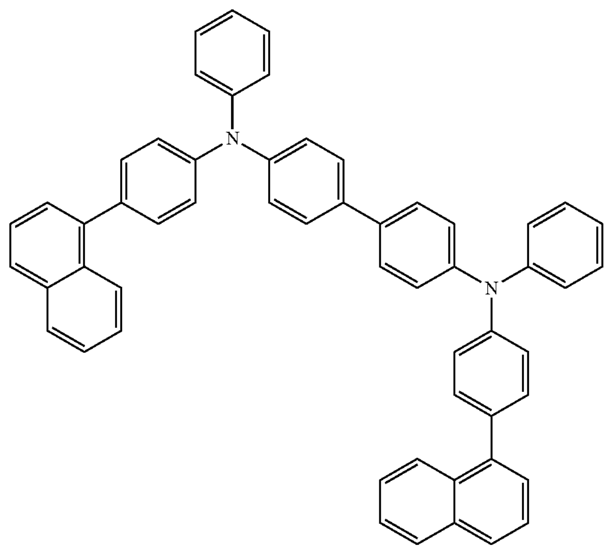
, -continued
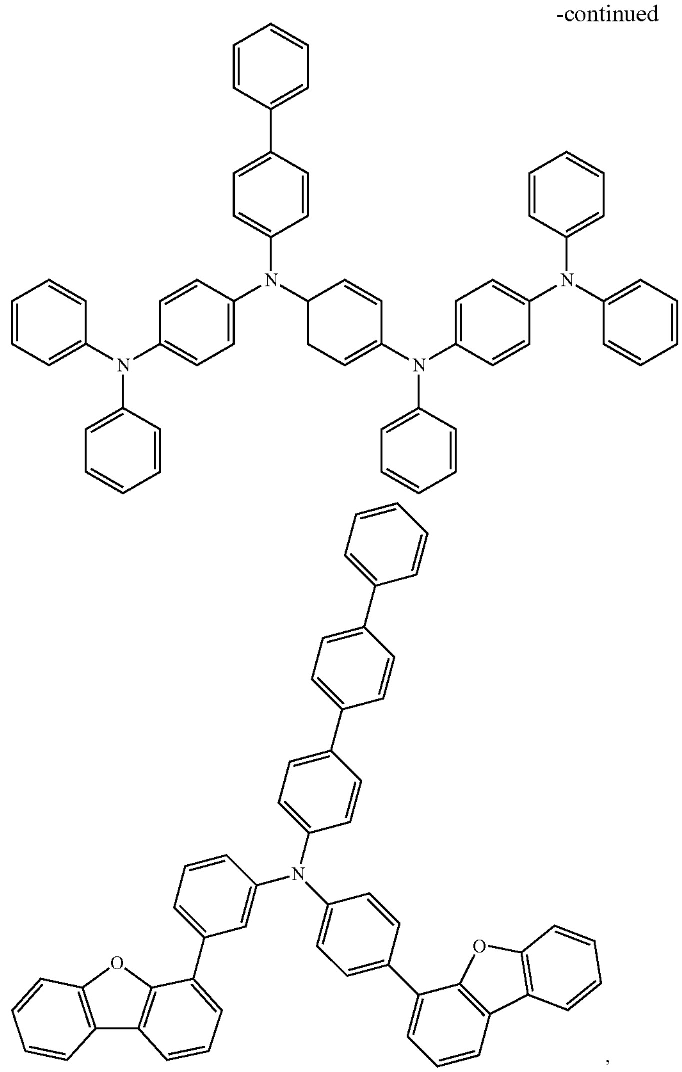
,
,
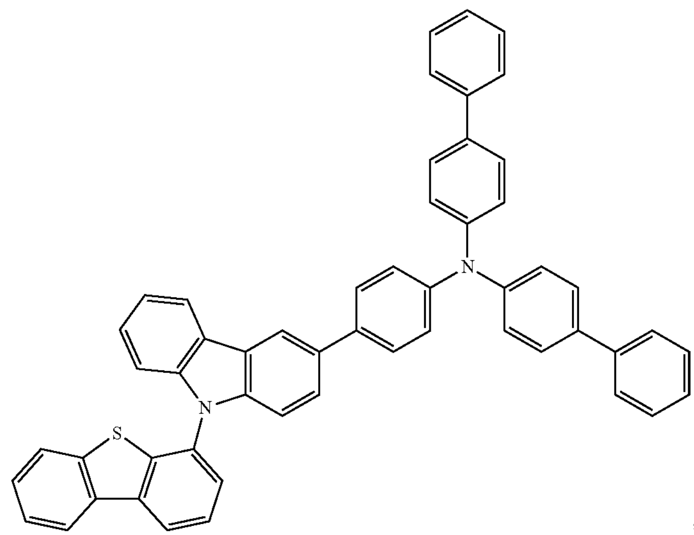
, -continued
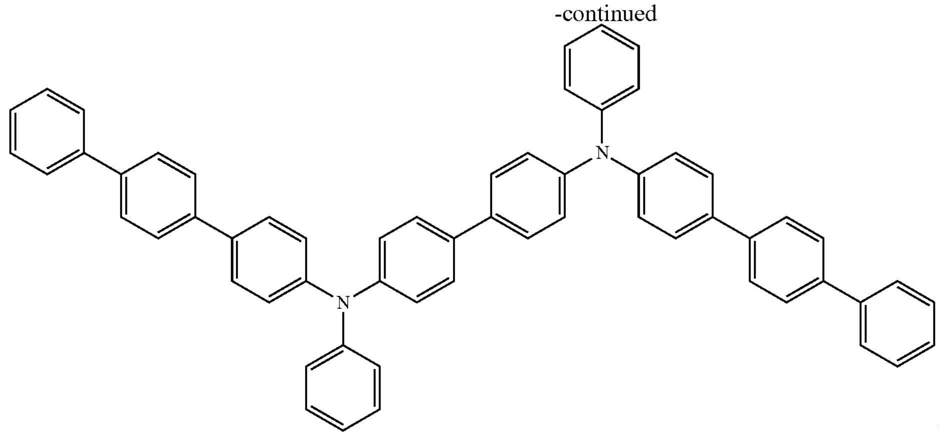
,
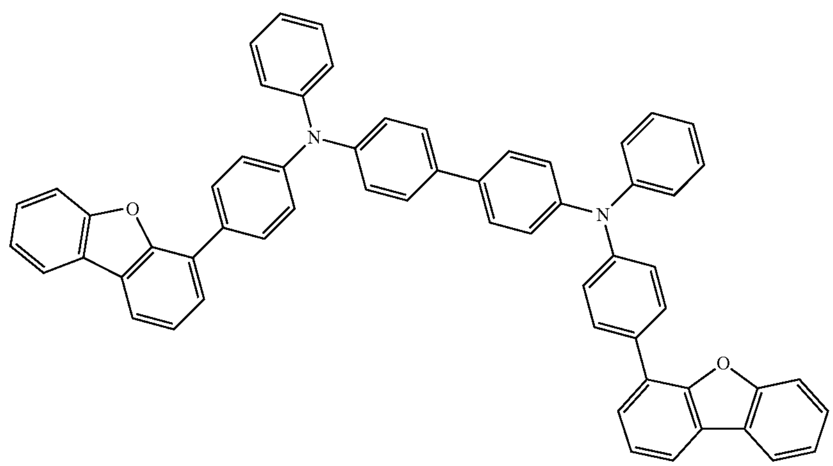
,
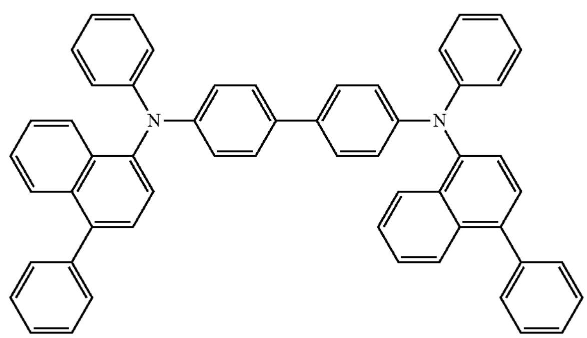
,
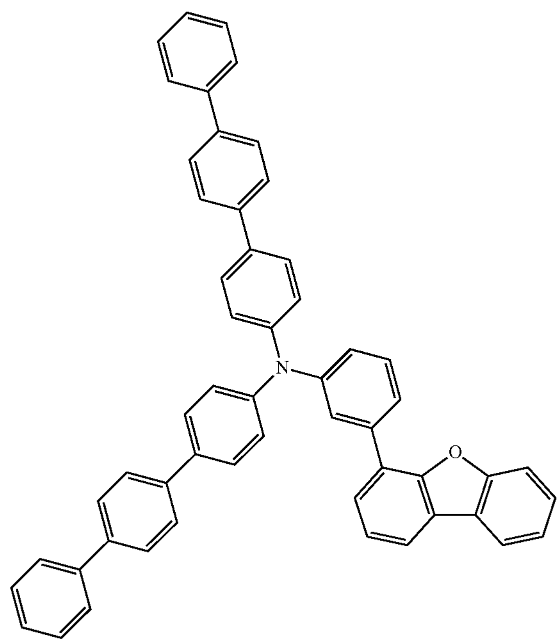
, -continued
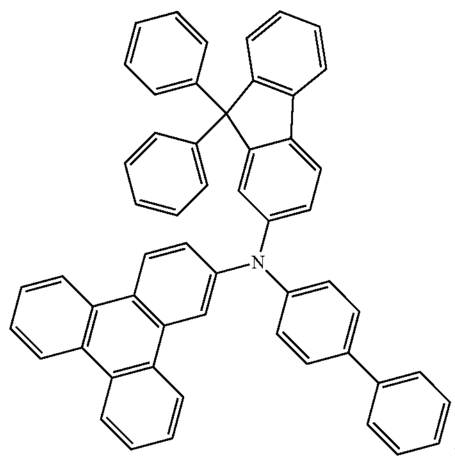
,
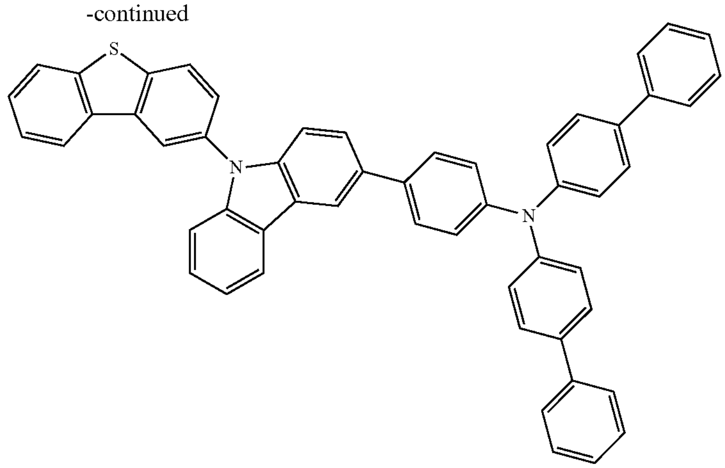
,
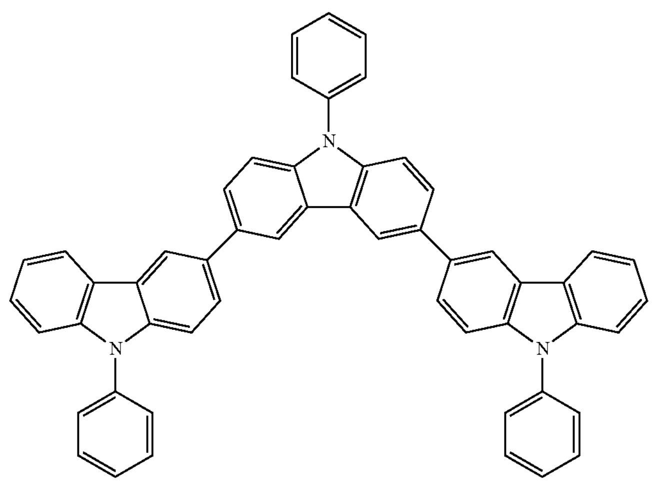
,
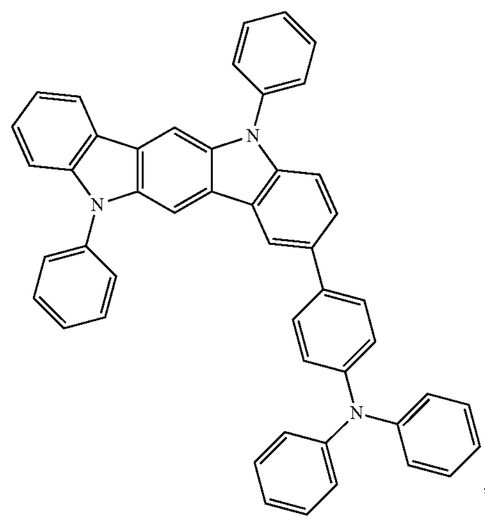
,
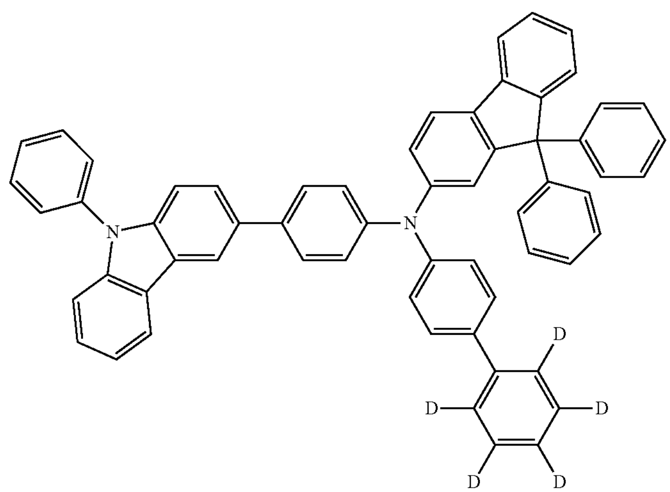
, -continued
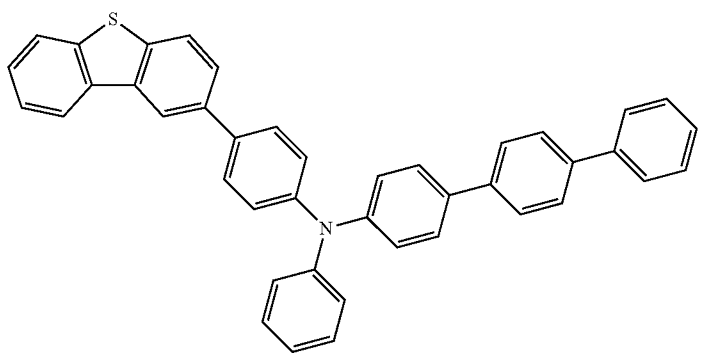
,
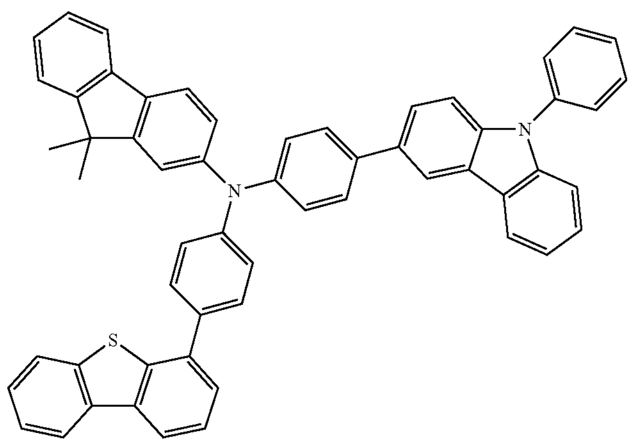
,
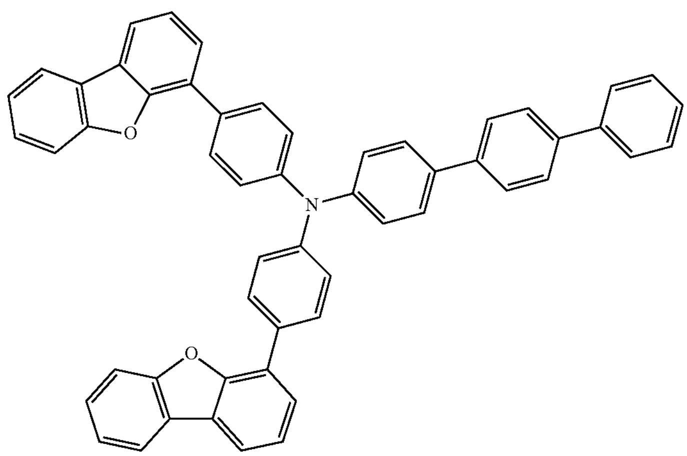
, -continued
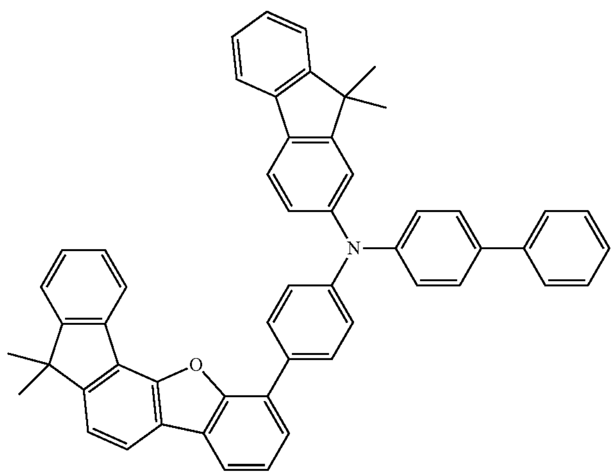
,
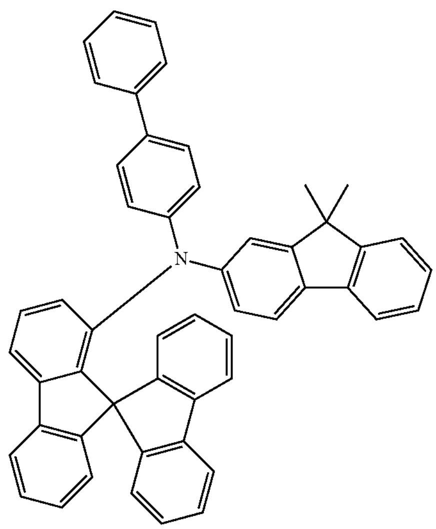
,
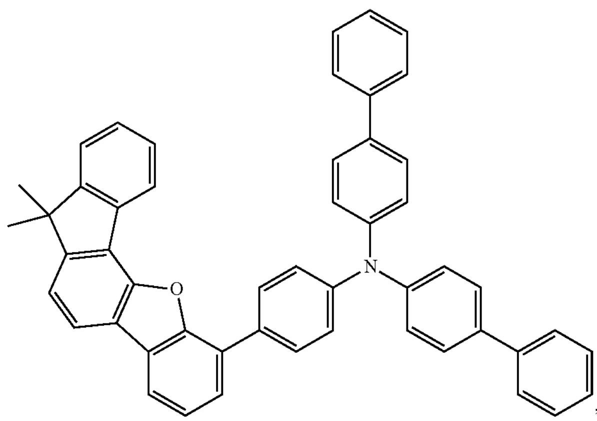
,
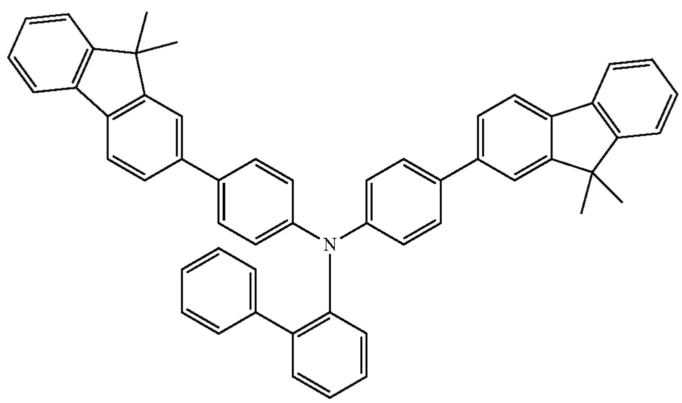
, -continued
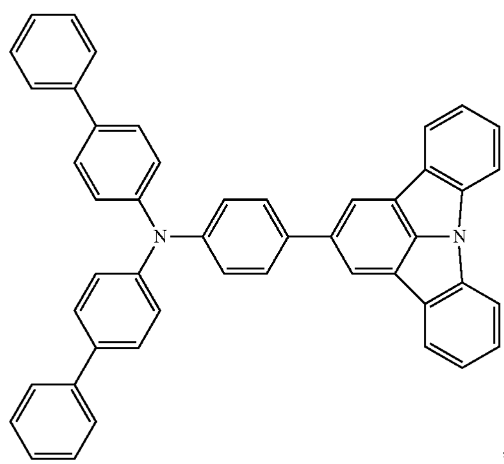
,
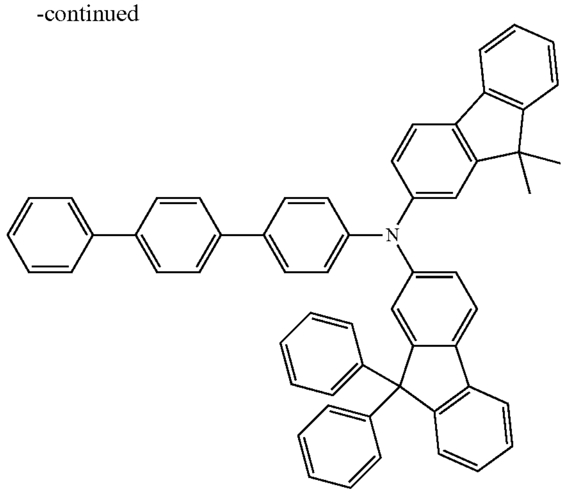
,
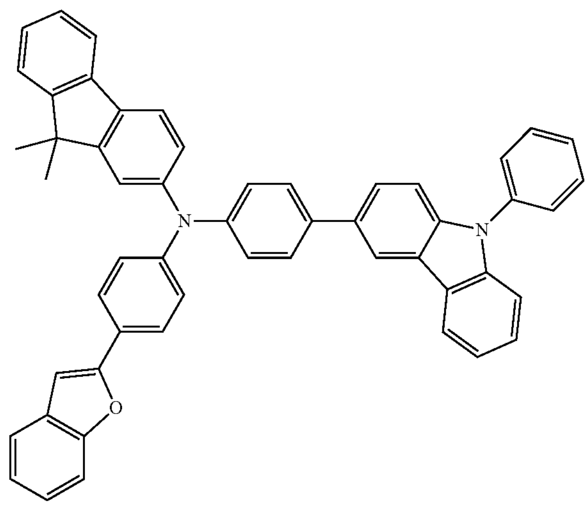
,
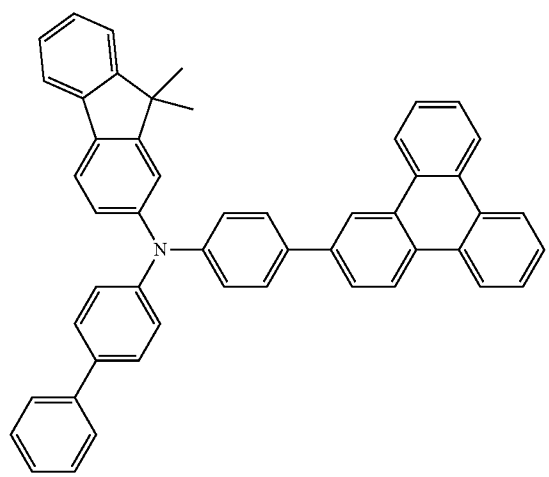
,
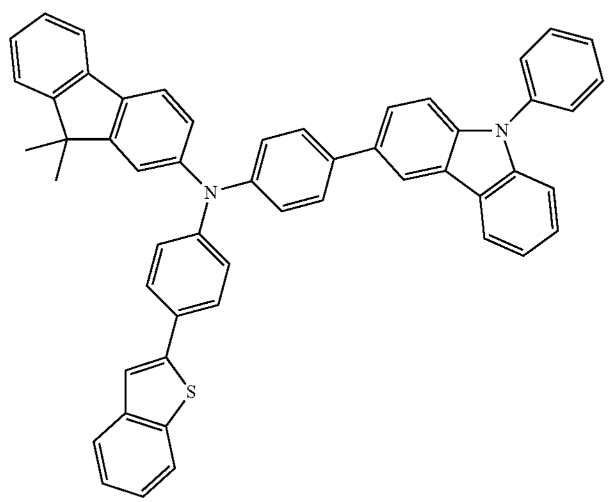
, -continued
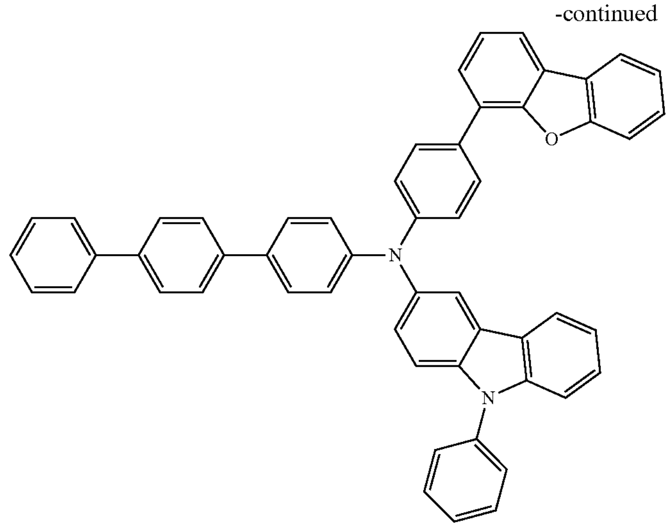
,
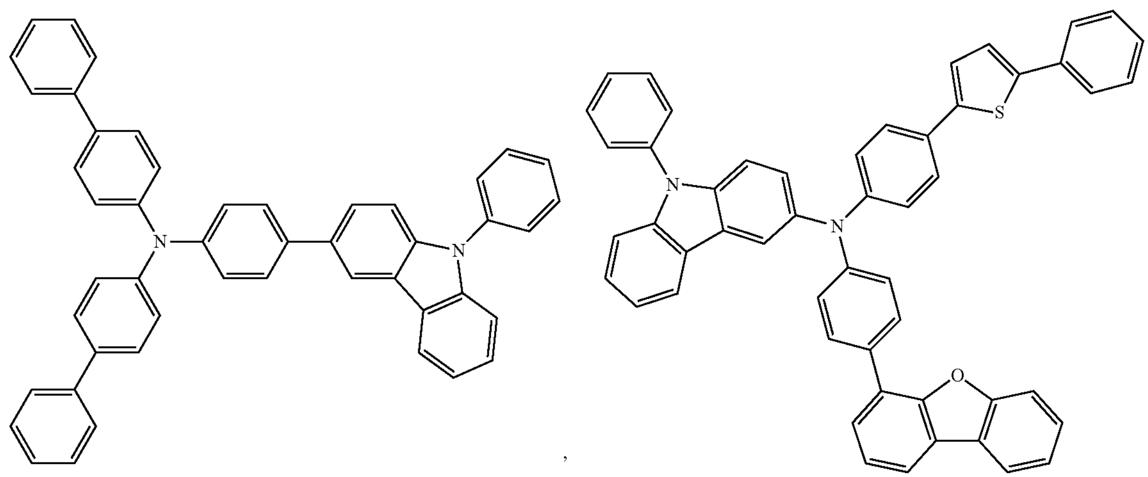
, ,
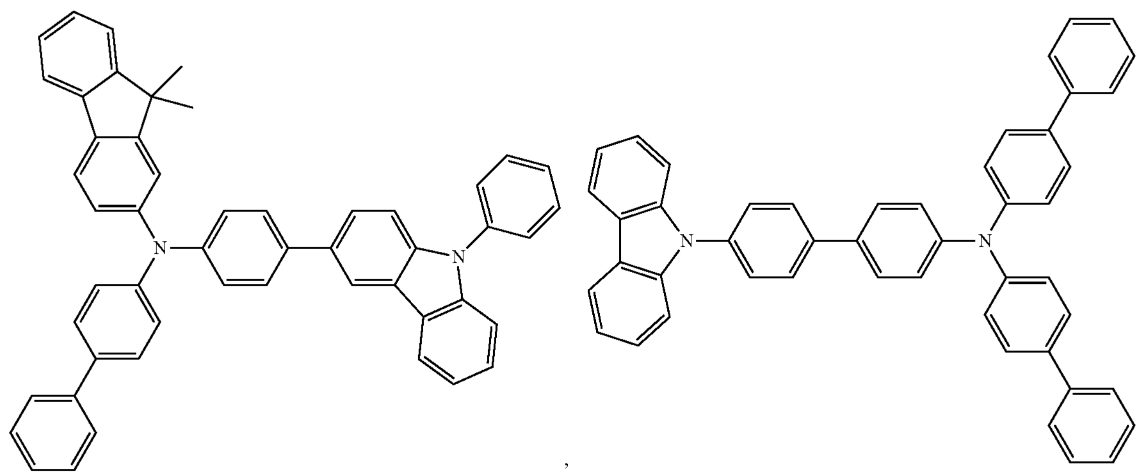
, , -continued
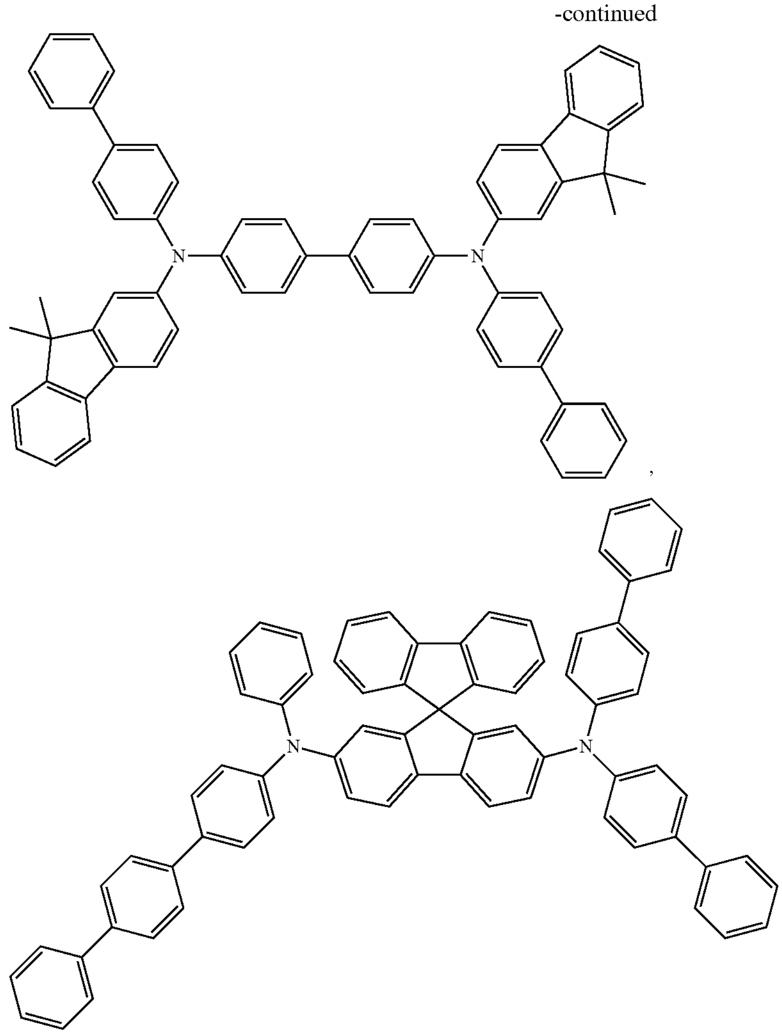
,
,
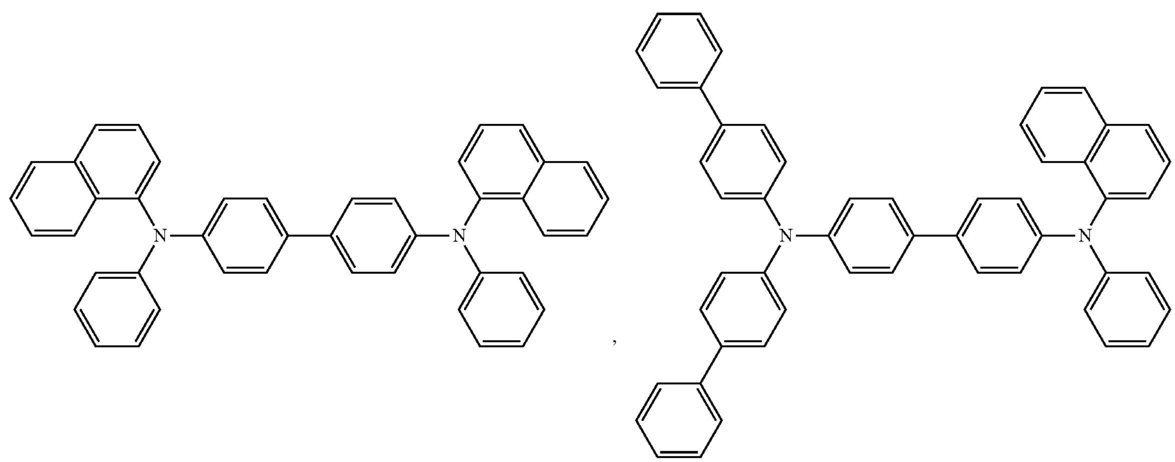
, , -continued
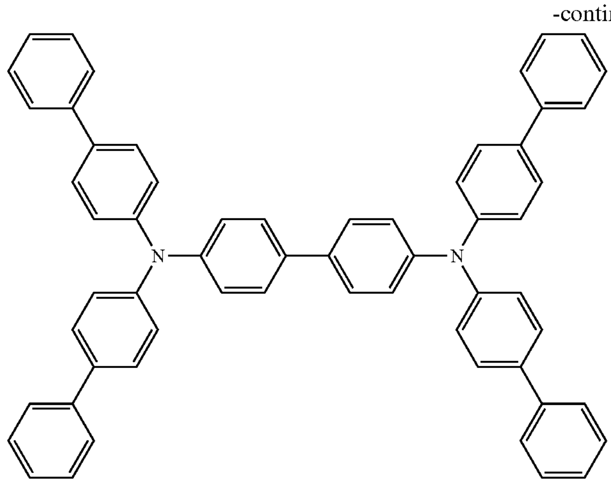
,
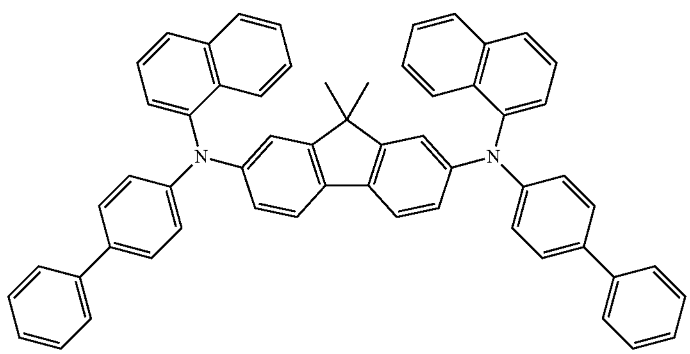
,
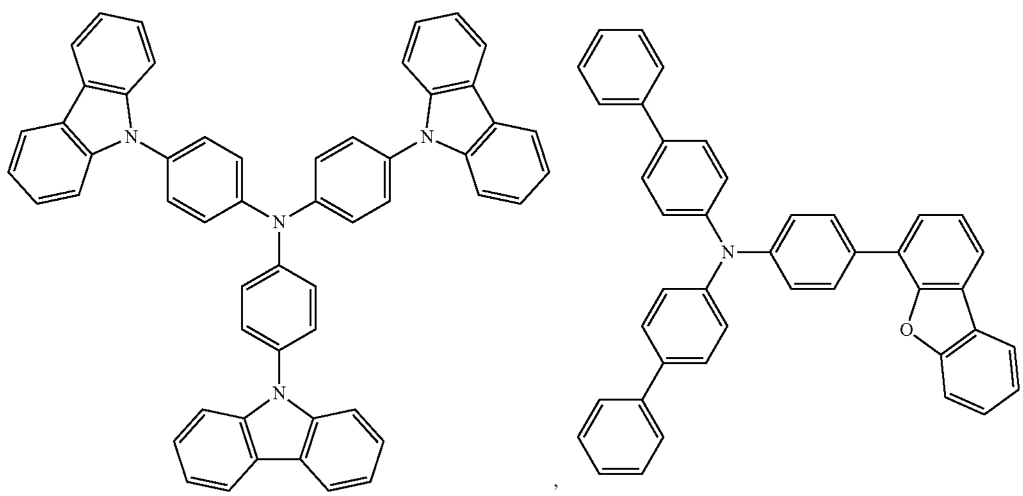
, , -continued

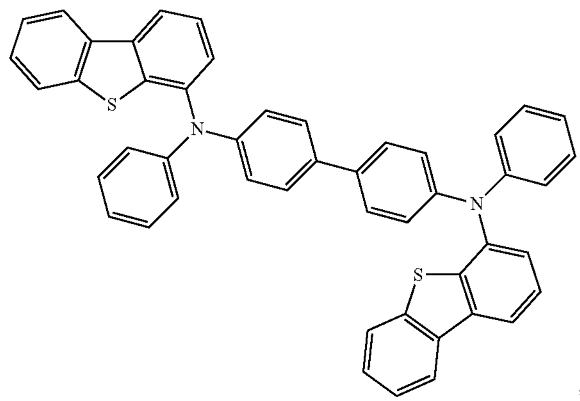

,

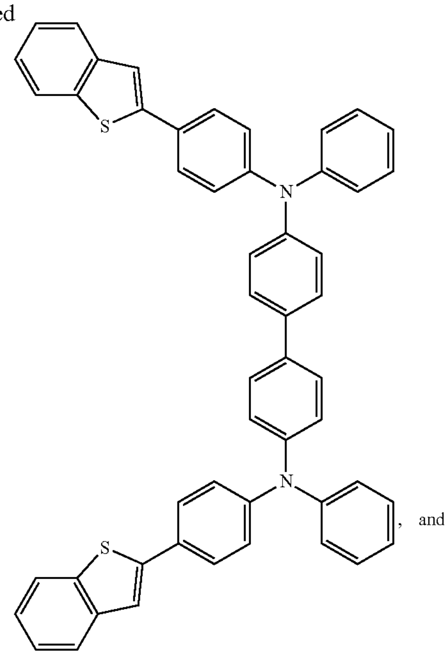

, and

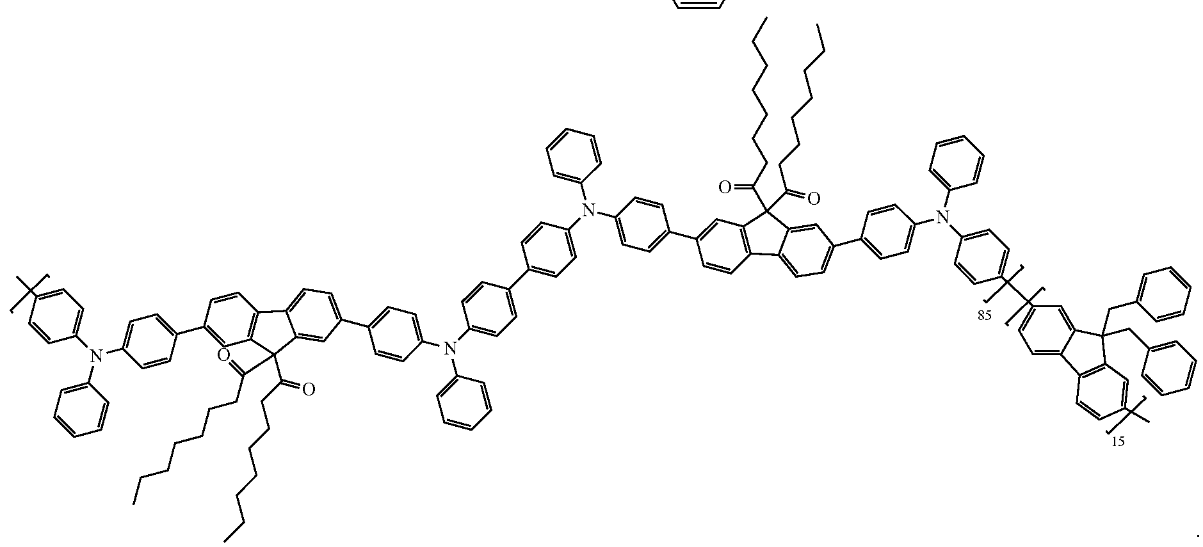

.

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

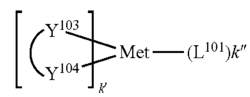

wherein Met is a metal; ($Y^{103}$-$Y^{104}$) is abidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

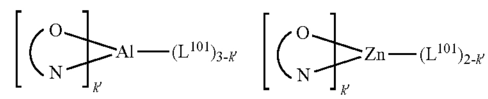

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as additional host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

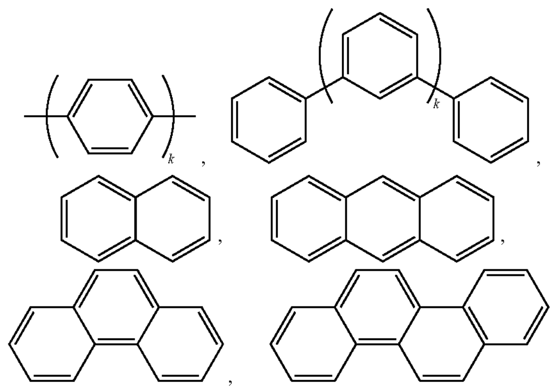

-continued

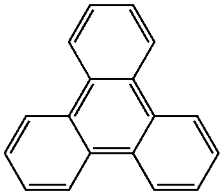,
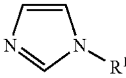,
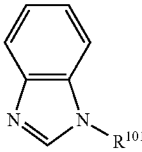,
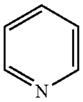,
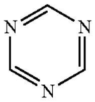,
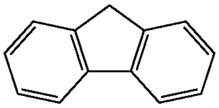,
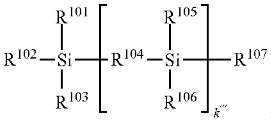,
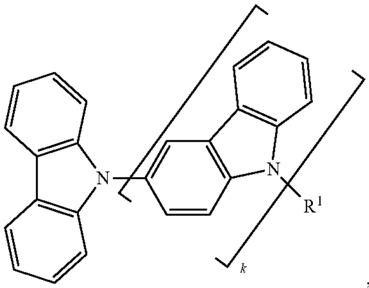,
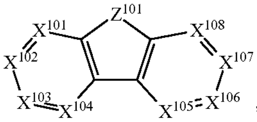,
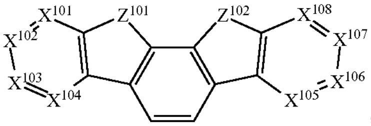,
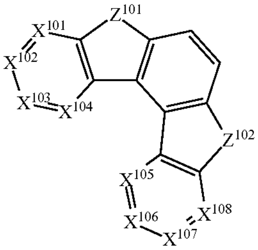,
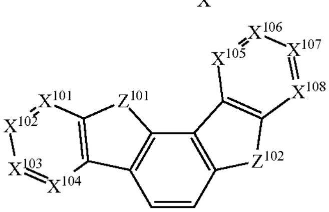,
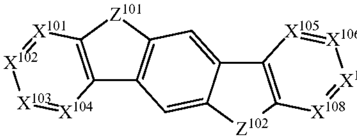, and -continued

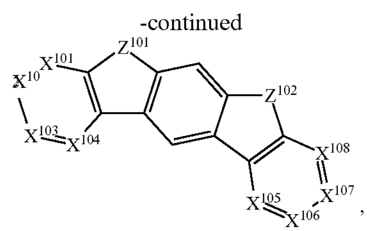

wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

Non-limiting examples of additional host materials that may be used in an OLED in combination with the materials disclosed herein are exemplified below together with references that disclose those materials: EP2034538, EP2034538A, EP2757608, P2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472.

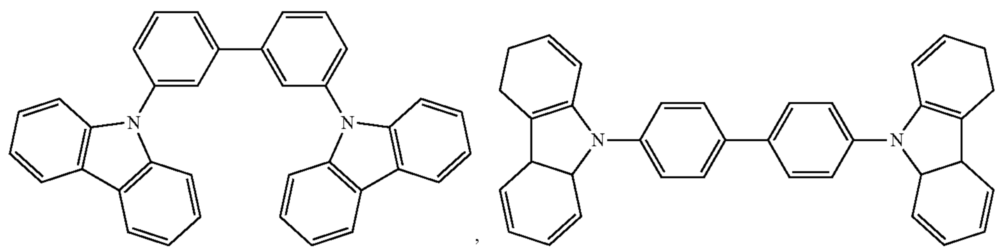

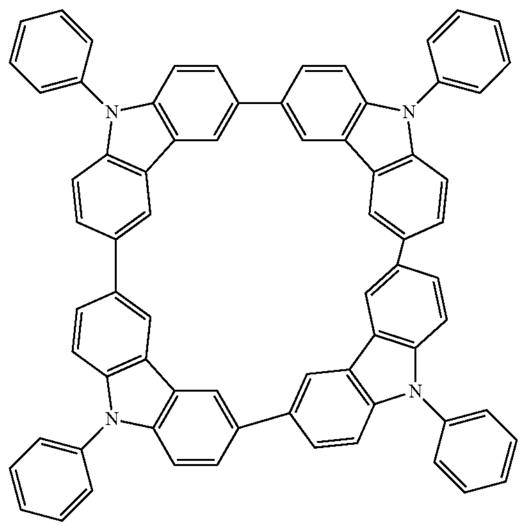

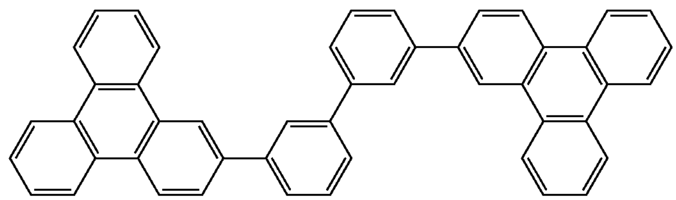

-continued
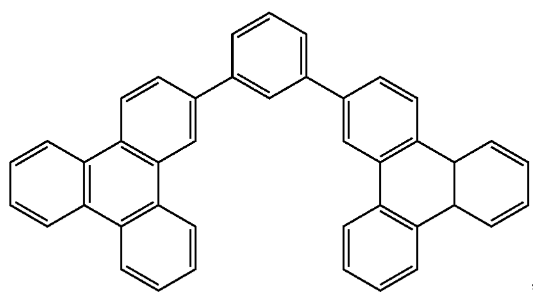
,
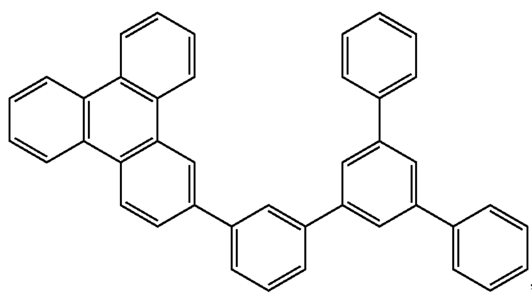
,
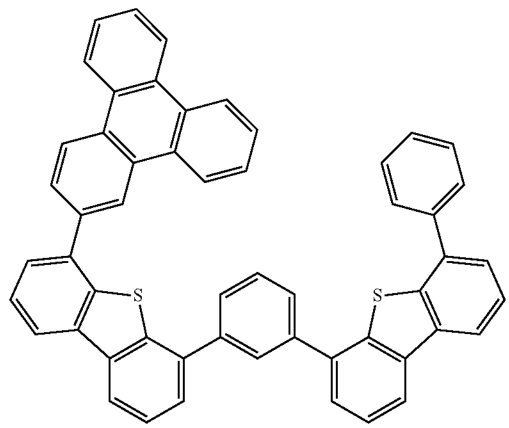
,
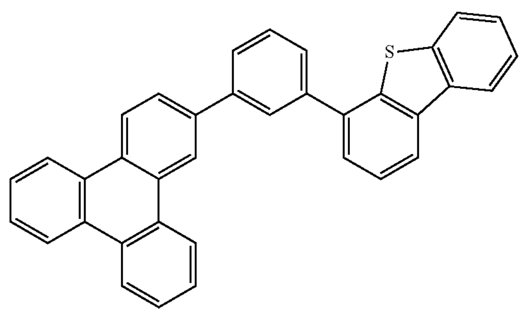
,
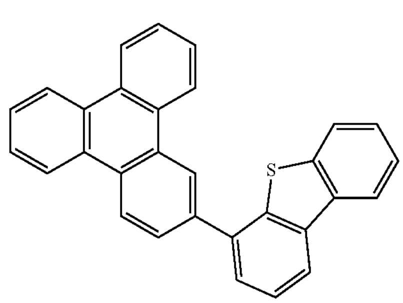
,
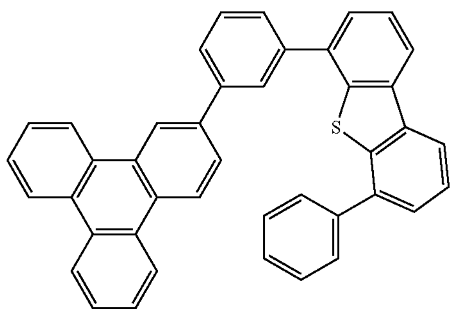
,
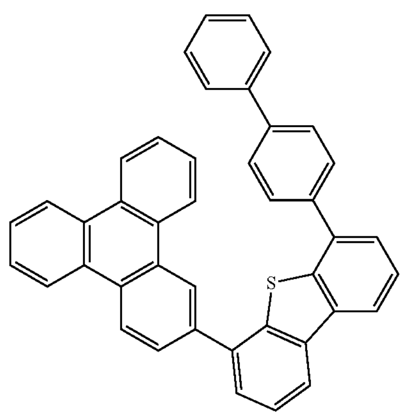
,
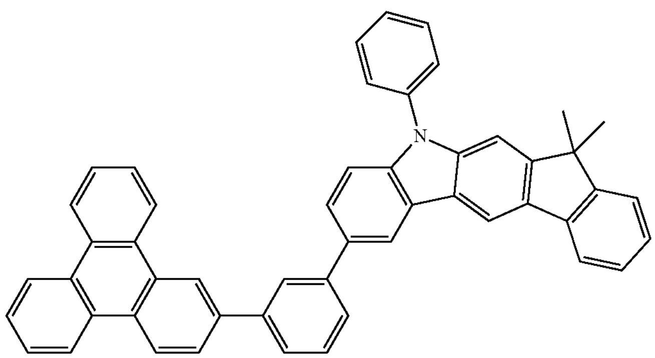
, -continued
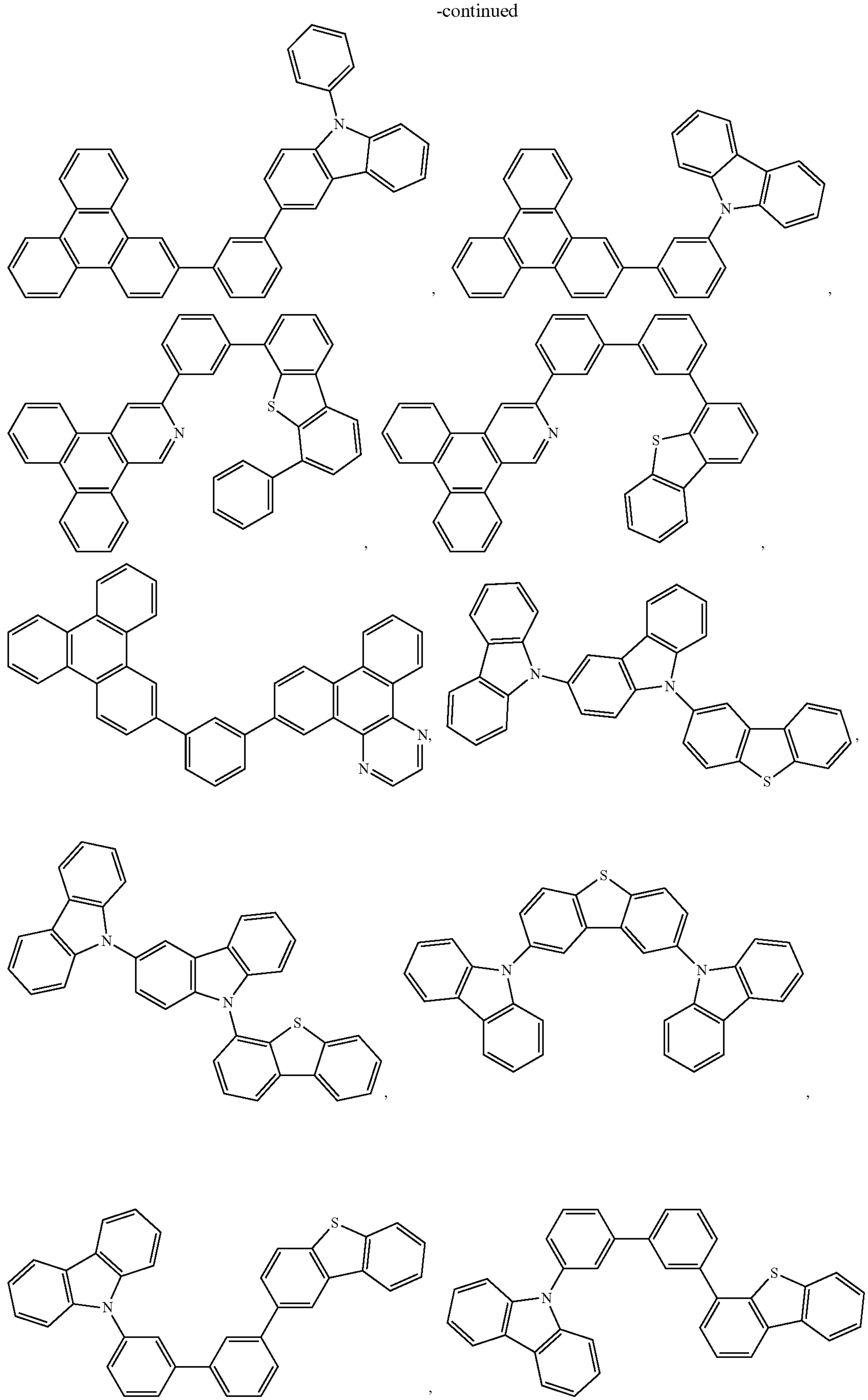

-continued
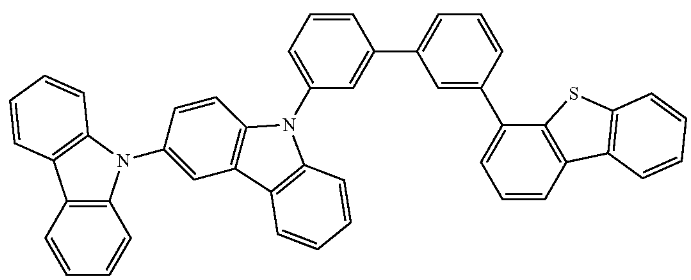
,
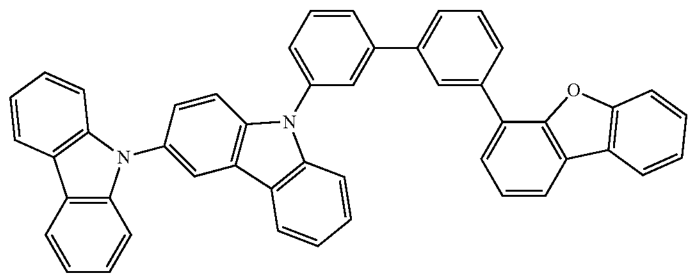
,
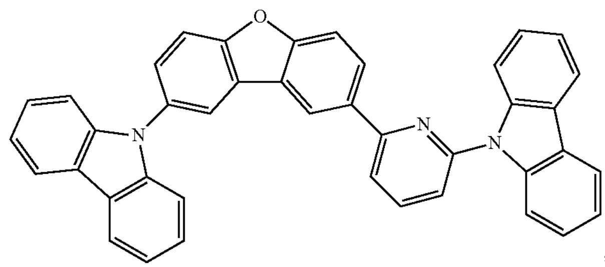
,
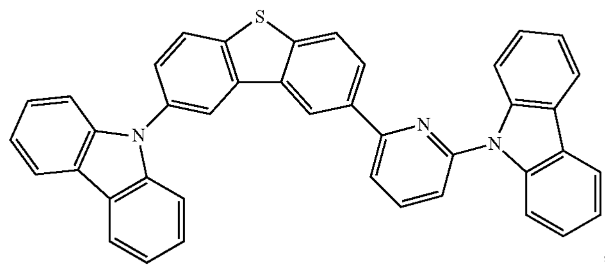
,
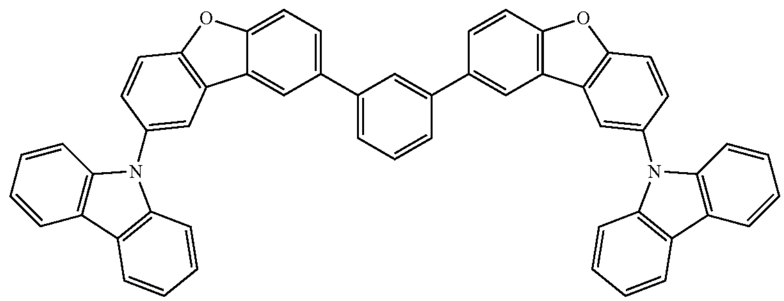
,
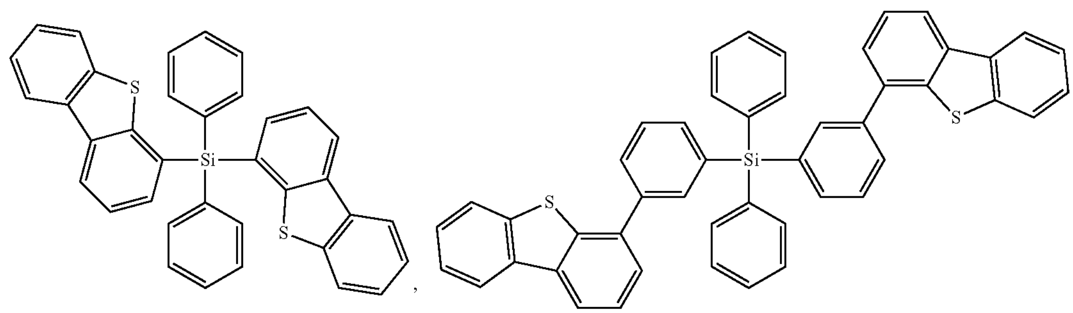
, , -continued
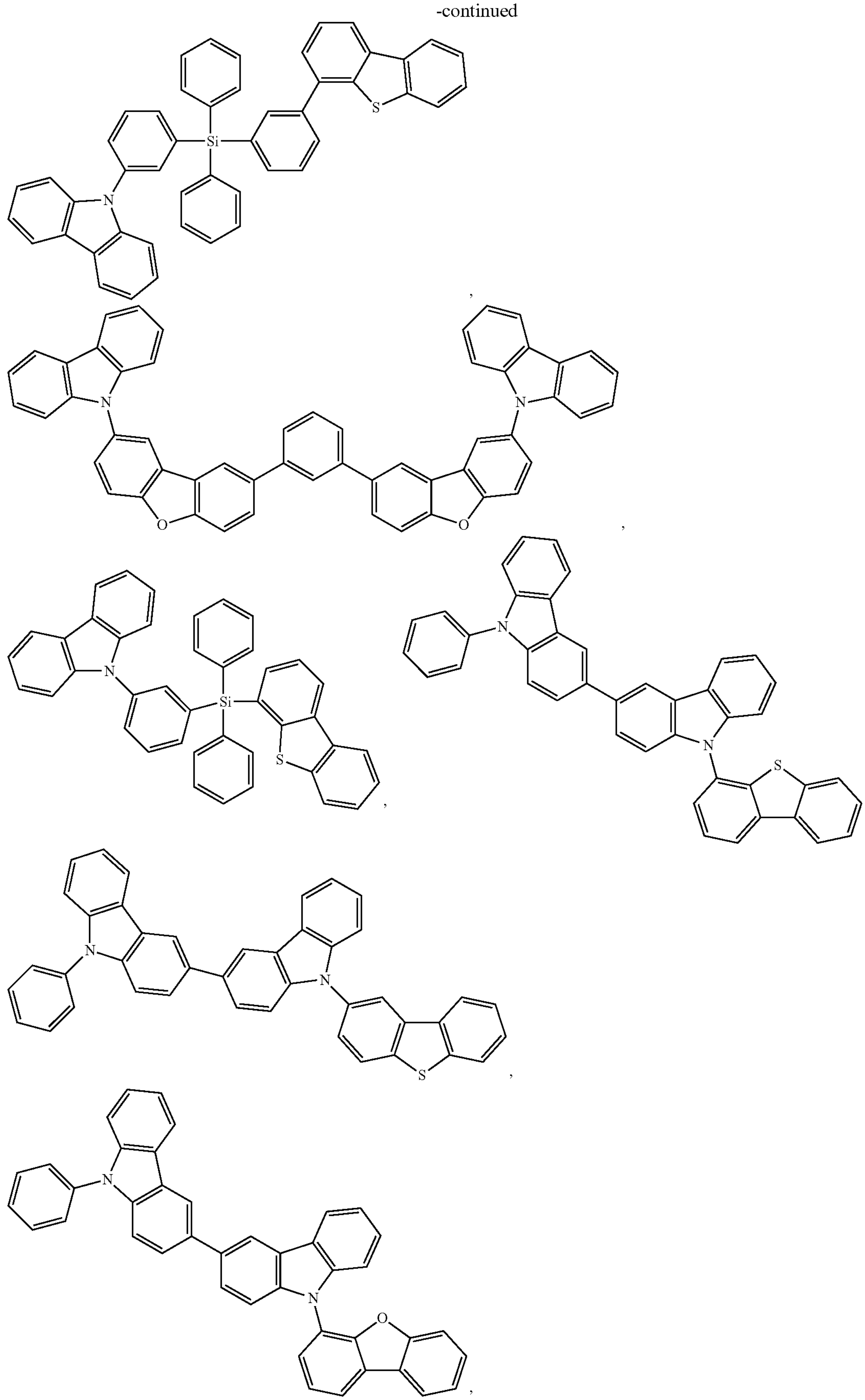
,
,
,
,
,
, -continued
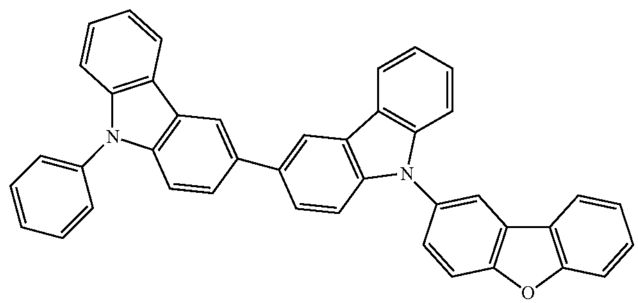
,
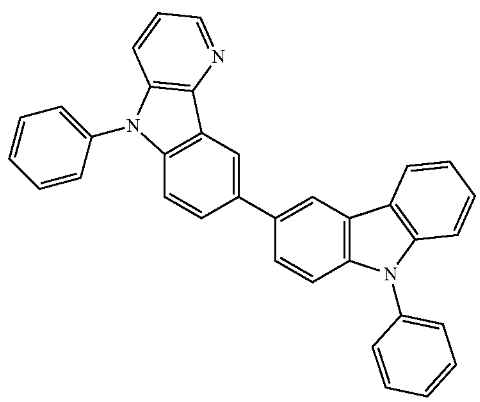
,
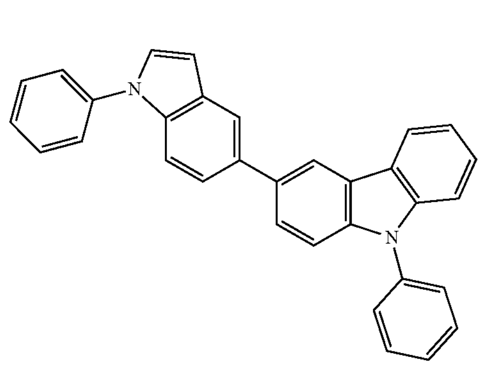
,
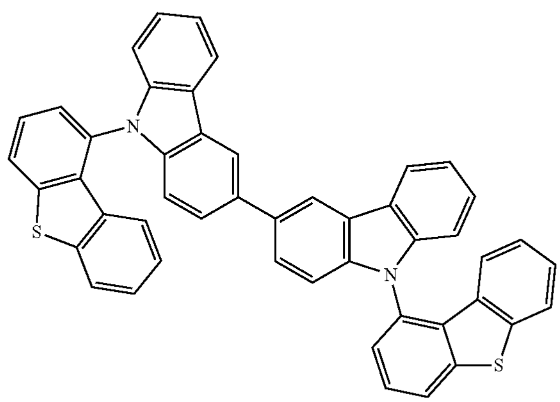
,
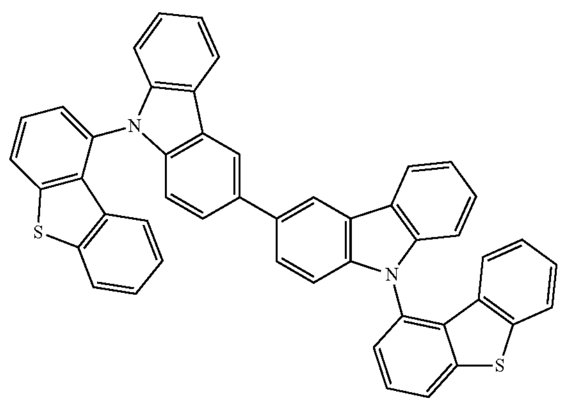
,
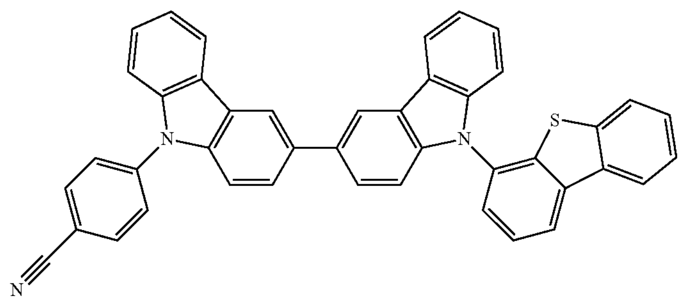
, -continued
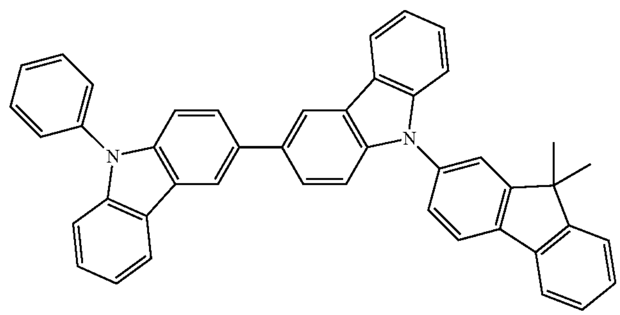
,
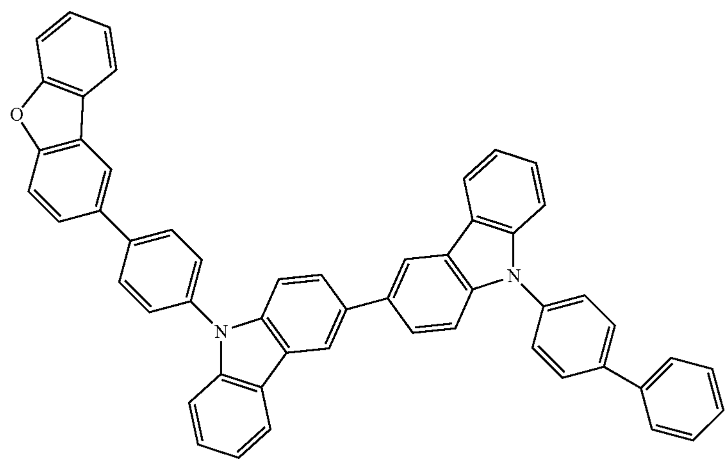
,
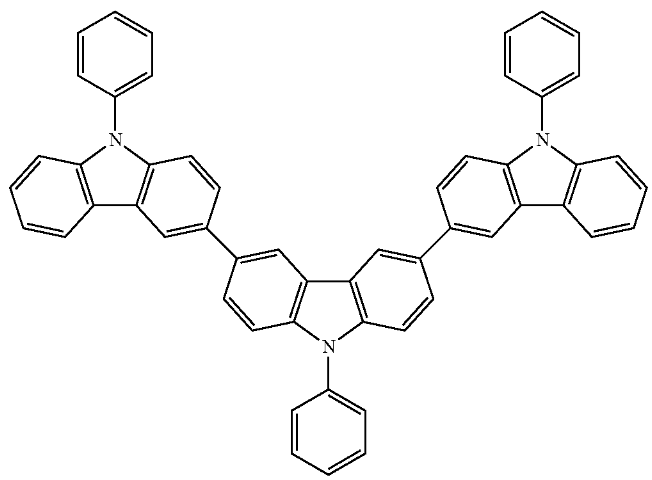
,
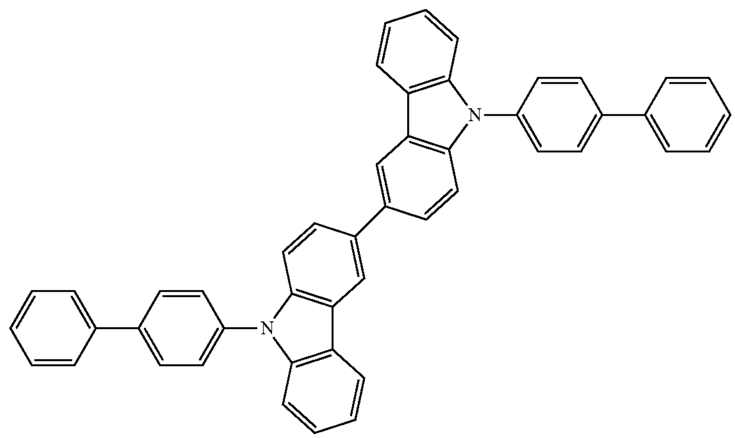
, -continued
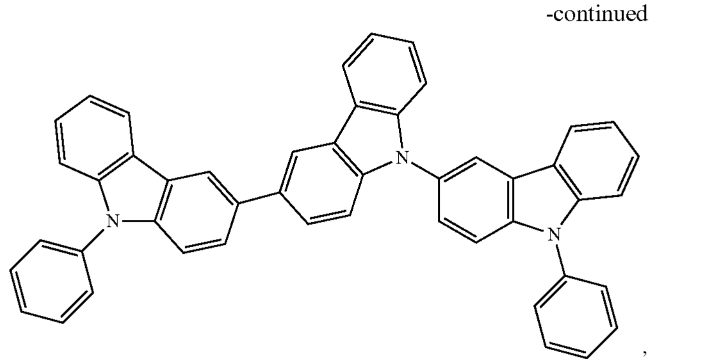
,
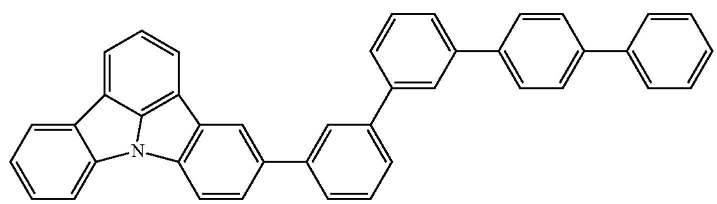
,
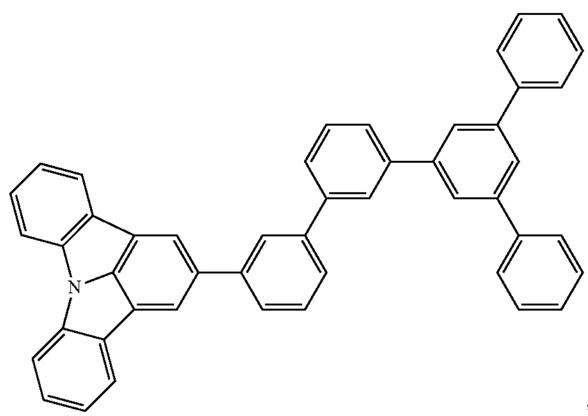
,
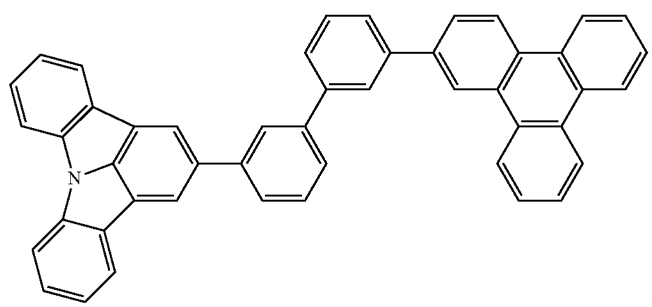
,
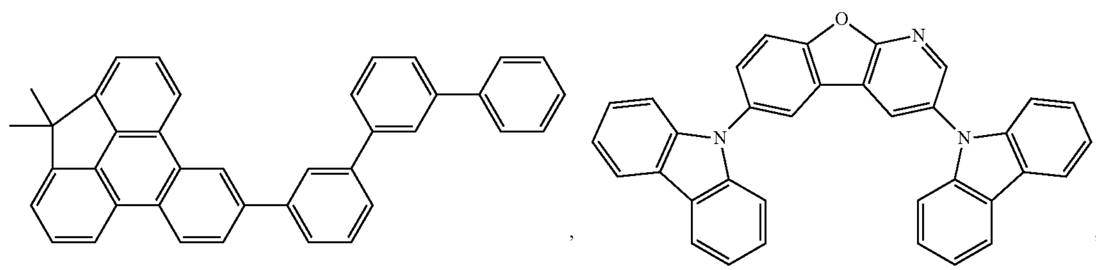
, , -continued
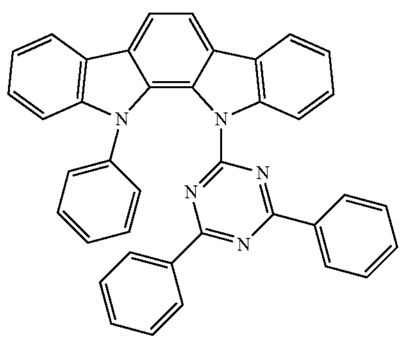
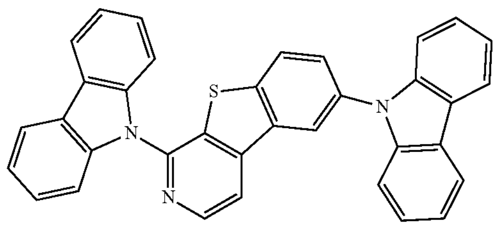
,
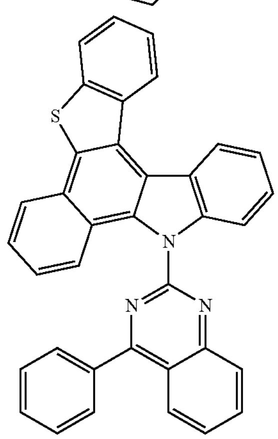
,
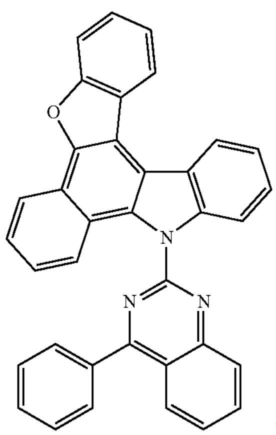
,
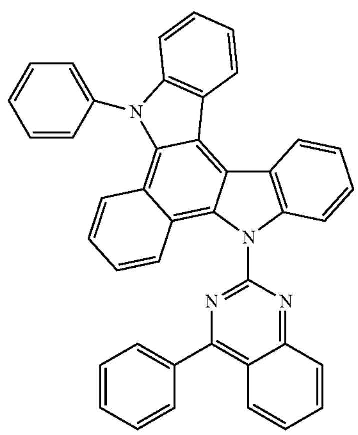
,,
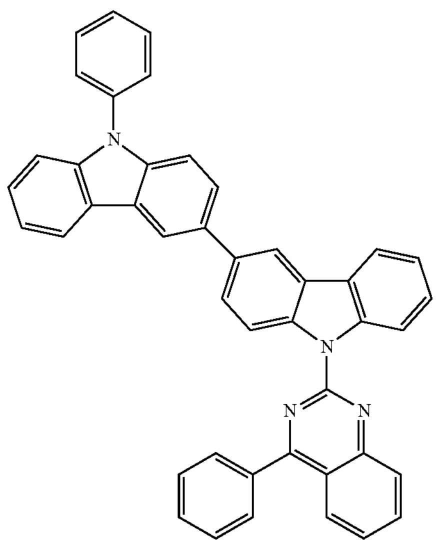
,
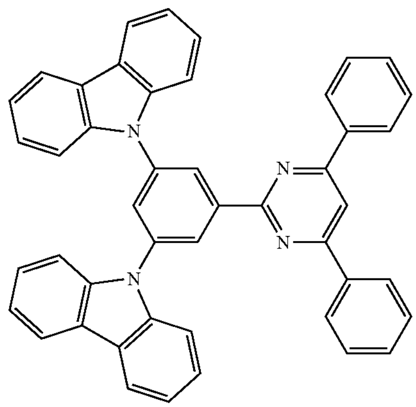
,
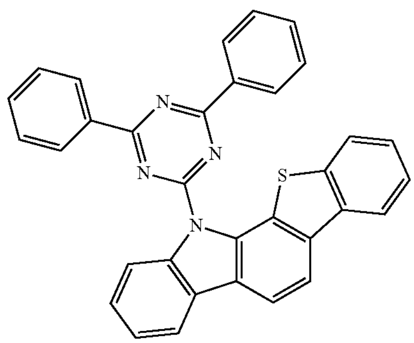
,
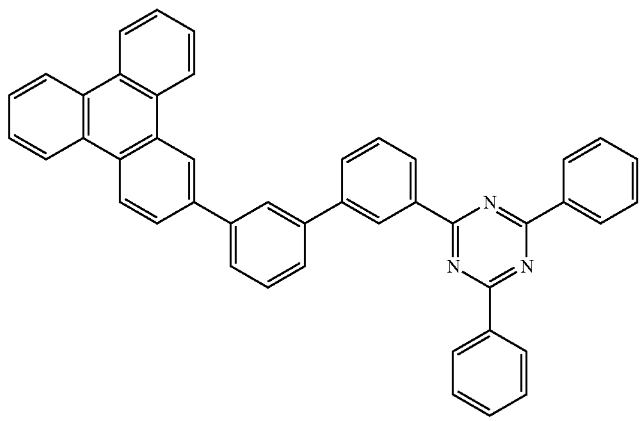
, -continued
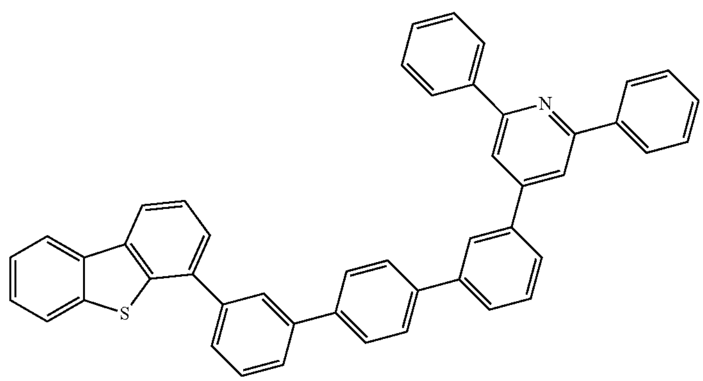
,
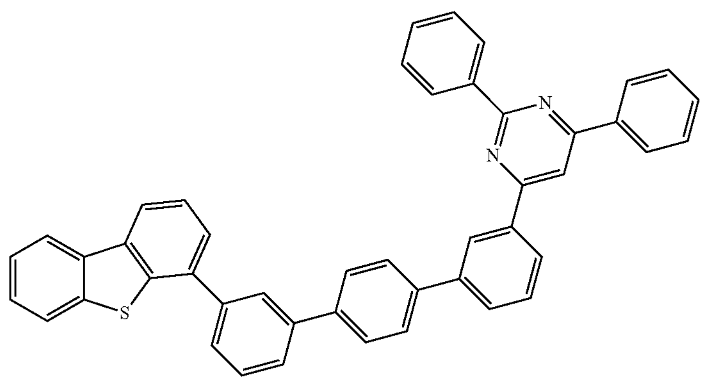
,
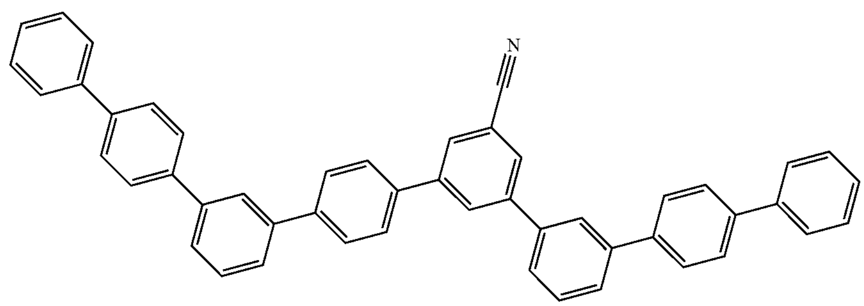
,
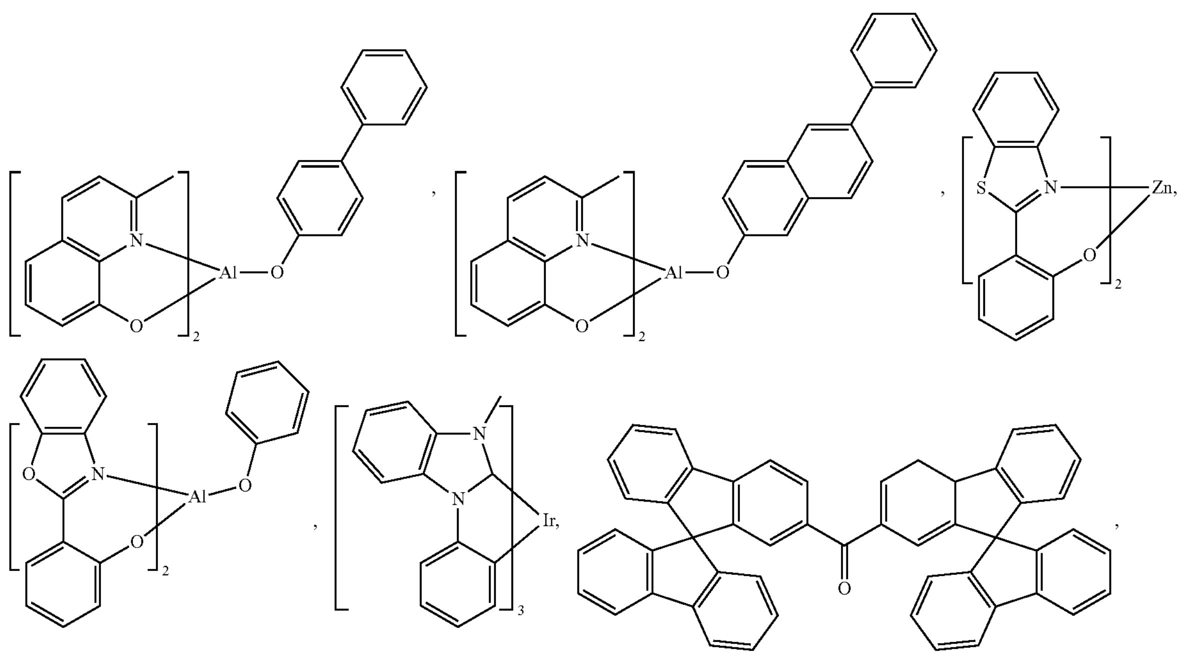

-continued

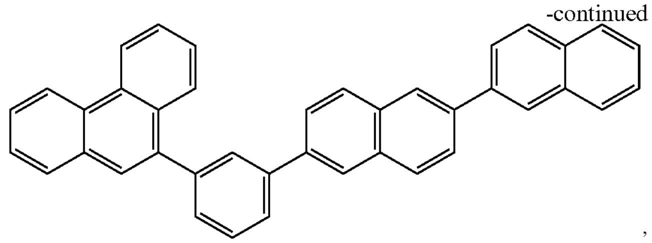

,

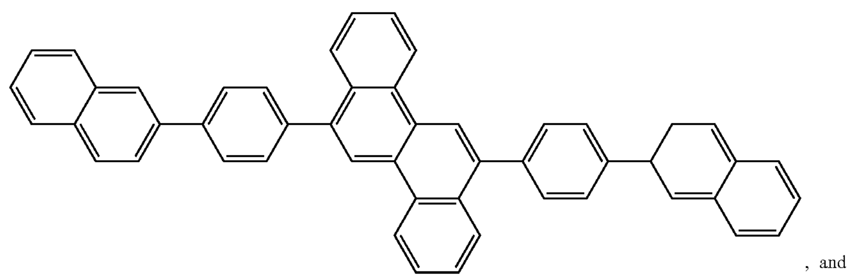

, and

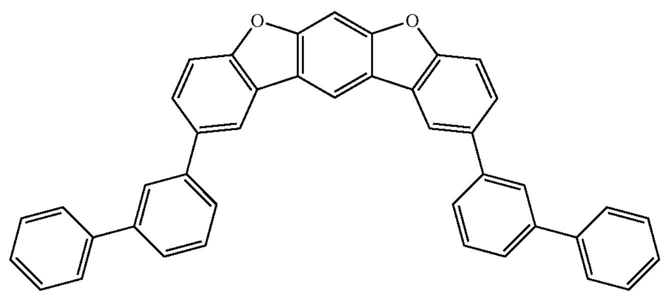 [SMILES: c1ccc(-c2cccc(-c3ccc4oc5cc6oc7ccc(-c8cccc(-c9ccccc9)c8)cc7c6cc5c4c3)c2)cc1]

.

Emitter:

An emitter dopant is not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

-continued
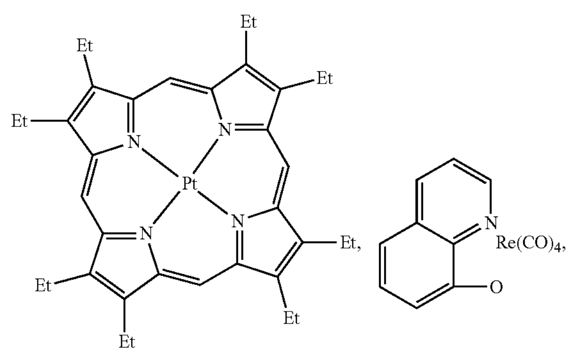
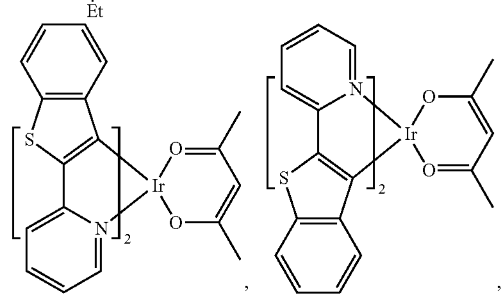
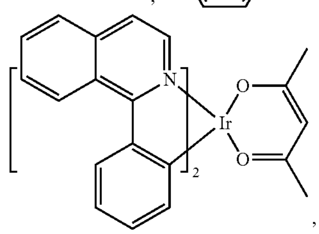
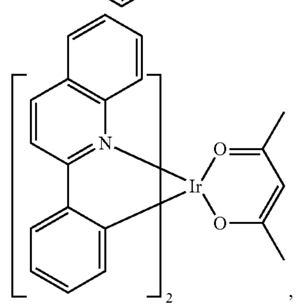
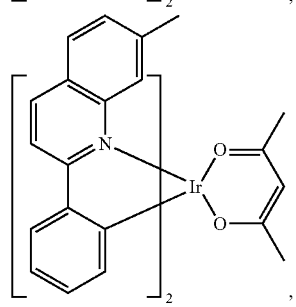
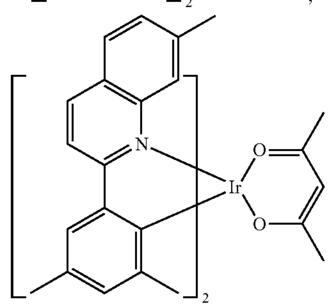
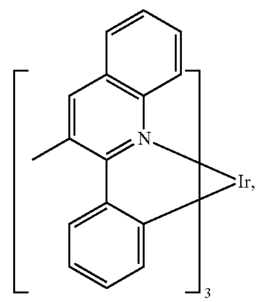
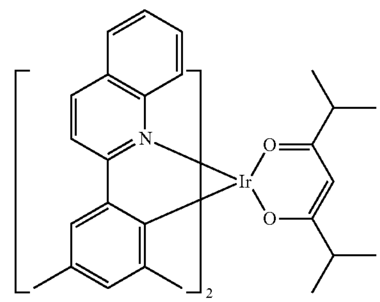
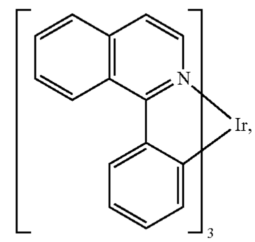
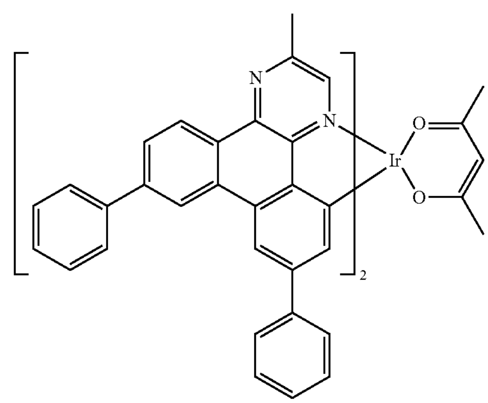
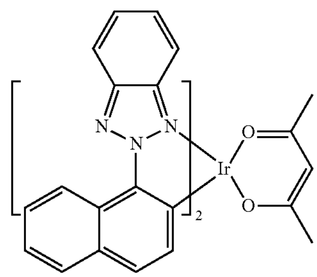

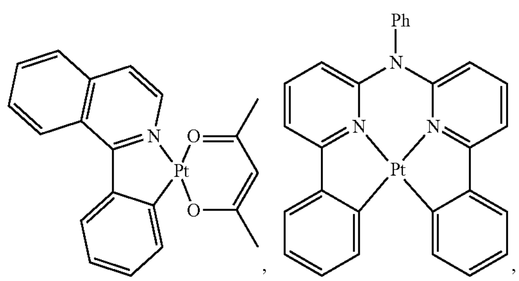
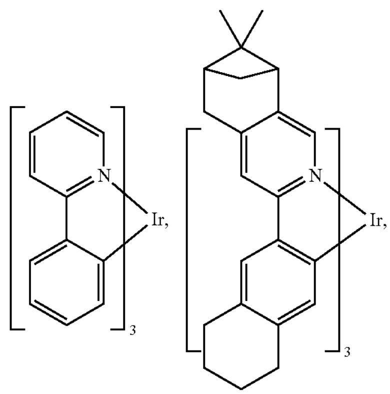
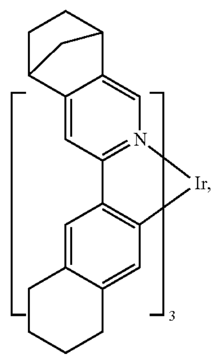
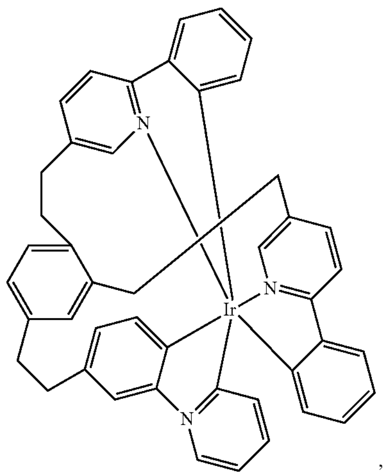
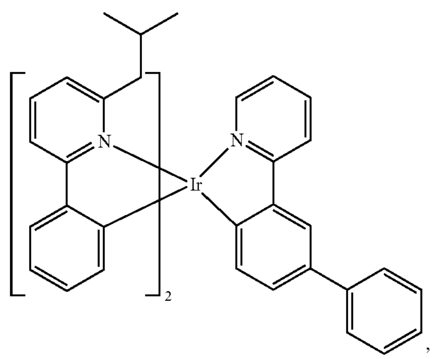
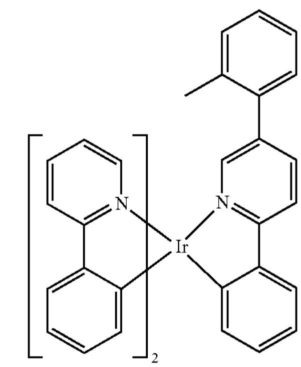
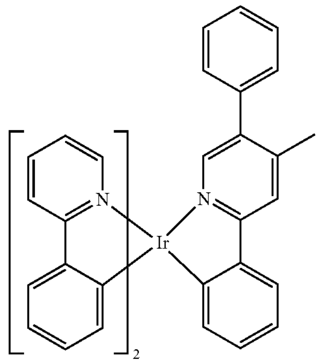
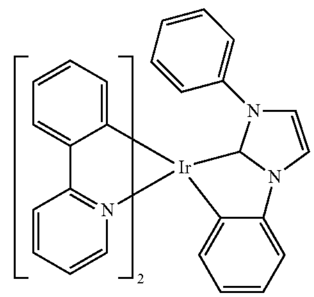
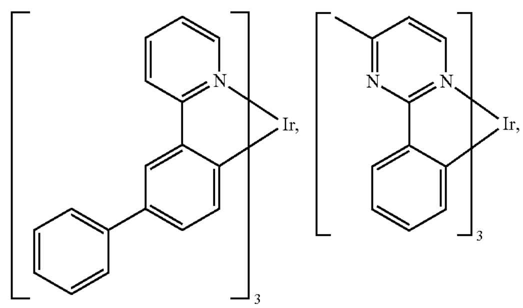

-continued
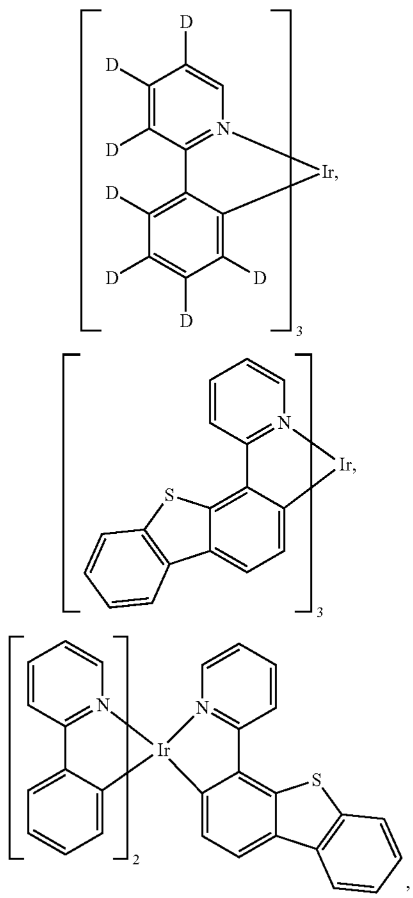
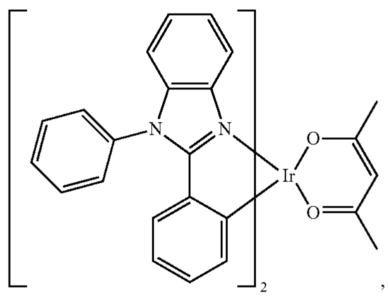
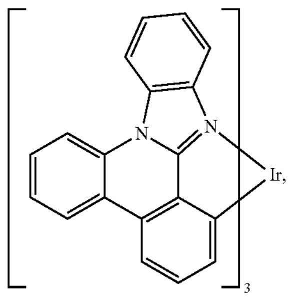
-continued
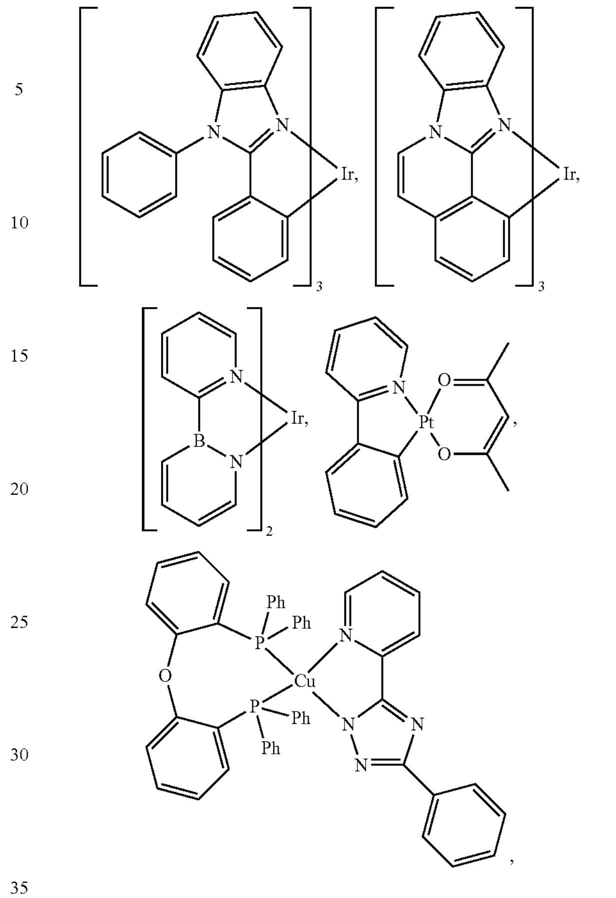
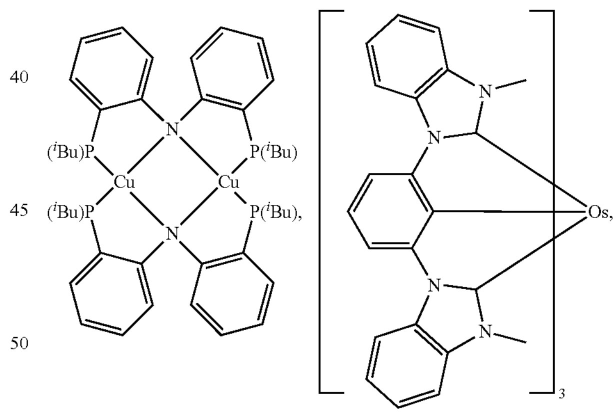
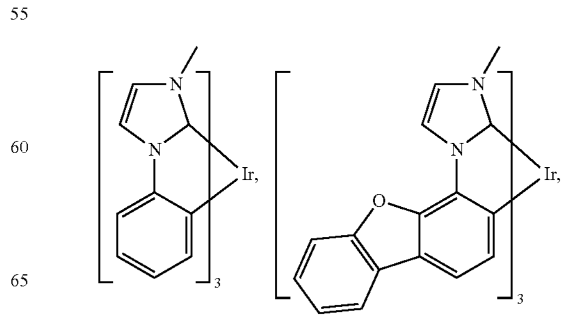

-continued
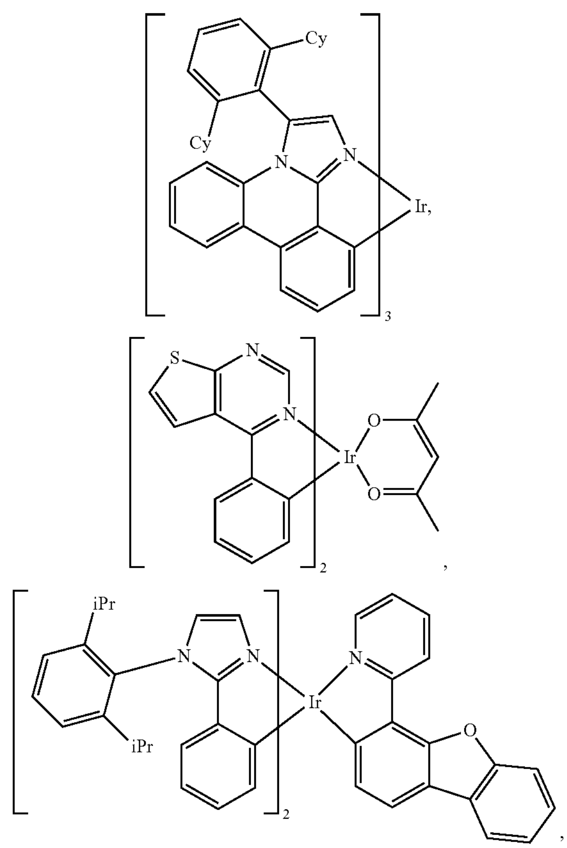
,
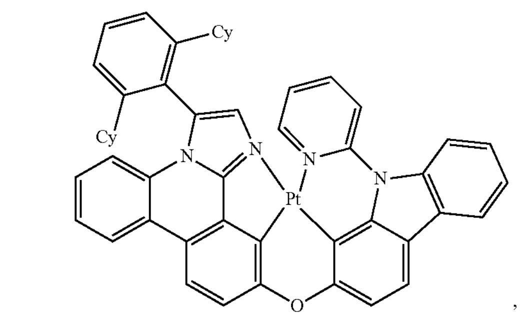
,
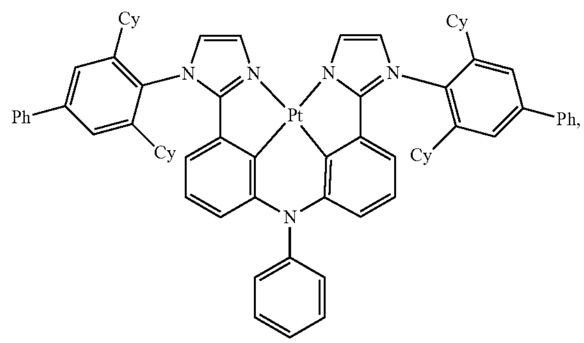
-continued
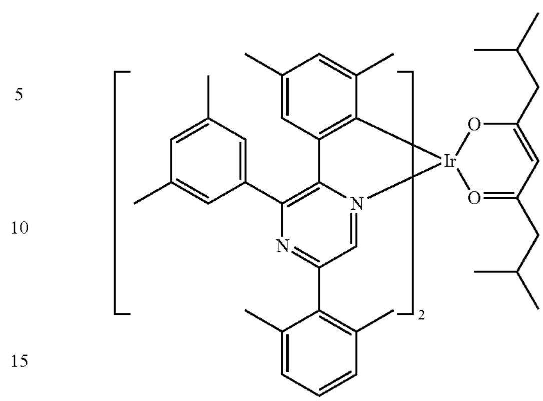
,
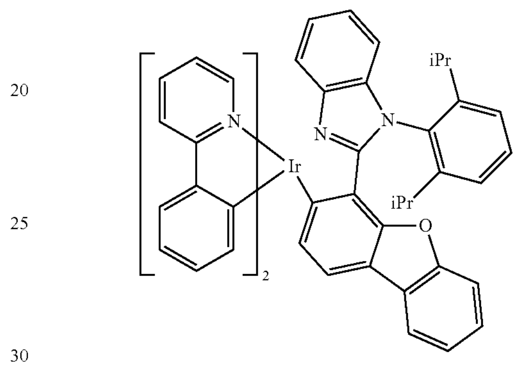
,
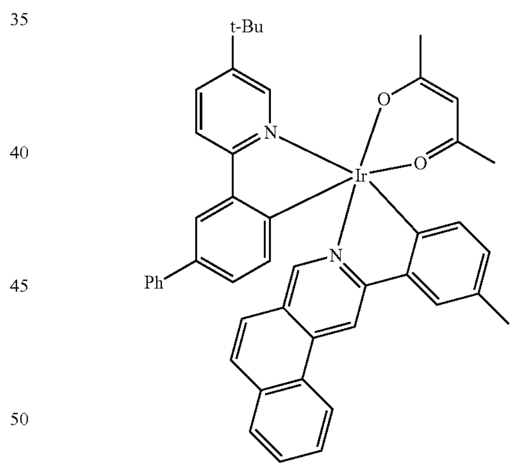
,
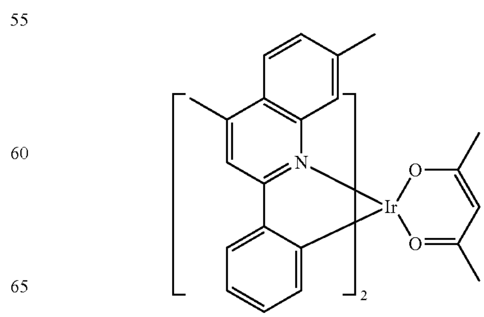
, -continued
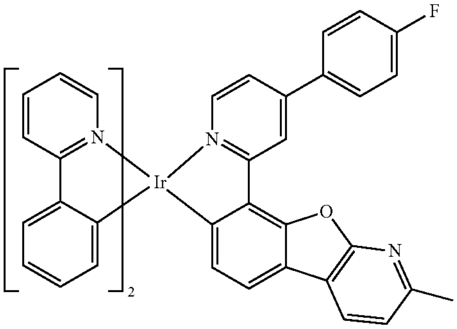
,
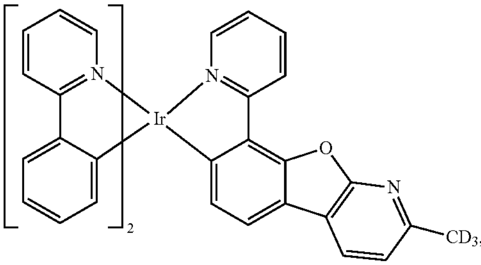
,
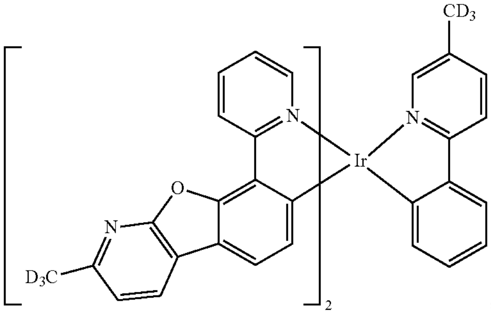
,
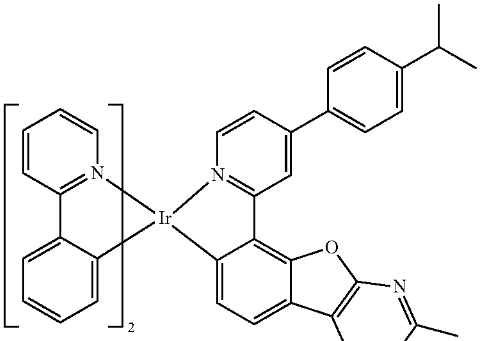
,
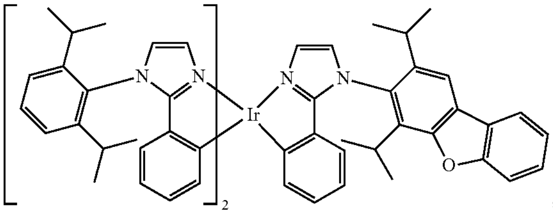
,
-continued
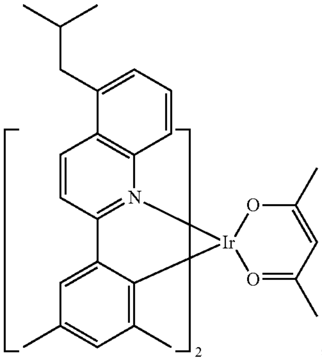
,
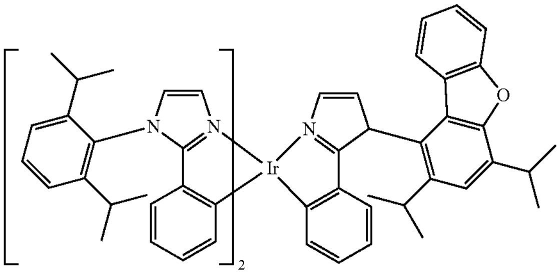
,
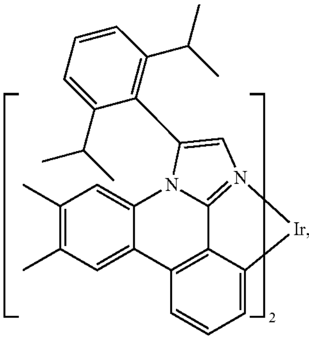
,
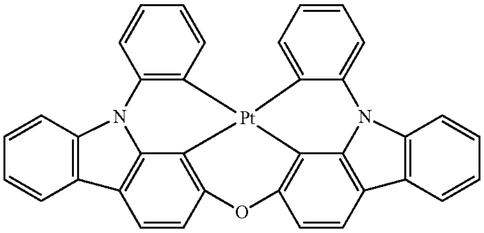
,
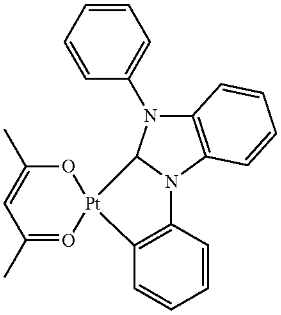
, -continued
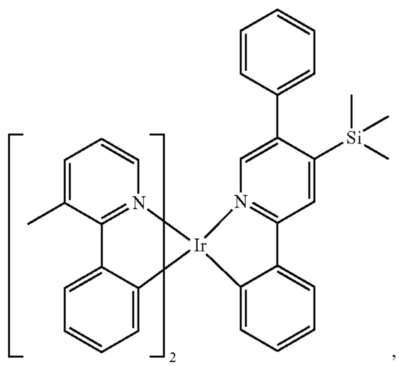
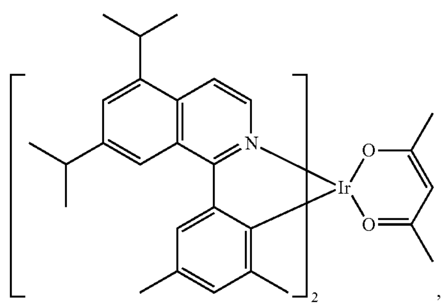
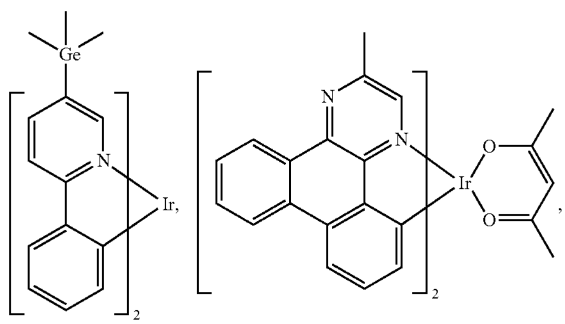
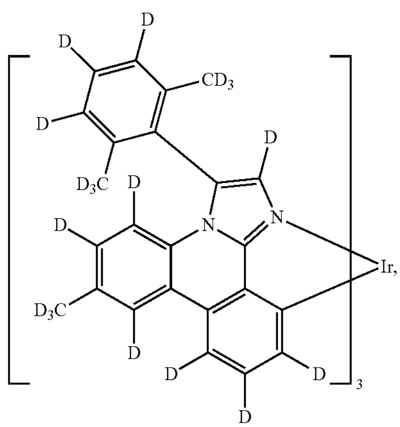
-continued
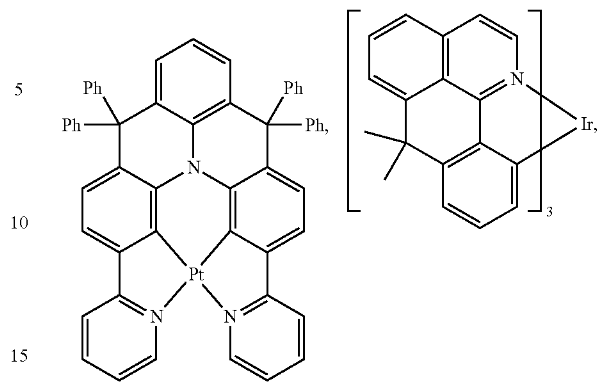
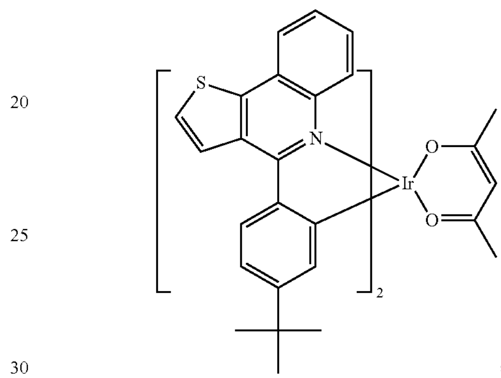
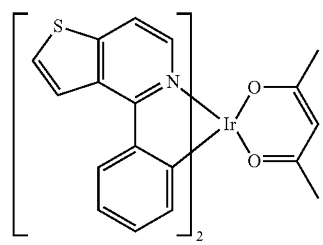
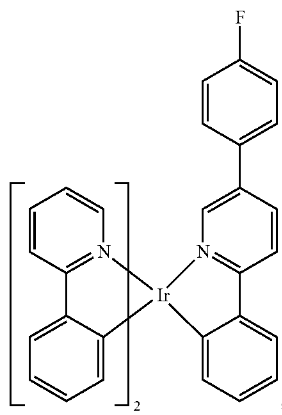

-continued
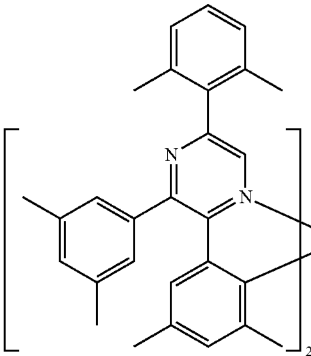
,
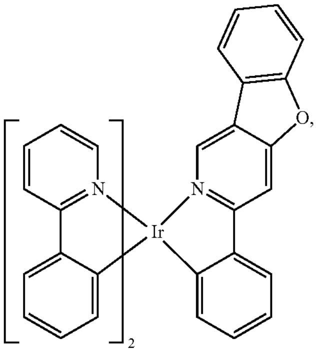
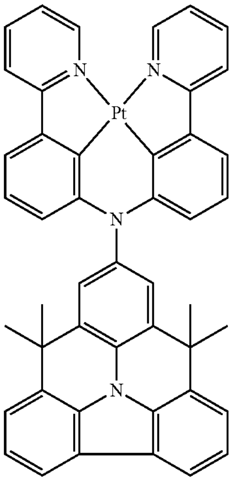
,
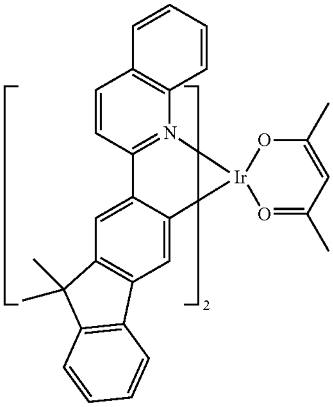
,
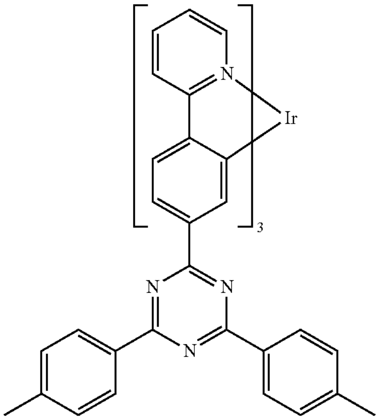
,
-continued
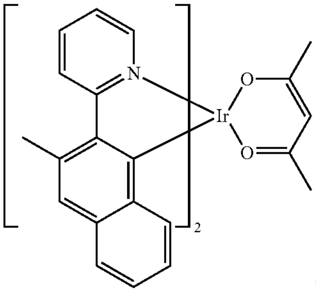
,
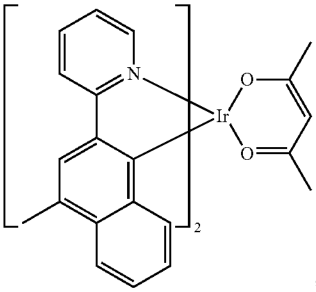
,
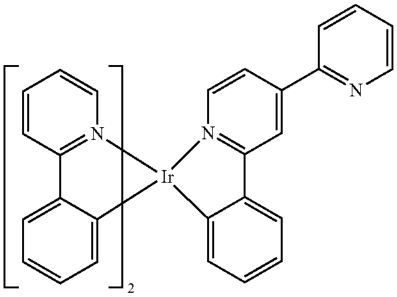
,
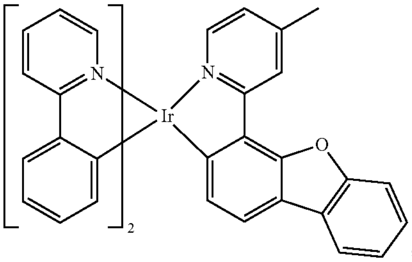
,
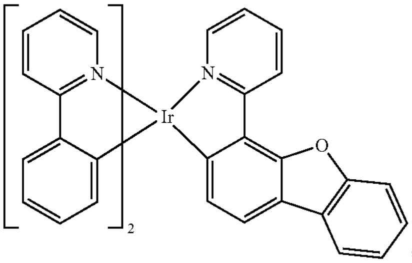
,
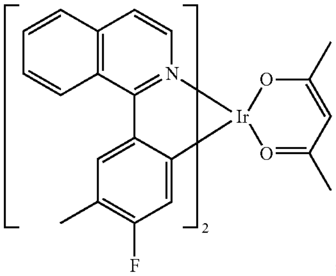
, -continued
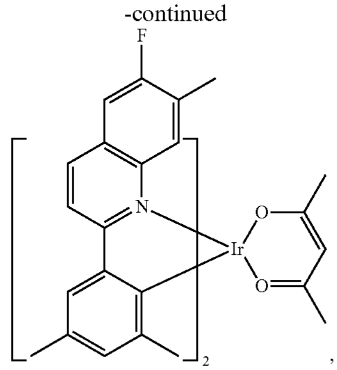
,
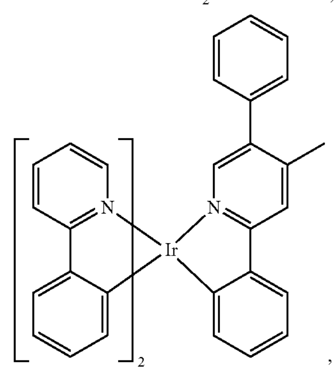
,
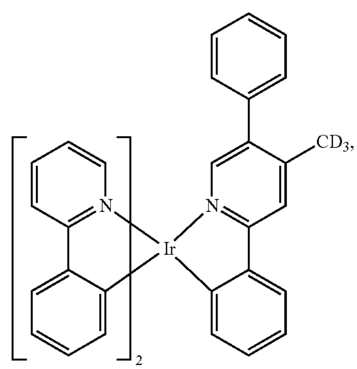
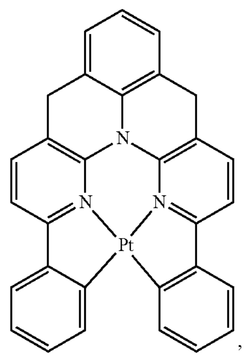
,
-continued
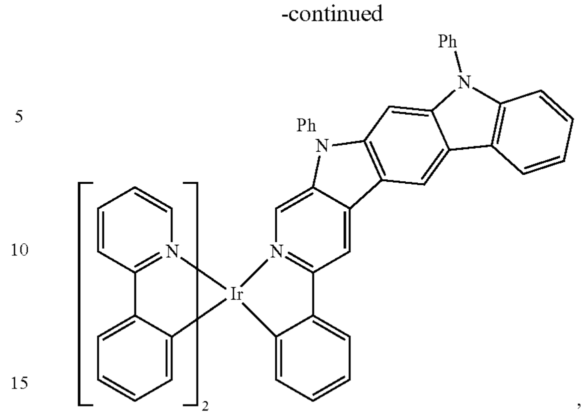
,
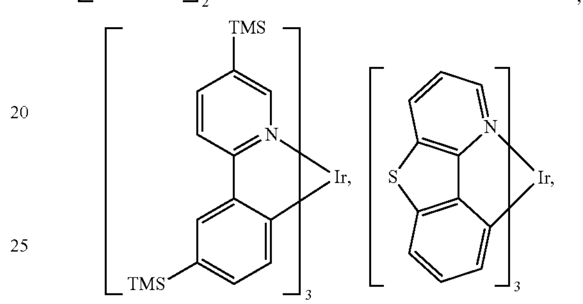
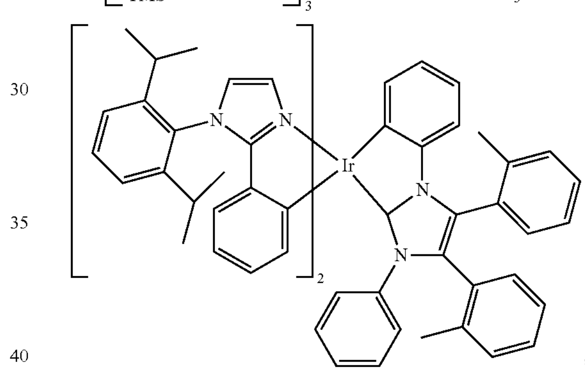
,
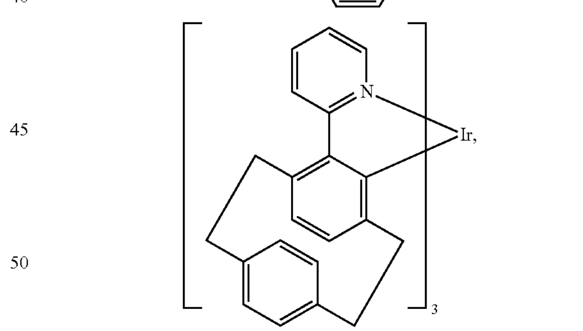
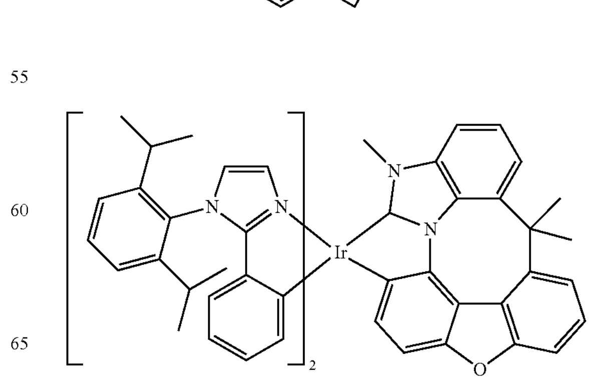
, -continued
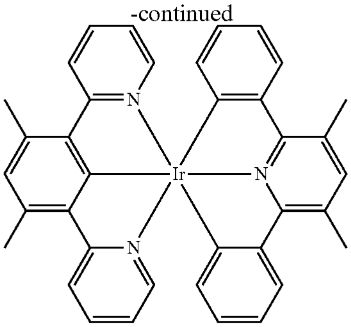
,
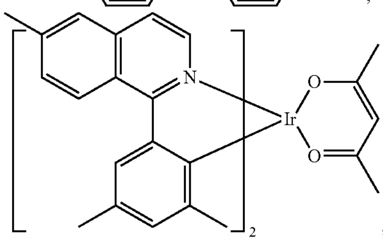
,
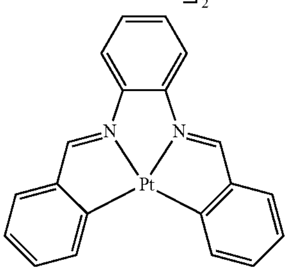
,
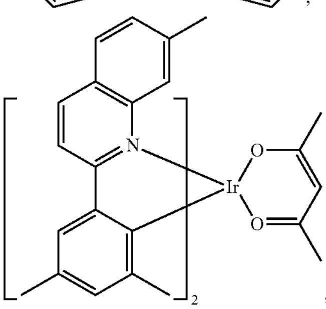
,
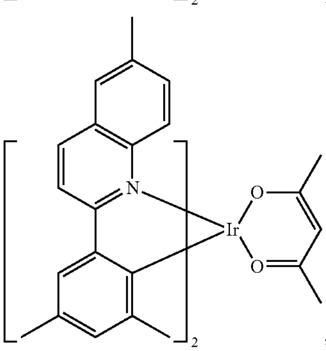
,
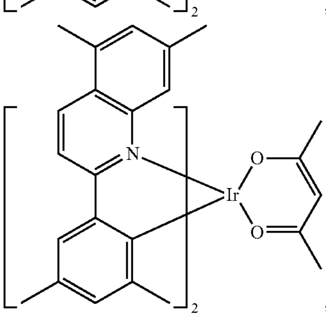
,
-continued
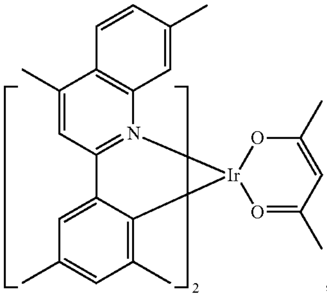
,
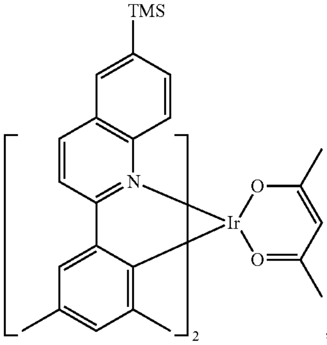
,
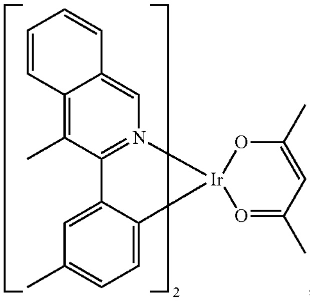
,
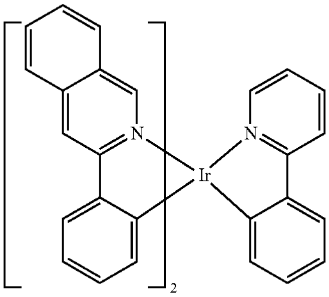
,
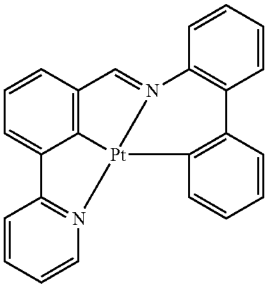
, -continued
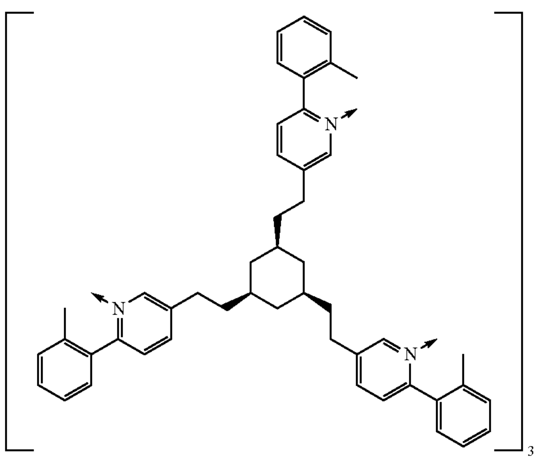
Ir,
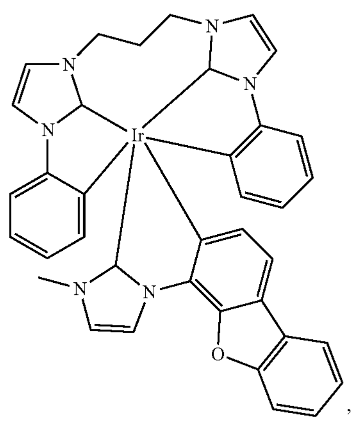
,
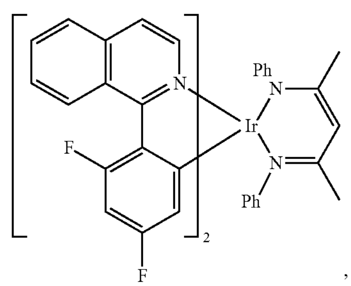
,
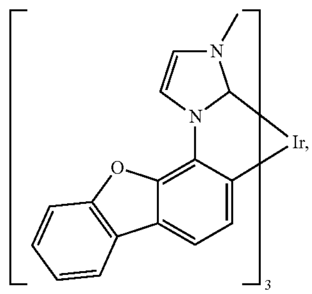
-continued
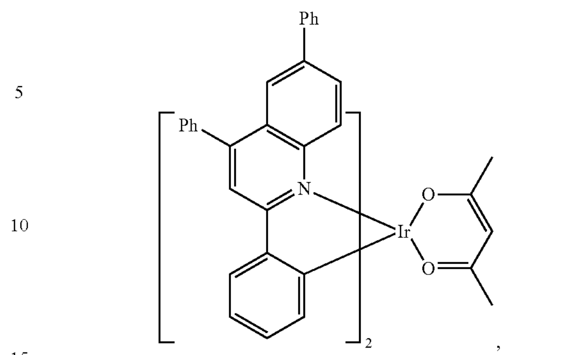
,
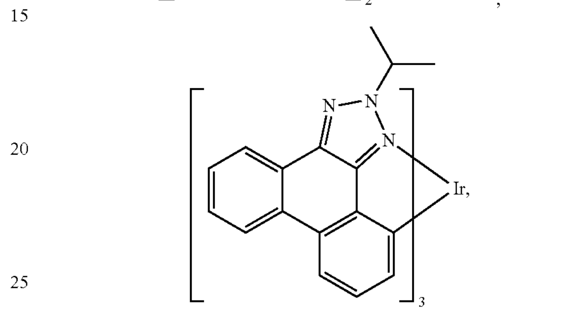
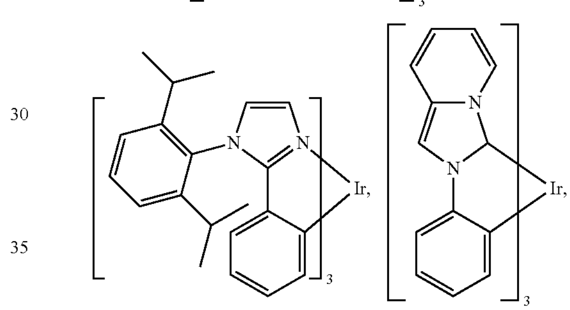
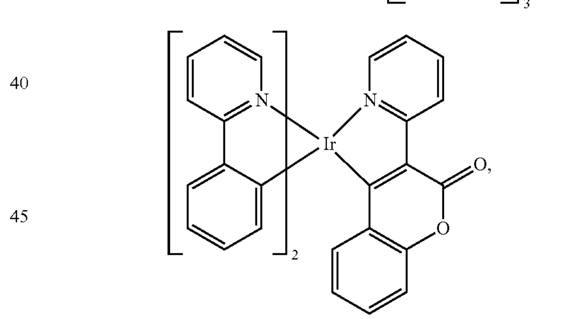
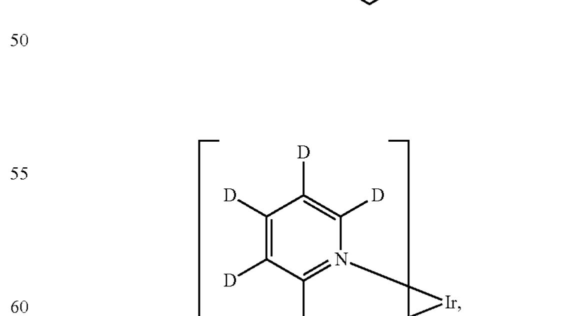
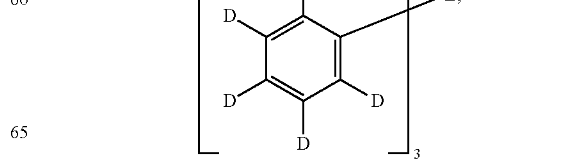

-continued

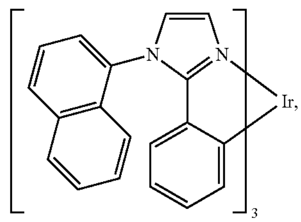

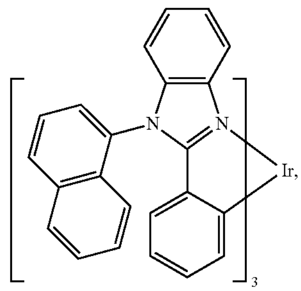

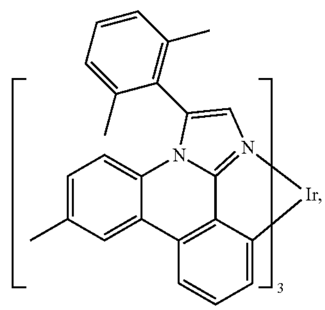

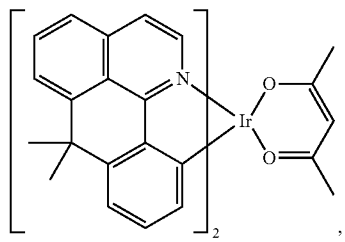

,

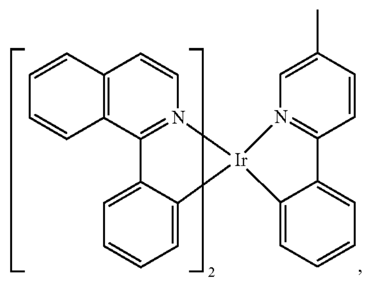

,

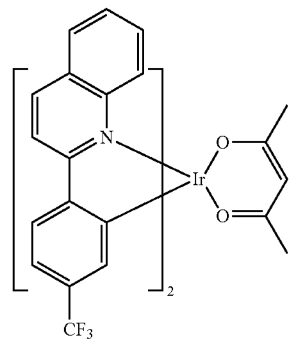

,

-continued

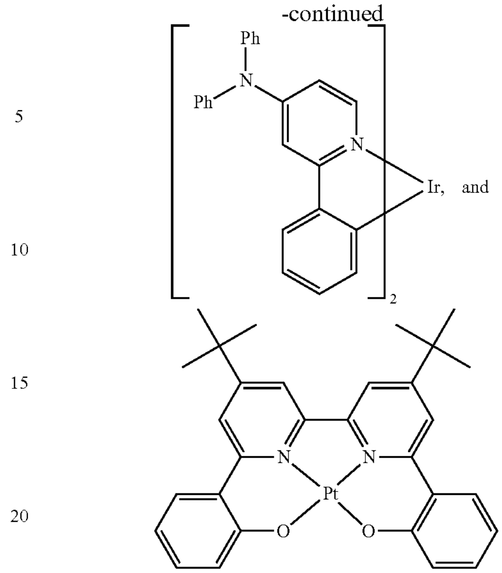

and

.

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

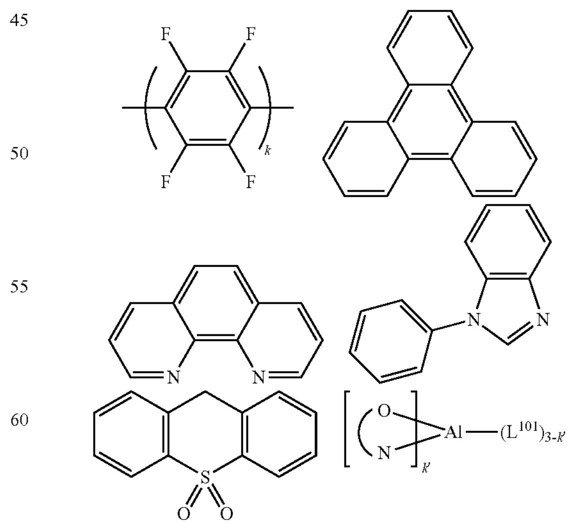

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

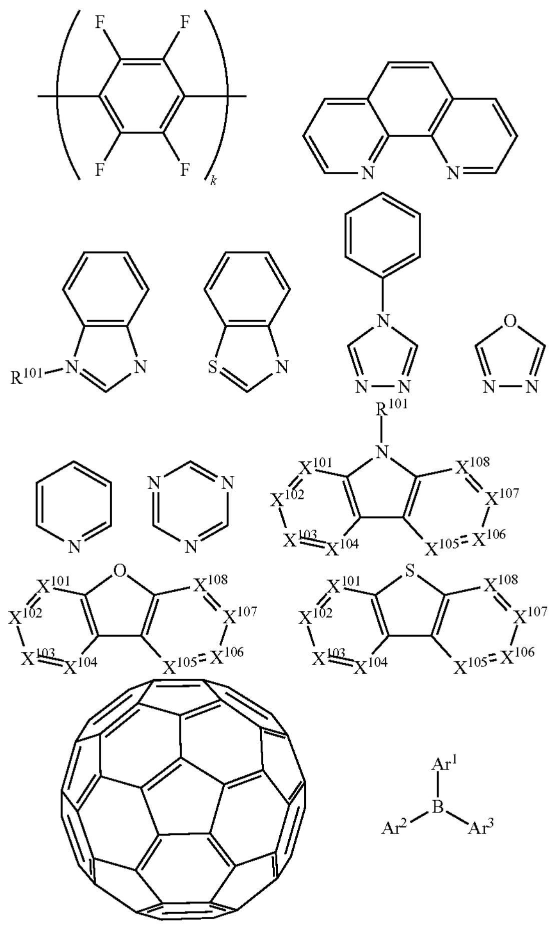

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contain, but are not limited to the following general formula:

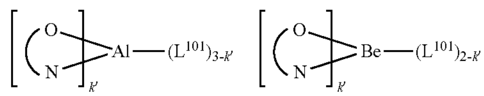

-continued

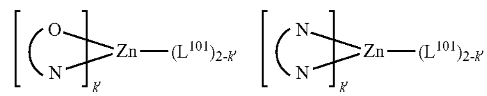

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535.

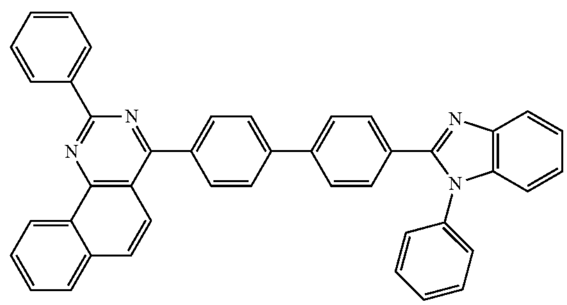

,

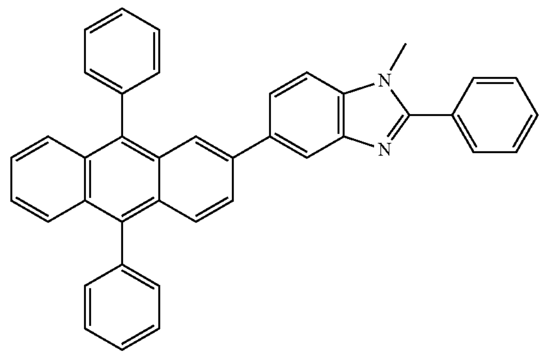

,

-continued
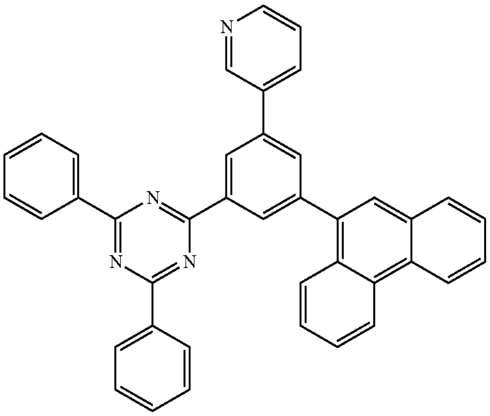
,
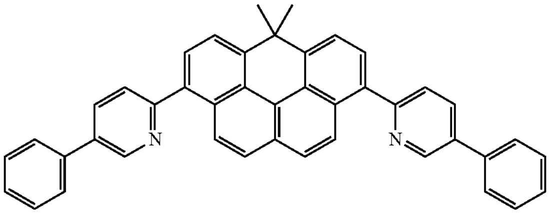
,
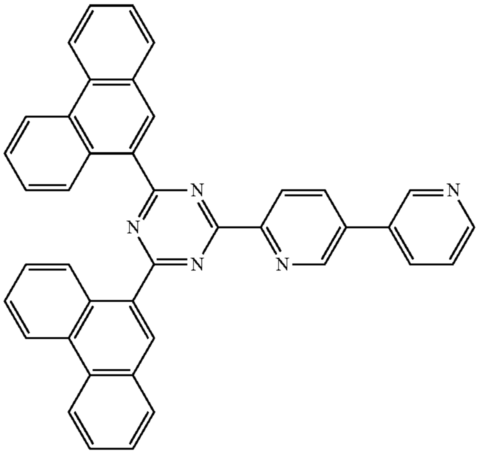
,
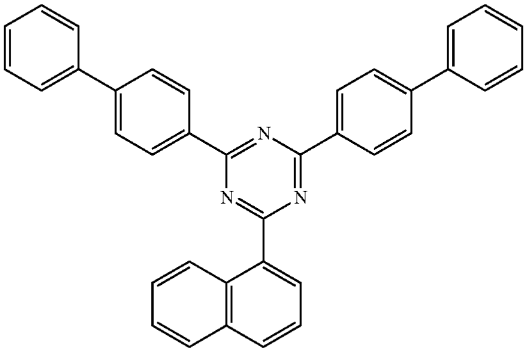
,
-continued
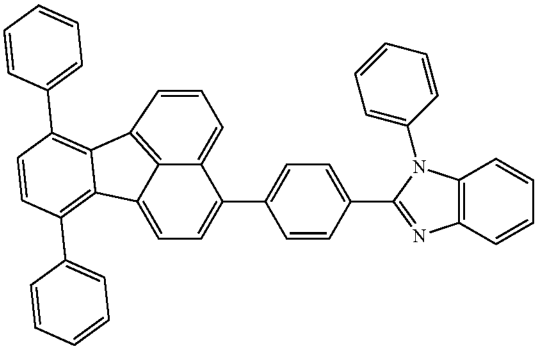
,
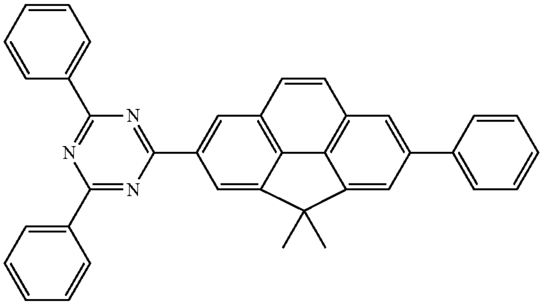
,
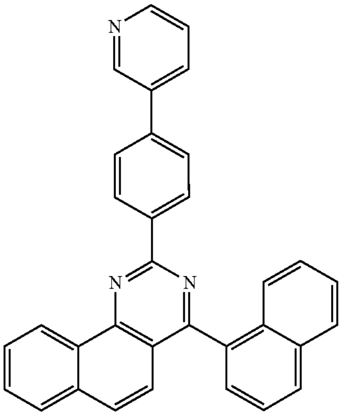
,
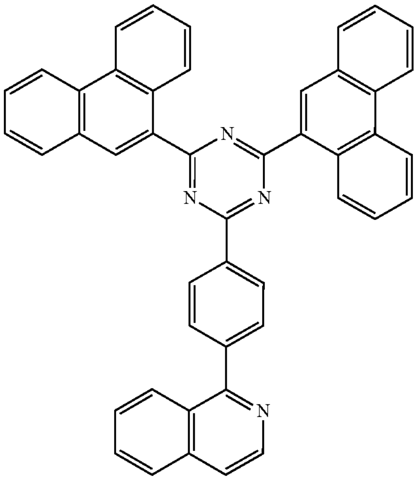
, -continued
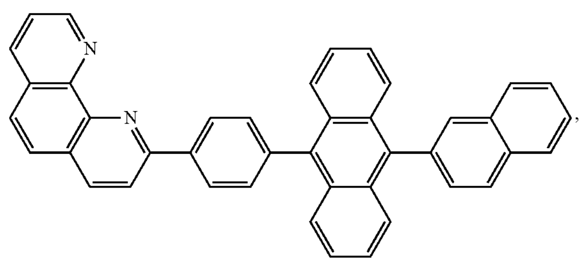
,
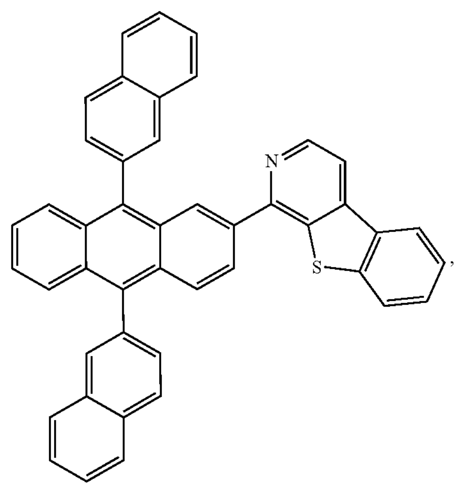
,
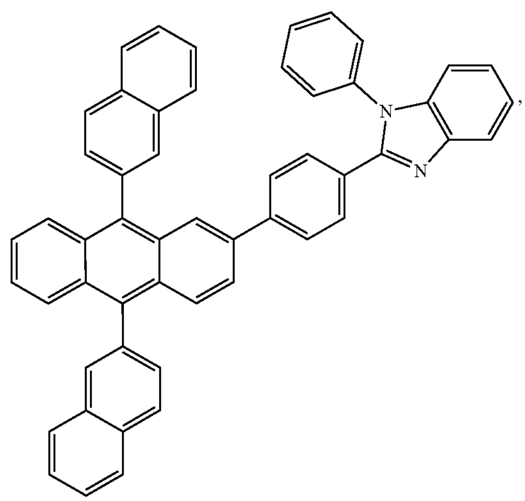
,
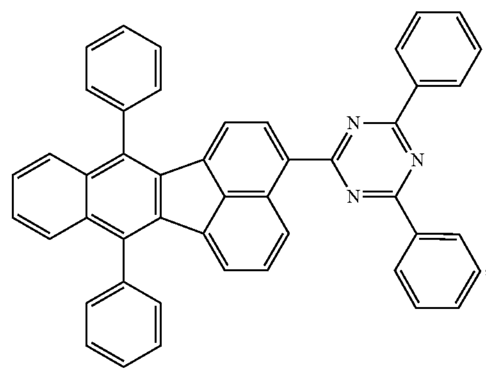
,
-continued
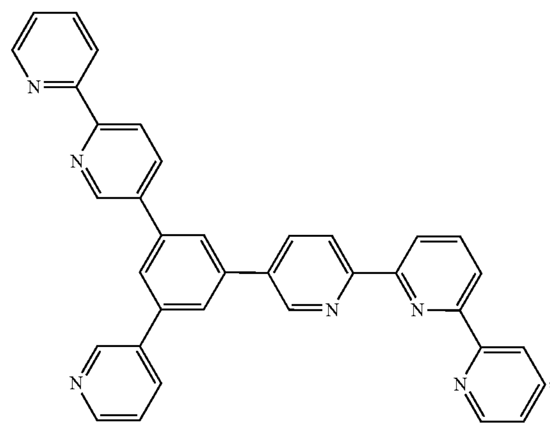
,
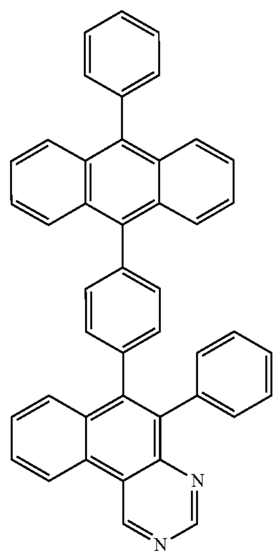
,
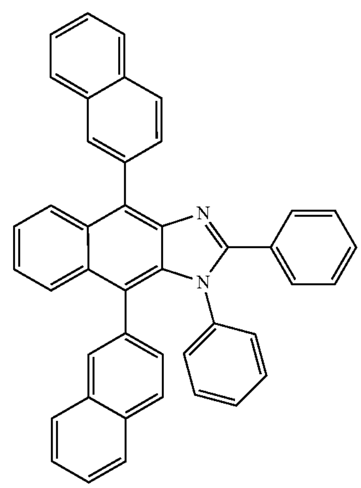
, -continued
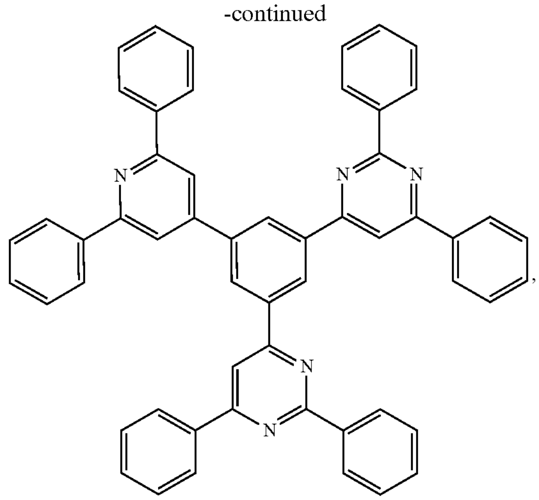
,
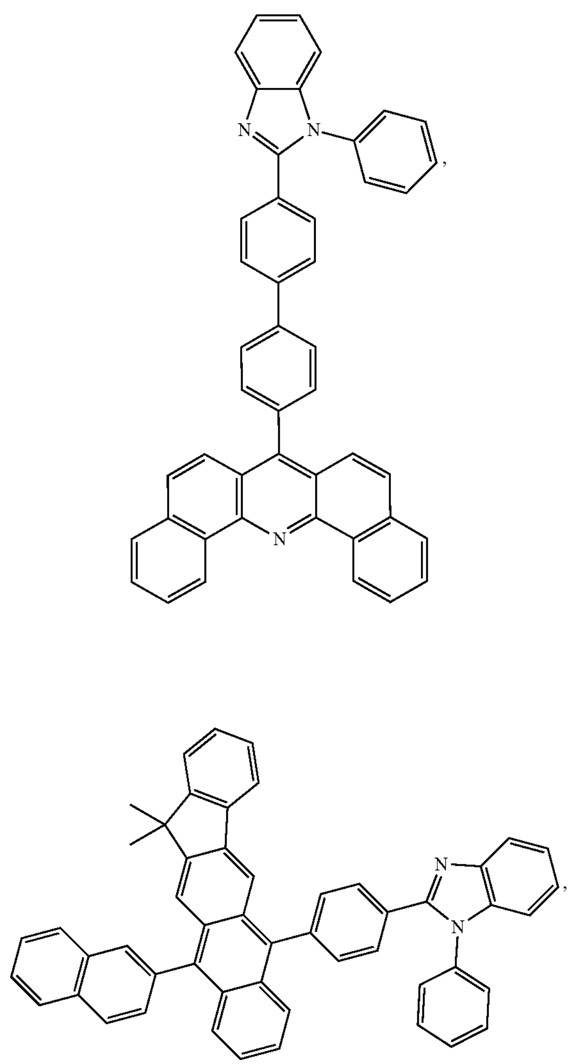
,
,
-continued
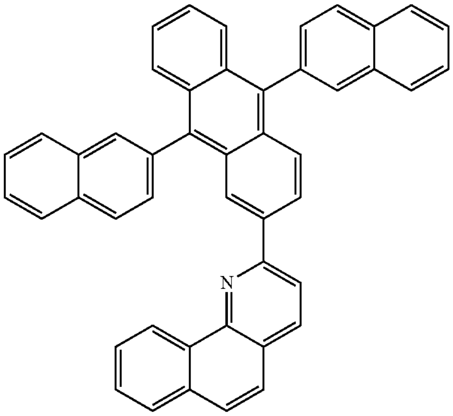
,
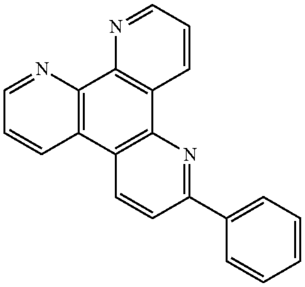
,
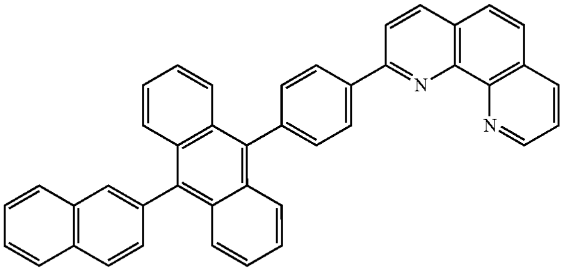
,
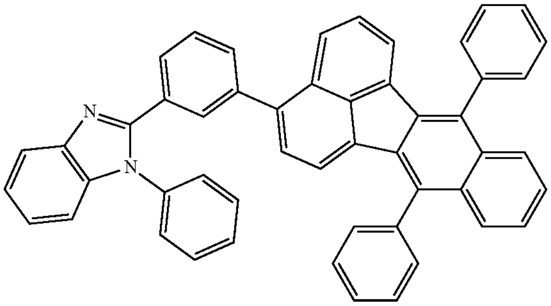
, -continued
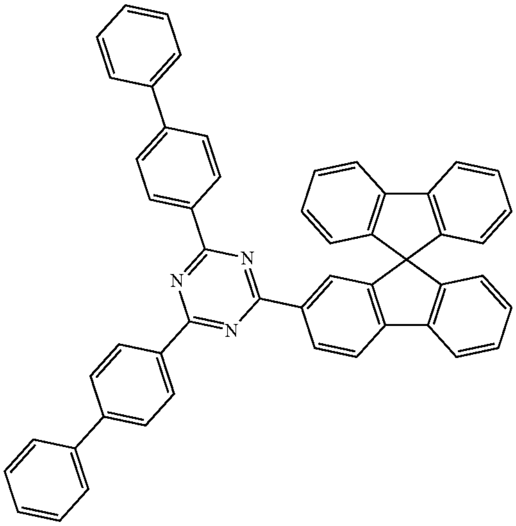
,
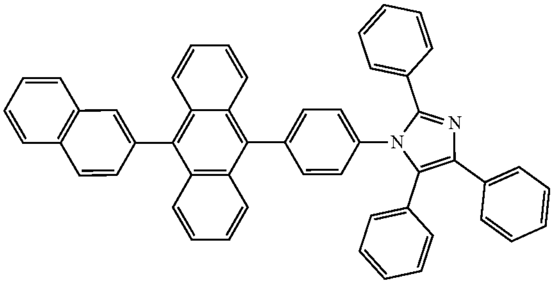
,
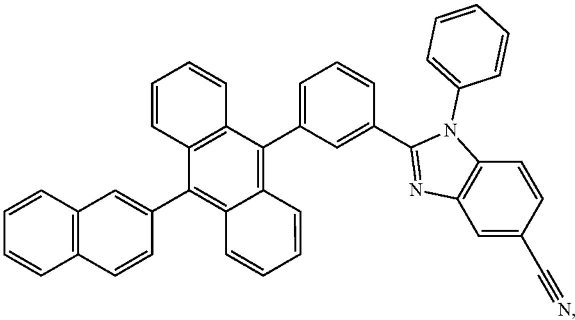
,
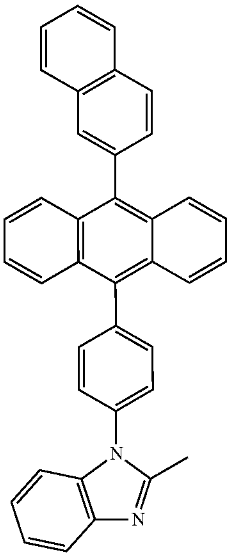
,
-continued
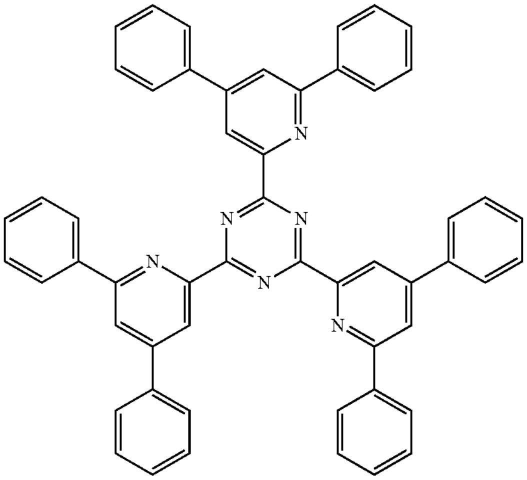
,
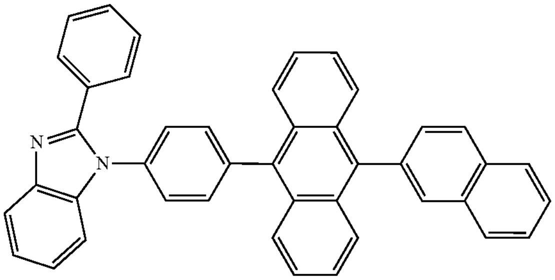
,
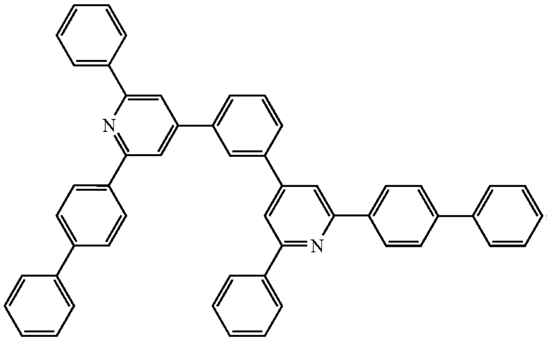
,
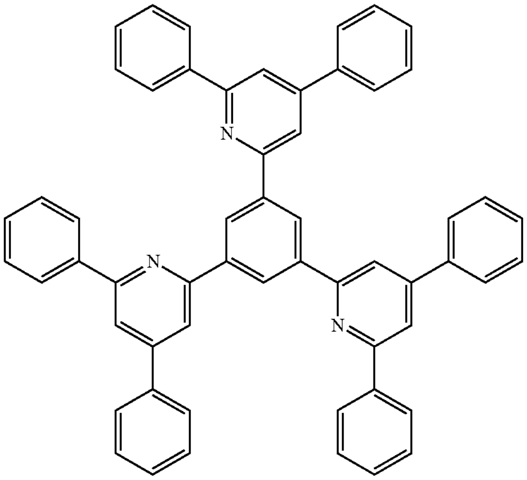
, -continued

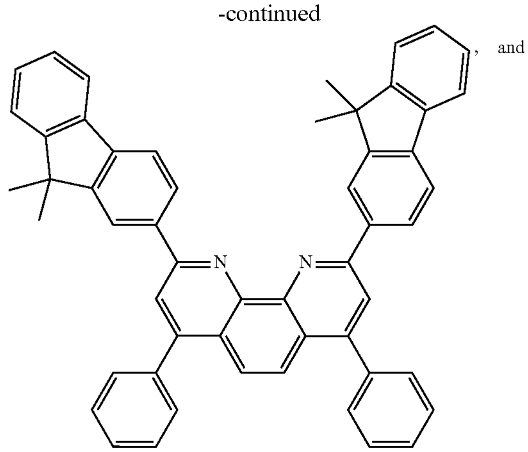

, and

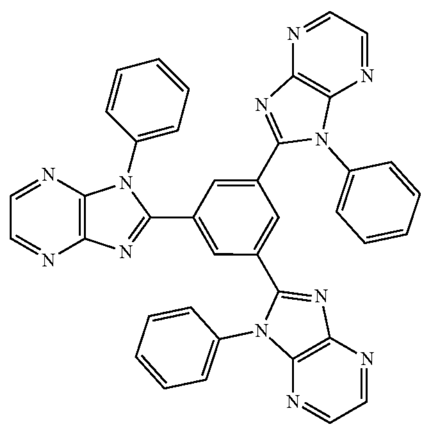

.

Charge Generation Layer (CGL):

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

Experimental

Materials Synthesis

Chemical abbreviations used throughout this document are as follows: $Pd_2(dba)_3$ is tri(dibenzylideneacetone) dipalladium(0), and SPhos is dicyclohexyl(2',6'-dimethoxy-[1,1'-biphenyl]-2-yl)phosphine.

Synthesis of Compound A2

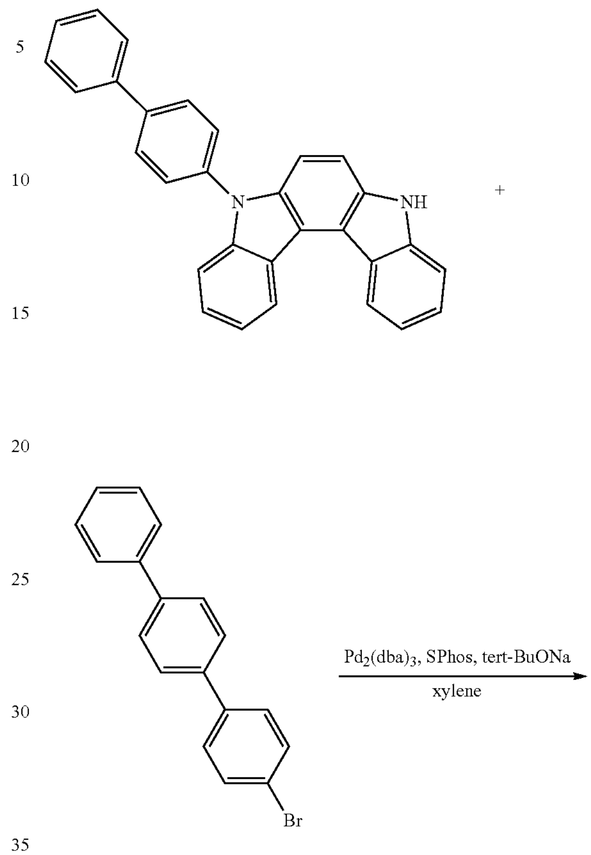

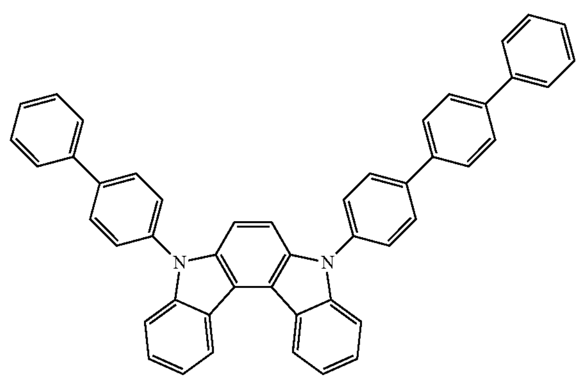

Compund A2

A mixture solution of 5-([1,1'-biphenyl]-4-yl)-5,8-dihydroindolo[2,3-c]carbazole (2 g, 4.90 mmol), 4-bromo-1,1':4',1"-terphenyl (1.817 g, 5.88 mmol), $Pd_2(dba)_3$ (0.224 g, 0.245 mmol), SPhos (0.201 g, 0.490 mmol) and tert-BuONa (1.18 g, 12.24 mmol) in xylene (80 ml) was refluxed under nitrogen for 16 h. The hot reaction mixture was filtered through a short plug of silica gel. Upon evaporation of the solvent, the residue was recrystallized from toluene and triturated with ethyl acetate to yield Compound A2 (1.84 g, 59%) as a white solid.

Synthesis of Compound B2

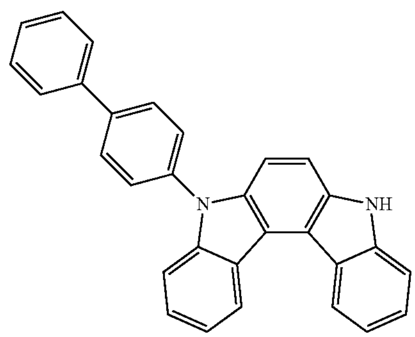

+

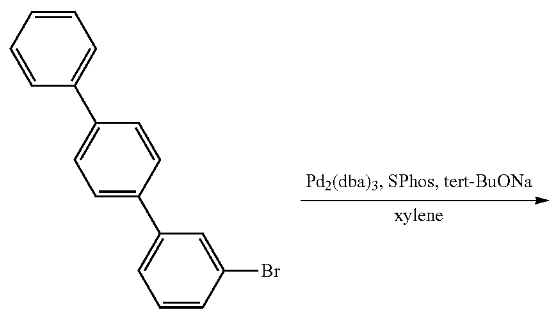

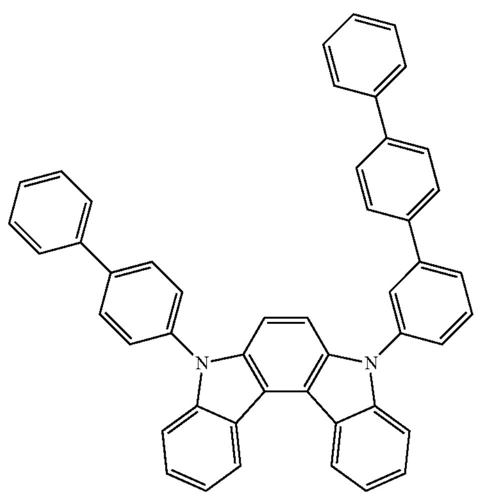

Compund B2

The procedure for the synthesis of Compound A2 was followed to synthesize Compound B2 from 5-([1,1'-biphenyl]-4-yl)-5,8-dihydroindolo[2,3-c]carbazole and 3-bromo-1,1': 4',1"-terphenyl. Compound B2 was synthesized as a white solid in a yield of 85%.

Synthesis of Compound D7

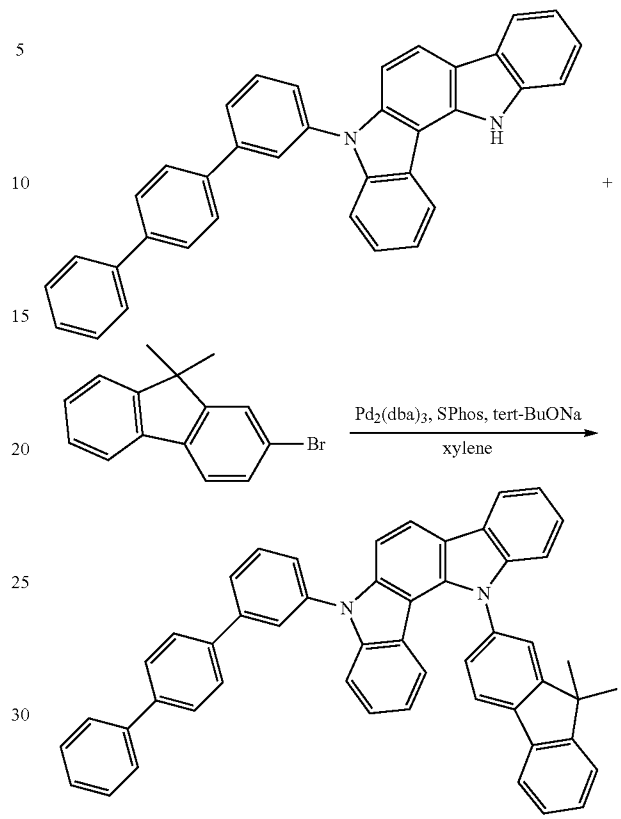

Compound D7

The procedure for the synthesis of Compound A2 was followed to synthesize Compound D7 from 5-([1,1': 4',1"-terphenyl]-3-yl)-5,12-dihydroindolo[3,2-a]carbazole and 2-bromo-9,9-dimethyl-9H-fluorene. Compound D7 was synthesized as a white solid in a yield of 50%.

Application in OLED.

All devices were fabricated by high vacuum (~$10^{-7}$ Torr) thermal evaporation. The anode electrode was 80 nm of indium tin oxide (ITO). The cathode electrode consisted of 1 nm of LiQ followed by 100 nm of A1. All devices were encapsulated with a glass lid sealed with an epoxy resin in a nitrogen glove box (<1 ppm of $H_2O$ and $O_2$) immediately after fabrication, and a moisture getter was incorporated inside the package.

Device Examples

A set of device examples have organic stacks consisting of, sequentially from the ITO surface, 10 nm of LG101 (from LG Chem) as the hole injection layer (HIL), 45 nm of PPh-TPD as the hole-transport layer (HTL), 40 nm of emissive layer (EML), 35 nm of compound EH-1 as the hole-blocking layer (HBL), followed by 35 nm of aDBT-ADN with 35 wt % LiQ as the electron-transport layer (ETL). The EML has two components: 90 wt % of the EML being the invented compounds (Compound A2 or Compound D7) or comparative compound (CC-1 or CC-2) as the host and 10 wt % of the EML being compound GD as the emitter. The chemical structures of the compounds used are shown below:

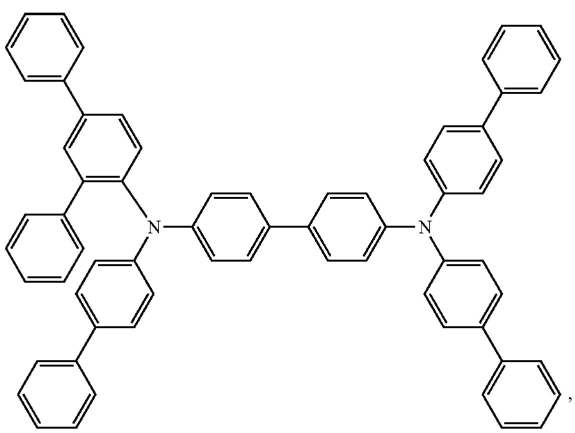
PPh-TPD
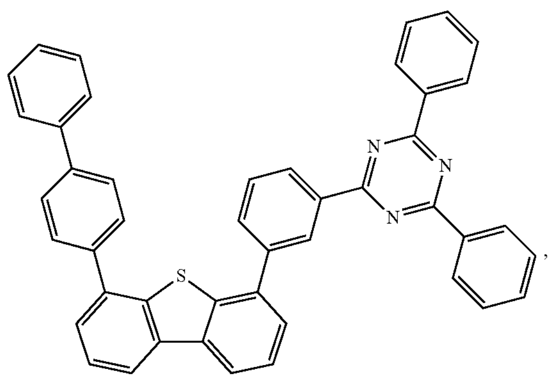
EH-1
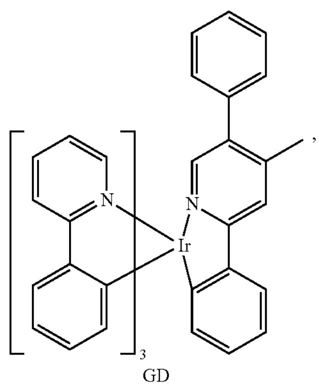
GD
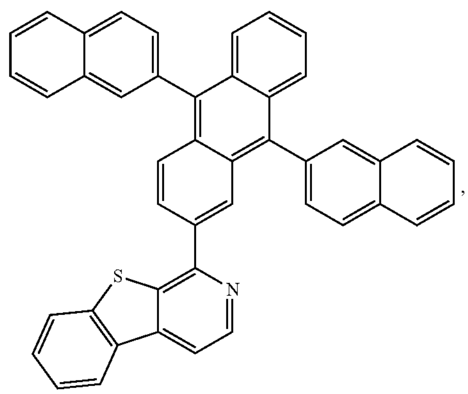
aDBT-ADN
-continued
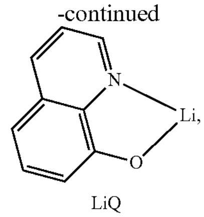
LiQ
Compound A2
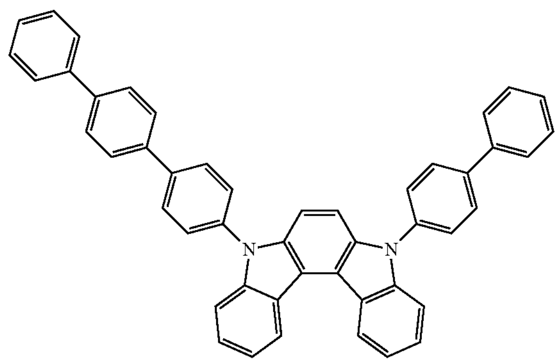
Compound D7
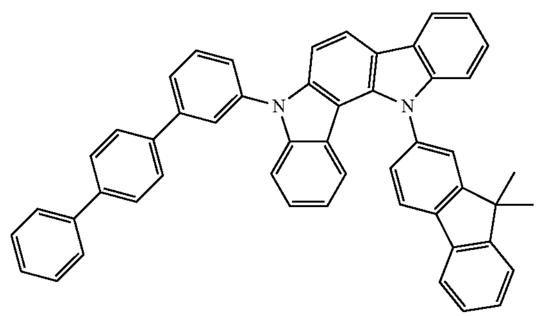
CC-1
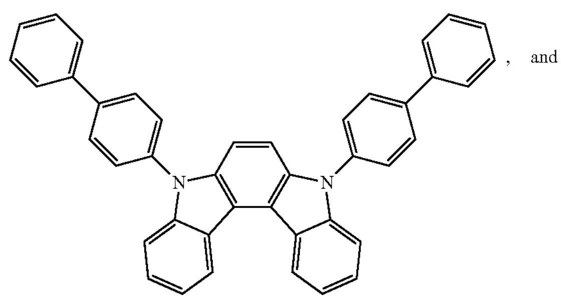
, and
CC-2
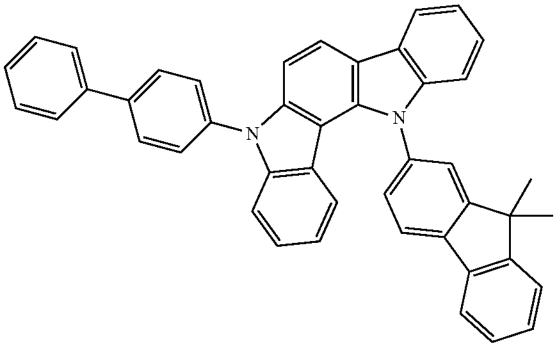
Provided in Table D1 below is a summary of the device data, emission color, power efficiency (PE) and relative lifetime LT97, recorded at 1000 nits for device examples. The relative lifetime LT80 (in arbitrary unit, A. U.), defined as the time it takes for a device to decay to 80% of its original luminescence under a constant operation current density that provides an initial luminescence of 1000 nits, is calculated from the measured value recorded at 40 $mA/cm^2$, assuming an acceleration factor of 1.8, and is normalized to that of Device C-1.

TABLE D1

| | EML | | Emission | PE | LT80 |
|---|---|---|---|---|---|
| Device ID | Host | Emitter | Color | [lm/W] | [A.U.] |
| Device 1 | Compound A2 | GD | Green | 41.2 | 177 |
| Device C-1 | CC-1 | GD | Green | 40.6 | 100 |
| Device 2 | Compound D7 | GD | Green | 17.7 | 246 |
| Device C-2 | CC-2 | GD | Green | 12.0 | 93 |

The device data in Table D1 shows that the inventive Compounds A2 and D7 produce longer lifetime, while maintaining equivalent or higher efficiency, than their corresponding comparative compounds CC-1 and CC-2, respectively. The enhanced performance of inventive compounds might be attributable to the extended conjugation of the terphenyl moiety than the biphenyl moiety, which could improve charge transport properties of the inventive compounds.

Provided in Table PM below is a summary of the compatibility of selected h- and e-hosts was evaluated by compositional analysis of films fabricated by single-source co-evaporation of the premixture of these two components. A first set of potential premixtures of selected h- and e-hosts are presented in Table PM.

TABLE PM

Potential premixtures comprising selected h- and e-hosts

| Premixtures | e-hosts | h-hosts |
|---|---|---|
| PM-1 | Compound F5 | Compound B2 |
| PM-2 | Compound F5 | Compound A3 |
| PM-3 | Compound F11 | Compound C2 |
| PM-4 | Compound F11 | Compound B15 |
| PM-5 | Compound F14 | Compound A9 |
| PM-6 | Compound F14 | Compound A38 |
| PM-7 | Compound F14 | Compound B22 |
| PM-8 | Compound F17 | Compound A3 |
| PM-9 | Compound F17 | Compound B2 |
| PM-10 | Compound F17 | Compound C5 |
| PM-11 | Compound H74 | Compound A35 |
| PM-12 | Compound H74 | Compound D1 |
| PM-13 | Compound H83 | Compound B2 |
| PM-14 | Compound H83 | Compound A3 |
| PM-15 | Compound H248 | Compound E14 |
| PM-16 | Compound M2 | Compound C1 |
| PM-17 | Compound M5 | Compound D6 |
| PM-18 | Compound G9 | Compound B2 |
| PM-19 | Compound M101 | Compound B5 |
| PM-20 | Compound G0 | Compound B2 |

Premixture PM-1: Compound F5 and Compound B2 were provided at a weight ratio of 1:1, physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The compositions of films were analyzed by high-performance liquid chromatography (HPLC) and the results are shown in Table 1.

TABLE 1

HPLC composition (%) of sequentially deposited films form a premixture (PM-1) comprising Compound F5 and Compound B2 with weight ratio 1:1. HPLC Conditions: C18 reverse column, 100% acetonitrile as mobile phase, detection wavelength wavelength 254 nm. Due to different absorption coefficients, the HPLC composition may or may not agree with the weight ratio.

| | F5 | B2 |
|---|---|---|
| Plate1 | 55.7 | 44.3 |
| Plate2 | 56.1 | 43.9 |
| Plate3 | 52.2 | 47.8 |
| Plate4 | 46.5 | 53.5 |

Premixture PM-9: Premixture PM-9 comprising Compound F17 and Compound B2 were evaluated in the same way as premixture PM-1, except that a weight ratio of 1:1 for Compound F17 and Compound B2 was used, and the results are presented in Table 2.

TABLE 2

HPLC composition (%) of sequentially deposited films from Premixture PM-9 comprising Compound E17 and Compound B2 with weight ratio 1:1. HPLC Conditions: C18 reverse column, 100% acetonitrile as mobile phase, detection wavelength wavelength 254 nm. Due to different absorption coefficients, the HPLC composition may or may not agree with the weight ratio.

| | F17 | B2 |
|---|---|---|
| Plate1 | 58.7 | 41.3 |
| Plate2 | 60.7 | 39.3 |
| Plate3 | 62.1 | 37.9 |
| Plate4 | 63.4 | 36.6 |
| Plate5 | 64.8 | 35.2 |

Premixture PM-13: Premixture PM-13 comprising Compound H83 and Compound B2 were evaluated in the same way as premixture PM-9, and the results are presented in Table 3.

TABLE 3

HPLC composition (%) of sequentially deposited films from Premixture PM-13 comprising Compound H83 and Compound B2 with weight ratio 1:1. HPLC Conditions: C18 reverse column, 100% acetonitrile as mobile phase, detection wavelength wavelength 254 nm. Due to different absorption coefficients, the HPLC composition may or may not agree with the weight ratio.

| | H83 | B2 |
|---|---|---|
| Plate1 | 53.4 | 46.6 |
| Plate2 | 55.0 | 45.0 |
| Plate3 | 55.6 | 44.4 |

Premixtures PM-18, PM-19, and PM-20: Each pair of premixable h-host and e-host at a weight ratio of 1:1 or 1:3 was physically mixed, grinded, and loaded into an evaporation source. The total weight of the mixture was 0.4 g. The premixed components were thermally co-evaporated at a rate of 2 Å/s in a vacuum chamber under a pressure less than $10^{-7}$ Torr until depletion, and deposited onto glass substrates. The substrates were replaced continuously after deposition of 400 Å of film without stopping the deposition and cooling the source. The compositions of the films were analyzed by high-performance liquid chromatography (HPLC) and the results are shown in Table 4.

TABLE 4

| Experimental HPLC data on Premixability for Premixtures PM-18, PM-19, and PM-20 | | | | | | | | | | | | |
|---|---|---|---|---|---|---|---|---|---|---|---|---|
| | | | Ratio in | H-Host/E-host ratio in deposited films [%] | | | | | | | | |
| Premixture | | | mixture | 1 | 2 | 3 | 4 | 5 | 6 | 7 | 8 | 9 |
| PM-18 | H-Host | B2 | 1 | 39.2 | 38.0 | 36.8 | 35.8 | 35.5 | 35.7 | 35.7 | 35.9 | 35.7 |
| | E-host | G9 | 1 | 60.8 | 62.0 | 63.2 | 64.2 | 64.5 | 64.3 | 64.3 | 64.1 | 64.3 |
| PM-19 | H-Host | B5 | 1 | 51.9 | 50.7 | 50.1 | 50.3 | 50.2 | 49.9 | 50.3 | 50.4 | |
| | E-host | M101 | 1 | 48.1 | 49.3 | 49.9 | 49.7 | 49.8 | 50.1 | 49.7 | 49.6 | |
| PM-20 | H-Host | B2 | 3 | 73.9 | 72.7 | 70.7 | 69.2 | 68.8 | 69.9 | 70.9 | | |
| | E-host | G10 | 1 | 26.1 | 27.3 | 29.3 | 30.8 | 31.2 | 30.1 | 29.1 | | |

The data in Tables 1, 2, 3, and 4 show that the ratio of the two components in premixtures PM-1, PM-9, PM-13, PM-18, PM-19, and PM-20 does not change significantly over a continuous single-source coevaporation. The minor fluctuations in the concentrations do not reveal any trend and can be explained by the accuracy of HPLC analysis. Normally, the change of the concentration before and after depositions within 5% throughout the process is considered to be good and useful for commercial OLED application. These experiments conclude that PM-1, PM-9 and PM-13 are stable premixtures for coevaporation. The coevaporation stability of these premixtures is believed to traceable to the unique chemical structures associated with these two classes of materials.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a formula selected from the group consisting of Formula I and Formula II:

Formula I and

Formula II

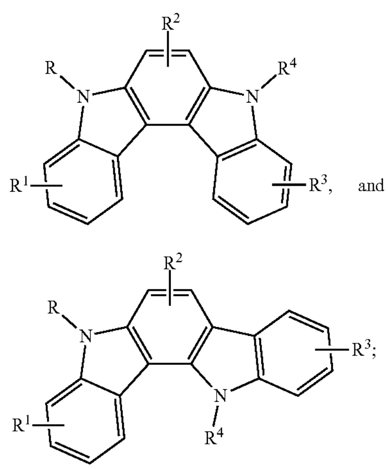

wherein R is selected from the group consisting of:

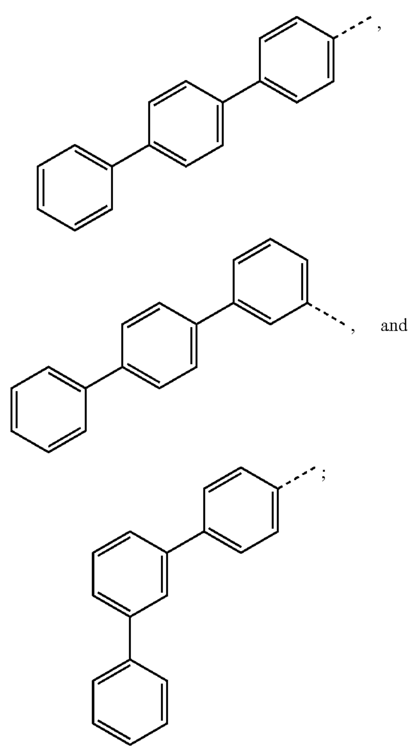

wherein $R^4$ is selected from the group consisting of

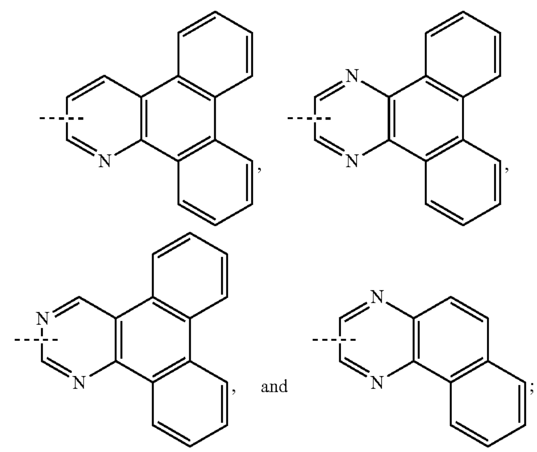

wherein $R^1$, $R^2$ and $R^3$ each independently represents mono to maximum allowable substitutions, or no substitution;

wherein $R^1$, $R^2$ and $R^3$ are each independently selected from the group consisting of hydrogen, deuterium, alkyl, alkenyl, alkyne, alkoxy, halogen, silyl, nitrile, nitro, aryl, heteroaryl and combinations thereof;

wherein any two adjacent substituents are optionally joined or fused into a ring;

wherein $R^4$, $R^1$, $R^2$, and $R^3$ are each independently, optionally, further substituted with one or more substituents selected from the group consisting of hydrogen, deuterium, alkyl, alkenyl, alkynyl, alkoxy, halogen, silyl, nitrile, nitro, aryl, heteroaryl, and combinations thereof; and wherein any hydrogen in the compound is optionally replaced with deuterium.

2. The compound of claim 1, wherein the compound is represented by Formula I.

3. The compound of claim 1, wherein the compound is represented by Formula II.

4. The compound of claim 1, wherein the compound is selected from the group consisting of:

Compound A32

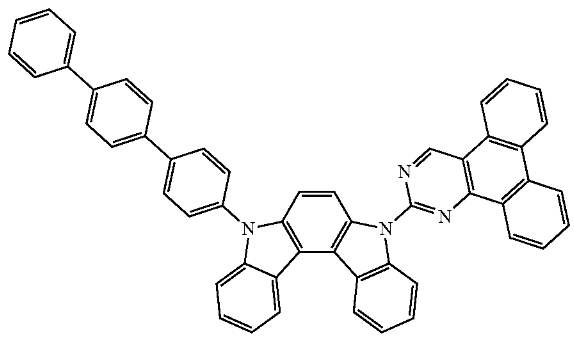

,

Compound A33

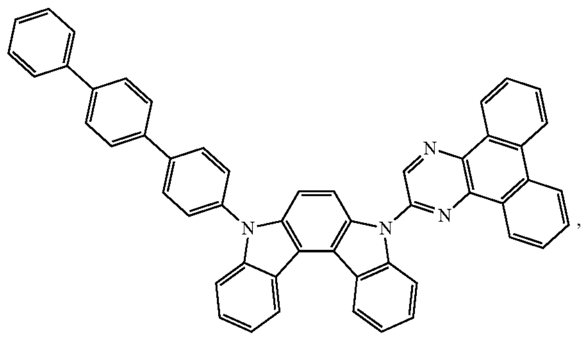

,

Compound B31

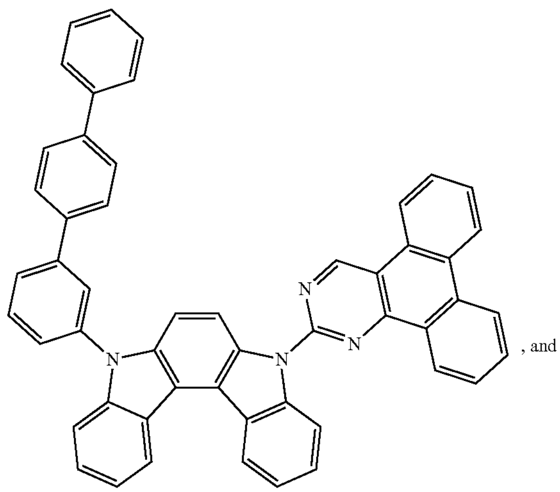

, and

Compound B32

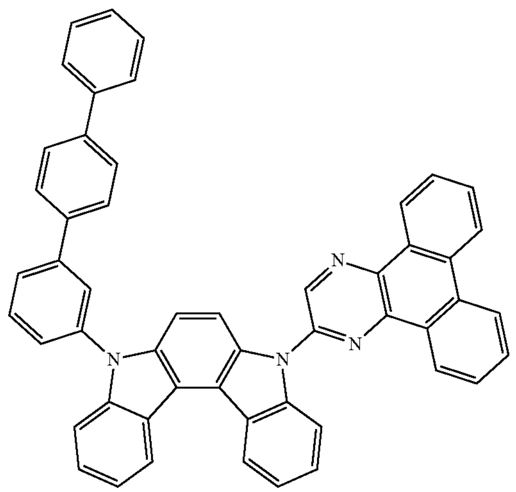

.

5. A composition comprising the compound of claim 1.

6. An organic light emitting device (OLED) comprising:

an anode;

a cathode; and an organic layer, disposed between the anode and the cathode, comprising a compound having a formula selected from the group consisting of Formula I and Formula II:

Formula I

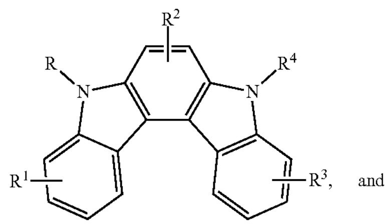

and

Formula II

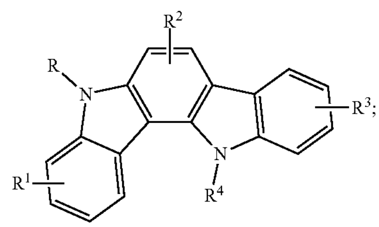

wherein R is selected from the group consisting of:

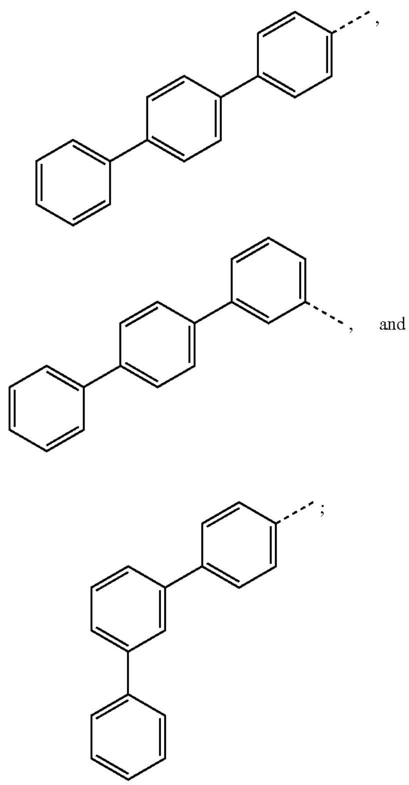

wherein $R^4$ is selected from the group consisting of

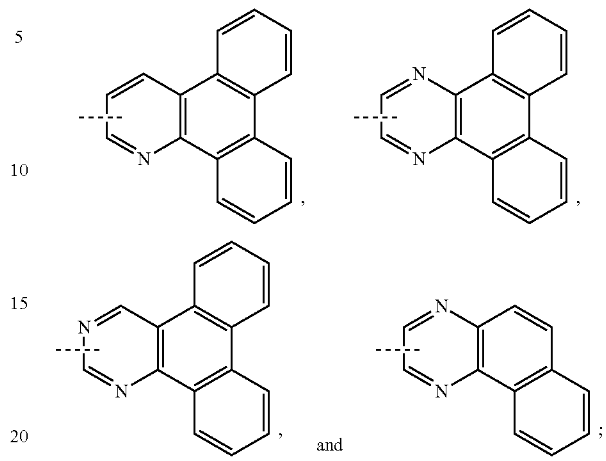

wherein $R^1$, $R^2$ and $R^3$ each independently represents mono to maximum allowable substitutions, or no substitution;

wherein $R^1$, $R^2$ and $R^3$ are each independently selected from the group consisting of hydrogen, deuterium, alkyl, alkenyl, alkyne, alkoxy, halogen, silyl, nitrile, nitro, aryl, heteroaryl and combinations thereof;

wherein any two adjacent substituents are optionally joined or fused into a ring;

wherein $R^4$, $R^1$, $R^2$, and $R^3$ are each independently, optionally, further substituted with one or more substituents selected from the group consisting of hydrogen, deuterium, alkyl, alkenyl, alkynyl, alkoxy, halogen, silyl, nitrile, nitro, aryl, heteroaryl, and combinations thereof; and wherein any hydrogen in the compound is optionally replaced with deuterium.

7. The OLED of claim 6, wherein the organic layer is an emissive layer and the compound of Formula I or Formula II is a host.

8. The OLED of claim 6, wherein the organic layer further comprises a phosphorescent emissive dopant; wherein the emissive dopant is a transition metal complex having at least one ligand or part of the ligand if the ligand is more than bidentate selected from the group consisting of:

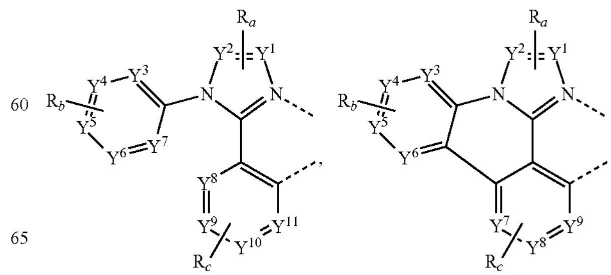

-continued

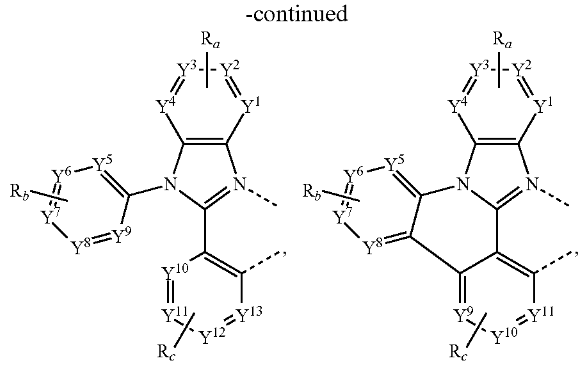

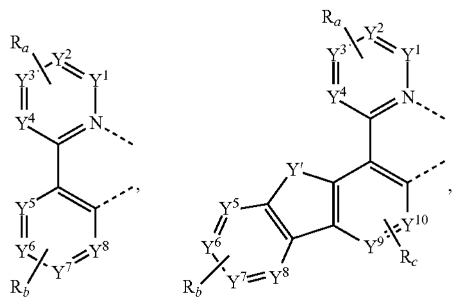

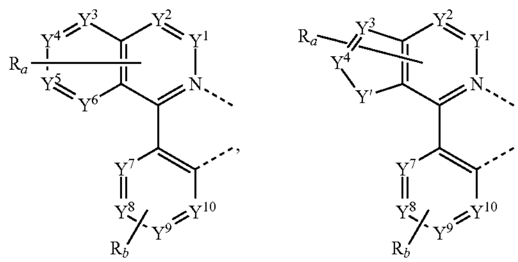

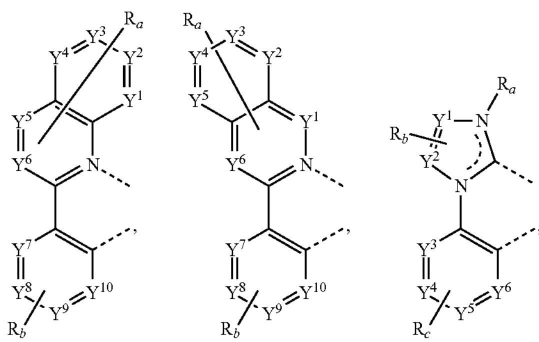

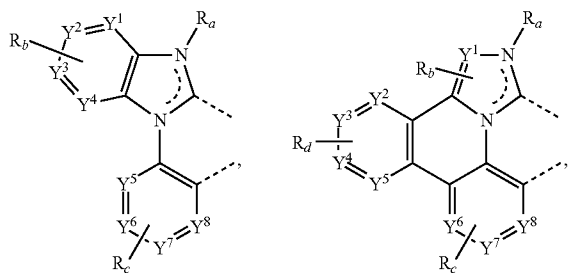

-continued

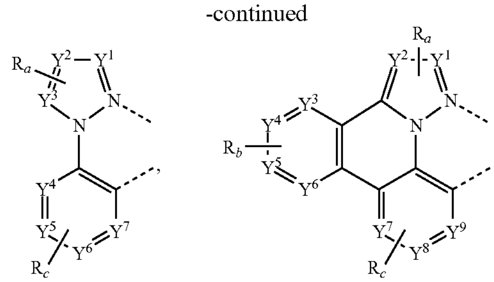

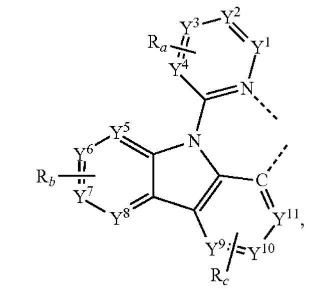

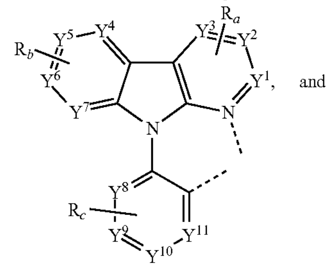

and

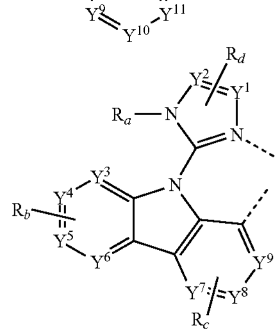

wherein each $Y^1$ to $Y^{13}$ are independently selected from the group consisting of carbon and nitrogen;

wherein Y' is selected from the group consisting of $BR_e$, $NR_e$, $PR_e$, O, S, Se, C═O, S═O, $SO_2$, $CR_eR_f$RR, $SiR_eR_f$, and $GeR_eR_f$;

wherein $R_e$ and $R_f$ are optionally fused or joined to form a ring;

wherein each $R_a$, $R_b$, $R_c$, and $R_d$ may independently represent from mono substitution to the maximum possible number of substitution, or no substitution;

wherein each $R_a$, $R_b$, $R_c$, $R_d$, $R_e$, and $R_f$ is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof; and wherein any two adjacent substituents of $R_a$, $R_b$, $R_c$, and $R_d$ are optionally fused or joined to form a ring or form a multidentate ligand.

9. The OLED of claim 6, wherein the organic layer is a blocking layer and the compound of Formula I or Formula II is a blocking material in the organic layer; or the organic layer is a transporting layer and the compound of Formula I or Formula II is a transporting material in the organic layer.

10. A consumer product comprising an organic light-emitting device (OLED) comprising:

an anode;

a cathode; and an organic layer, disposed between the anode and the cathode, comprising a compound having a formula selected from the group consisting of Formula I and Formula II:

Formula I

Formula II

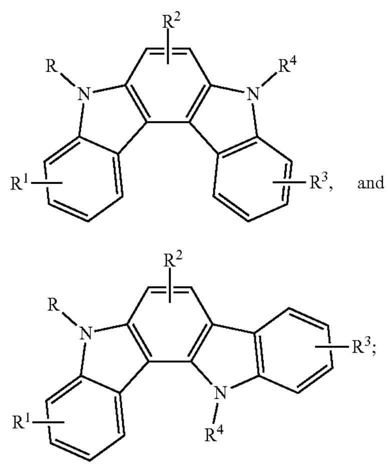

and wherein R is selected from the group consisting of:

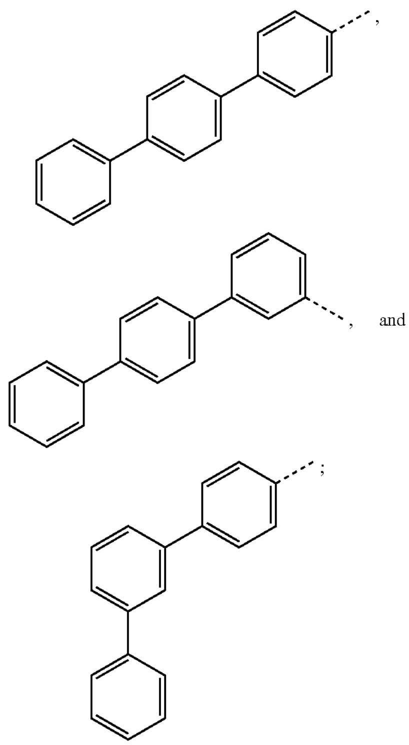

, , and ;

wherein $R^4$ is selected from the group consisting of

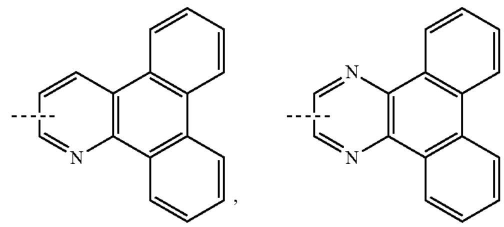

, ,

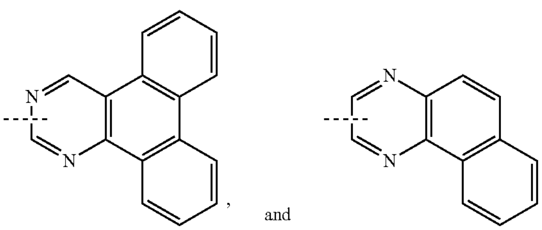

, and ;

wherein $R^1$, $R^2$ and $R^3$ each independently represents mono to maximum allowable substitutions, or no substitution;

wherein $R^1$, $R^2$ and $R^3$ are each independently selected from the group consisting of hydrogen, deuterium, alkyl, alkenyl, alkyne, alkoxy, halogen, silyl, nitrile, nitro, aryl, heteroaryl and combinations thereof;

wherein any two adjacent substituents are optionally joined or fused into a ring;

wherein $R^4$, $R^1$, $R^2$, and $R^3$ are each independently, optionally, further substituted with one or more substituents selected from the group consisting of hydrogen, deuterium, alkyl, alkenyl, alkynyl, alkoxy, halogen, silyl, nitrile, nitro, aryl, heteroaryl, and combinations thereof; and wherein any hydrogen in the compound is optionally replaced with deuterium.

11. The consumer product of claim 10, wherein the consumer product is selected from the group consisting of a flat panel display, a curved display, a computer monitor, a medical monitor, a television, a billboard, a light for interior or exterior illumination and/or signaling, a heads-up display, a fully or partially transparent display, a flexible display, a rollable display, a foldable display, a stretchable display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video walls comprising multiple displays tiled together, a theater or stadium screen, and a sign.

* * * * *